United States Patent
Nakano et al.

(10) Patent No.: US 9,537,111 B2
(45) Date of Patent: Jan. 3, 2017

(54) COMPOUND, MATERIAL FOR ORGANIC ELECTROLUMINESCENCE DEVICE, AND ORGANIC ELECTROLUMINESCENCE DEVICE

(75) Inventors: Yuki Nakano, Chiba (JP); Masaki Numata, Chiba (JP); Hideaki Nagashima, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 517 days.

(21) Appl. No.: 14/116,896

(22) PCT Filed: May 9, 2012

(86) PCT No.: PCT/JP2012/061914
§ 371 (c)(1),
(2), (4) Date: Feb. 14, 2014

(87) PCT Pub. No.: WO2012/153780
PCT Pub. Date: Nov. 15, 2012

(65) Prior Publication Data
US 2014/0183486 A1    Jul. 3, 2014

(30) Foreign Application Priority Data
May 11, 2011 (JP) .................. 2011-106725

(51) Int. Cl.
*H01L 51/50* (2006.01)
*H01L 51/00* (2006.01)
(Continued)

(52) U.S. Cl.
CPC ............ *H01L 51/50* (2013.01); *C07D 209/86* (2013.01); *C07D 307/91* (2013.01); *C07D 333/20* (2013.01); *C07D 333/76* (2013.01); *C07D 407/10* (2013.01); *C07D 417/14* (2013.01); *C07D 491/048* (2013.01);
(Continued)

(58) Field of Classification Search
None
See application file for complete search history.

(56) References Cited

U.S. PATENT DOCUMENTS

2007/0104976 A1*  5/2007  Iwakuma ............... C09K 11/06
                                                        428/690
2009/0017330 A1    1/2009  Iwakuma et al.
(Continued)

FOREIGN PATENT DOCUMENTS

JP      2814435 B2      8/1998
JP      2002-540572 A   11/2002
(Continued)

OTHER PUBLICATIONS

International Search Report issued Jun. 12, 2012 in PCT/JP2012/061914.
(Continued)

*Primary Examiner* — Gregory Clark
(74) *Attorney, Agent, or Firm* — Oblon, McClelland, Maier & Neustadt, L.L.P.

(57) ABSTRACT

A specific material for organic electroluminescence device having m-phenylene skeleton in its molecule realizes a highly heat-resistant and long lifetime organic electroluminescence device capable of driving at low voltage with high efficiency.

21 Claims, 1 Drawing Sheet

(51) Int. Cl.
*C09K 11/06* (2006.01)
*H05B 33/14* (2006.01)
*C07D 333/20* (2006.01)
*C07D 333/76* (2006.01)
*C07D 407/10* (2006.01)
*C07D 417/14* (2006.01)
*C07D 491/048* (2006.01)
*C07D 209/86* (2006.01)
*C07D 307/91* (2006.01)

(52) U.S. Cl.
CPC .......... *C09K 11/06* (2013.01); *H01L 51/0071* (2013.01); *H01L 51/0073* (2013.01); *H01L 51/0074* (2013.01); *H05B 33/14* (2013.01); *C09K 2211/1007* (2013.01); *C09K 2211/1044* (2013.01); *C09K 2211/1059* (2013.01); *C09K 2211/1088* (2013.01); *C09K 2211/1092* (2013.01); *H01L 51/0072* (2013.01); *H01L 51/5016* (2013.01); *H01L 51/5056* (2013.01); *H01L 51/5088* (2013.01); *H01L 51/5096* (2013.01)

(56) References Cited

U.S. PATENT DOCUMENTS

2009/0017331 A1    1/2009    Iwakuma et al.
2009/0224658 A1    9/2009    Iwakuma et al.
2010/0187984 A1    7/2010    Lin et al.
2011/0006670 A1    1/2011    Katakur et al.

FOREIGN PATENT DOCUMENTS

| | | |
|---|---|---|
| JP | 2003-081988 A | 3/2003 |
| JP | 2003-133075 A | 5/2003 |
| JP | 2003-515897 A | 5/2003 |
| JP | 2003-526876 A | 9/2003 |
| JP | 2007-067383 A | 3/2007 |
| JP | 2008-074939 A | 4/2008 |
| JP | 2009-263579 A | 11/2009 |
| JP | 2011-084531 A | 4/2011 |
| WO | WO 2005/057987 A1 | 6/2005 |
| WO | WO 2007/142083 A1 | 12/2007 |
| WO | WO 2009/008099 A1 | 1/2009 |
| WO | WO 2010/004877 A1 | 1/2010 |
| WO | WO 2010/083359 A2 | 7/2010 |
| WO | WO 2011/004639 A1 | 1/2011 |

OTHER PUBLICATIONS

C.W. Tang, et al., "Organic electroluminescent diodes" Applied Physics Letters, vol. 51, No. 12, Sep. 21, 1987 pp. 913-915.

M.A. Baldo, et al. "Very high-efficiency green organiz light-emitting devices based on electrophosphorescence" Applied Physics Letters, vol. 75, No. 1, Jul. 5, 1999, 4 Pages.

* cited by examiner

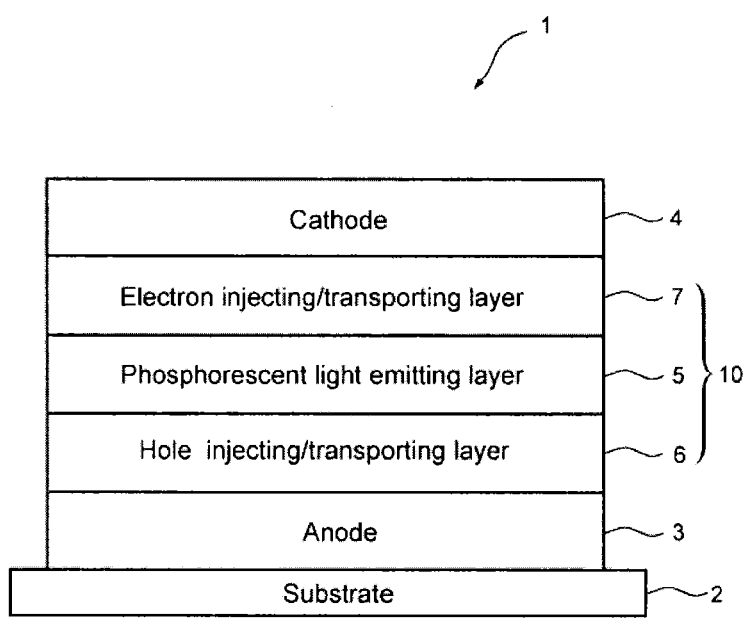

COMPOUND, MATERIAL FOR ORGANIC ELECTROLUMINESCENCE DEVICE, AND ORGANIC ELECTROLUMINESCENCE DEVICE

CROSS REFERENCE TO RELATED APPLICATIONS

The present application is a 35 U.S.C. §371 national stage patent application of International patent application PCT/JP2012/061914, filed on May 9, 2012, published as WO/2012/153780 on Nov. 15, 2012, the text of which is incorporated by reference, and claims the benefit of the filing date of Japanese application no. 2011-106725, filed on May 11, 2011, the text of which is also incorporated by reference.

TECHNICAL FIELD

The present invention relates to novel compounds, materials for organic electroluminescence device, and organic electroluminescence devices employing the materials, particularly relates to materials for realizing an organic electroluminescence device with a high emission efficiency and a long lifetime and organic electroluminescence devices.

BACKGROUND ART

In recent years, many studies have been actively made on an organic thin-film light emitting device that emits light upon recombination of electrons injected from a cathode and holes injected from an anode in an organic light emitting body interposed between both the electrodes. The light emitting device has been attracting attention because the device is thin and emits light with high luminance under a low driving voltage, and multi-color emission can be obtained by selecting light emitting materials.

Since an organic thin-film light emitting device with high luminance emission has been reported by C. W. Tang of Kodak, many studies have been made by research facilities. The typical organic thin-film light emitting device reported by a Kodak research group is successively constructed by an ITO glass substrate, a hole transporting layer including an diamine compound, a light emitting layer including tris(8-quinolinolato)aluminum(III), and a Mg:Ag cathode and emits green light with a luminance of 1,000 cd/m$^2$ at a driving voltage of about 10 V (Non-Patent Document 1).

Many researches have been made on the applications of the organic thin-film light emitting device to display, etc. because of its possibility of a wide selection of emission colors by using various emitting materials in the light emitting layer. Particularly, the research on the materials which emit three primary red, green, blue colors has been made most actively, and the intensive research has been made to improve their properties.

One of the most important problems in the organic thin-film light emitting device is to achieve both high emission efficiency and low driving voltage. Patent Document 1 reports that a highly efficient light-emitting device is obtained by forming a light emitting layer wherein a several percent of a dopant material is doped to a host material. The host material is required to have a high carrier mobility and a uniform film-forming property, and the dopant material is required to have a high fluorescent quantum yield and a uniform dispersibility.

A fluorescent (emission from singlet state) material has been generally used as the dopant material. To improve the emission efficiency, the use of a phosphorescent (emission from triplet state) material has been studied, and a Princeton University group has demonstrated that the phosphorescent material drastically improved the emission efficiency as compared with the known fluorescent material (Non-Patent Document 2). As the phosphorescent dopant material, metal complexes having a central metal, such as iridium, osmium, rhodium, palladium and platinum, have been disclosed (Patent Documents 2 to 4). As the host material to be combinedly used with the phosphorescent dopant material, carbazole derivatives, aromatic amine derivatives, quinolinol metal complexes, etc. have been disclosed (Patent Documents 2 to 6). However, a device achieving both a sufficient emission efficiency and a low driving voltage is not obtained by the known host material.

The host material, the hole transporting material, and the electron transporting material existing around the phosphorescent dopant in an phosphorescent organic electroluminescence device are required to have a high triplet excited energy, i.e., have a wide gap capable of energetically confining the excitons of emitting dopant for achieving a high internal quantum efficiency; a high carrier injection and transport ability for achieving a high power conversion efficiency to allow a driving at low voltage; and a high chemical and heat stability for achieving a long lifetime. The device performance may be optimized by optimizing the chemical structure of material. If the performance (mainly carrier balance) can be simply controlled by modifying the chemical structure of material, the study on the material can be significantly facilitated.

However, the material for organic electroluminescence device, such as the host material, the hole transporting material and the electron transporting material, which meets the above requirements is not yet reported.

Patent Documents 7 to 9 disclose compounds having a carbazole ring, etc. at the terminal end.

PRIOR ART DOCUMENTS

Patent Documents

Patent Document 1: JP Patent 2814435
Patent Document 2: JP 2003-526876A
Patent Document 3: JP 2003-515897A
Patent Document 4: JP 2003-81988A
Patent Document 5: JP 2003-133075A
Patent Document 6: JP 2002-540572A
Patent Document 7: WO2009/008099
Patent Document 8: WO2010/004877
Patent Document 9: WO2005/057987

Non-Patent Documents

Non-Patent Document 1: Applied Physics Letters, 1987, vol. 51, No. 12, pp 913-915
Non-Patent Document 2: Applied Physics Letters, 1999, vol. 75, No. 1, p. 4

SUMMARY OF THE INVENTION

Problem to be Solved by the Invention

The present invention has been made in consideration of the above problems in order to provide highly heat-resistant, long-lifetime organic EL devices which can be driven at lower voltages with high efficiency, and also provide materials for organic EL device and novel compounds which realize such devices.

Means for Solving Problem

As a result of extensive research for achieving the above object, the inventors have found that the above problems are solved by a specific material having a m-phenylene skeleton in its molecule and an organic electroluminescence device employing such a material. The present invention is based on this finding.

The present invention provides:

1. A compound represented by formula (1-1) or formula (1-2):

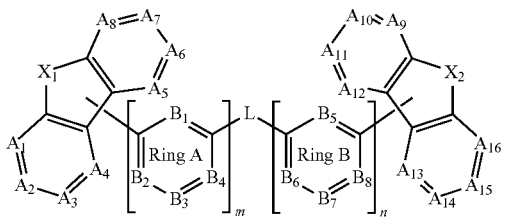

(1-1)

in formula (1-1):

$X_1$ represents an oxygen atom, a sulfur atom, or $-N(R_A)-$;

$X_2$ represents an oxygen atom, a sulfur atom, or $-N(R_B)-$;

each of $A_1$ to $A_8$ independently represents $=C(R_A)-$ or $=N-$;

each of $A_9$ to $A_{16}$ independently represents $=C(R_B)-$ or $=N-$;

each of $B_1$ to $B_8$ independently represents $=C(R)-$ or $=N-$;

each of m and n independently represents an integer of 1 to 3;

L represents an oxygen atom, a sulfur atom, $-N(R)-$, $-Si(R_1)(R_2)-$ or a linker represented by any one of formulae (2-1), (3-1), (4-1), (5-1), and (6-1):

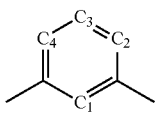

(2-1)

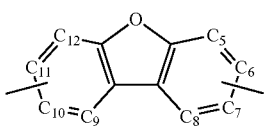

(3-1)

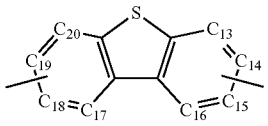

(4-1)

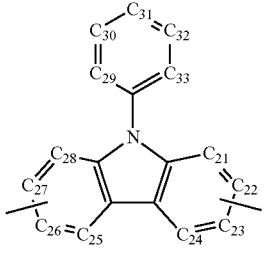

(5-1)

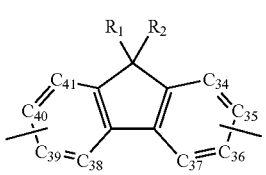

(6-1)

in formulae (2-1), (3-1), (4-1), (5-1), and (6-1):

each of $C_1$ to $C_4$ and $C_{29}$ to $C_{33}$ independently represents $=C(R)-$;

each of $C_5$ to $C_8$, $C_{13}$ to $C_{16}$, $C_{21}$ to $C_{24}$, and $C_{34}$ to $C_{37}$ independently represents $=C(R_B)-$;

each of $C_9$ to $C_{12}$, $C_{17}$ to $C_{20}$, $C_{25}$ to $C_{28}$, and $C_{38}$ to $C_{41}$ independently represents $=C(R_A)-$;

provided that when m=n=1 and both of $X_1$ and $X_2$ represent oxygen atoms, L does not represent the formula (2-1);

when m=n=1 and both of $X_1$ and $X_2$ represent sulfur atoms, L does not represent the formula (2-1); and when m=n=1 or m=n=2, $X_1$ and $X_2$ cannot both be nitrogen atoms;

R represents a hydrogen atom, a deuterium atom, or $R_C$;

each of $R_1$ and $R_2$ independently represents a hydrogen atom, a deuterium atom or $R_C$, or $R_1$ and $R_2$ are boned to each other to represent a divalent group represented by $-(CR_3R_4)_p-$;

$R_A$ represents a hydrogen atom, a deuterium atom, $R_C$, or a single bond bonded to ring A;

$R_B$ represents a hydrogen atom, a deuterium atom, $R_C$, or a single bond bonded to ring B;

$R_C$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atom, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or $-P(=O)R_3R_4$;

each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and p represents an integer of 5 to 8;

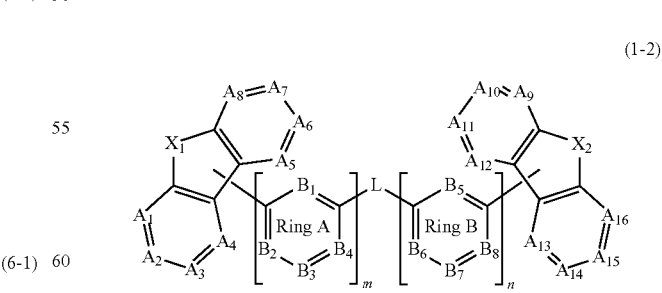

(1-2)

in formula (1-2):

$X_1$ represents an oxygen atom, a sulfur atom, or $-N(R_A)-$;

$X_2$ represents an oxygen atom, a sulfur atom, or $-N(R_B)-$;

each of $A_1$ to $A_8$ independently represents $=C(R_A)-$ or $=N-$;
each of $A_9$ to $A_{16}$ independently represents $=C(R_B)-$ or $=N-$;
at least one of $A_1$ to $A_{16}$ represents $=N-$;
each of $B_1$ to $B_8$ independently represents $=C(R)-$ or $=N-$;
each of m and n independently represents an integer of 1 to 3;
L represents an oxygen atom, a sulfur atom, $-N(R)-$, $-Si(R_1)(R_2)-$, or a linker represented by any one of formulae (2-2), (3-2), (4-2), (5-2), and (6-2):

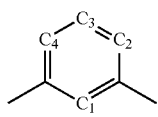
(2-2)

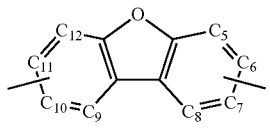
(3-2)

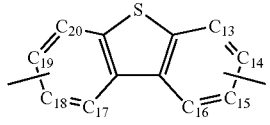
(4-2)

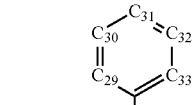
(5-2)

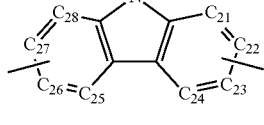

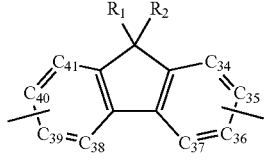
(6-2)

in formulae (2-2), (3-2), (4-2), (5-2), and (6-2):
each of $C_1$ to $C_4$ and $C_{29}$ to $C_{33}$ independently represents $=C(R)-$ or $=N-$;
each of $C_5$ to $C_8$, $C_{13}$ to $C_{16}$, $C_{21}$ to $C_{24}$, and $C_{34}$ to $C_{37}$ independently represents $=C(R_B)-$ or $=N-$; and each of $C_9$ to $C_{12}$, $C_{17}$ to $C_{20}$, $C_{25}$ to $C_{28}$, and $C_{38}$ to $C_{41}$ independently represents $=C(R_A)-$ or $=N-$;
R represents a hydrogen atom, a deuterium atom, or $R_C$;
each of $R_1$ and $R_2$ independently represents a hydrogen atom, a deuterium atom or $R_C$, or $R_1$ and $R_2$ are boned to each other to represent a divalent group represented by $-(CR_3R_4)_p-$;
$R_A$ represents a hydrogen atom, a deuterium atom, $R_C$, or a single bond bonded to ring A;
$R_B$ represents a hydrogen atom, a deuterium atom, $R_C$, or a single bond bonded to ring B;
$R_C$ independently represents, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or $-P(=O)R_3R_4$;
each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and
p represents an integer of 5 to 8;

2. The compound according to item 1, wherein each of R, $R_1$, $R_2$, $R_A$, and $R_B$ independently represents a hydrogen atom, a deuterium atom, a single bond, a substituted or unsubstituted alkyl group having 1 to 5 carbon atoms, a substituted or unsubstituted aryl group having 6 to 18 ring carbon atoms, a substituted or unsubstituted heteroaryl group having 5 to 18 ring atoms, or $-P(=O)(R_3)(R_4)$;

3. The compound according to item 1 or 2, wherein at least one of m and n is 2 or 3;

4. The compound according to any one of items 1 to 3, wherein the compound is represented by formula (7):

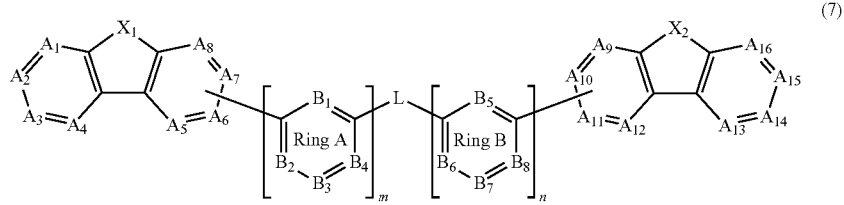
(7)

wherein $X_1$, $X_2$, $A_1$ to $A_{16}$, $B_1$ to $B_8$, L, m, and n are the same as defined above with respect to $X_1$, $X_2$, $A_1$ to $A_{16}$, $B_1$ to $B_8$, L, m, and n of the formula (1-1), or $X_1$, $X_2$, $A_1$ to $B_8$, L, m, and n of the formula (1-2);

5. The compound according to any one of items 1 to 4, wherein the compound is represented by formula (8):

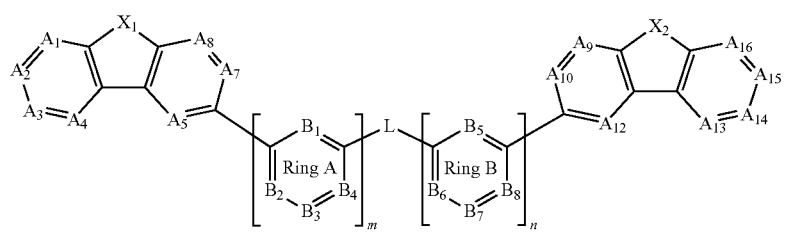

(8)

wherein $X_1$, $X_2$, $A_1$ to $A_5$, $A_7$ to $A_{10}$, $A_{12}$ to $A_{16}$, $B_1$ to $B_8$, L, m, and n are the same as defined above with respect to $X_1$, $X_2$, $A_1$ to $A_5$, $A_7$ to $A_{10}$, $A_{12}$ to $A_{16}$, $B_1$ to $B_8$, L, m, and n of the formula (1-1), or $X_1$, $X_2$, $A_1$ to $A_5$, $A_7$ to $A_{10}$, $A_{12}$ to $A_{16}$, $B_1$ to $B_8$, L, m, and n of the formula (1-2);

6. The compound according to any one of items 1 to 5, wherein the compound is represented by formula (9):

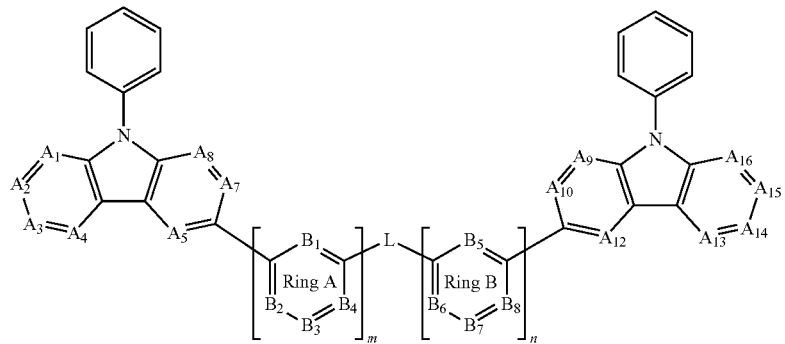

(9)

wherein $A_1$ to $A_5$, $A_7$ to $A_{10}$, $A_{12}$ to $A_{16}$, $B_1$ to $B_8$, L, m, and n are the same as defined above with respect to $A_1$ to $A_5$, $A_7$ to $A_{10}$, $A_{12}$ to $A_{16}$, $B_1$ to $B_8$, L, m, and n of the formula (1-1), or $A_1$ to $A_5$, $A_7$ to $A_{10}$, $A_{12}$ to $A_{16}$, $B_1$ to $B_8$, L, m, and n of the formula (1-2);

7. The compound according to any one of items 1 to 3, wherein the compound is represented by formula (10):

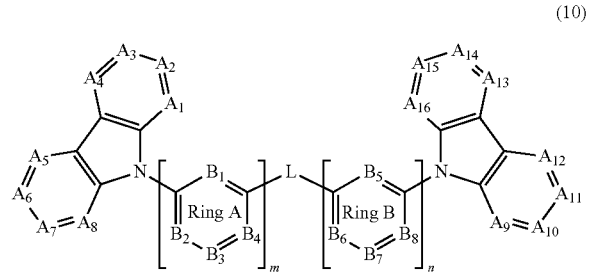

(10)

wherein $A_1$ to $A_{16}$, $B_1$ to $B_8$, L, m, and n are the same as defined above with respect to $A_1$ to $A_{16}$, $B_1$ to $B_8$, L, m, and n of the formula (1-1), or $A_1$ to $A_{16}$, $B_1$ to $B_8$, L, m, and n of the formula (1-2);

8. The compound according to any one of items 1 to 7, wherein the compound has a molecular weight of 1000 or less;

9. The compound according to any one of items 1 to 8, wherein the compound has a triplet energy of 2.90 eV or more;

10. A material for organic electroluminescence device comprising the compound according to any one of items 1 to 9;

11. An organic electroluminescence device comprising at least one organic thin film layer between a cathode and anode, wherein the at least one organic thin film layer comprises a light emitting layer and at least one layer of the at least one organic thin film layer comprises the material for organic electroluminescence device according to item 10;

12. The organic electroluminescence device according to item 11, wherein the light emitting layer comprises the material for organic electroluminescence device;

13. The organic electroluminescence device according to item 12, wherein the light emitting layer comprises the material for organic electroluminescence device as a host material;

14. The organic electroluminescence device according to any one of items 11 to 13, wherein an electron transporting layer is disposed between the light emitting layer and the cathode, and a hole blocking layer comprising the material for organic electroluminescence device is disposed between the light emitting layer and the electron transporting layer;

15. The organic electroluminescence device according to any one of items 11 to 14, wherein a hole transporting layer is disposed between the light emitting layer and the anode, and an electron blocking layer comprising the material for organic electroluminescence device is disposed between the light emitting layer and the hole transporting layer;

16. The organic electroluminescence device according to any one of items 11 to 15, wherein the light emitting layer comprises a phosphorescent material;

17. The organic electroluminescence device according to item 16, wherein the phosphorescent material is a compound comprising a metal selected from iridium (Ir), osmium (Os) and platinum (Pt);
18. The organic electroluminescence device according to item 17, wherein the compound comprising a metal is an ortho-metallated complex;
19. The organic electroluminescence device according to any one of items 11 to 18, wherein an interfacial region between the cathode and the organic thin film layer comprises a reducing dopant;
20. The organic electroluminescence device according to any one of items 11 to 19, wherein an electron injecting layer is disposed between the light emitting layer and the cathode, and the electron injecting layer comprises a nitrogen-containing ring derivative; and
21. The organic electroluminescence device according to any one of items 11 to 20, wherein a hole transporting layer is disposed between the light emitting layer and the anode, and the hole transporting layer comprises the material for organic electroluminescence device.

Effect of the Invention

According to the present invention, a long lifetime organic electroluminescence device which can be driven at low voltage with high efficiency, and a material for organic EL device and a novel compound which realize such an organic electroluminescence device are provided.

BRIEF DESCRIPTION OF DRAWINGS

FIG. 1 is a schematic cross-sectional view of an example of the organic EL device of the invention.

MODE FOR CARRYING OUT THE INVENTION

Compound and Material for Organic Electroluminescence Device

The compound of the invention is represented by formula (1-1) or (1-2). The material for organic electroluminescence device (also referred to as "material for organic EL device") of the invention comprises the compound represented by formula (1-1) or (1-2):

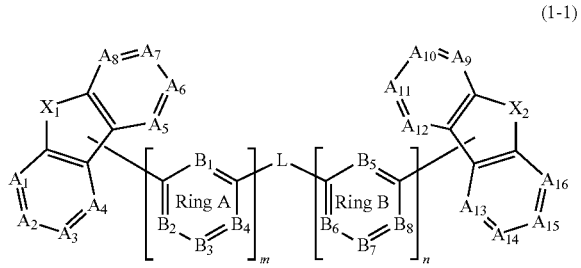

(1-1)

in formula (1-1):
$X_1$ represents an oxygen atom, a sulfur atom, or —N($R_A$)—;
$X_2$ represents an oxygen atom, a sulfur atom, or —N($R_B$)—;
each of $A_1$ to $A_8$ independently represents =C($R_A$)— or =N—;
each of $A_9$ to $A_{16}$ independently represents =C($R_B$)— or =N—;

each of $B_1$ to $B_8$ independently represents =C(R)— or =N—; each of m and n independently represents an integer of 1 to 3;
L represents an oxygen atom, a sulfur atom, —N(R)—, —Si($R_1$)($R_2$)— or a linker represented by any one of formulae (2-1), (3-1), (4-1), (5-1), and (6-1):

(2-1)

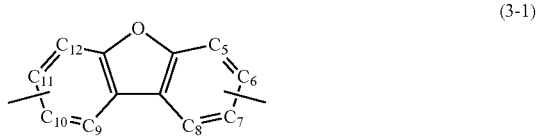

(3-1)

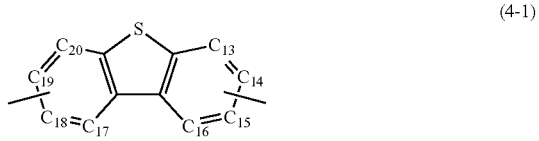

(4-1)

(5-1)

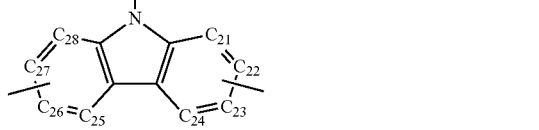

(6-1)

in formulae (2-1), (3-1), (4-1), (5-1), and (6-1):
each of $C_1$ to $C_4$ and $C_{29}$ to $C_{33}$ independently represents =C(R)—;
each of $C_5$ to $C_8$, $C_{13}$ to $C_{16}$, $C_{21}$ to $C_{24}$, and $C_{34}$ to $C_{37}$ independently represents =C($R_B$)—;
each of $C_9$ to $C_{12}$, $C_{17}$ to $C_{20}$, $C_{25}$ to $C_{28}$, and $C_{38}$ to $C_{41}$ independently represents =C($R_A$)—;
provided that when m=n=1 and both of $X_1$ and $X_2$ represent oxygen atoms, L does not represent the formula (2-1);
when m=n=1 and both of $X_1$ and $X_2$ represent sulfur atoms, L does not represent the formula (2-1); and
when m=n=1 or m=n=2, $X_1$ and $X_2$ cannot both be nitrogen atoms;
R represents a hydrogen atom, a deuterium atom, or $R_C$;
each of $R_1$ and $R_2$ independently represents a hydrogen atom, a deuterium atom, or $R_C$, or $R_1$ and $R_2$ are boned to each other to represent a divalent group represented by —(CR$_3$R$_4$)$_p$—;
$R_A$ represents a hydrogen atom, a deuterium atom, $R_C$, or a single bond bonded to ring A;
$R_B$ represents a hydrogen atom, a deuterium atom, $R_C$, or a single bond bonded to ring B;
$R_C$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atom, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or $-P(=O)R_3R_4$;

each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and p represents an integer of 5 to 8; or

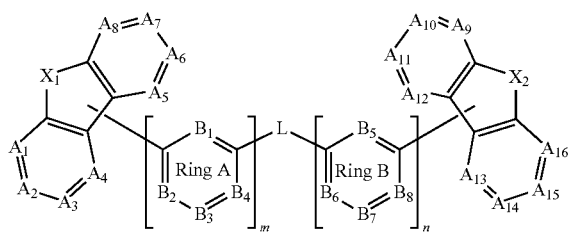
(1-2)

in formula (1-2):

$X_1$ represents, an oxygen atom, a sulfur atom, or $-N(R_A)-$;

$X_2$ represents, an oxygen atom, a sulfur atom, or $-N(R_B)-$;

each of $A_1$ to $A_8$ independently represents $=C(R_A)-$ or $=N-$;

each of $A_9$ to $A_{16}$ independently represents $=C(R_B)-$ or $=N-$;

at least one of $A_1$ to $A_{16}$ represents $=N-$;

each of $B_1$ to $B_8$ independently represents $=C(R)-$ or $=N-$;

each of m and n independently represents an integer of 1 to 3;

L represents an oxygen atom, a sulfur atom, $-N(R)-$, $-Si(R_1)(R_2)-$, or a linker represented by any one of formulae (2-2), (3-2), (4-2), (5-2), and (6-2):

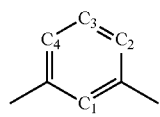
(2-2)

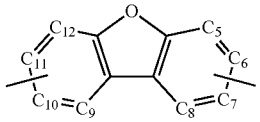
(3-2)

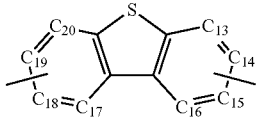
(4-2)

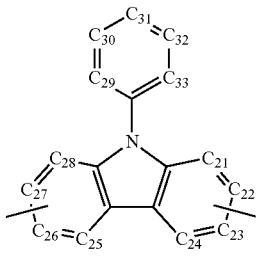
(5-2)

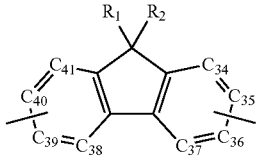
(6-2)

in formulae (2-2), (3-2), (4-2), (5-2), and (6-2):

each of $C_1$ to $C_4$ and $C_{29}$ to $C_{33}$ independently represents $=C(R)-$ or $=N-$;

each of $C_5$ to $C_8$, $C_{13}$ to $C_{16}$, $C_{21}$ to $C_{24}$, and $C_{34}$ to $C_{37}$ independently represents $=C(R_B)-$ or $=N-$; and each of $C_9$ to $C_{12}$, $C_{17}$ to $C_{20}$, $C_{25}$ to $C_{28}$, and $C_{38}$ to $C_{41}$ independently represents $=C(R_A)-$ or $=N-$;

R represents a hydrogen atom, a deuterium atom, or $R_C$;

each of $R_1$ and $R_2$ independently represents a hydrogen atom, a deuterium atom or $R_C$, or $R_1$ and $R_2$ are boned to each other to represent a divalent group represented by $-(CR_3R_4)_p-$;

$R_A$ represents a hydrogen atom, a deuterium atom, $R_C$, or a single bond bonded to ring A;

$R_B$ represents a hydrogen atom, a deuterium atom, $R_C$, or a single bond bonded to ring B;

$R_C$ independently represents, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or $-P(=O)R_3R_4$;

each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and p represents an integer of 5 to 8.

At least one of m and n is preferably represents 2 or 3.

Preferably, each of $X_1$ and $X_2$ independently represents an oxygen atom or a sulfur atom.

Each of R, $R_1$, $R_2$, $R_A$, $R_B$, and $R_C$ is preferably unsubstituted.

The compound and the material for organic EL device are preferably represented by any one of formulae (7) to (11):

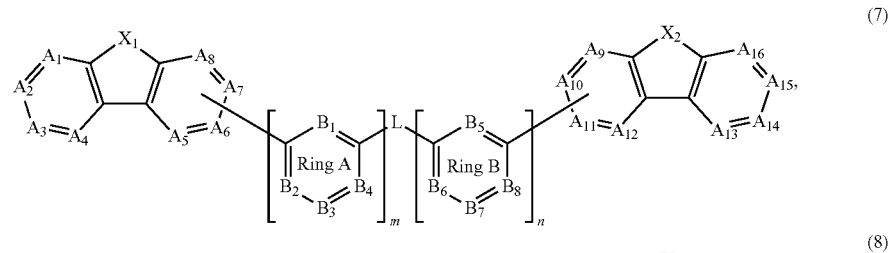

(7)

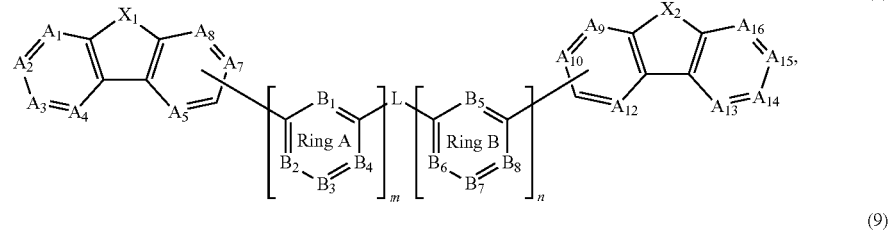

(8)

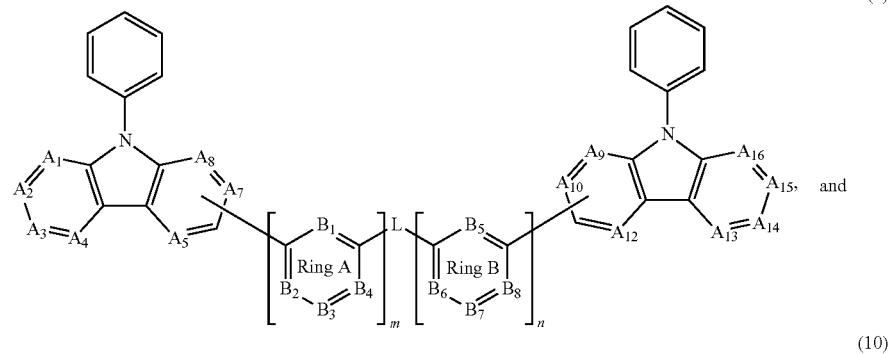

(9)

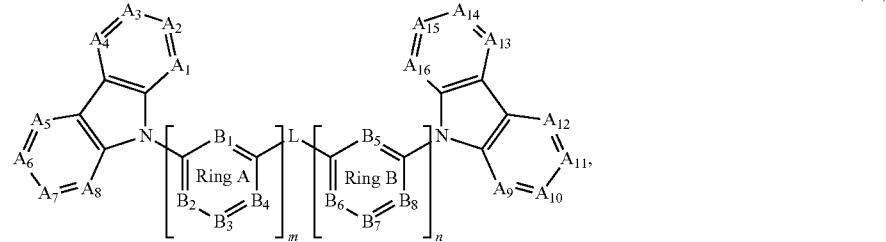

(10)

In formulae (1-1) and (1-2), one of $X_1$ and $A_1$ to $A_8$ one is bonded to the ring A, and one of $X_2$ and $A_9$ to $A_{16}$ is bonded to the ring B.

In formulae (1-1) and (1-2):
R groups, if any, may be the same or different;
$R_A$ groups, if any, may be the same or different;
$R_B$ groups, if any, may be the same or different;
$R_C$ groups, if any, may be the same or different;
$R_3$ groups, if any, may be the same or different; and
$R_4$ groups, if any, may be the same or different.

In formulae (1-1) and (1-2), when m represents 2 or 3, rings A may be the same or different, and when n represent 2 or 3, rings B may be the same or different.

in formula (7), $X_1$, $X_2$, $A_1$ to $A_{16}$, $B_1$ to $B_8$, L, m, and n are the same as defined above with respect to $X_1$, $X_2$, $A_1$ to $A_{16}$, $B_1$ to $B_8$, L, m, and n of the formula (1-1), or $X_1$, $X_2$, $A_1$ to $A_{16}$, $B_1$ to $B_8$, L, m, and n of the formula (1-2);

in formula (8), $X_1$, $X_2$, $A_1$ to $A_5$, $A_7$ to $A_{10}$, $A_{12}$ to $A_{16}$, $B_1$ to $B_8$, L, m, and n are the same as defined above with respect to $X_1$, $X_2$, $A_1$ to $A_5$, $A_7$ to $A_{10}$, $A_{12}$ to $A_{16}$, $B_1$ to $B_8$, L, m, and n of the formula (1-1), or $X_1$, $X_2$, $A_1$ to $A_5$, $A_7$ to $A_{10}$, $A_{12}$ to $A_{16}$, $B_1$ to $B_8$, L, m, and n of the formula (1-2);

in formula (9), $A_1$ to $A_5$, $A_7$ to $A_{10}$, $A_{12}$ to $A_{16}$, $B_1$ to $B_8$, L, m, and n are the same as defined above with respect to $A_1$ to $A_5$, $A_7$ to $A_{10}$, $A_{12}$ to $A_{16}$, $B_1$ to $B_8$, L, m, and n of the formula (1-1), or $A_1$ to $A_5$, $A_7$ to $A_{10}$, $A_{12}$ to $A_{16}$, $B_1$ to $B_8$, L, m, and n of the formula (1-2); and in formula (10), $A_1$ to $A_{16}$, $B_1$ to $B_8$, L, m, and n are the same as defined above with respect to $A_1$ to $A_{16}$, $B_1$ to $B_8$, L, m, and n of the formula (1-1), or $A_1$ to $A_{16}$, $B_1$ to $B_8$, L, m, and n of the formula (1-2).

In a preferred embodiment of the compound and the for organic EL device, one of $A_5$ to $A_8$ is bonded to the ring A, and one of $A_9$ to $A_{12}$ is bonded to the ring B.

In a more preferred embodiment, $A_6$ is bonded to the ring A, and $A_{11}$ is bonded to the ring B.

(11)

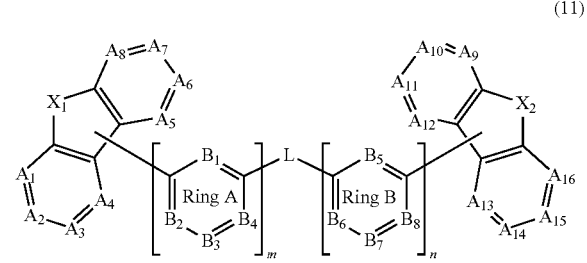

in formula (11):

each of $X_1$ and $X_2$ independently represents an oxygen atom or a sulfur atom;

each of $A_1$ to $A_8$ independently represents =C($R_A$)— or =N—;

each of $A_9$ to $A_{16}$ independently represents =C($R_B$)— or =N—;

each of $B_1$ to $B_8$ independently represents =C(R)— or =N—; one of m and n represents an integer of 1 to 3 and the other represents 2 or 3;

L represents an oxygen atom, a sulfur atom, —N(R)—, or a linker represented by any one of formulae (2-3), (3-3), (4-3), (5-3), and (6-3):

(2-3)

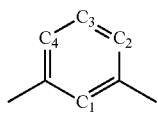

(3-3)

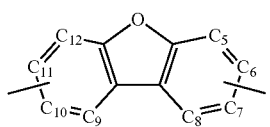

(4-3)

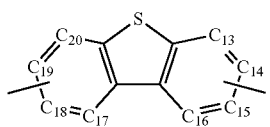

(5-3)

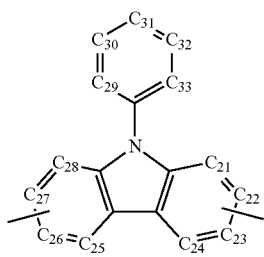

(6-3)

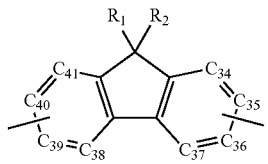

in formulae (2-3), (3-3), (4-3), (5-3), and (6-3):

each of $C_1$ to $C_4$ and $C_{29}$ to $C_{33}$ independently represents =C(R)— or =N—;

each of $C_5$ to $C_8$, $C_{13}$ to $C_{16}$, $C_{21}$ to $C_{24}$, and $C_{34}$ to $C_{37}$ independently represents =C($R_B$)— or =N—;

each of $C_9$ to $C_{12}$, $C_{17}$ to $C_{20}$, $C_{25}$ to $C_{28}$, and $C_{38}$ to $C_{41}$ independently represents =C($R_A$)— or =N—;

R represents a hydrogen atom, a deuterium atom, or $R_C$;

each of $R_1$ and $R_2$ independently represents a hydrogen atom, a deuterium atom or $R_C$, or $R_1$ and $R_2$ are boned to each other to represent a divalent group represented by —(CR$_3$R$_4$)$_p$—;

$R_A$ represents a hydrogen atom, a deuterium atom, $R_C$, or a single bond bonded to ring A;

$R_B$ represents a hydrogen atom, a deuterium atom, $R_C$, or a single bond bonded to ring B;

$R_C$ represents a substituted or unsubstituted alkyl group having 1 to 5 carbon atoms, a substituted or unsubstituted aryl group having 6 to 18 ring carbon atoms, or a substituted or unsubstituted heteroaryl group having 5 to 18 ring atoms; and an optional substituent for $R_C$ is selected from the group consisting of an alkyl group having 1 to 4 carbon atoms, a cycloalkyl group having 3 to 12 ring carbon atoms, an alkoxy group having 1 to 4 carbon atoms, a cycloalkoxy group having 3 to 6 ring carbon atoms, an aryl group having 6 to 18 ring carbon atoms, a heteroaryl group having 5 to 18 ring atoms, an aryloxy group having 6 to 18 ring carbon atoms, an amino group, an alkylamino group having 1 to 4 carbon atoms, a silyl group, an alkylsilyl group having 1 to 6 carbon atoms, a fluorine atom, and a cyano group.

The details of $X_1$, $X_2$, $A_1$ to $A_{16}$, $B_1$ to $B_8$, m, and n in formula (11) are the same as $X_1$, $X_2$, $A_1$ to $A_{16}$, $B_1$ to $B_8$, m, and n in formula (1-1), and $X_1$, $X_2$, $A_1$ to $A_{16}$, $B_1$ to $B_8$, m, and n in formula (1-2).

In formula (11), one of $X_1$ and $A_1$ to $A_8$ is bonded to the ring A, and one of $X_2$ and $A_9$ to $A_{16}$ is bonded to the ring B.

Examples of the alkyl group include a methyl group, an ethyl group, a propyl group, an isopropyl group, a n-butyl group, a s-butyl group, an isobutyl group, a t-butyl group, and a n-pentyl group.

Examples of the alkoxy group include those including the alkyl group mentioned above.

Examples of the amino group substituted with an alkyl group having 1 to 30 carbon atoms and/or an aryl group having 6 to 30 ring carbon atoms include amino groups substituted with the alkyl group mentioned above and/or the aryl group described below.

Examples of the silyl group substituted with an alkyl group having 1 to 30 carbon atoms and/or an aryl group having 6 to 30 ring carbon atoms include silyl groups substituted with the alkyl group mentioned above and/or the aryl group described below.

Examples of the cycloalkyl group include a cyclopropyl group, a cyclobutyl group, a cyclopentyl group, and a cyclohexyl group.

Examples of the cycloalkoxy group include those including the cycloalkyl group mentioned above.

The aryl group having 6 to 18 ring carbon atoms may be a non-fused aryl group or a fused aryl group, and examples thereof include a phenyl group, a naphthyl group, a phenanthryl group, a biphenylyl group, a terphenylyl group, a fluoranthenyl group, a triphenylenyl group, a phenanthrenyl group, and a 9,9-dimethylfluorenyl group.

Examples of the aryloxy group include those including the aryl group mentioned above.

Examples of the heteroaryl group having 5 to 18 ring atoms include a pyrrolyl group, a pyrazinyl group, a pyridinyl group, a pyrimidinyl group, a pyridazinyl group, a triazinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a thienyl group, a pyrrolidinyl group, a dioxanyl group, a piperidinyl group, a morpholinyl group, a piperazinyl group, a carbazolyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzimidazolyl group, a pyranyl group, and a benzo[c]dibenzofuranyl group.

Examples of the fluoroalkyl group having 1 to 30 carbon atoms include the alkyl group mentioned above, wherein one or more hydrogen atoms are replaced by a fluorine atom.

The aralkyl group having 7 to 30 carbon atoms includes the alkyl group mentioned above which is substituted with the aryl group mentioned above, and examples thereof include a benzyl group, a 1-phenylethyl group, a 2-phenylethyl group, a 1-phenylisopropyl group, a 2-phenylisopropyl group, and a phenyl-tert-butyl group.

The optional substituent referred to by "substituted or unsubstituted" may include an alkyl group, an alkoxy group, a fluoroalkyl group, an aryl group, a heteroaryl group, an aryloxy group, an aralkyl group, a silyl group, an amino group, a fluorine atom, and a cyano group. Examples thereof are the same as mentioned above.

When $X_1$ represents —N($R_A$)—, $R_A$ is preferably the alkyl group, the aryl group, the heteroaryl group, the aryloxy group, or the aralkyl group.

When any one of $A_1$ to $A_8$ represents =C($R_A$)—, $R_A$ is preferably the alkyl group, the aryl group, the heteroaryl group, the fluoroalkyl group, the cycloalkyl group, the silyl group, a cyano group, the alkoxy group, the aryloxy group, the aralkyl group, a hydroxyl group, a nitro group, the amino group, or the phosphine oxide group.

When any one of $C_9$ to $C_{12}$, $C_{17}$ to $C_{20}$, $C_{25}$ to $C_{28}$, and $C_{38}$ to $C_{41}$ represents =C($R_A$)—, $R_A$ is preferably the alkyl group, the aryl group, the heteroaryl group, the fluoroalkyl group, the cycloalkyl group, the silyl group, a cyano group, the alkoxy group, the aryloxy group, the aralkyl group, the hydroxyl group, a nitro group, the amino group, or the phosphine oxide group.

When $X_2$ represents —N($R_B$)—, $R_B$ is preferably the alkyl group, the aryl group, the heteroaryl group, the aryloxy group, or the aralkyl group.

When any one of $A_9$ to $A_{16}$ represents =C($R_B$)—, $R_B$ is preferably the alkyl group, the aryl group, the heteroaryl group, the fluoroalkyl group, the cycloalkyl group, the silyl group, a cyano group, the alkoxy group, the aryloxy group, the aralkyl group, a hydroxyl group, a nitro group, the amino group, or the phosphine oxide group.

When any of $C_5$ to $C_8$, $C_{13}$ to $C_{16}$, $C_{21}$ to $C_{24}$, and $C_{34}$ to $C_{37}$ represents =C($R_B$)—, $R_B$ is preferably the alkyl group, the aryl group, the heteroaryl group, the fluoroalkyl group, the cycloalkyl group, the silyl group, a cyano group, the alkoxy group, the aryloxy group, the aralkyl group, a hydroxyl group, a nitro group, the amino group, or the phosphine oxide group.

When any one of $B_1$ to $B_8$ represents =C(R)—, R is preferably the alkyl group, the aryl group, the heteroaryl group, the fluoroalkyl group, the cycloalkyl group, the silyl group, a cyano group, the alkoxy group, the aryloxy group, the aralkyl group, a hydroxyl group, a nitro group, the amino group, or the phosphine oxide group.

When L represents —N(R)—, R is preferably the alkyl group, the aryl group, the heteroaryl group, the aryloxy group, or the aralkyl group.

When any one of $C_1$ to $C_4$ and $C_{29}$ to $C_{33}$ represents =C(R)—, R is preferably the alkyl group, the aryl group, the heteroaryl group, the fluoroalkyl group, the cycloalkyl group, the silyl group, a cyano group, the alkoxy group, the aryloxy group, the aralkyl group, a hydroxyl group, a nitro group, the amino group, or the phosphine oxide group.

$R_C$ is preferably the alkyl group, the aryl group, the heteroaryl group, the fluoroalkyl group, the cycloalkyl group, the silyl group, a cyano group, the alkoxy group, the aryloxy group, the aralkyl group, a hydroxyl group, a nitro group, the amino group, or the phosphine oxide group.

In view of the heat resistance of the compound, L is preferably a fused ring and more preferably a dibenzofurandiyl group, a dibenzothiophenediyl group, a quinoxalinediyl group, or a carbazolediyl group.

Examples of the compounds for the material for organic electroluminescence device represented by any of formulae (1-1), (1-2), and (7) to (11) are shown below.

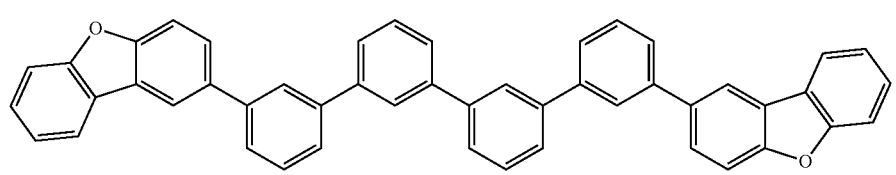

(1)

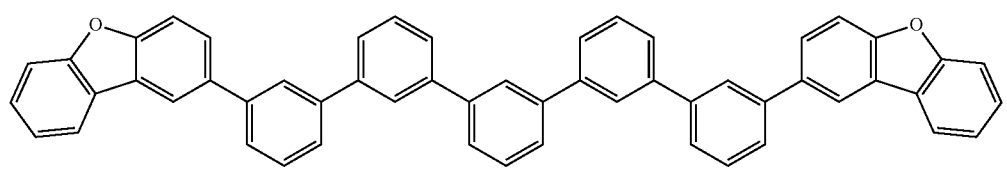

(2)

-continued
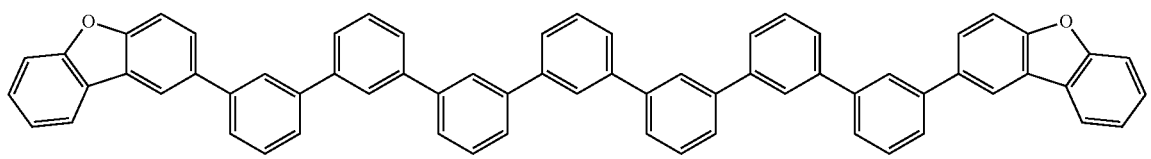
(3)
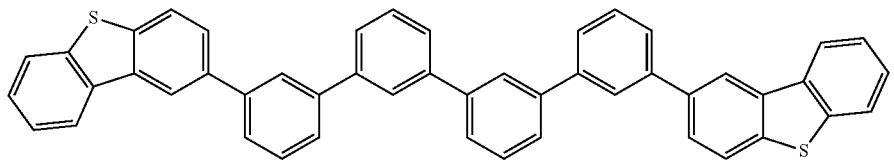
(4)
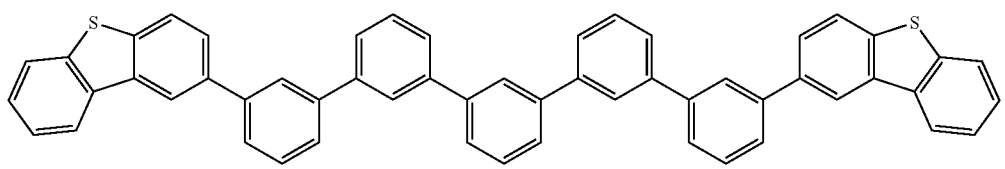
(5)
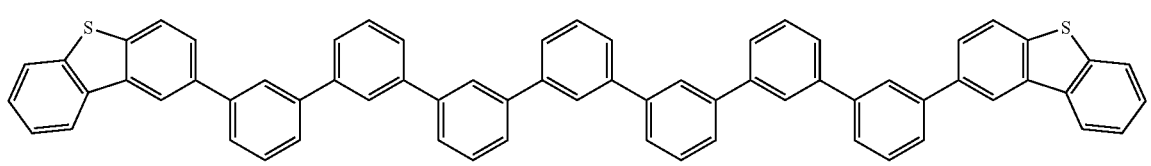
(6)
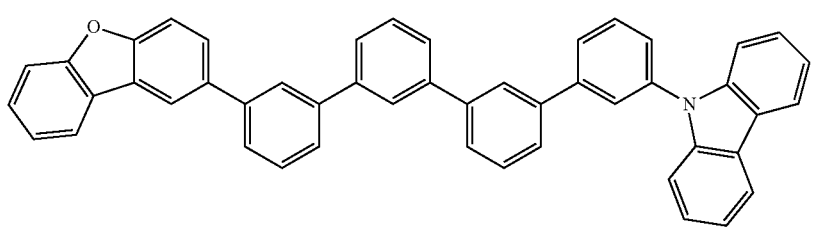
(7)
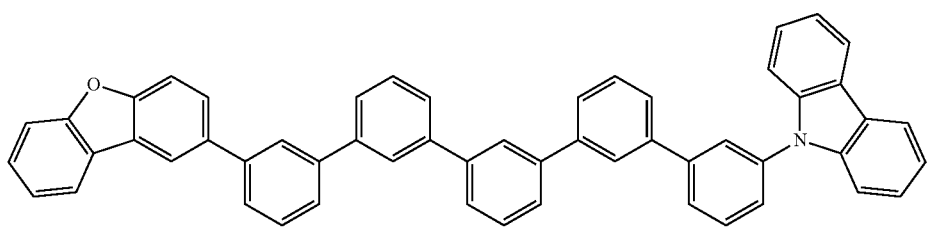
(8)
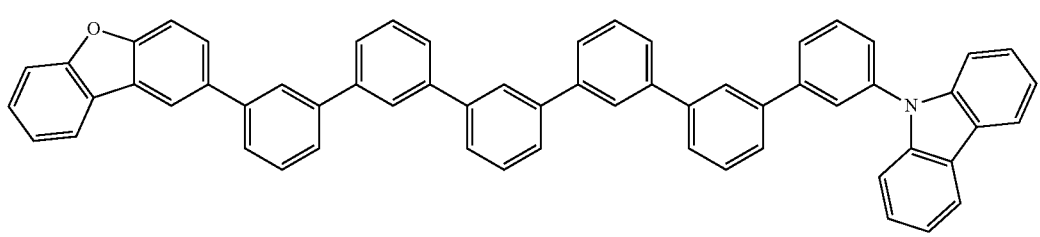
(9)

-continued
(10)
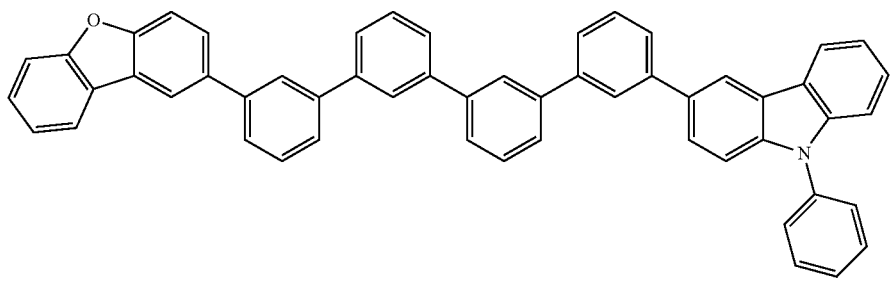
(11)
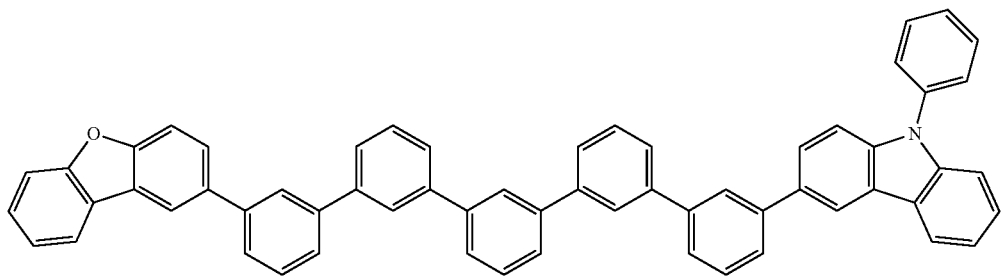
(12)
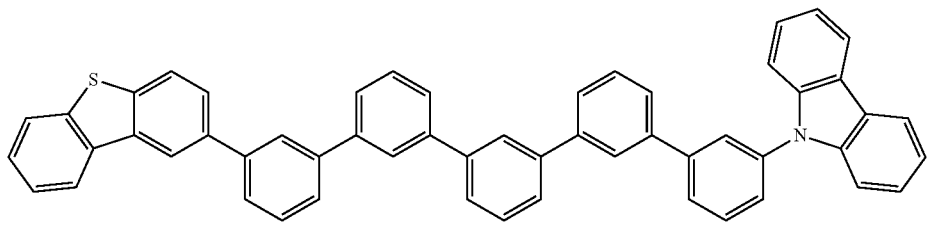
(13)
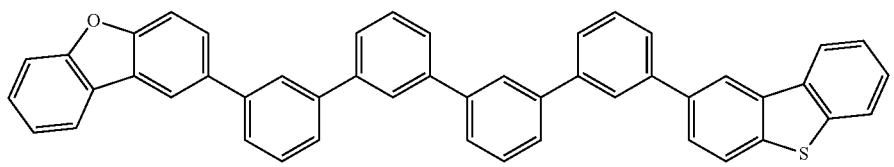
(14)
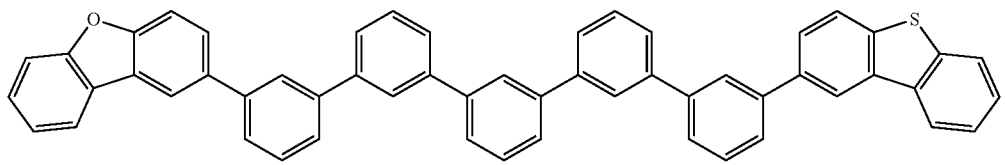
(15)
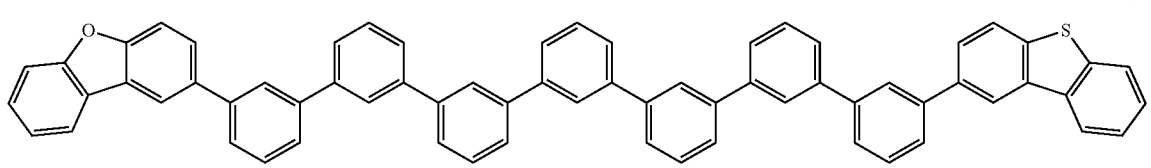
(16)
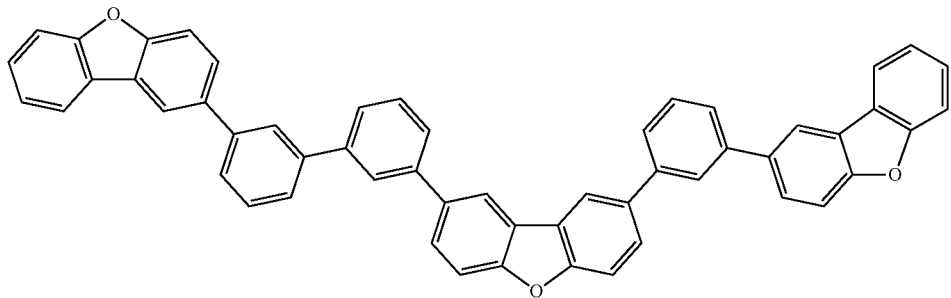

-continued
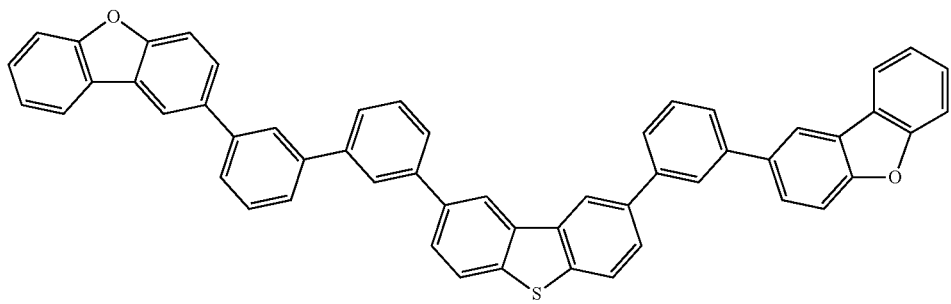
(17)
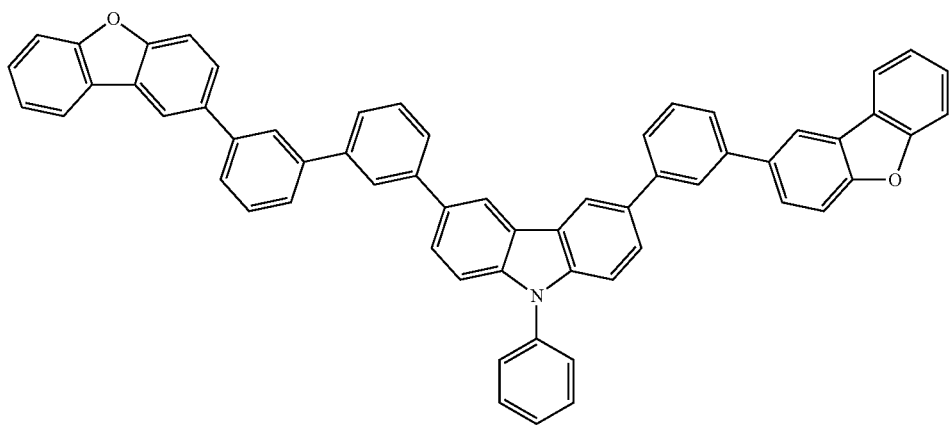
(18)
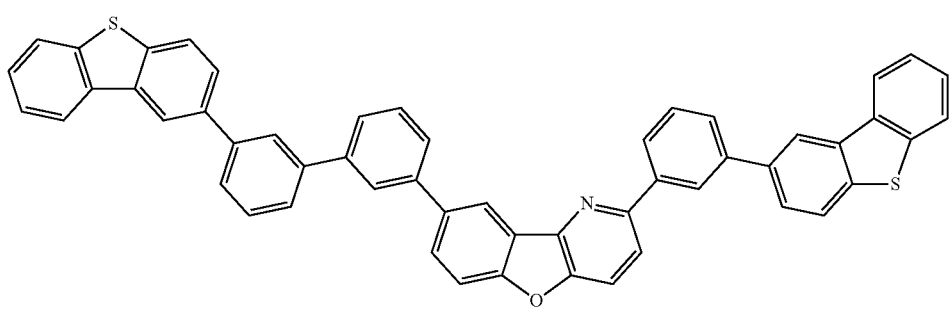
(19)
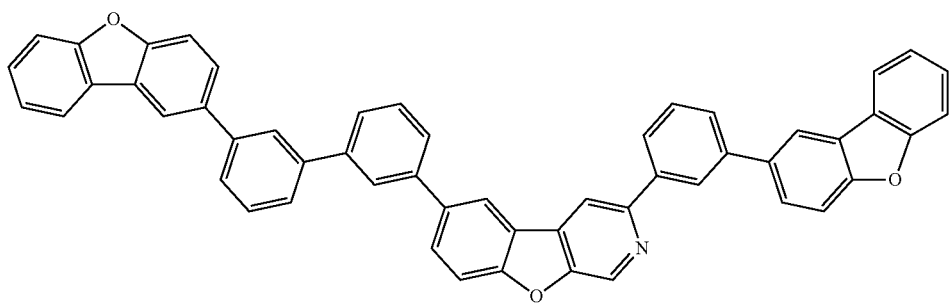
(20)
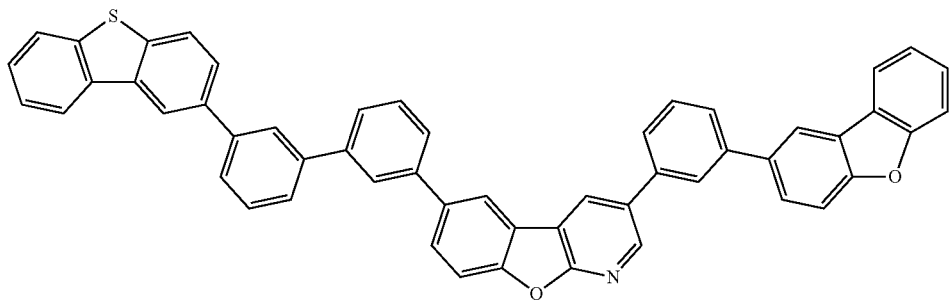
(21)

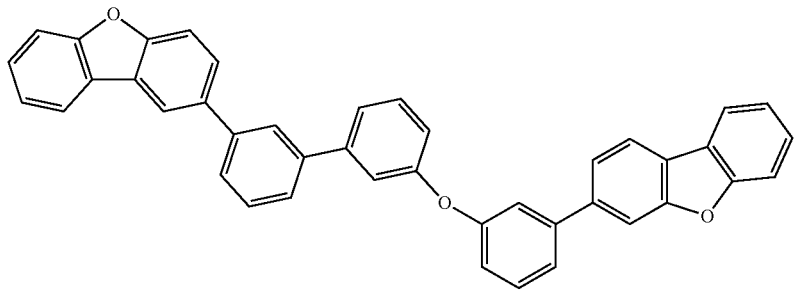
(22)
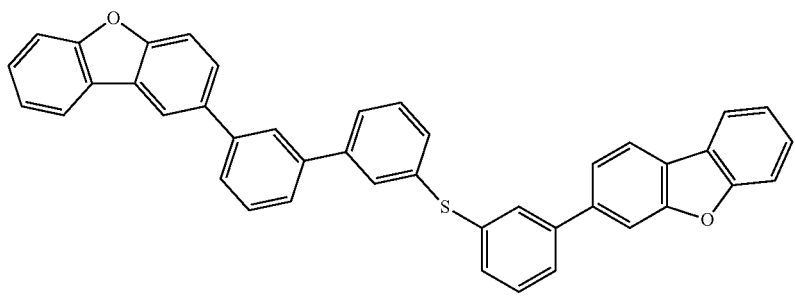
(23)
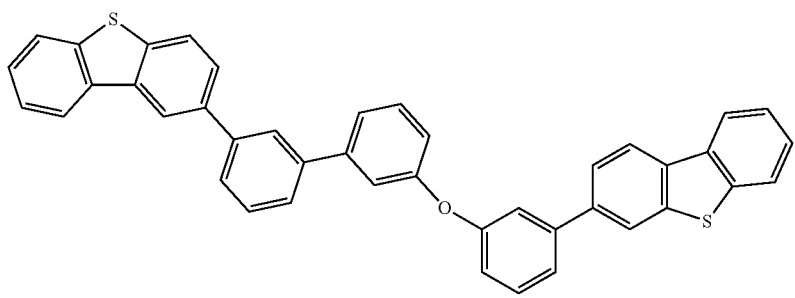
(24)
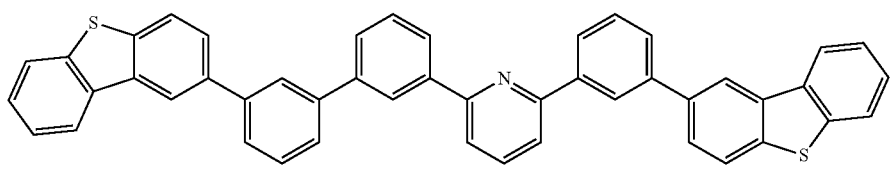
(25)
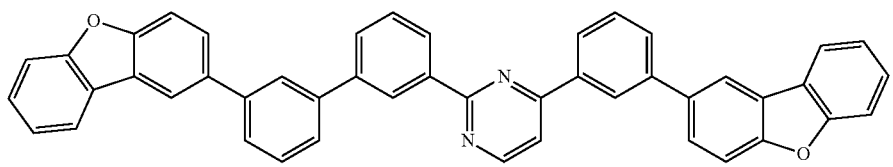
(26)
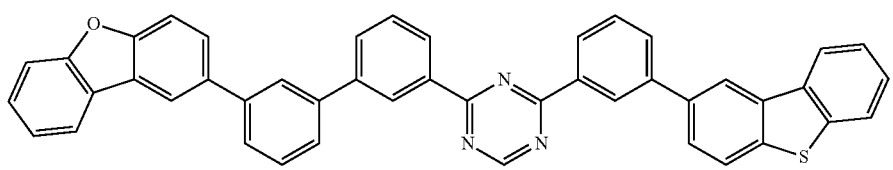
(27)

(28)
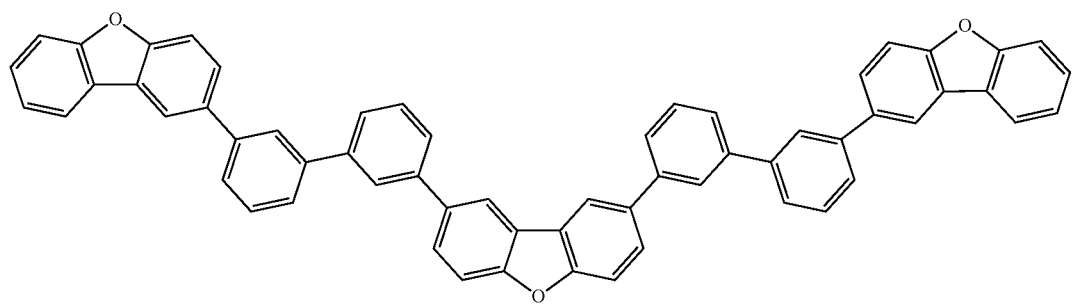
(29)
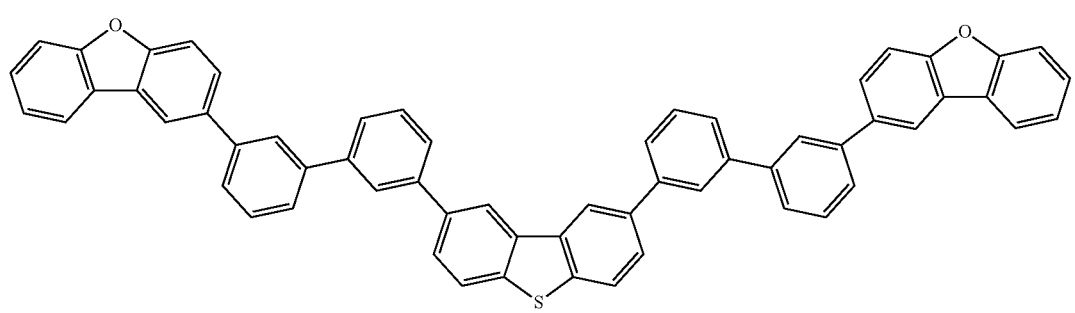
(30)
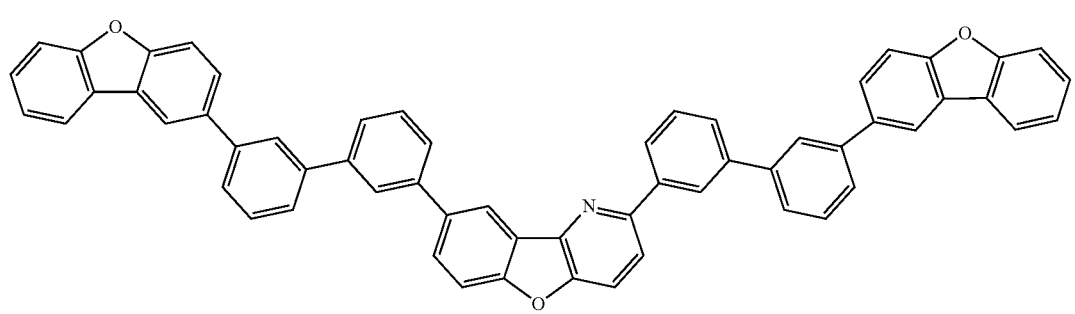
(31)
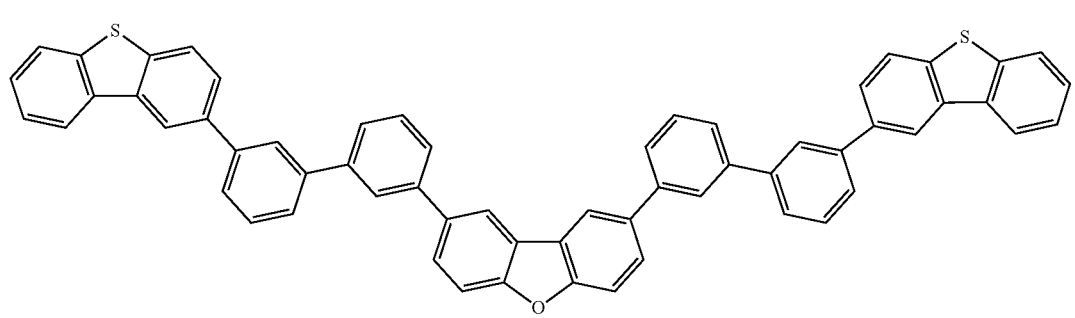
(32)
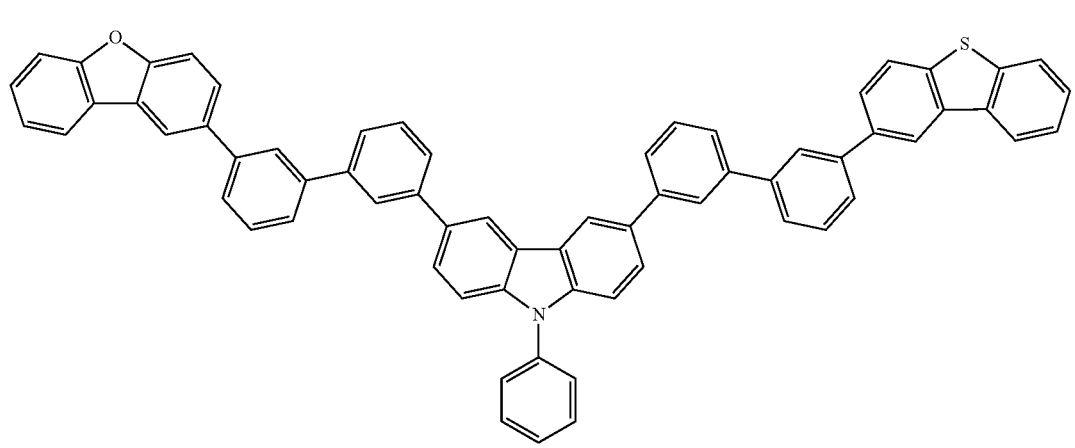

-continued
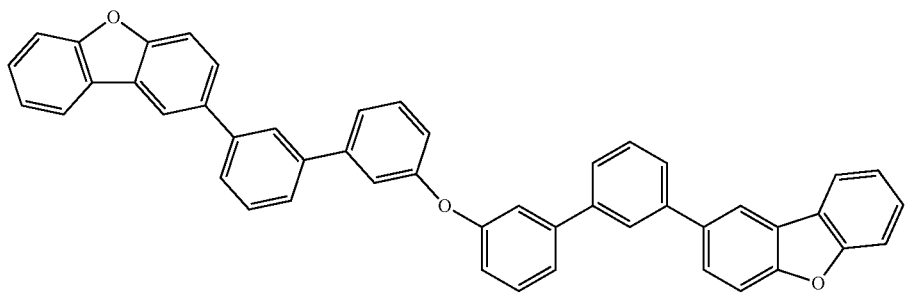
(33)
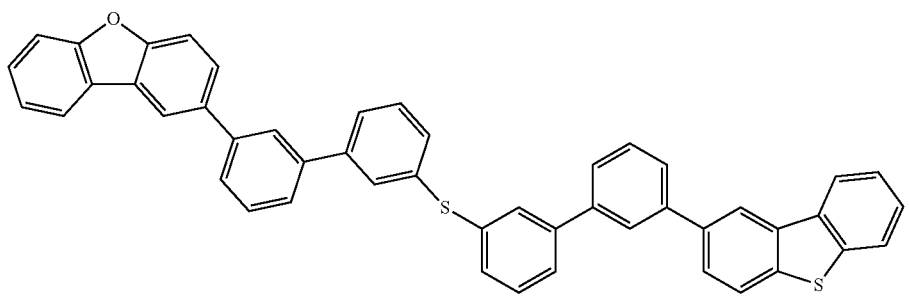
(34)
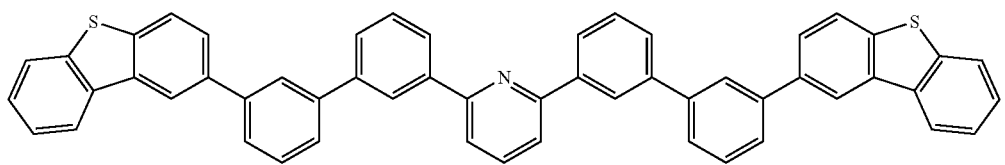
(35)
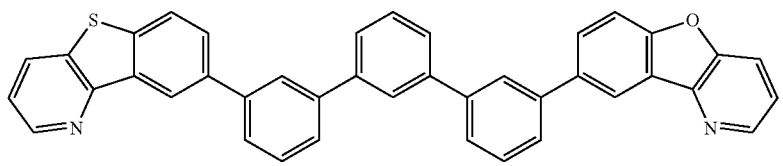
(36)
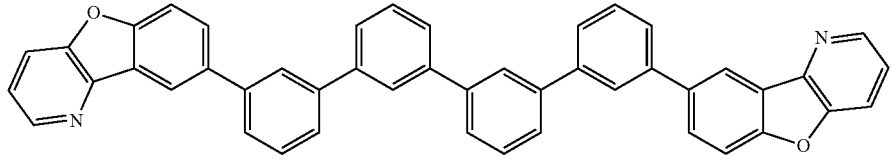
(37)
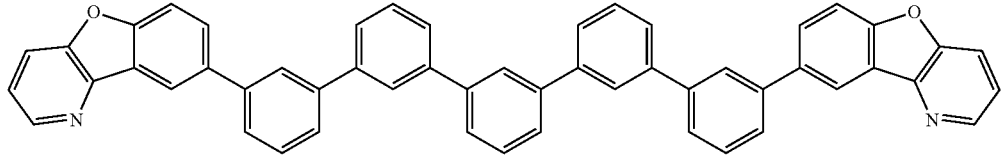
(38)
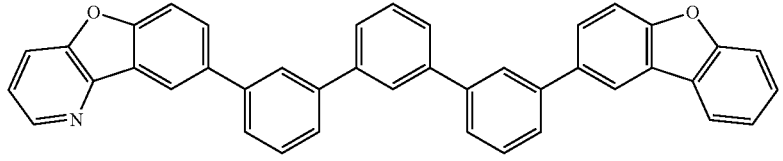
(39)
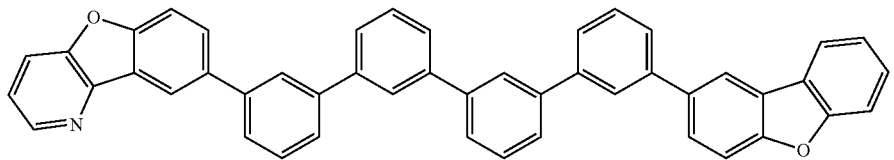
(40)

-continued
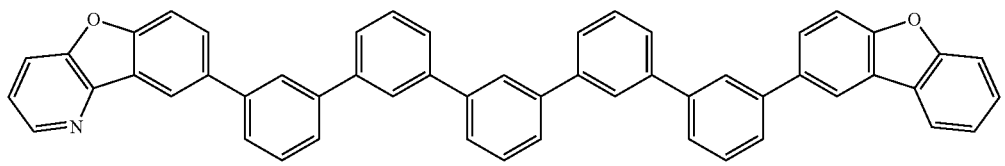
(41)
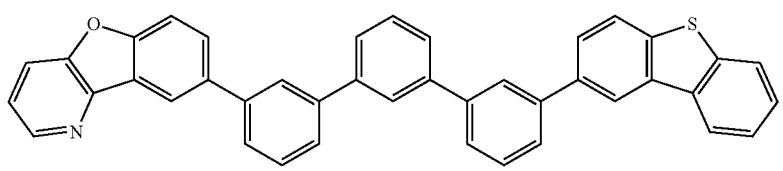
(42)
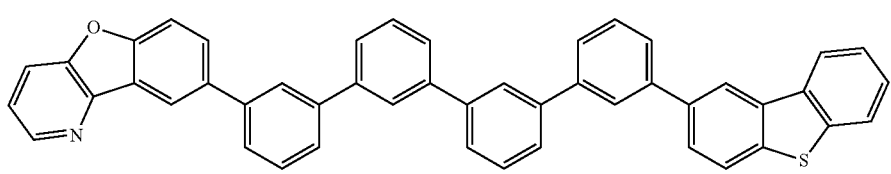
(43)
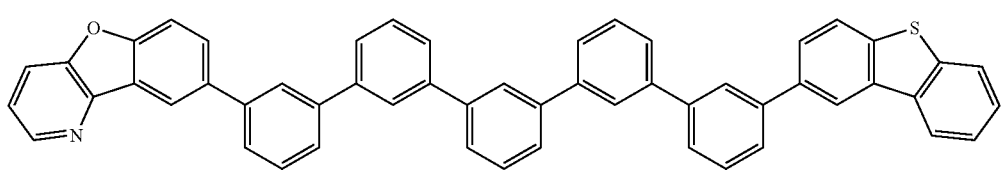
(44)
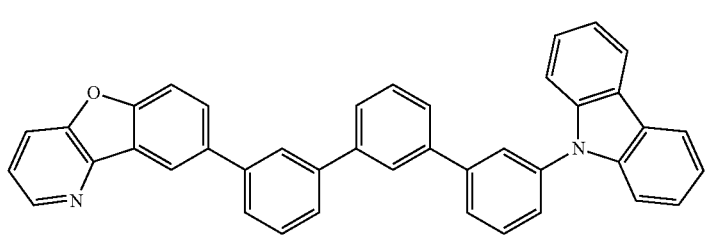
(45)
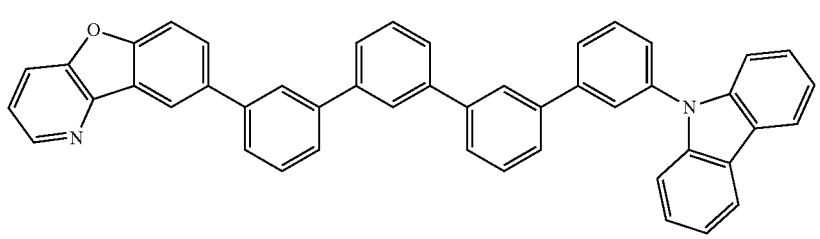
(46)
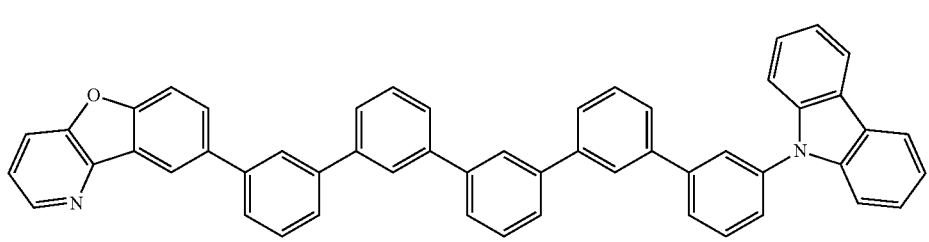
(47)

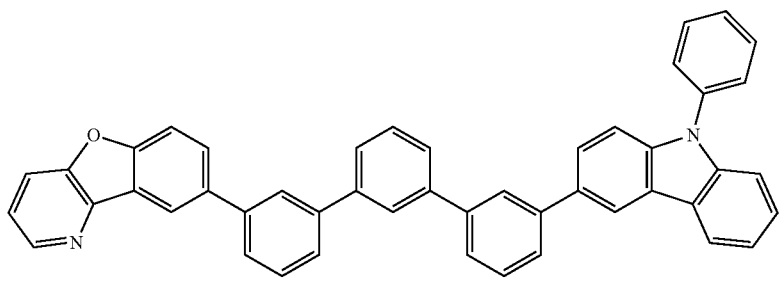
(48)
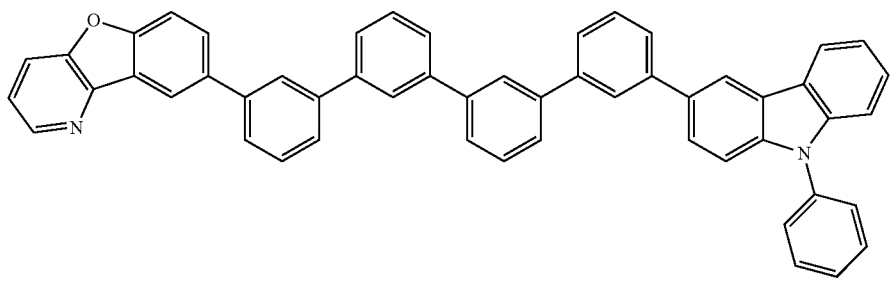
(49)
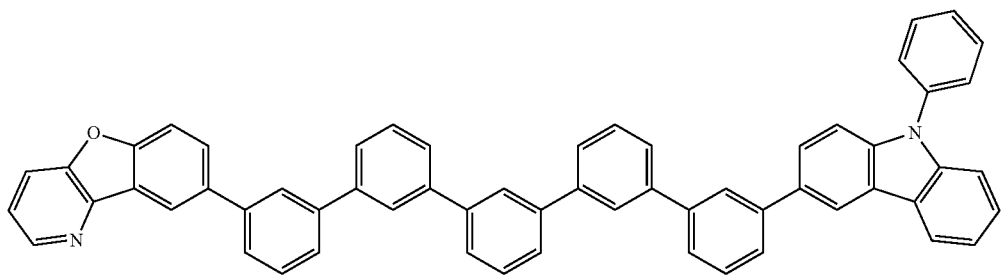
(50)
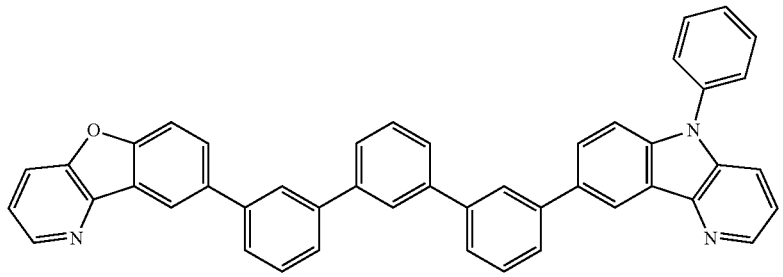
(51)
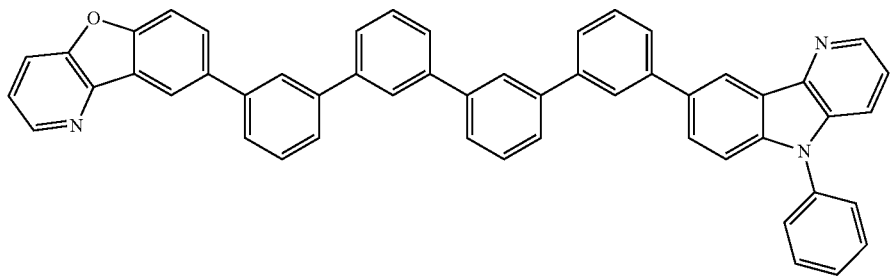
(52)

-continued
(53)
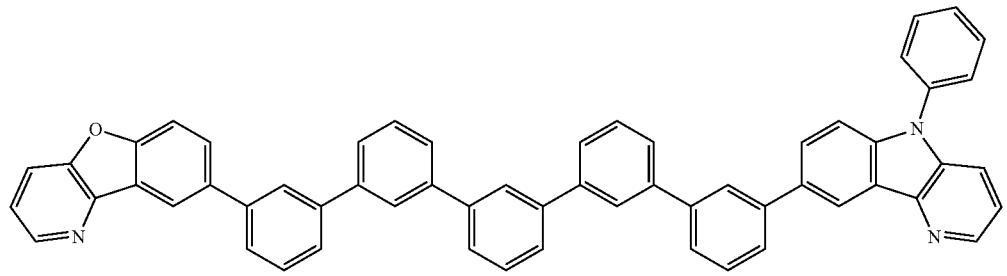
(54)
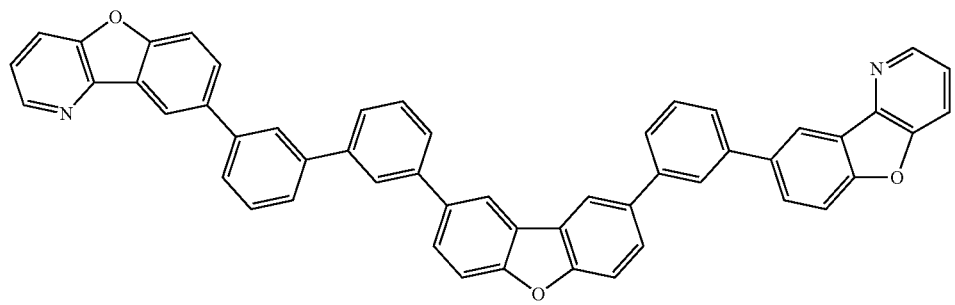
(55)
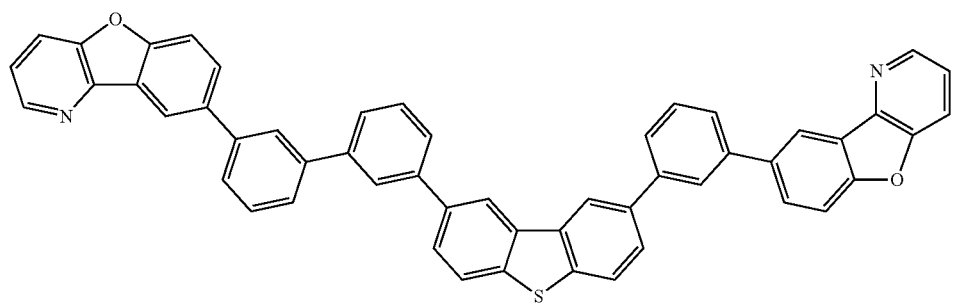
(56)
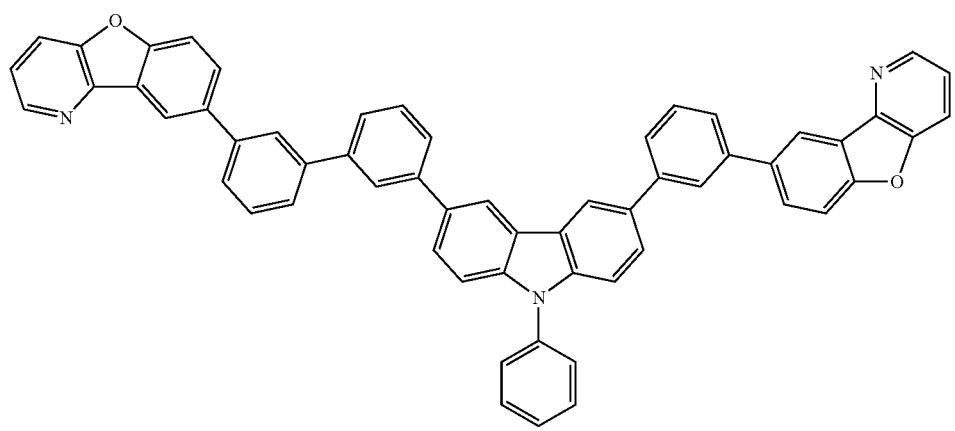
(57)
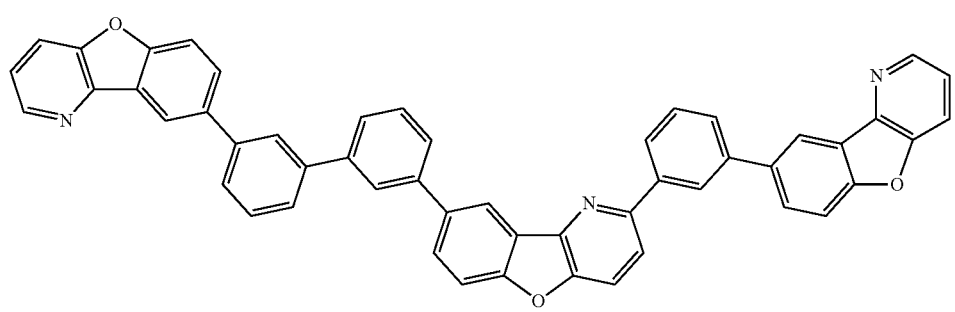

-continued
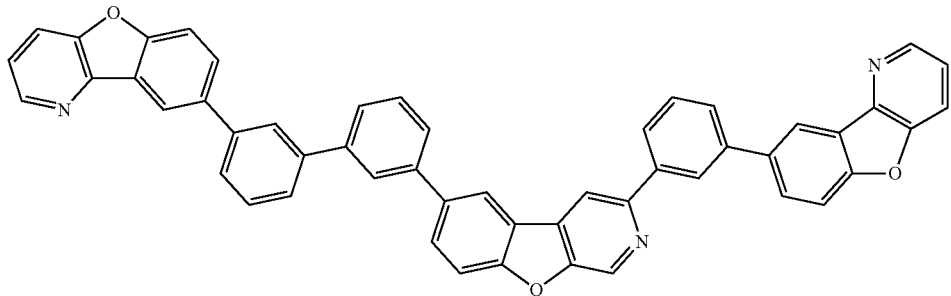
(58)
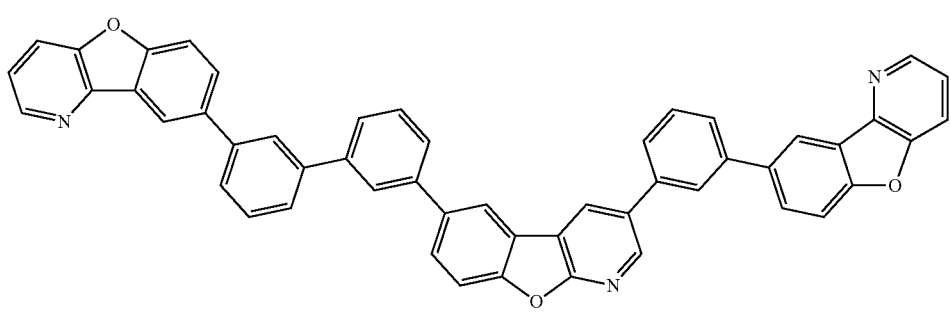
(59)
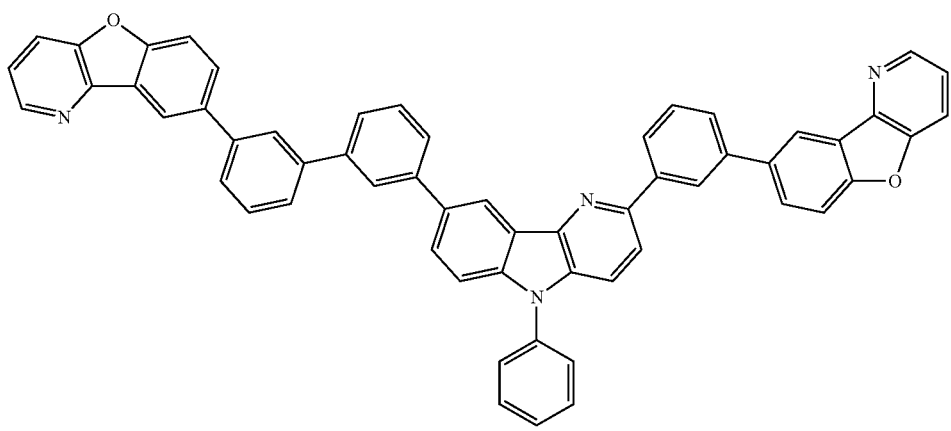
(60)
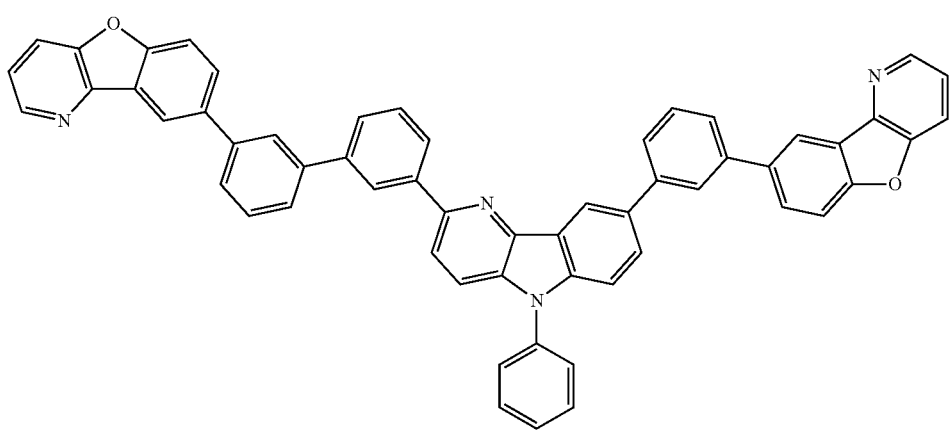
(61)

-continued
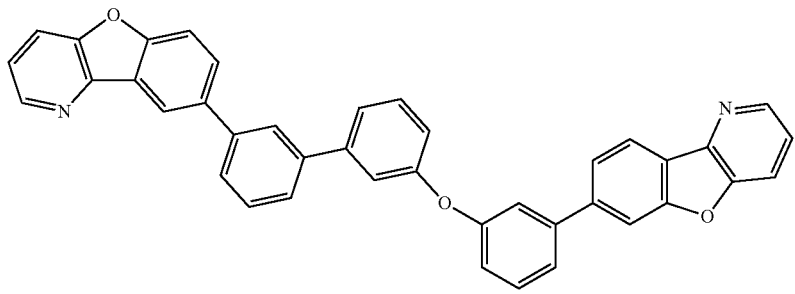
(62)
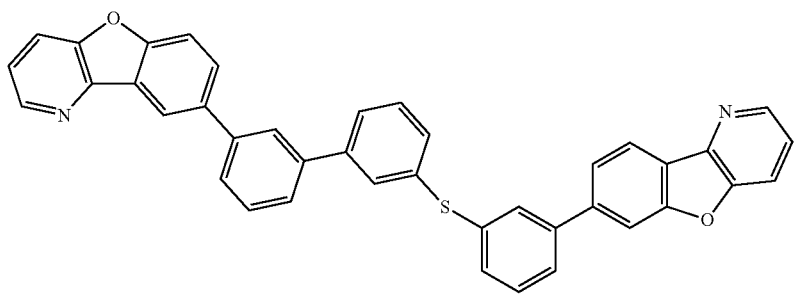
(63)
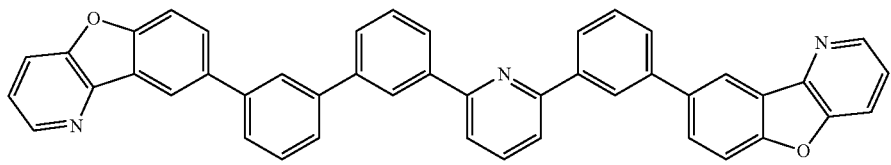
(64)
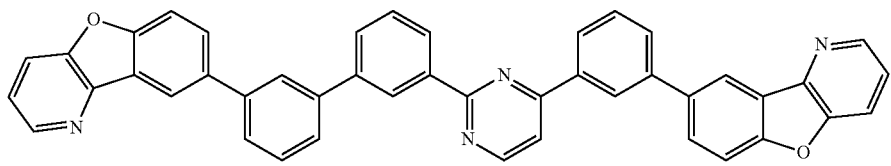
(65)
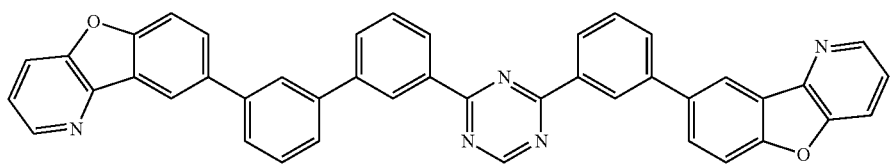
(66)
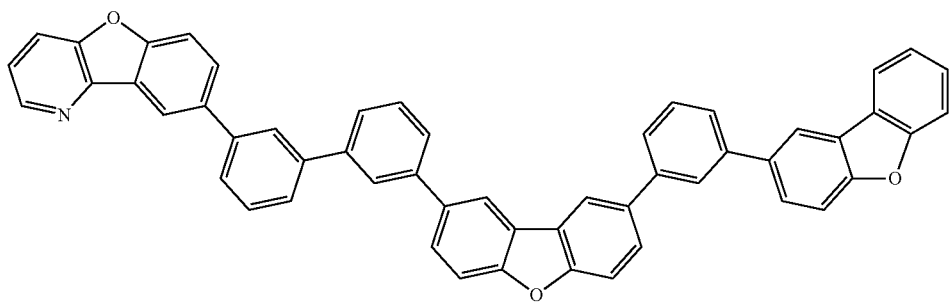
(67)

-continued (68)

(69)

(70)

(71)

-continued
(72)
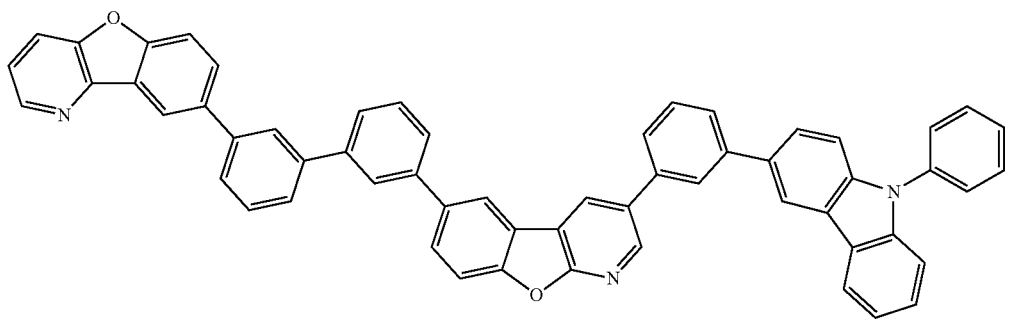
(73)
(74)
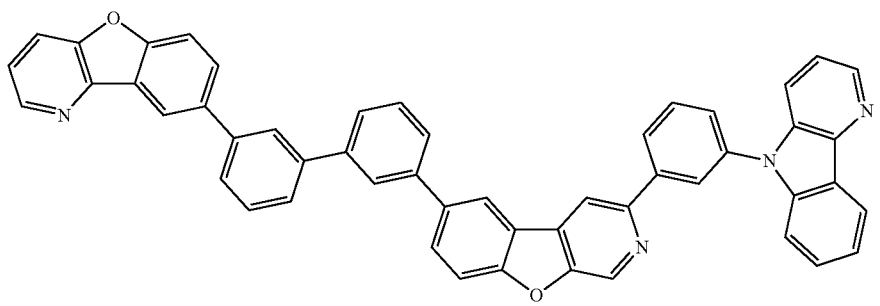
(75)
(76)
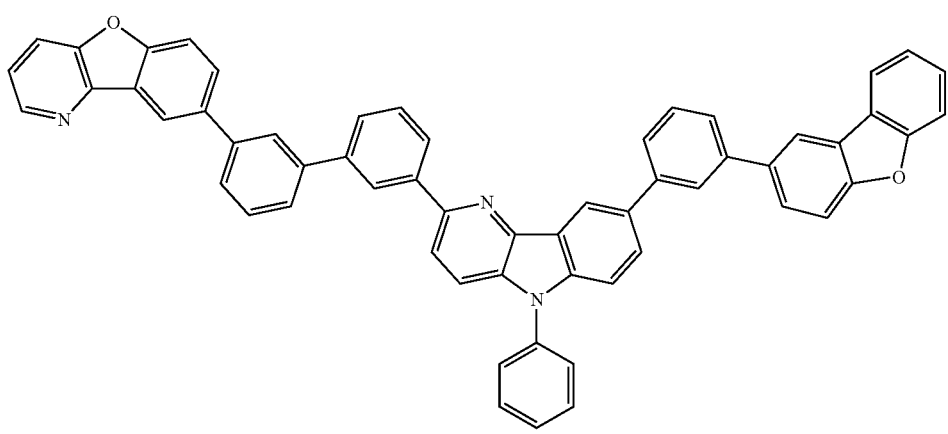

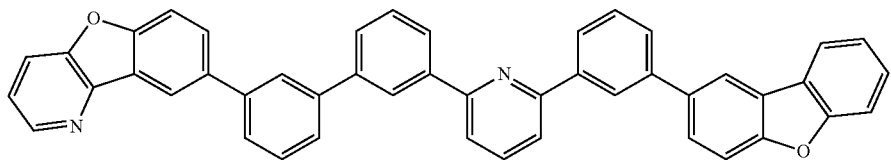
(77)
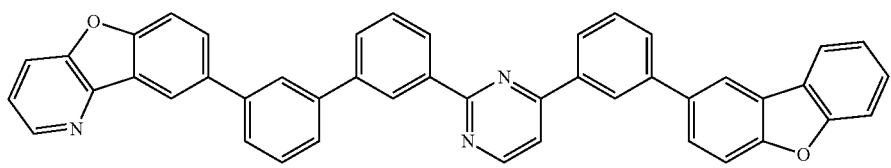
(78)
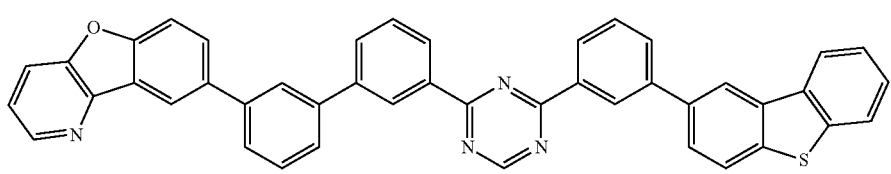
(79)
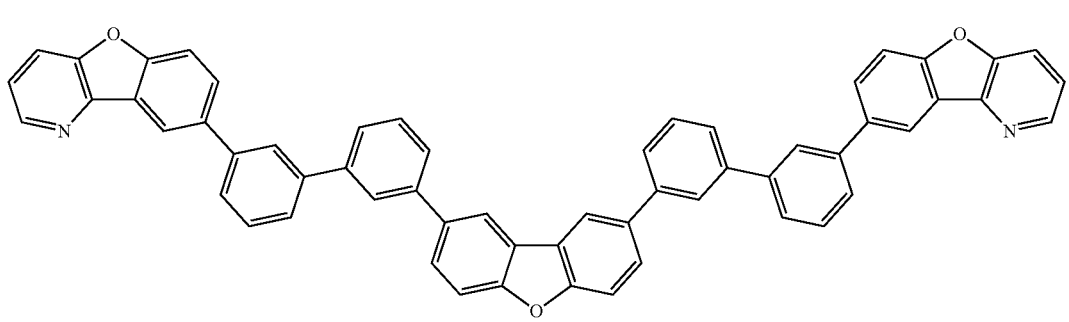
(80)
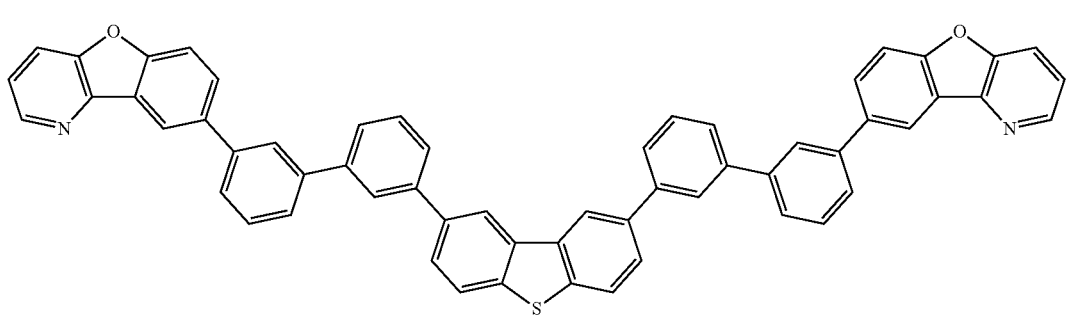
(81)
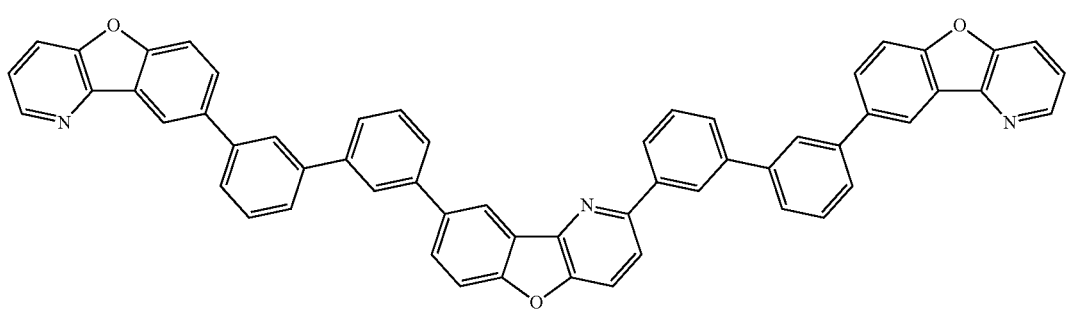
(82)

-continued
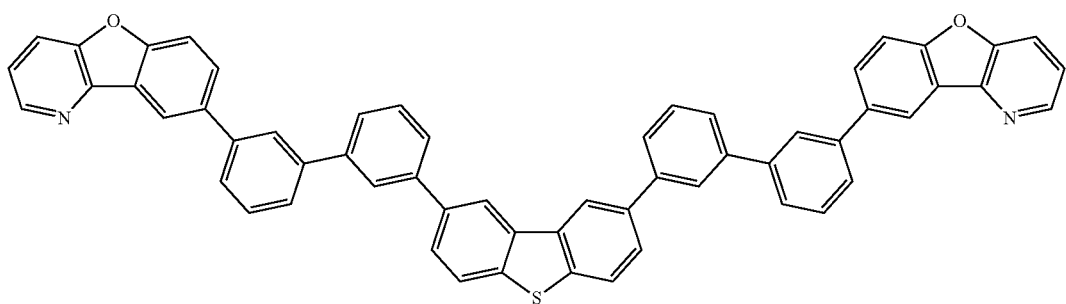
(83)
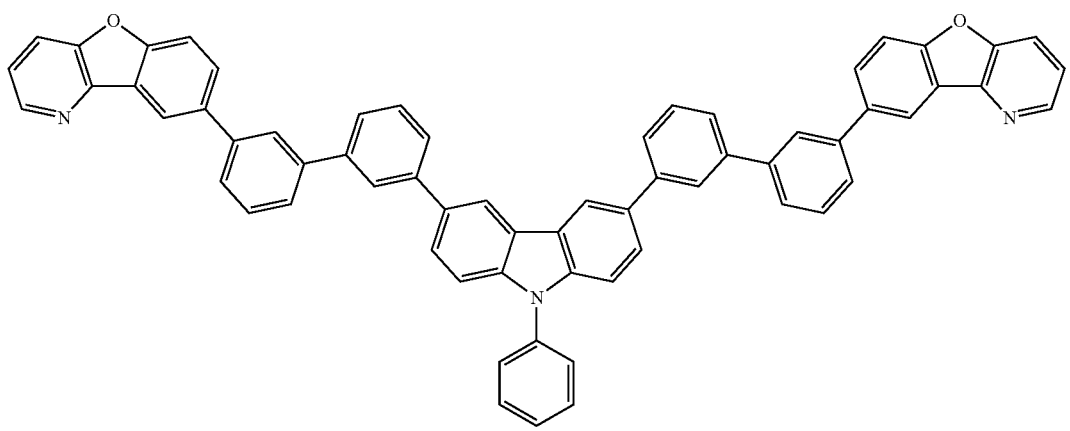
(84)
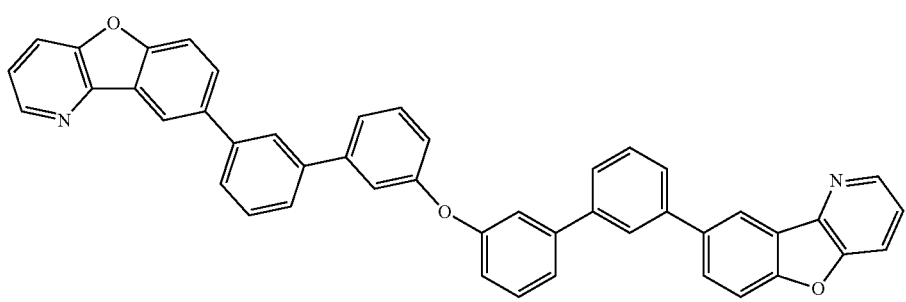
(85)
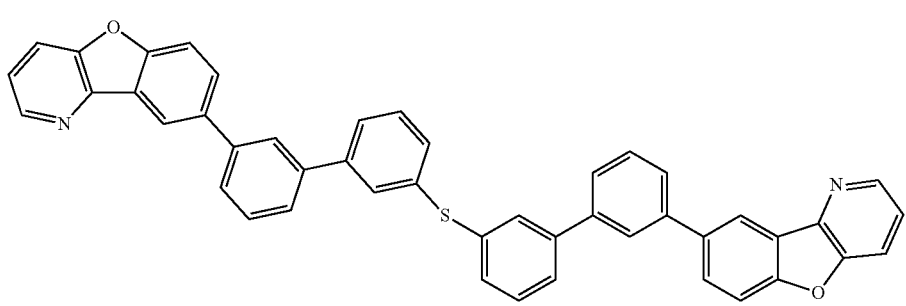
(86)
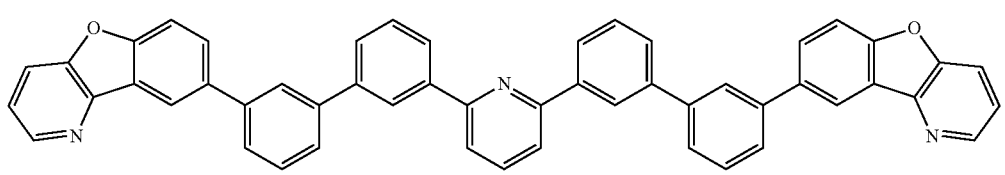
(87)

-continued
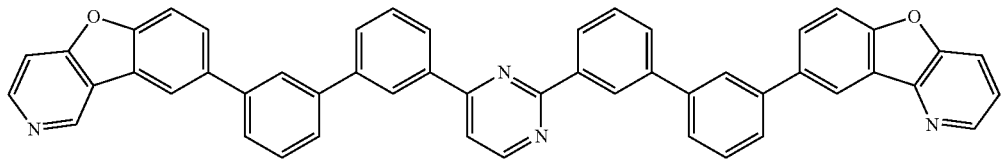
(88)
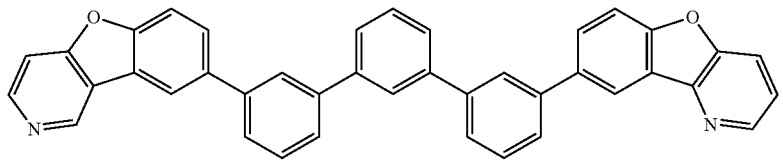
(89)
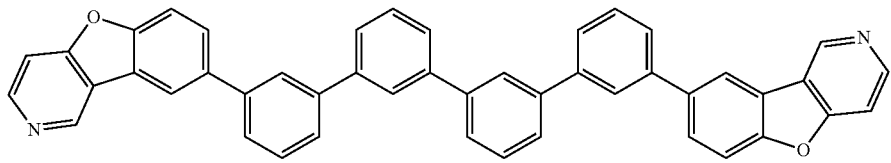
(90)
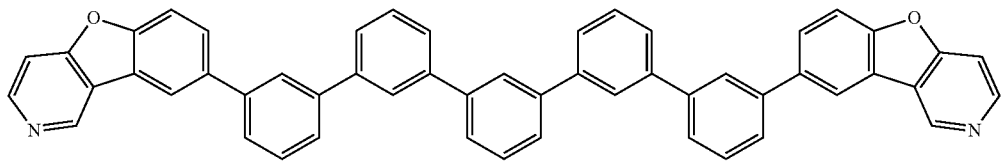
(91)
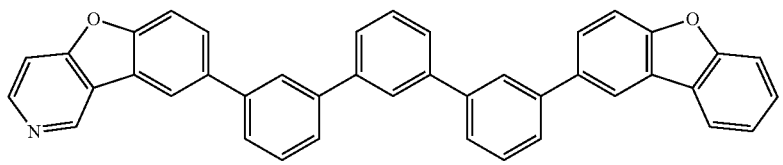
(92)
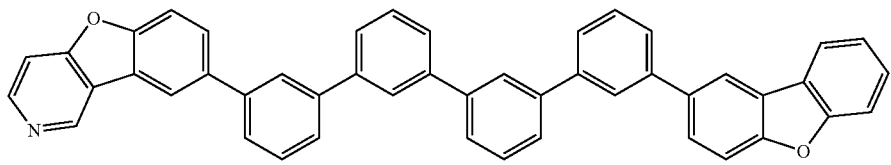
(93)
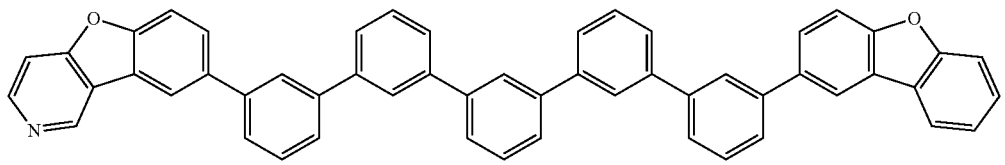
(94)
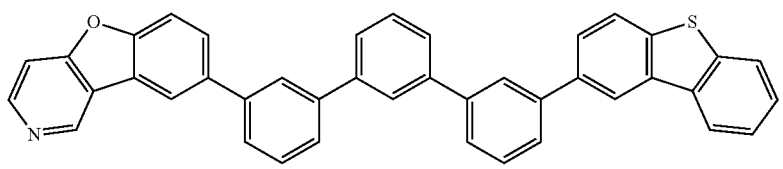
(95)
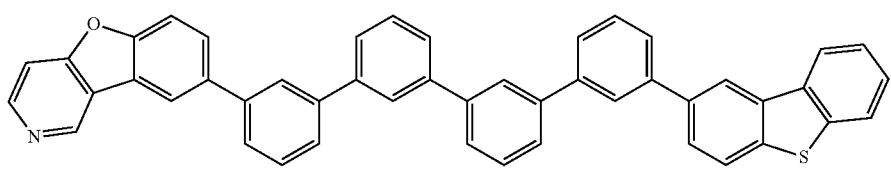
(96)

-continued
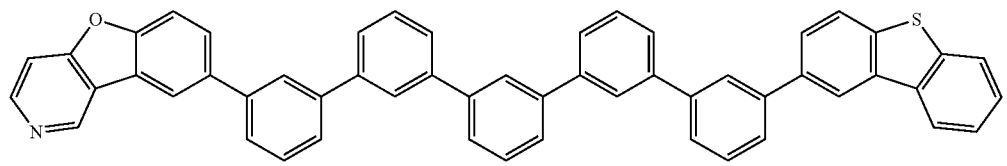
(97)
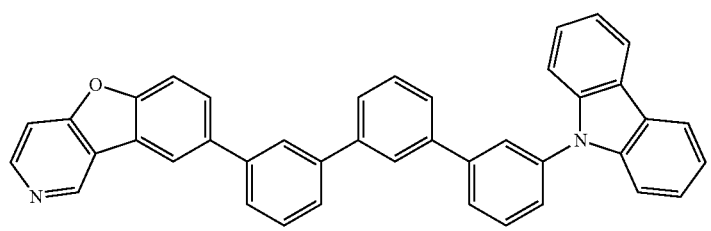
(98)
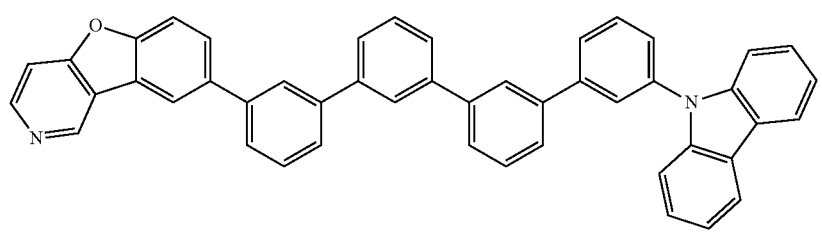
(99)
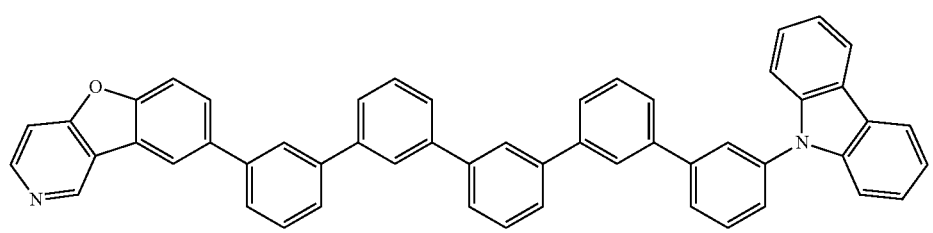
(100)
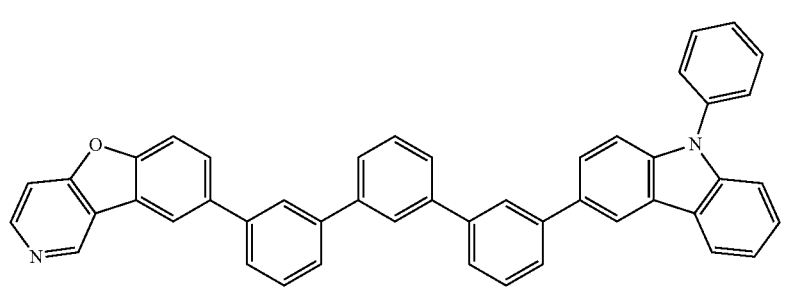
(101)
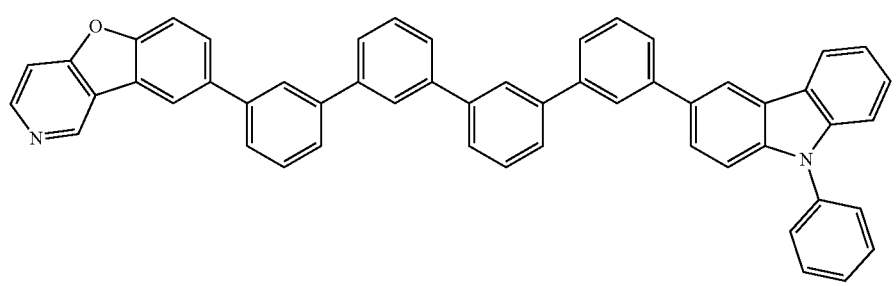
(102)

-continued
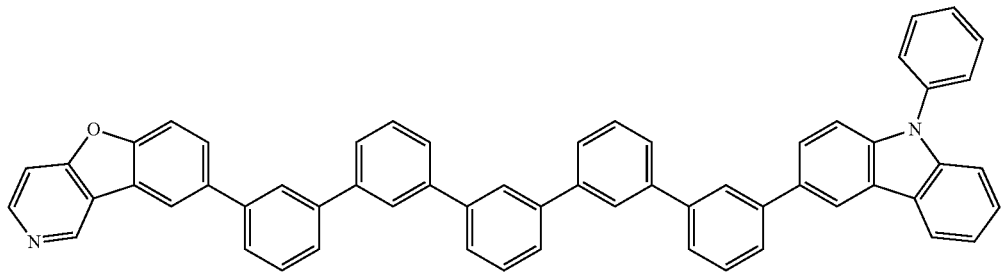
(103)
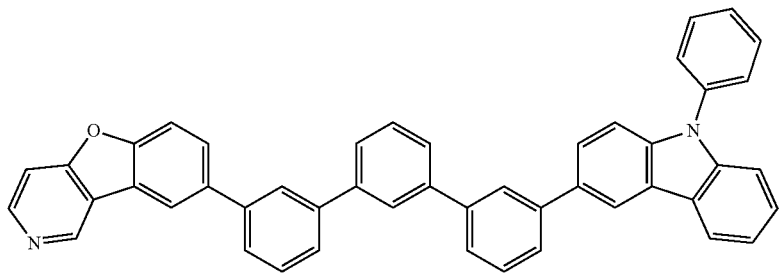
(104)
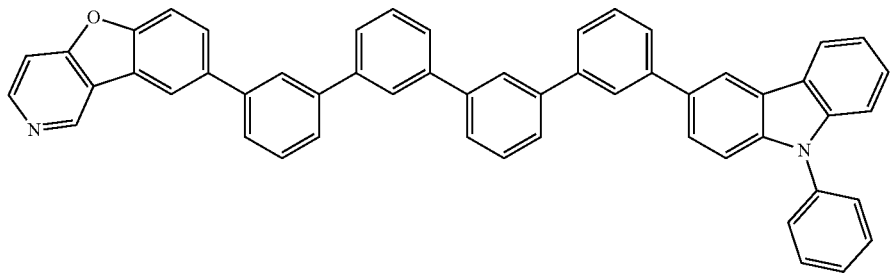
(105)
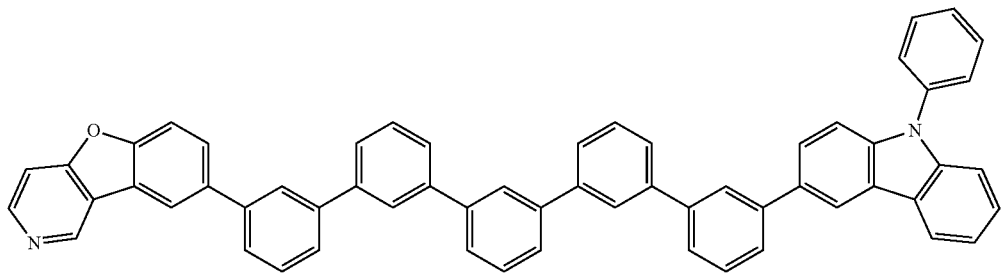
(106)
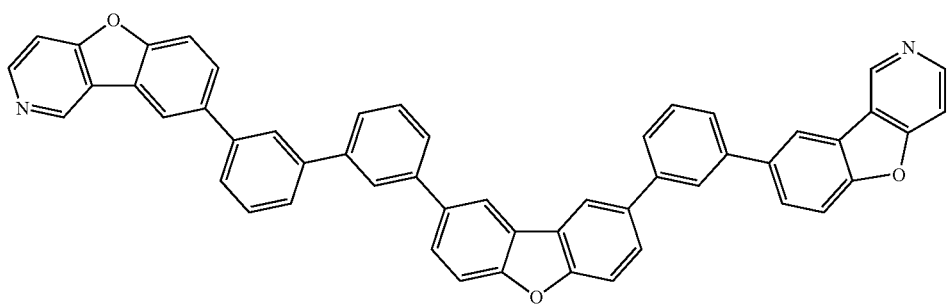
(107)

-continued
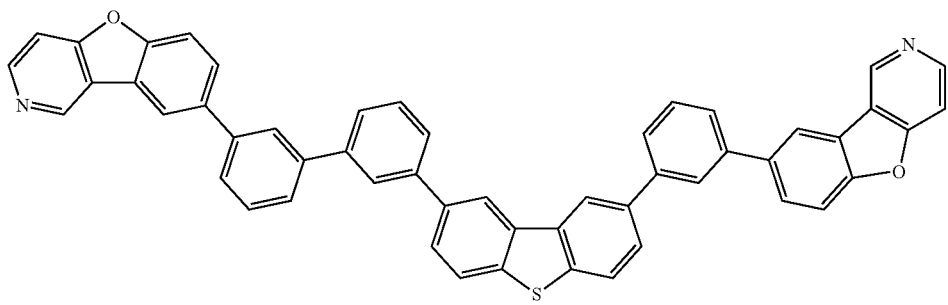
(108)
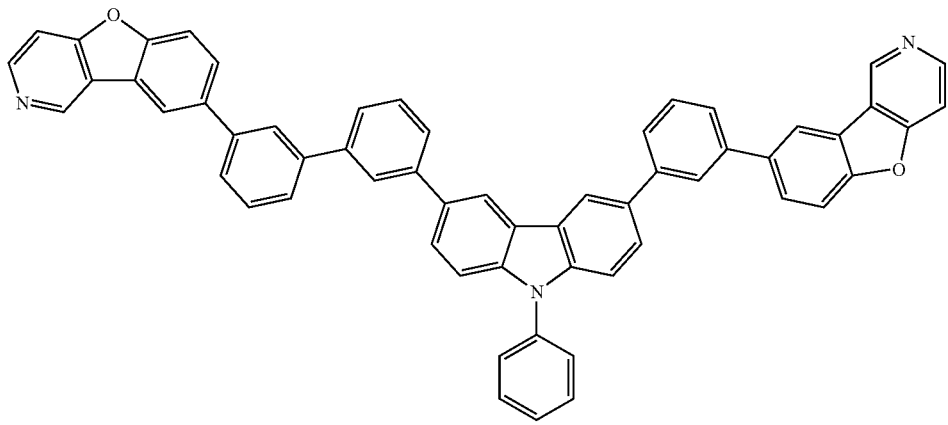
(109)
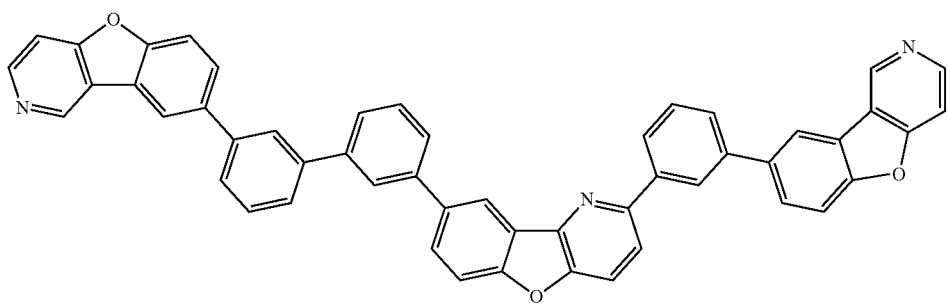
(110)
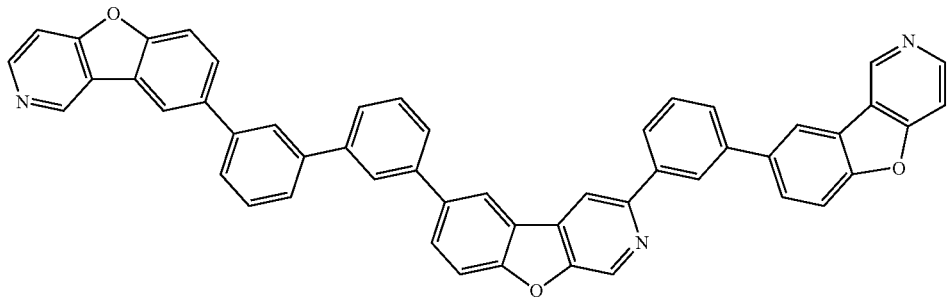
(111)
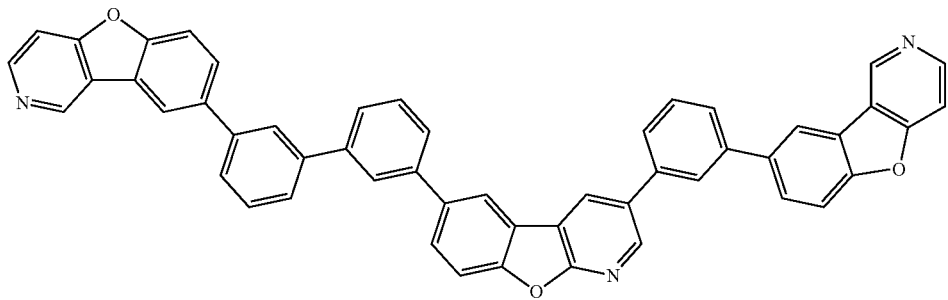
(112)

-continued
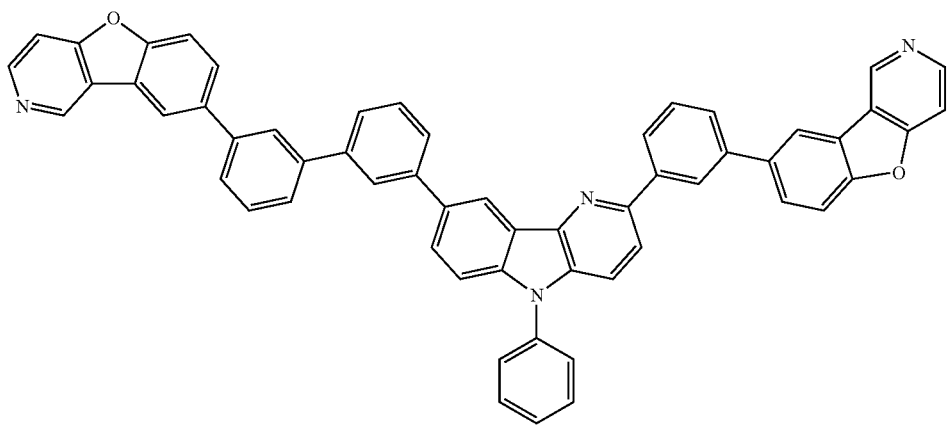
(113)
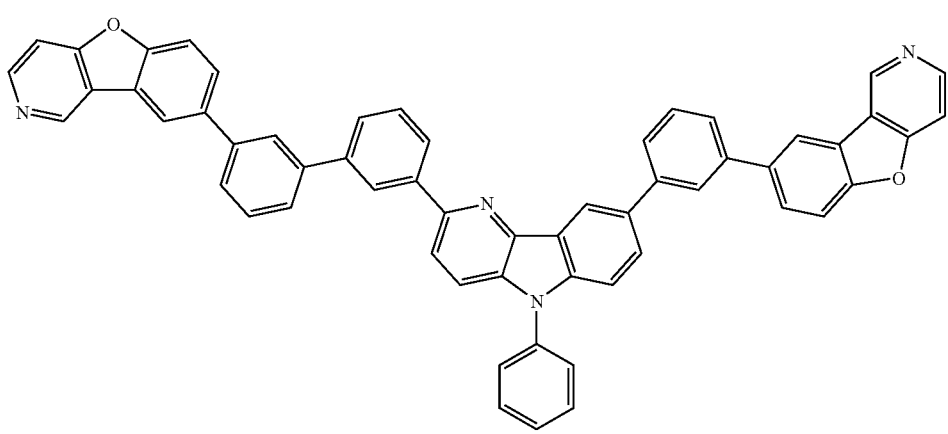
(114)
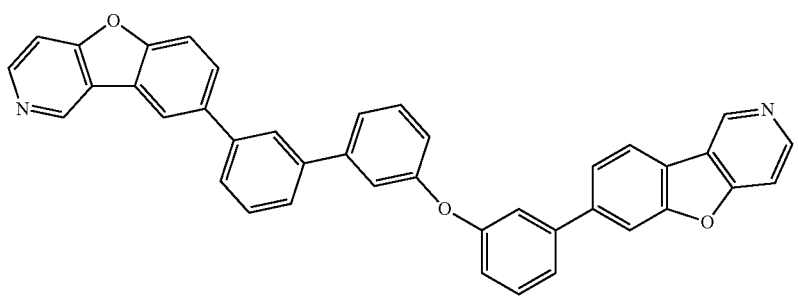
(115)
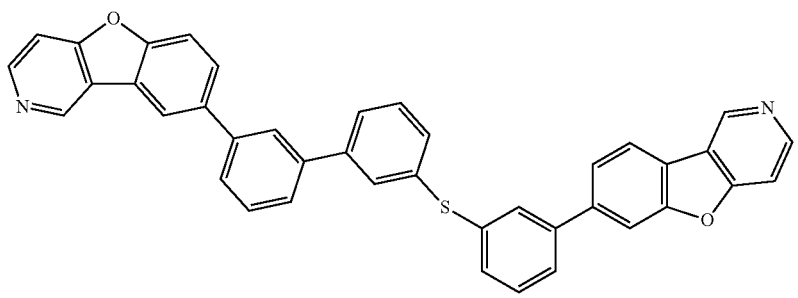
(116)
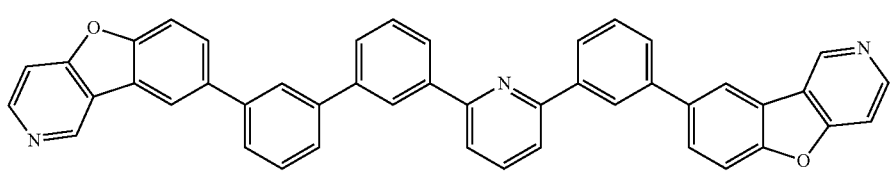
(117)

-continued
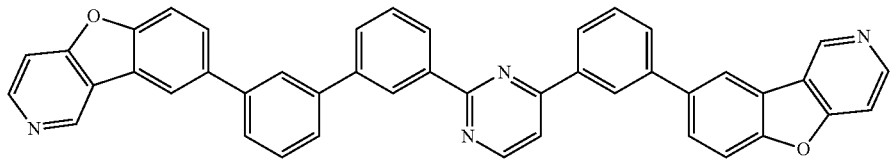
(118)
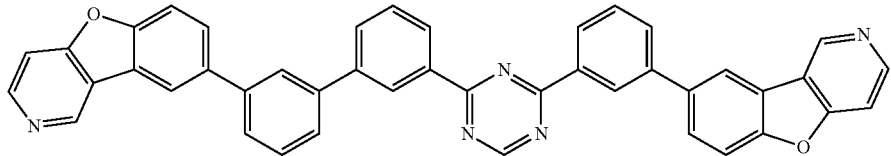
(119)
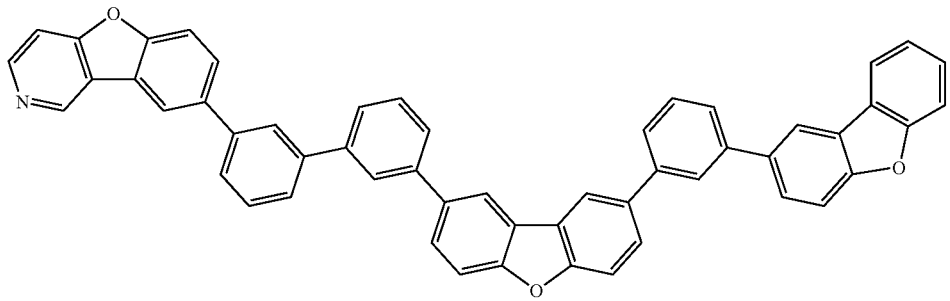
(120)
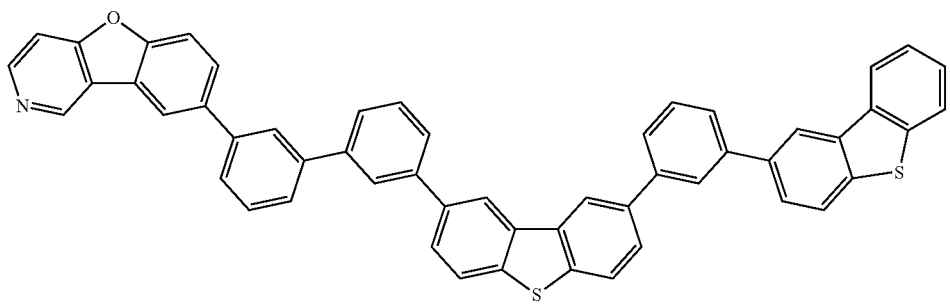
(121)
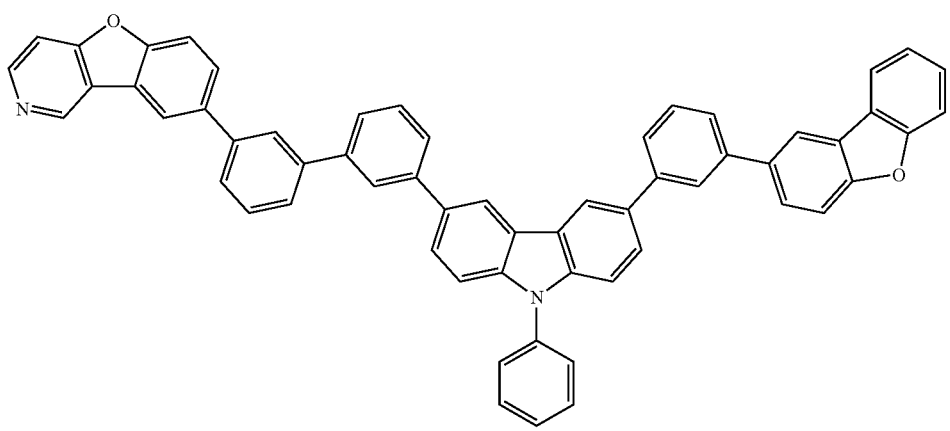
(122)

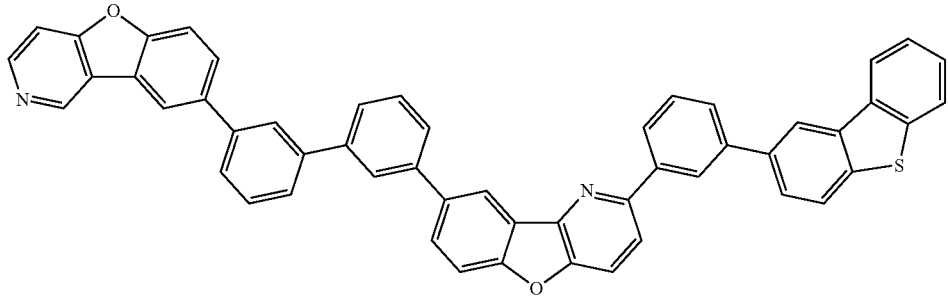
(123)
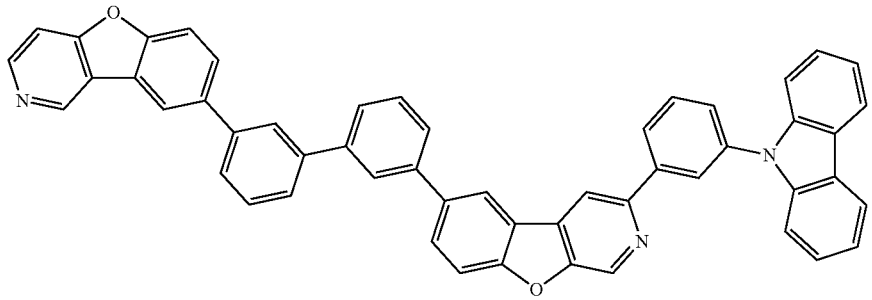
(124)
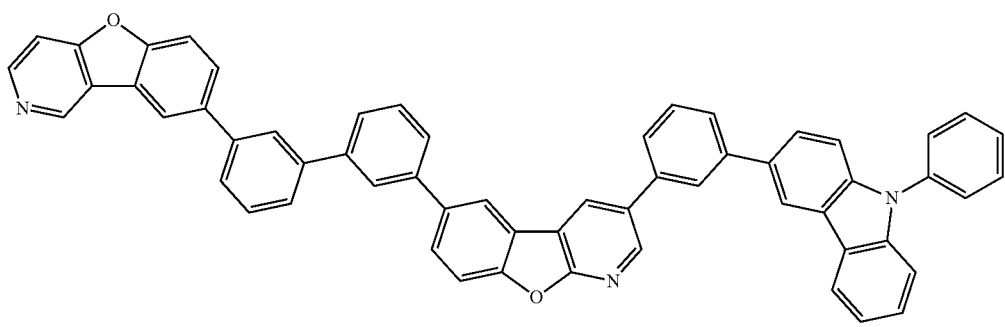
(125)
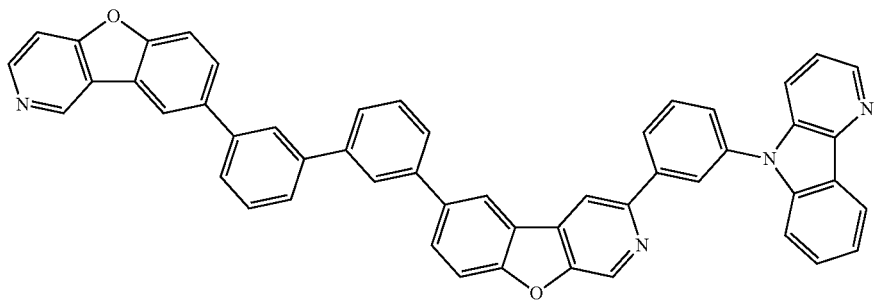
(126)

-continued
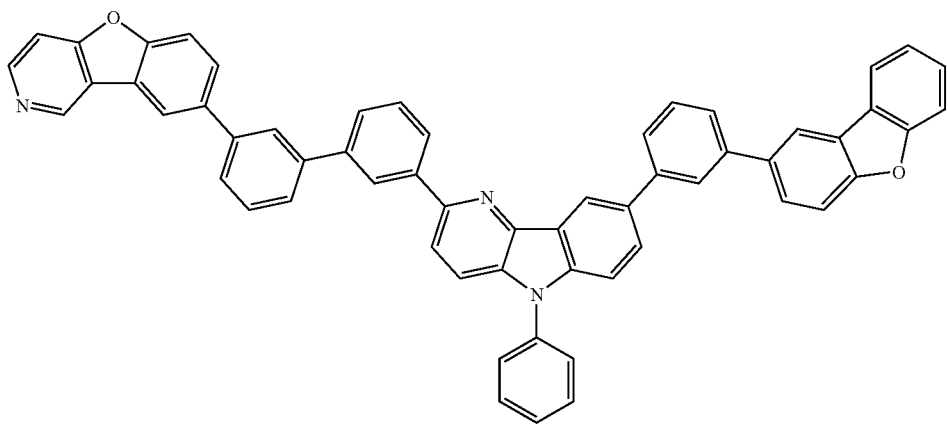
(127)
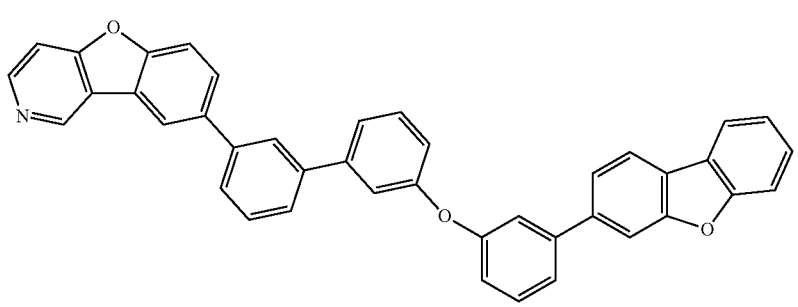
(128)
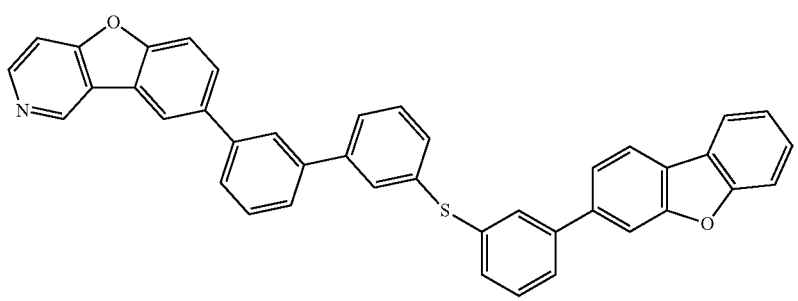
(129)
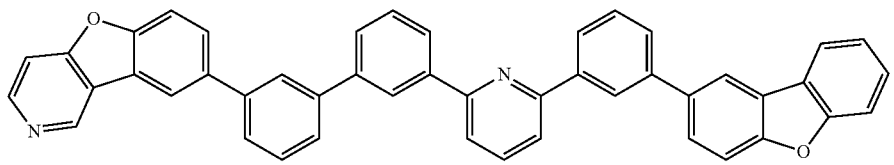
(130)
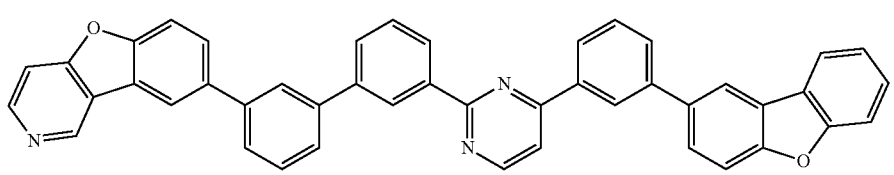
(131)
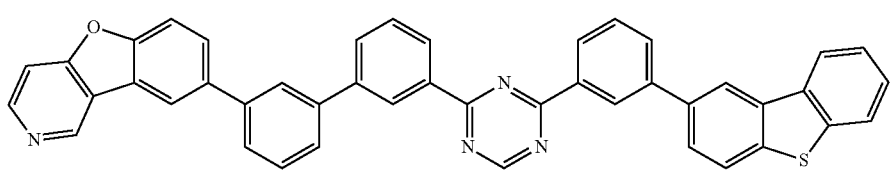
(132)

-continued
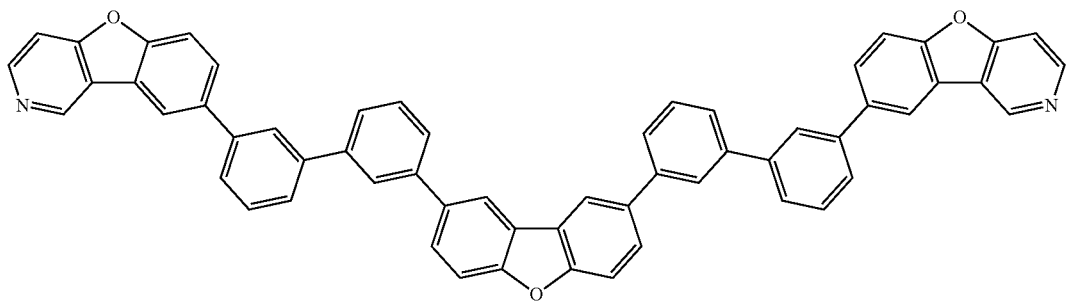
(133)
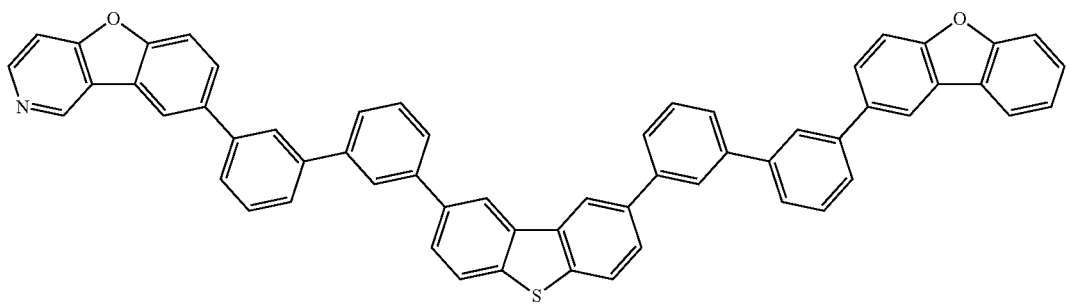
(134)
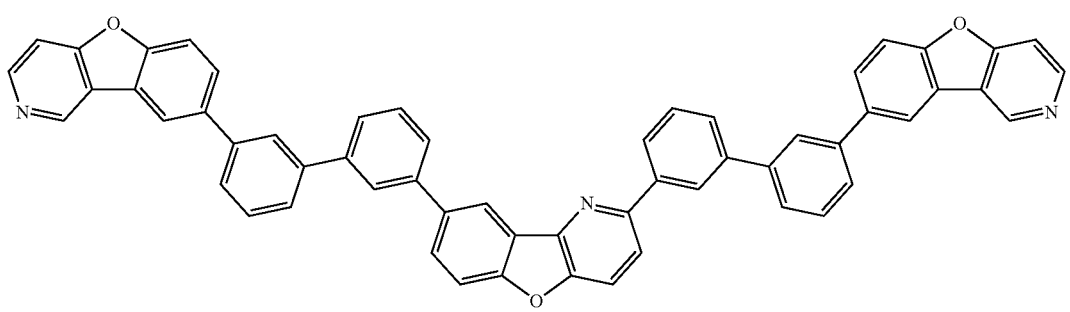
(135)
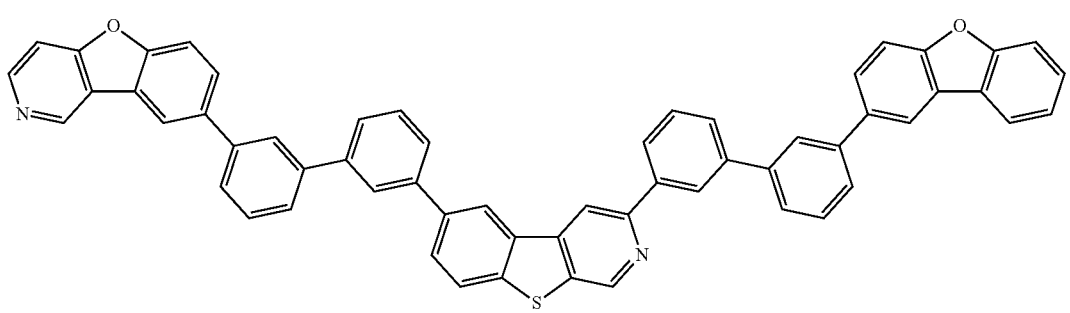
(136)
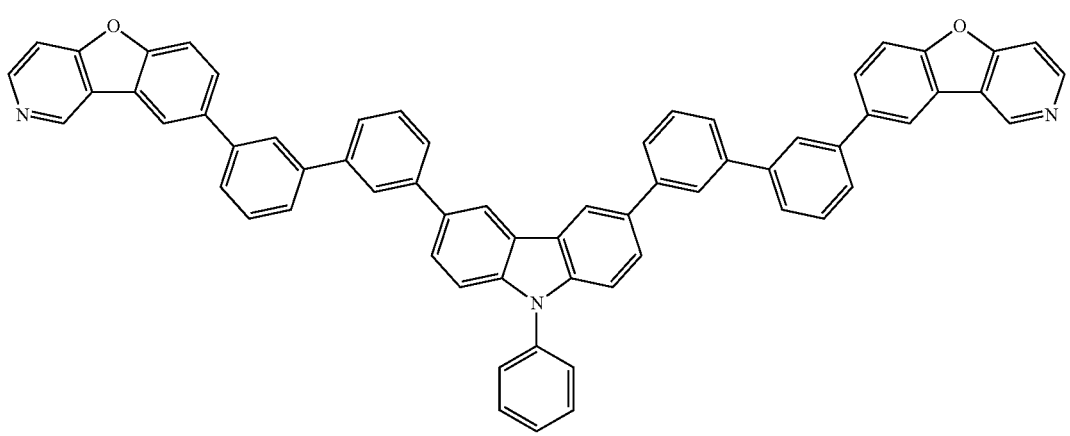
(137)

-continued
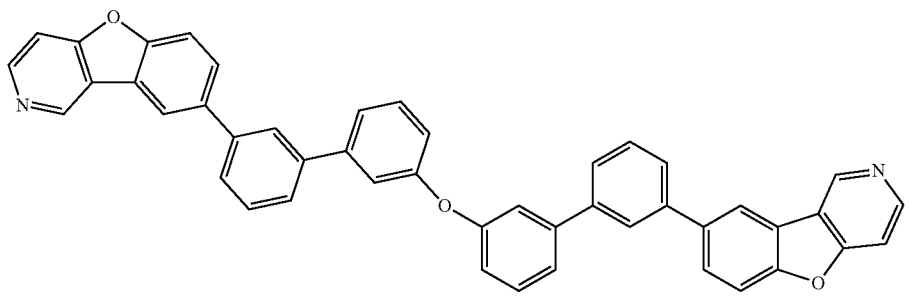
(138)
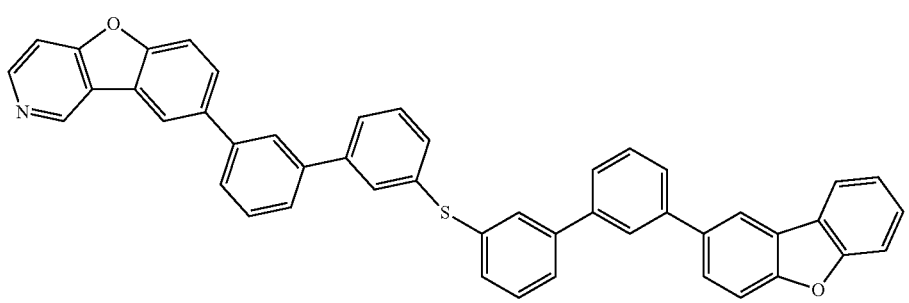
(139)
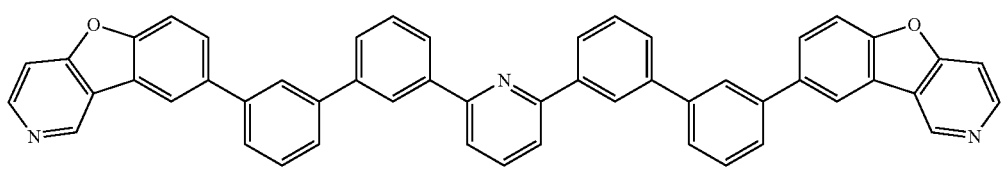
(140)
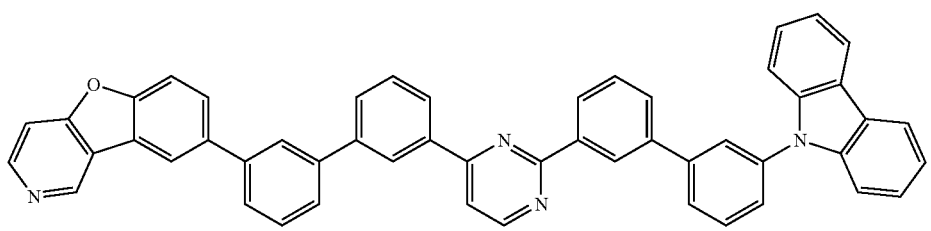
(141)
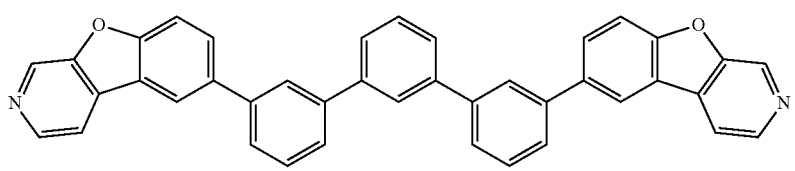
(142)
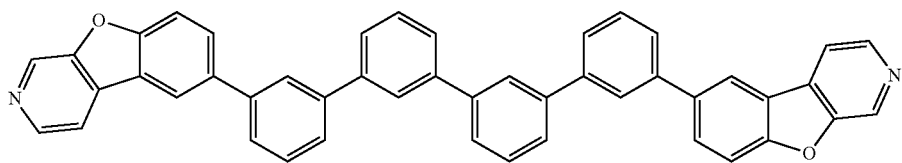
(143)
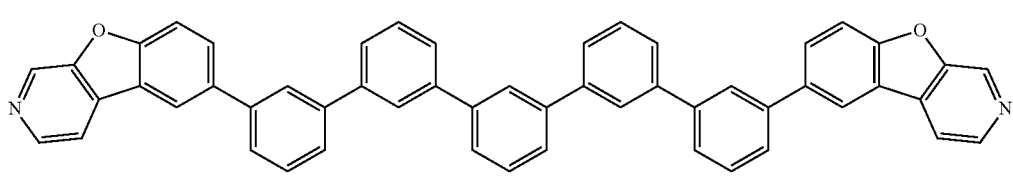
(144)

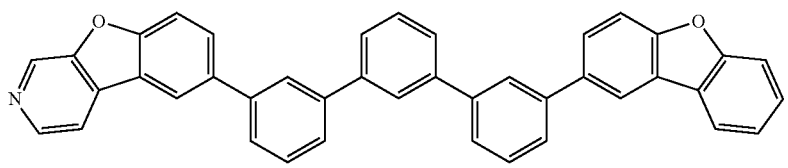
(145)
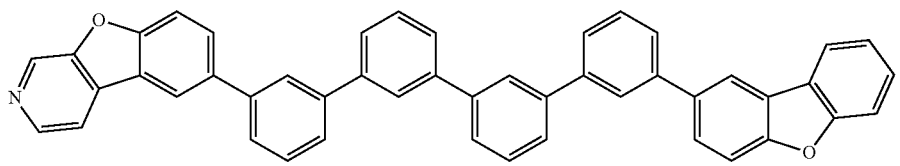
(146)
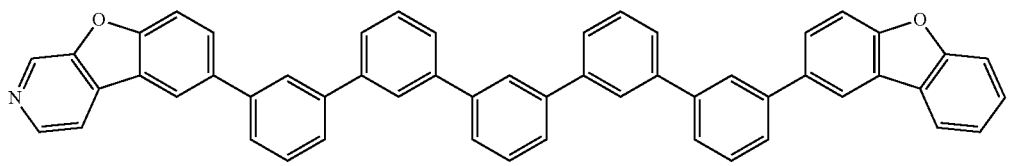
(147)
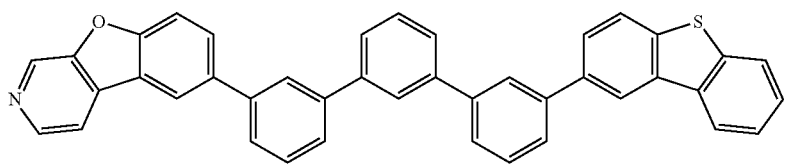
(148)
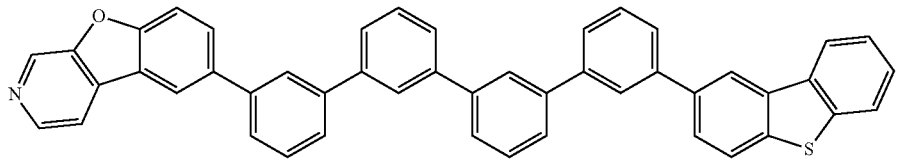
(149)
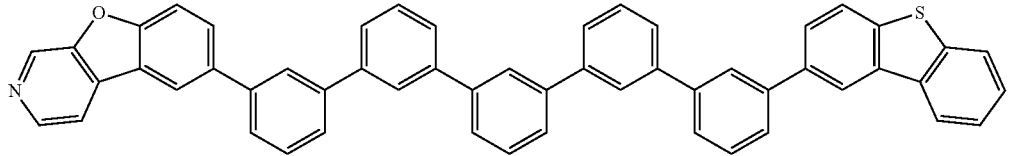
(150)
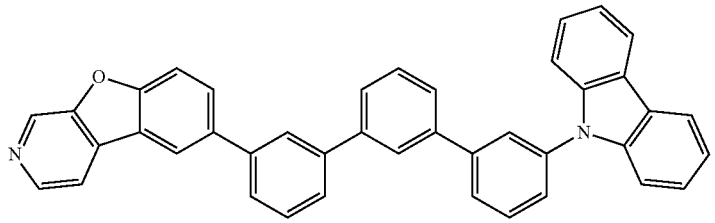
(151)
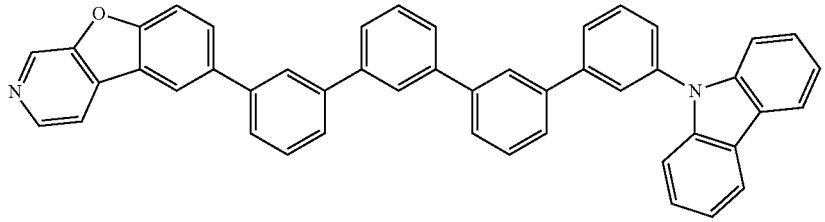
(152)

(153)
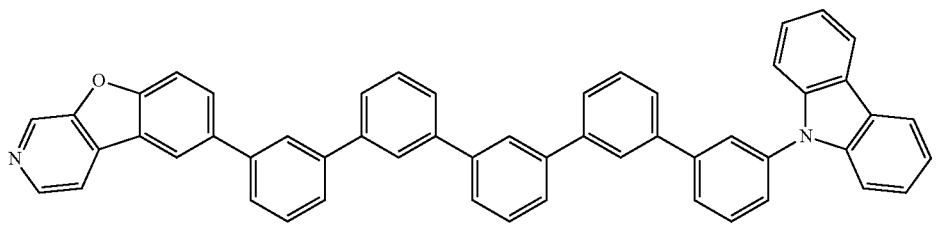
(154)
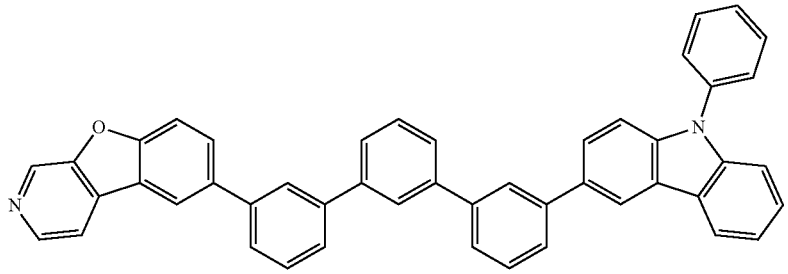
(155)
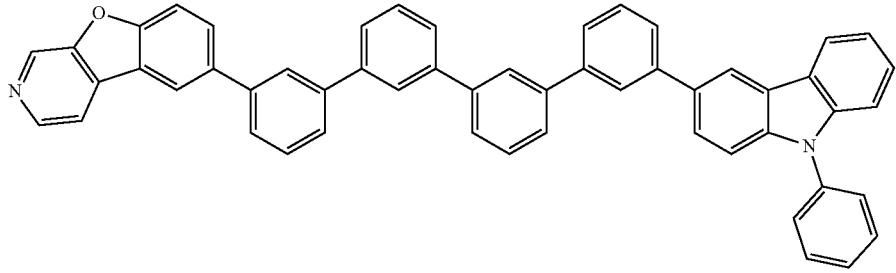
(156)
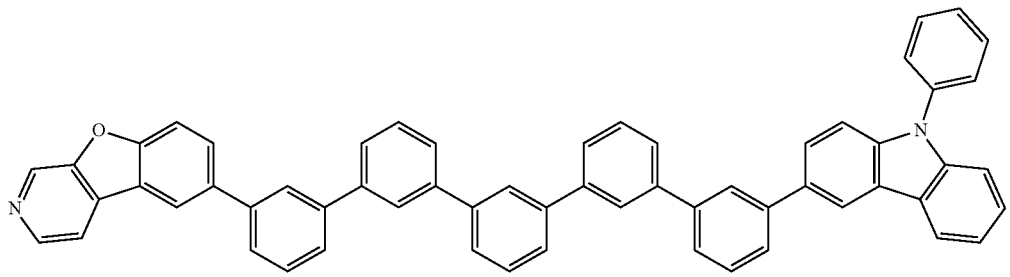
(157)
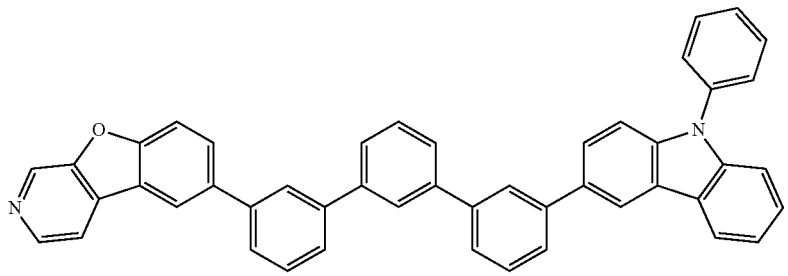
(158)
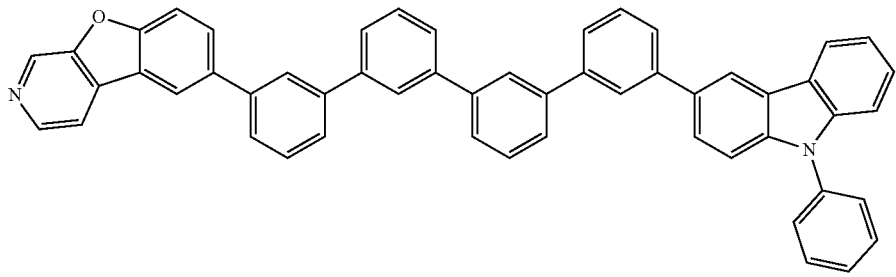

-continued
(159)
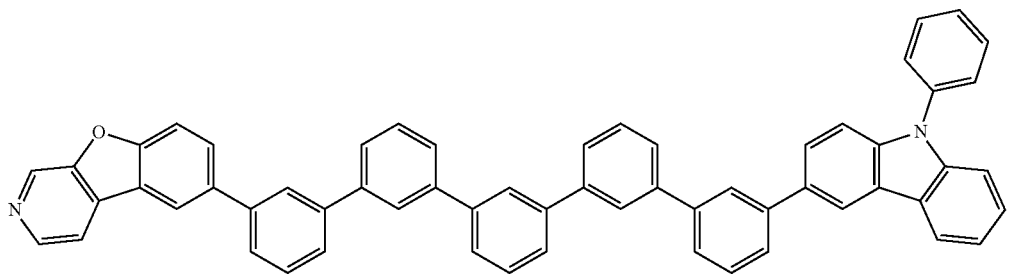
(160)
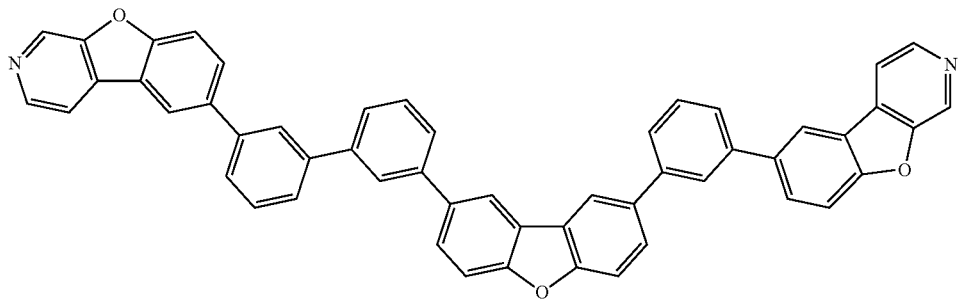
(161)
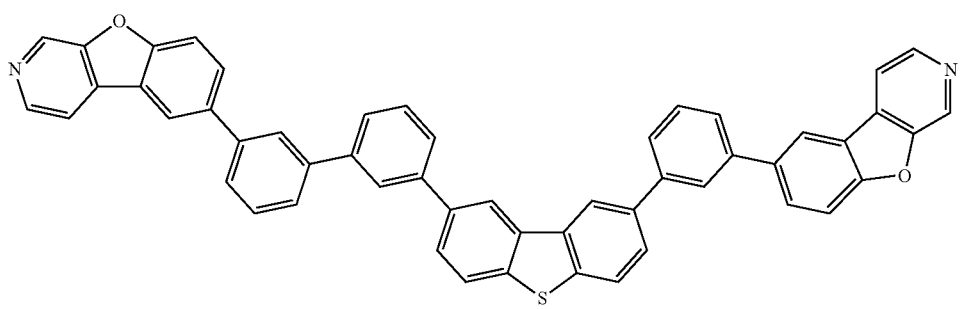
(162)
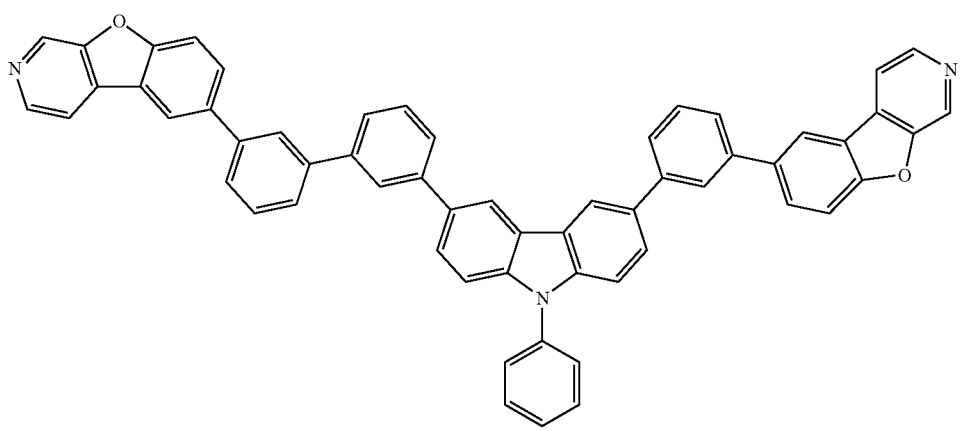
(163)
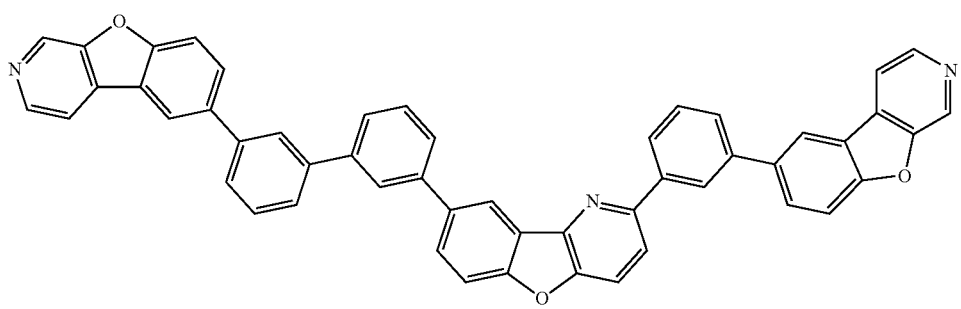

-continued
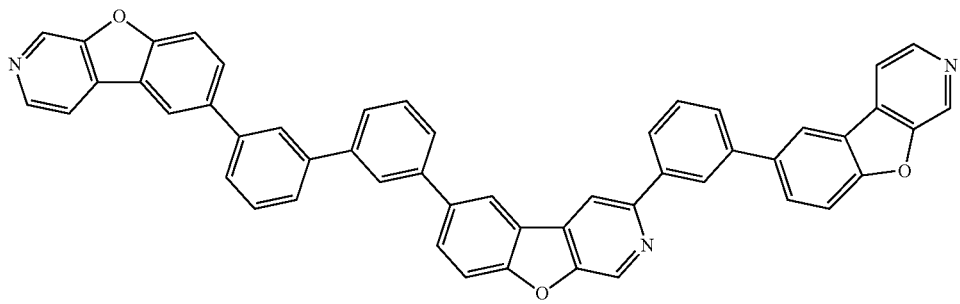
(164)
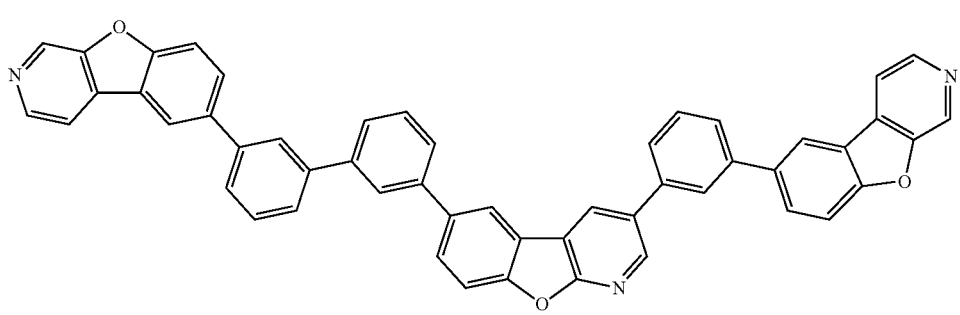
(165)
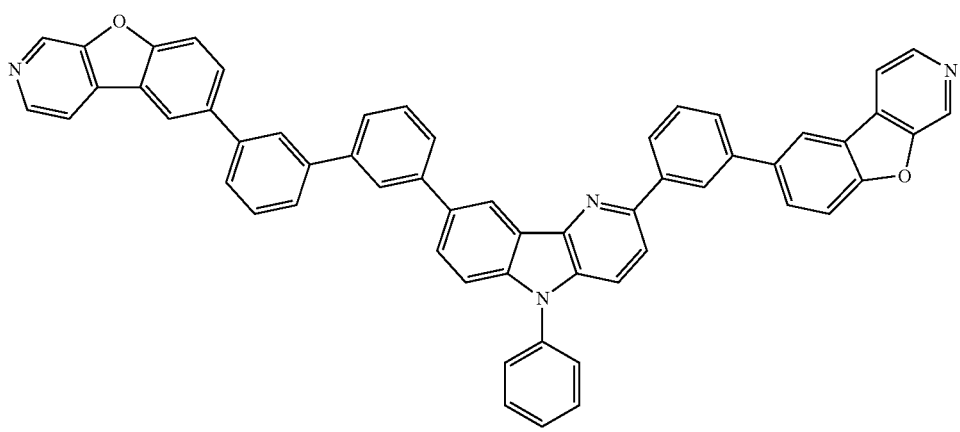
(166)
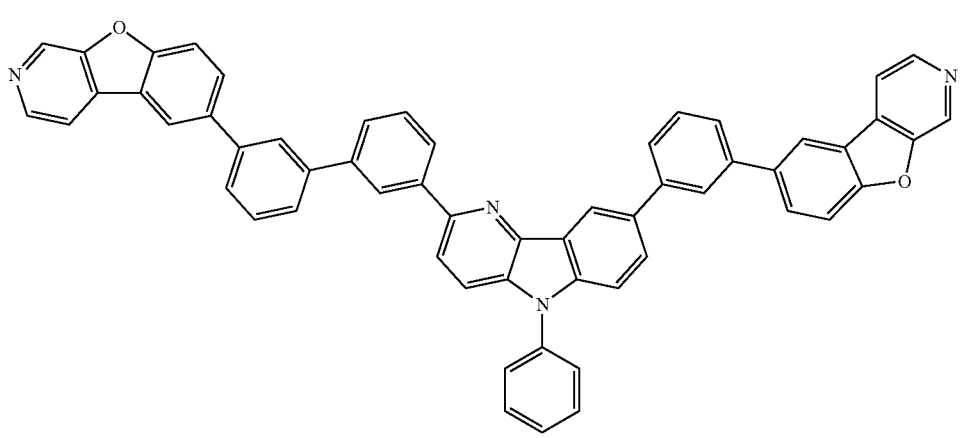
(167)

-continued
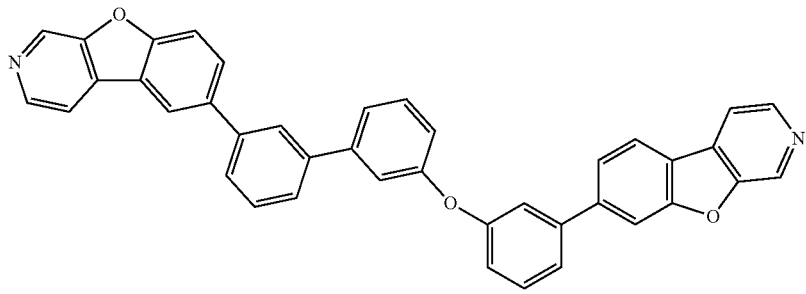
(168)
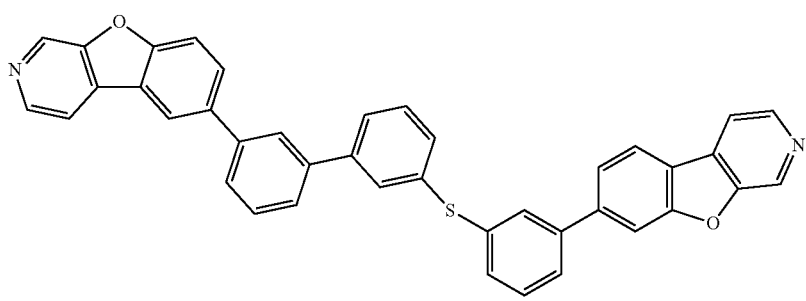
(169)
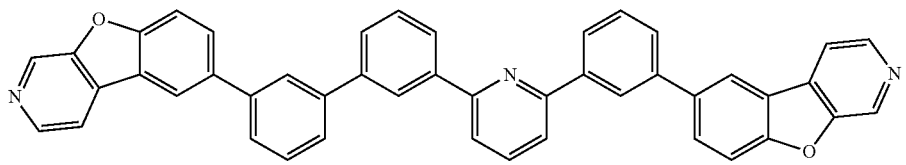
(170)
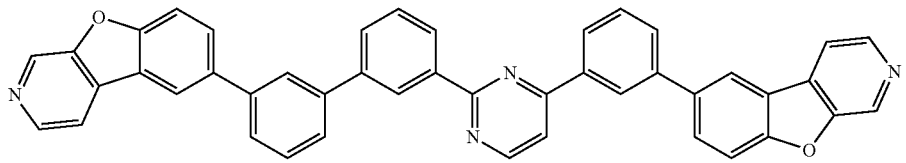
(171)
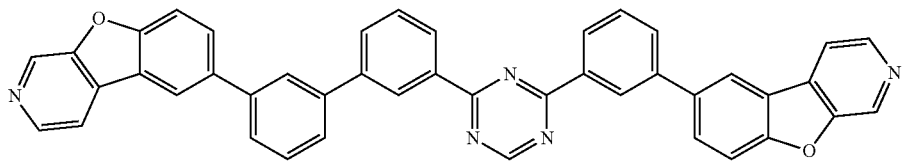
(172)
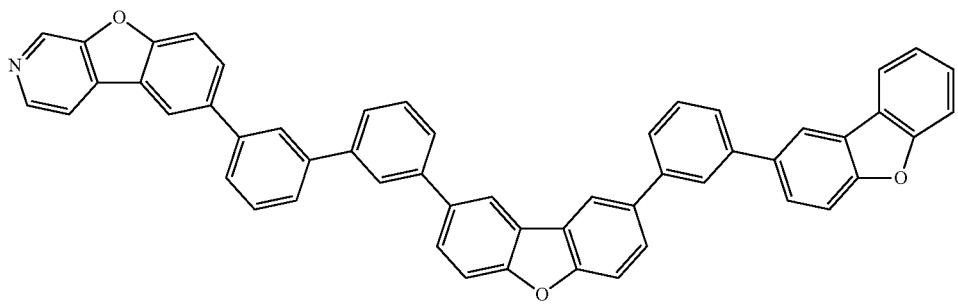
(173)

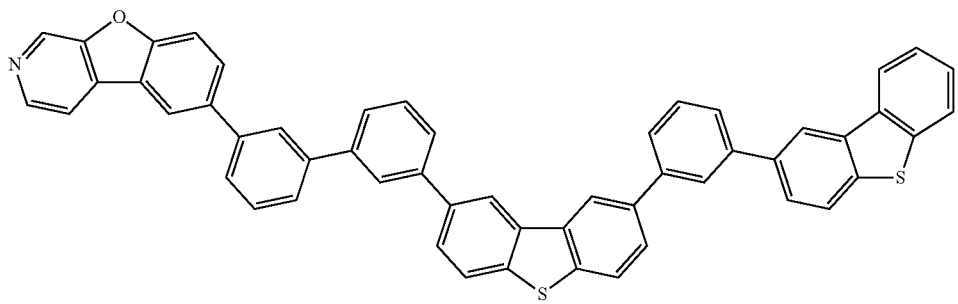
(174)
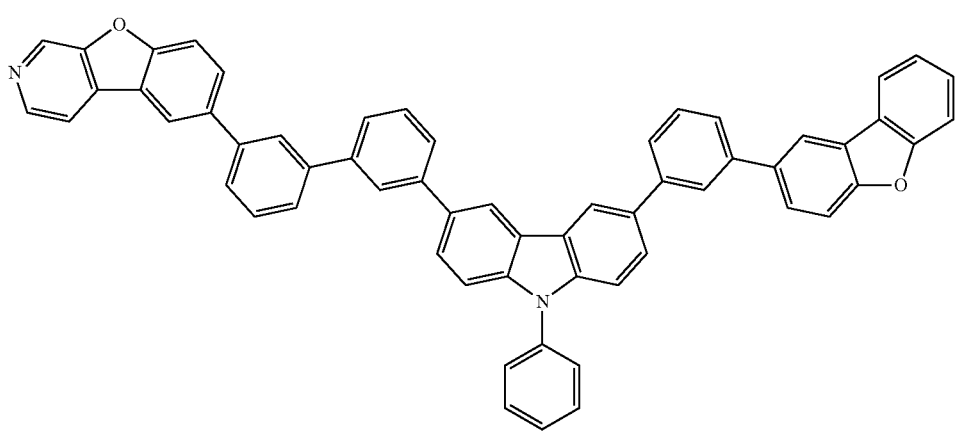
(175)
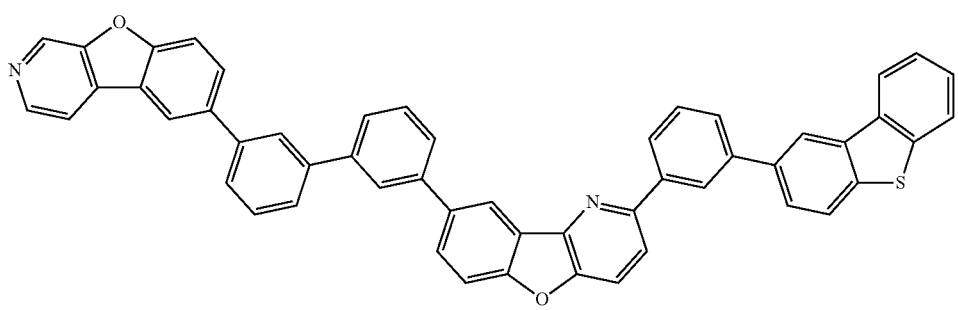
(176)
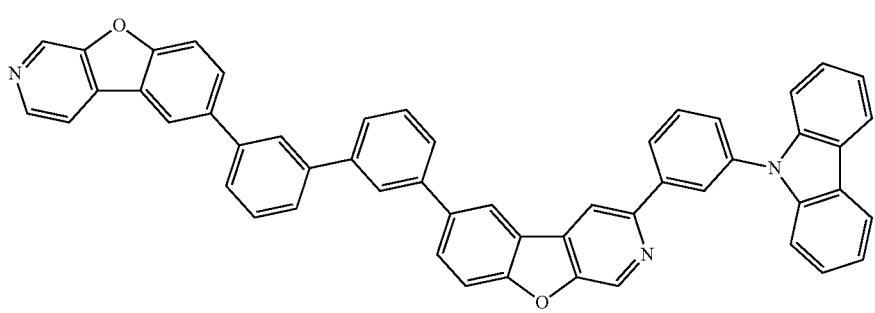
(177)

-continued
(178)
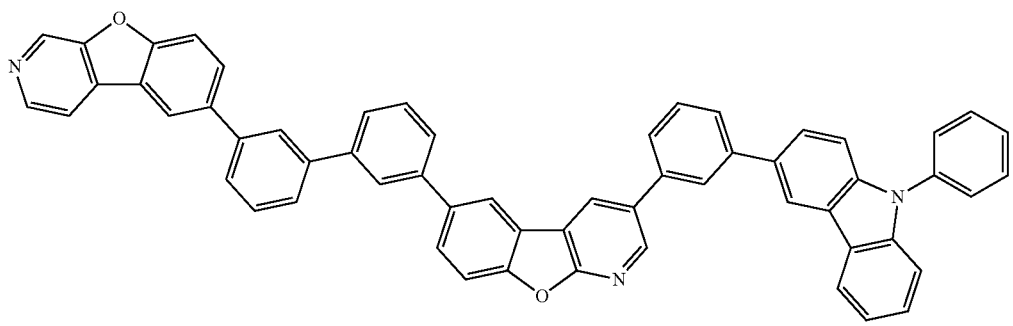
(179)
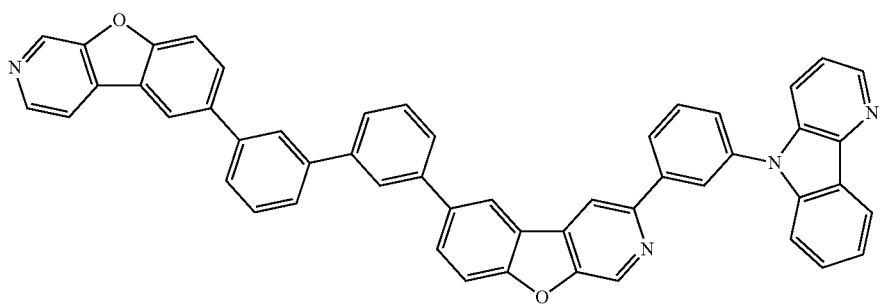
(180)
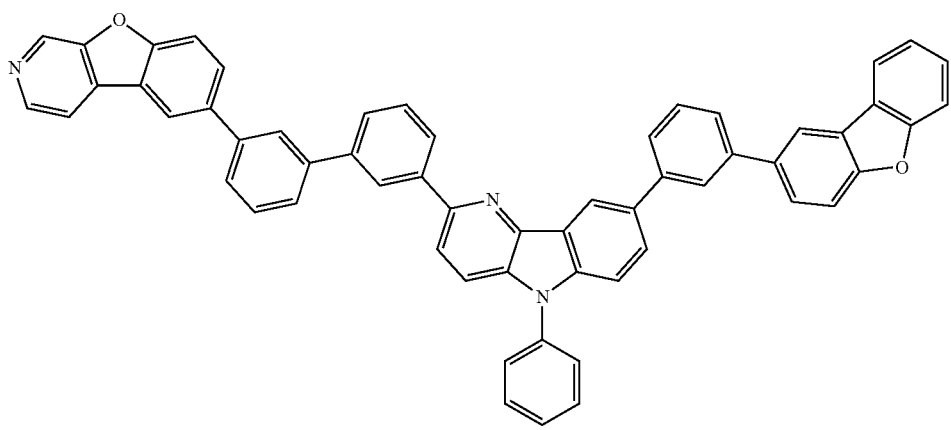
(181)
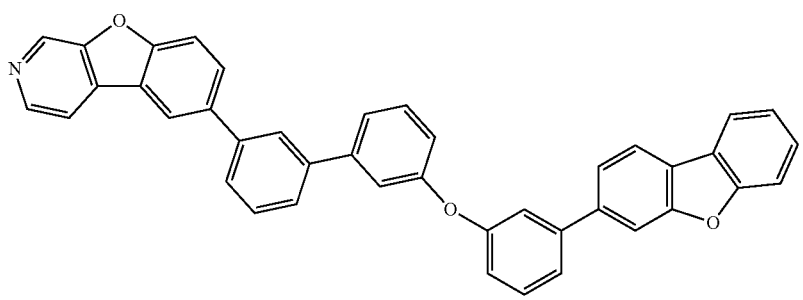
(182)
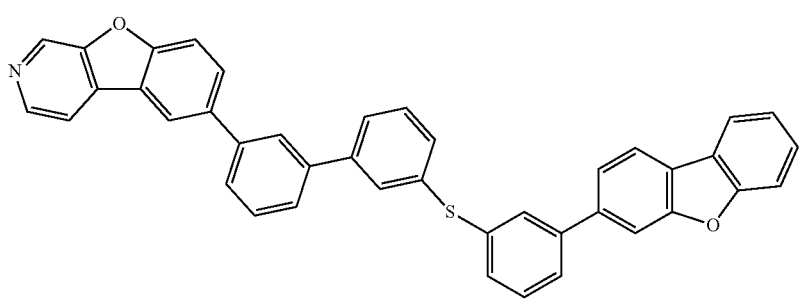

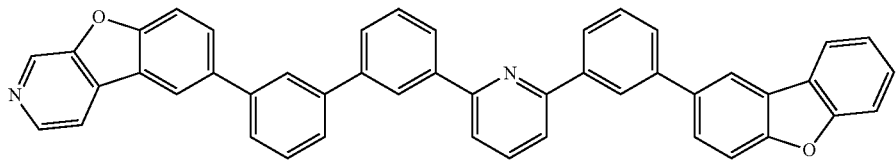
(183)
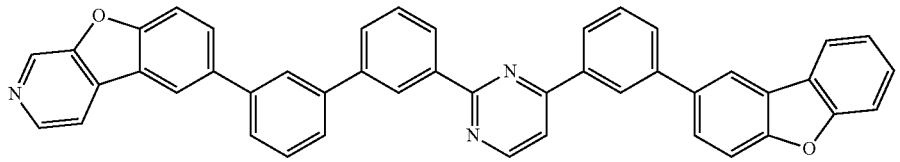
(184)
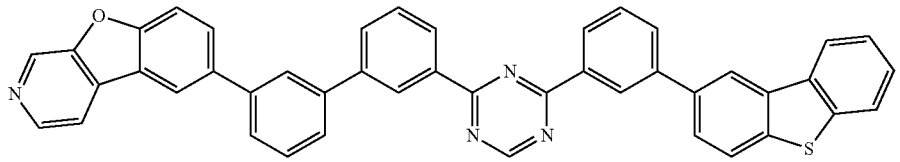
(185)
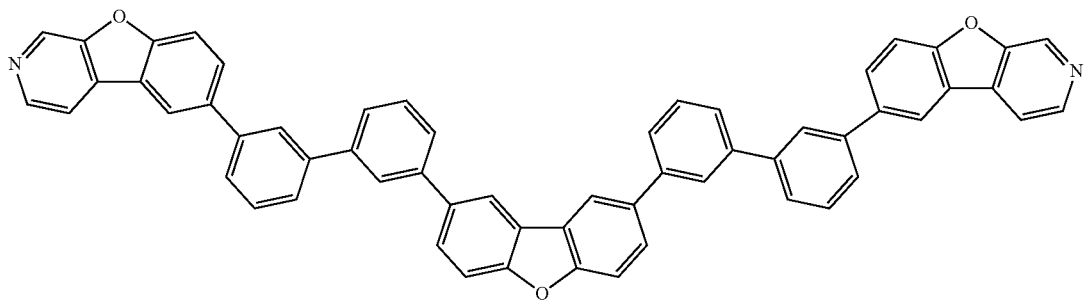
(186)
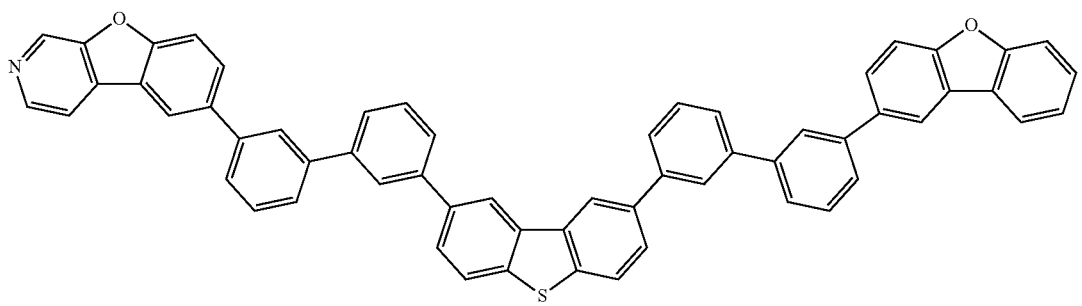
(187)
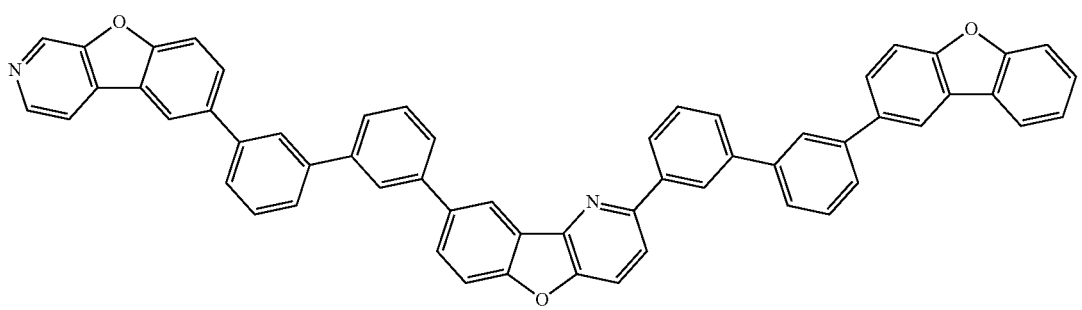
(188)

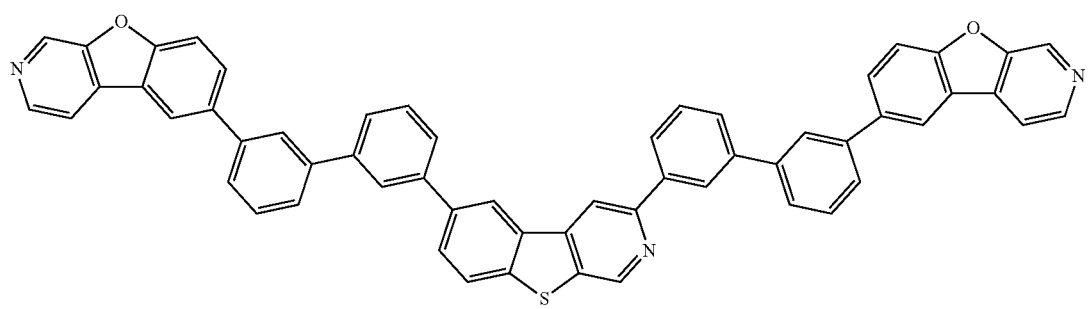
(189)
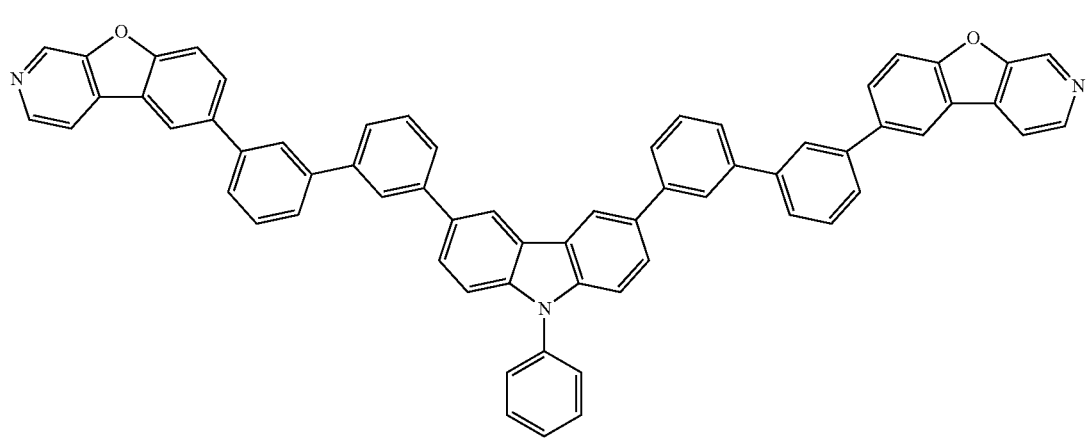
(190)
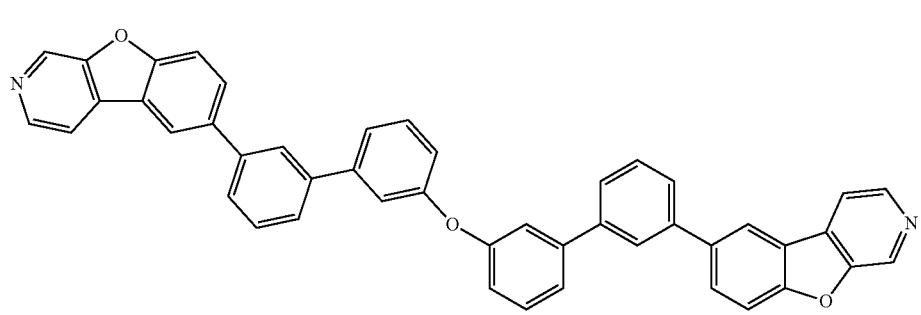
(191)
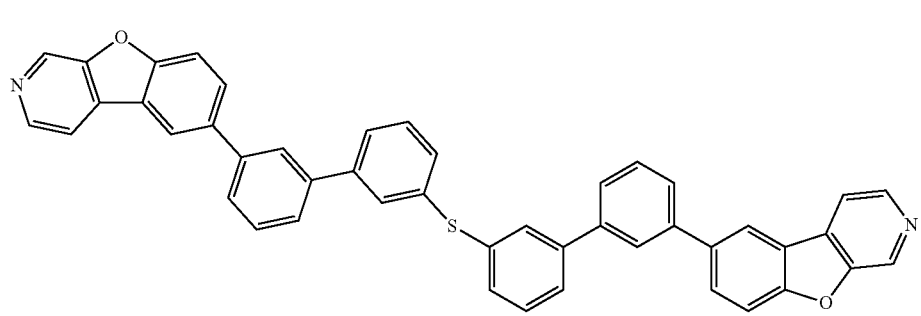
(192)
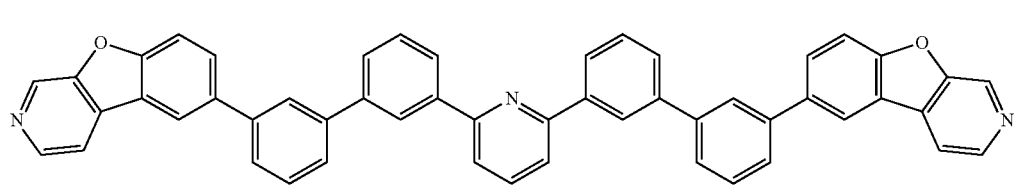
(193)

-continued
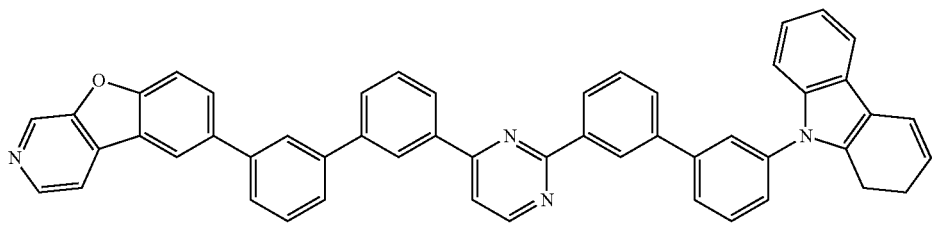
(194)
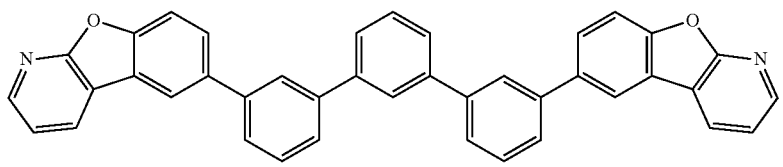
(195)
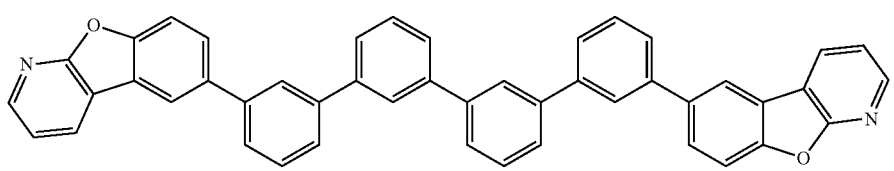
(196)
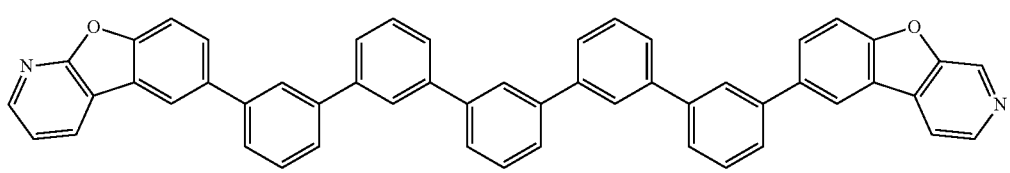
(197)
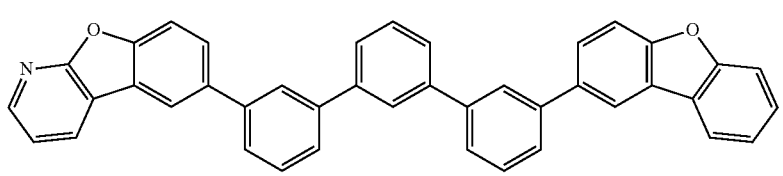
(198)
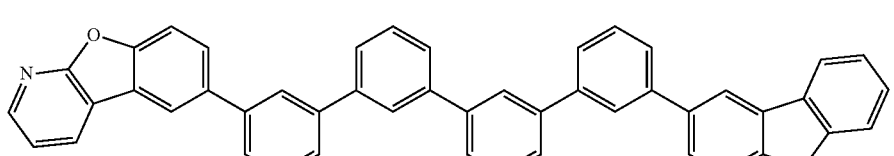
(199)
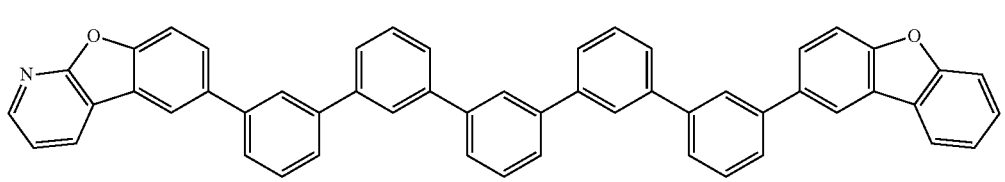
(200)
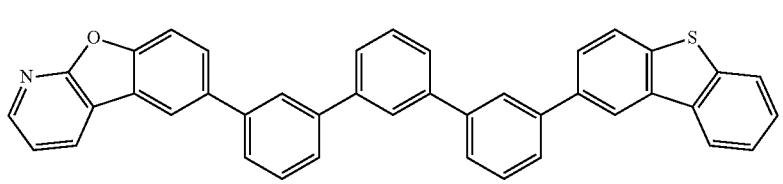
(201)
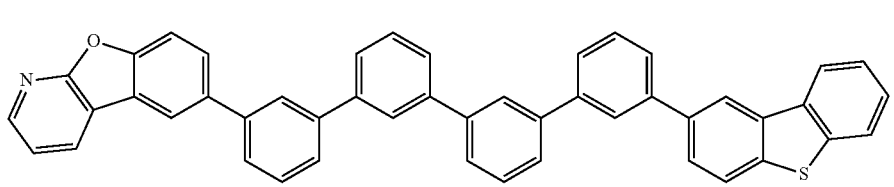
(202)

(203)
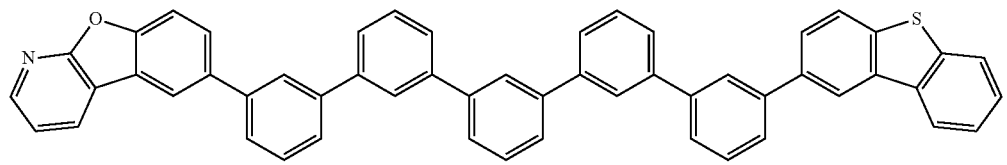
(204)
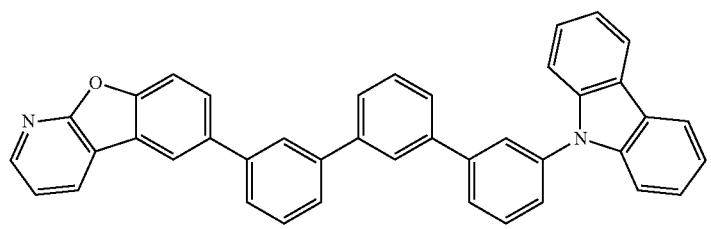
(205)
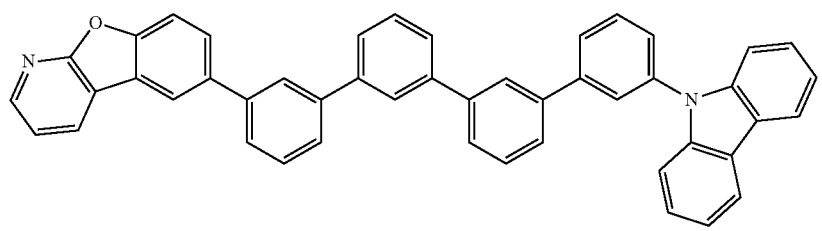
(206)
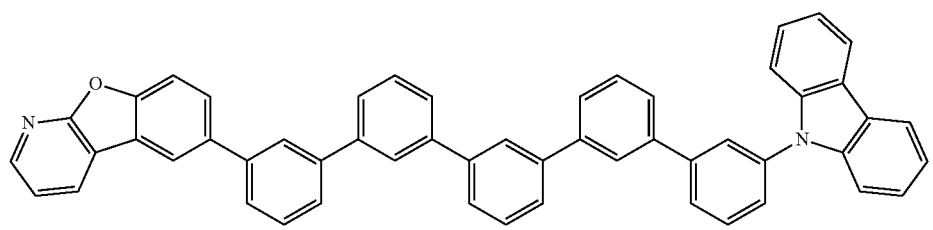
(207)
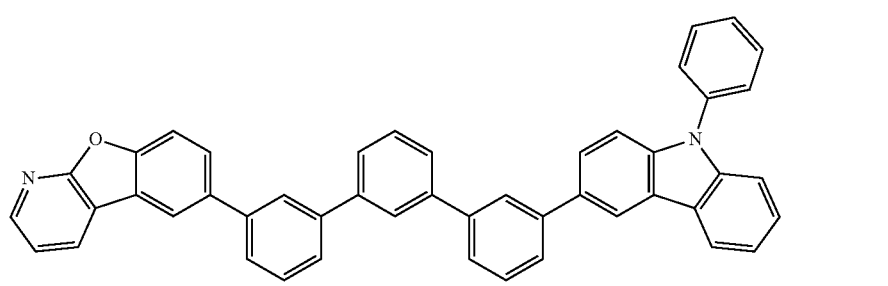
(208)
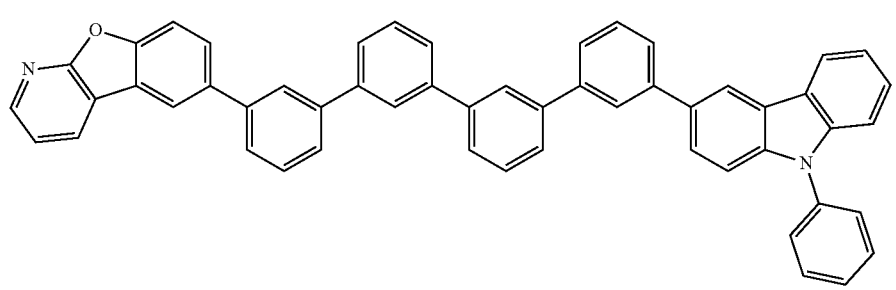

-continued
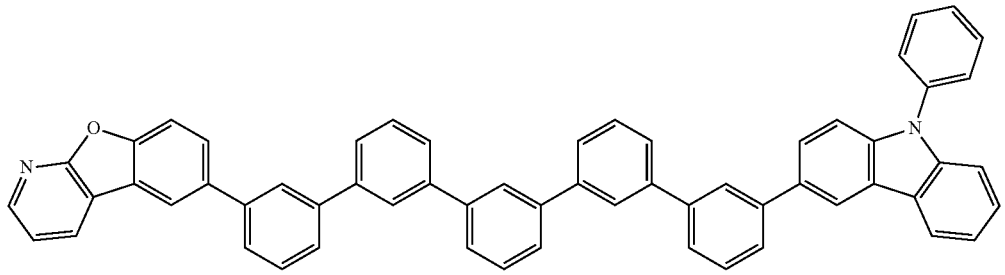
(209)
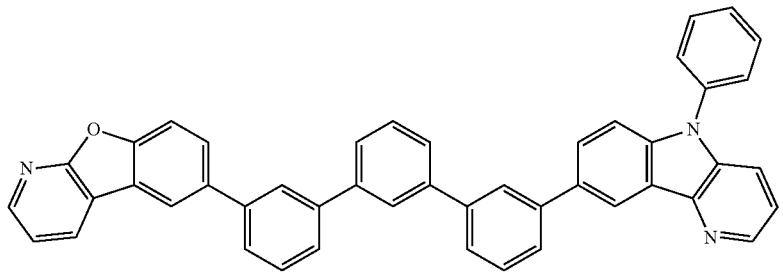
(210)
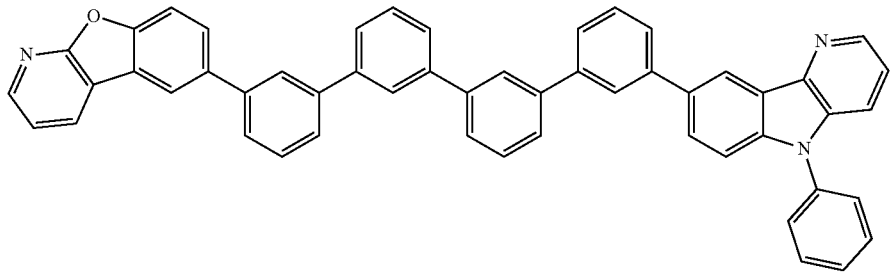
(211)
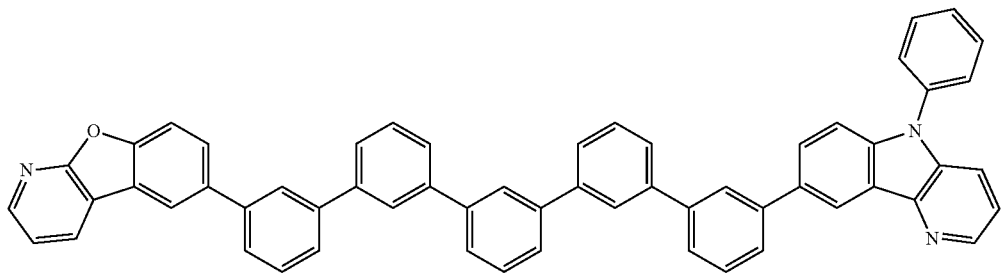
(212)
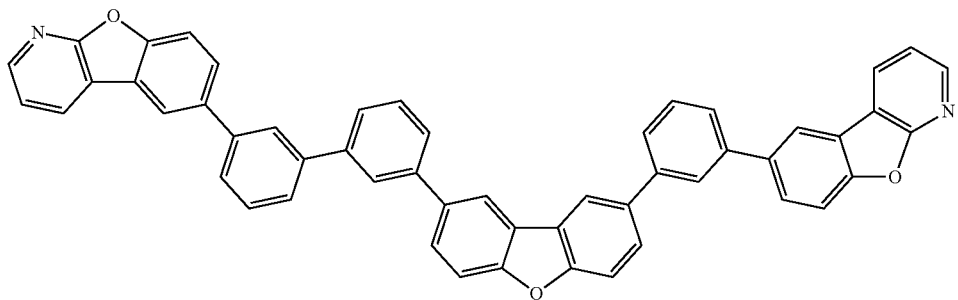
(213)

-continued
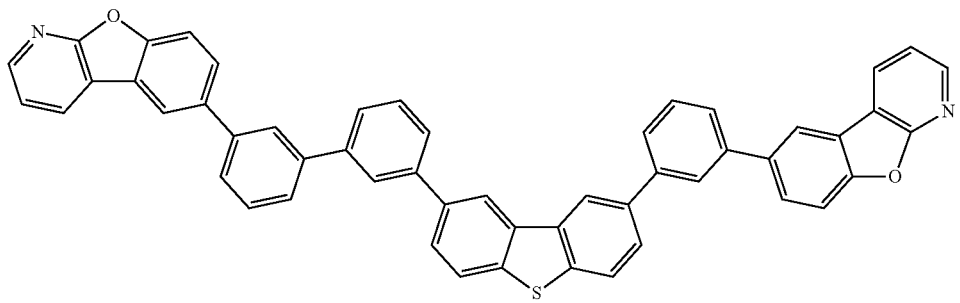
(214)
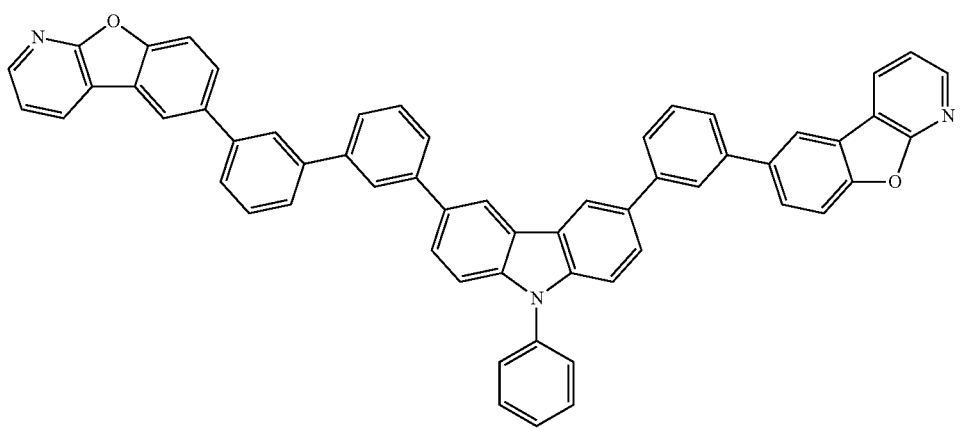
(215)
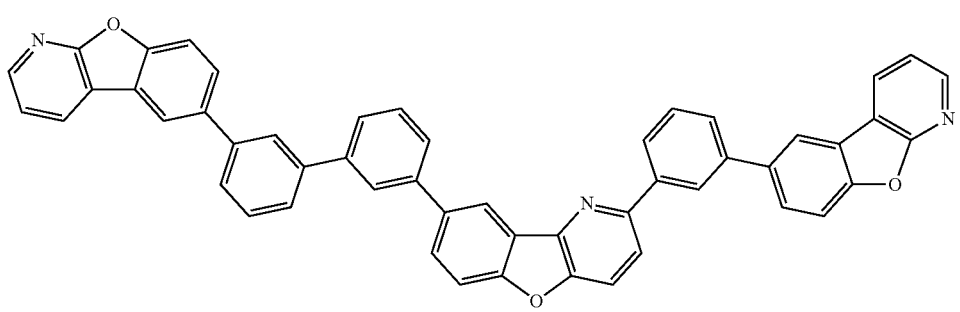
(216)
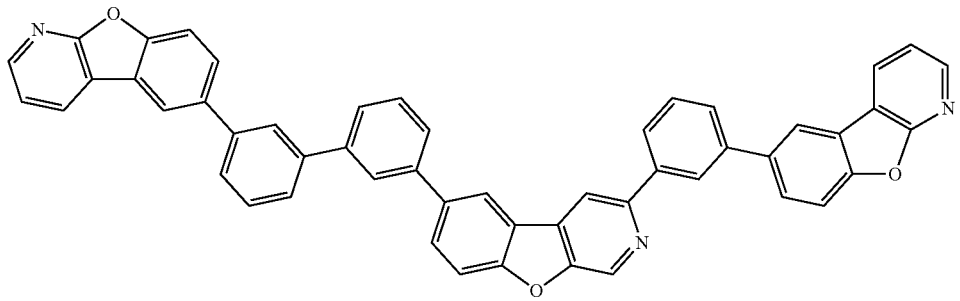
(217)
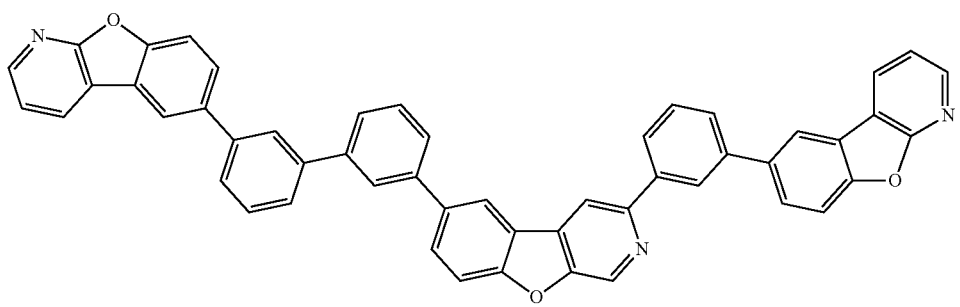
(218)

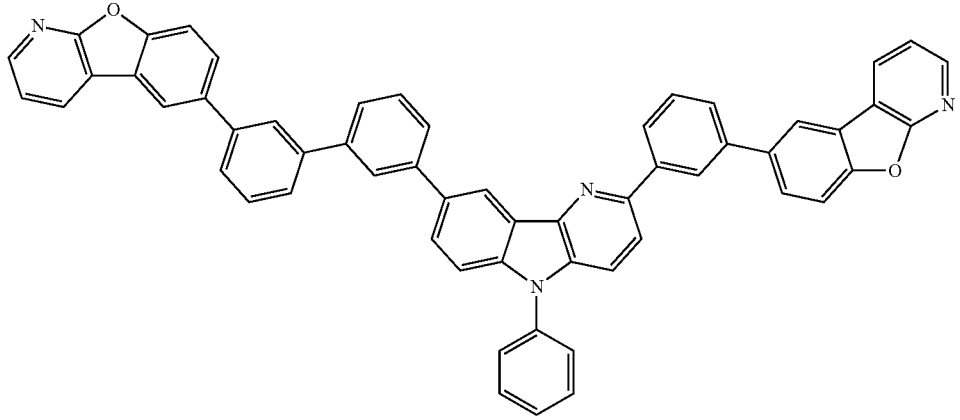
(219)
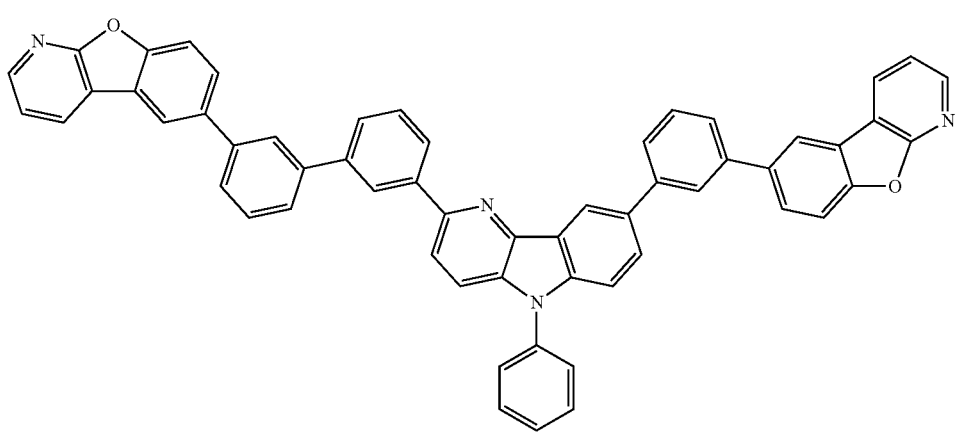
(220)
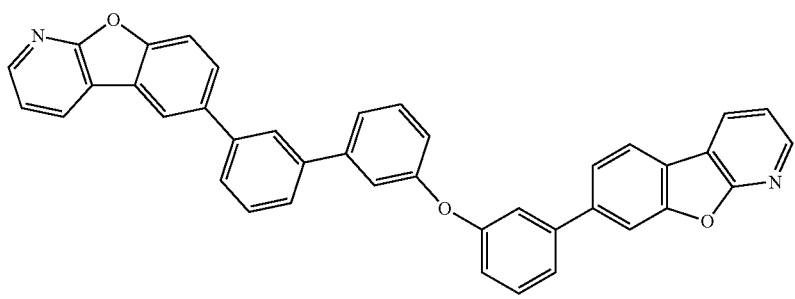
(221)
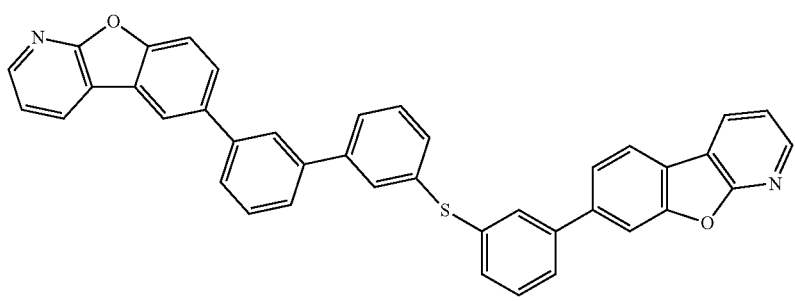
(222)
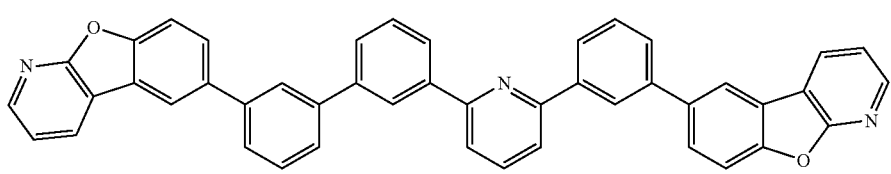
(223)

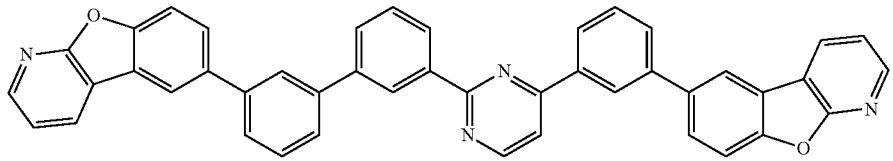
(224)
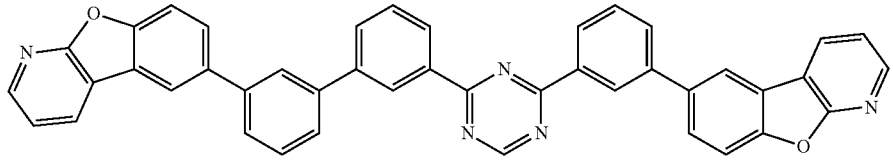
(225)
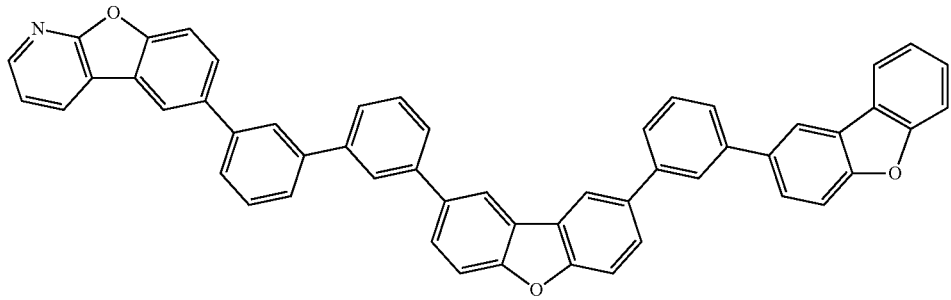
(226)
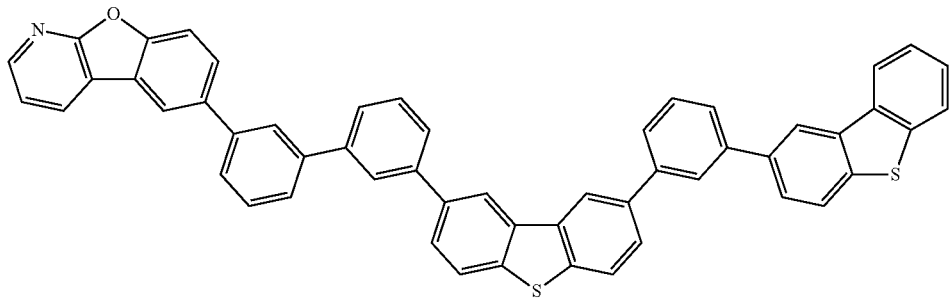
(227)
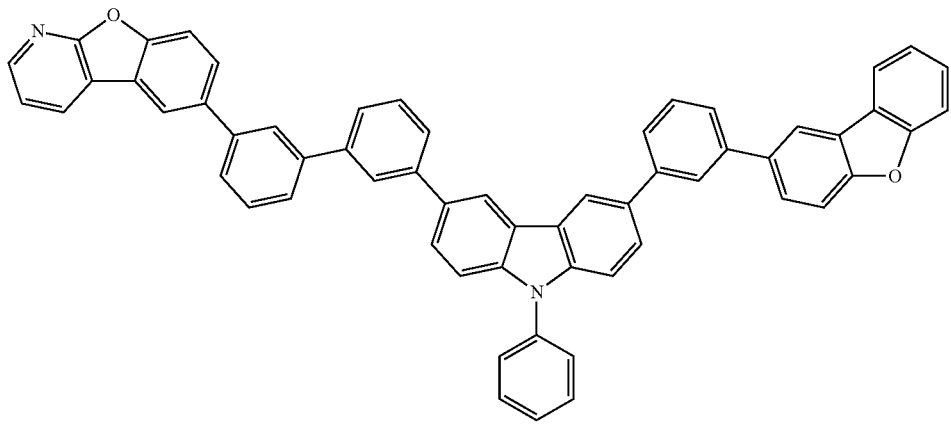
(228)

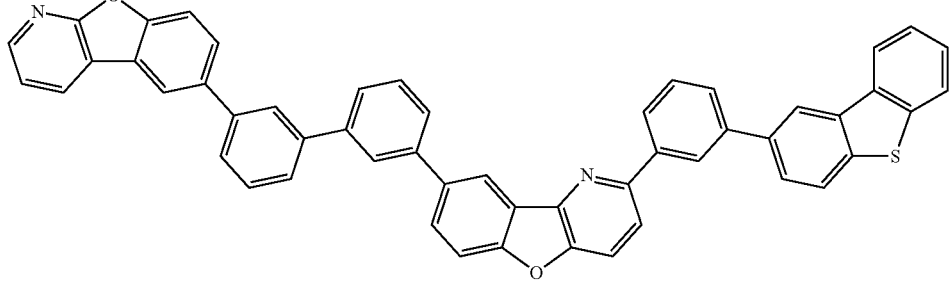
(229)
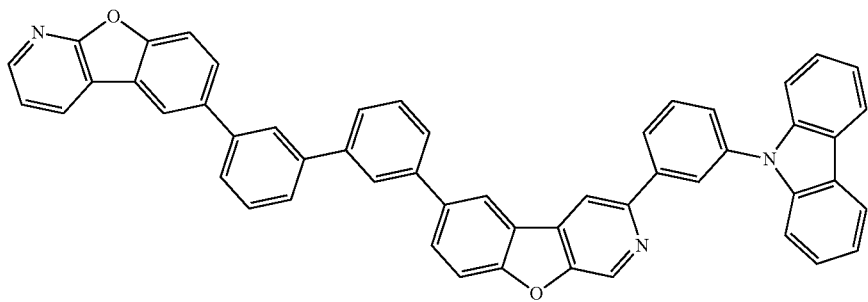
(230)
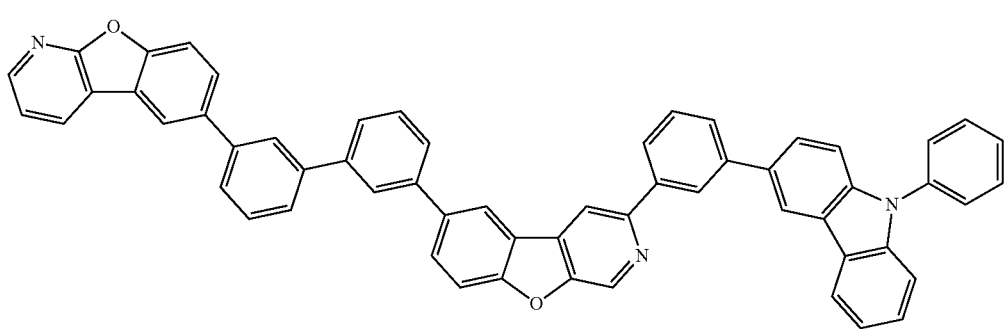
(231)
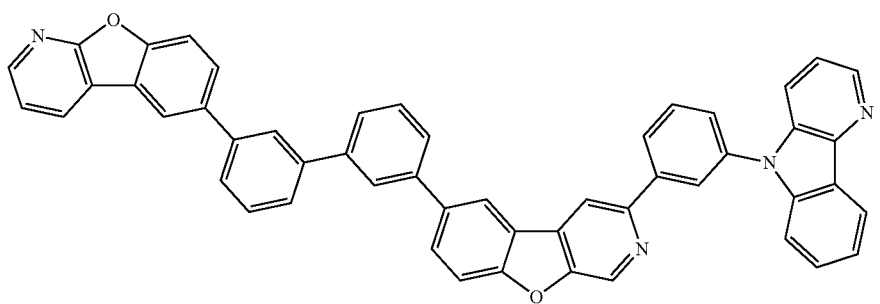
(232)

-continued
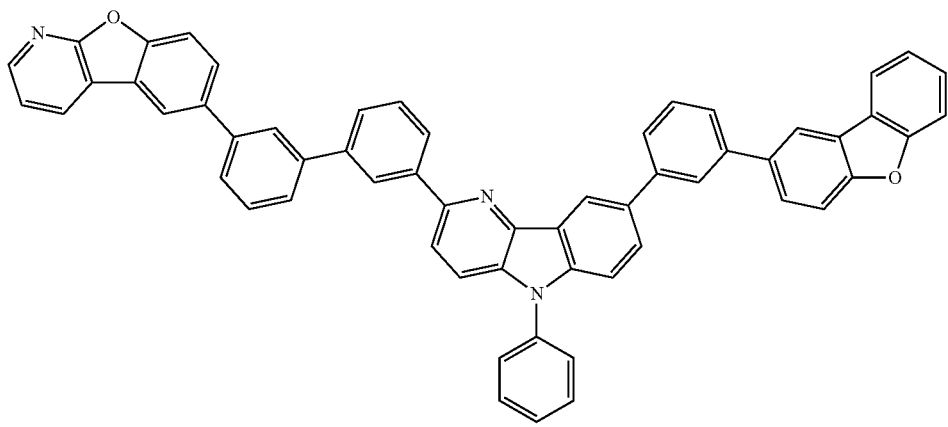
(233)
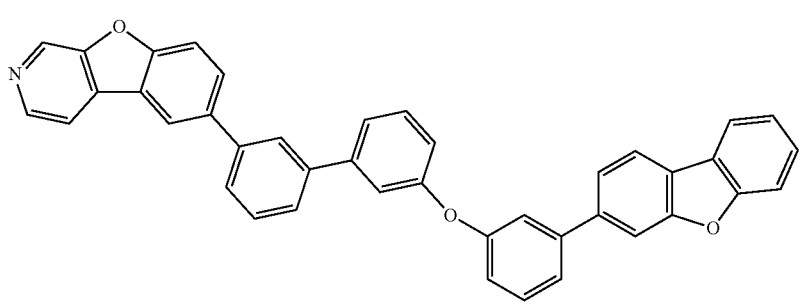
(234)
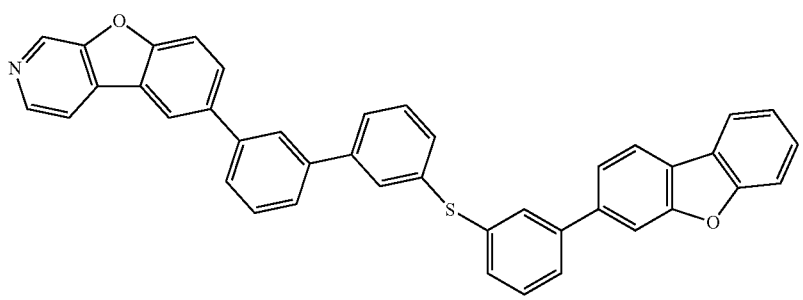
(235)
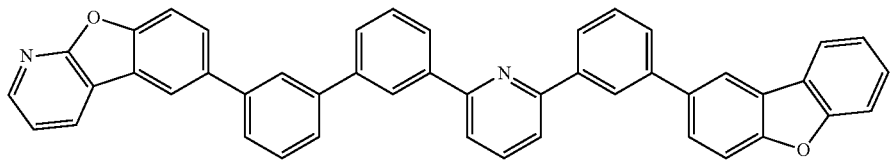
(236)
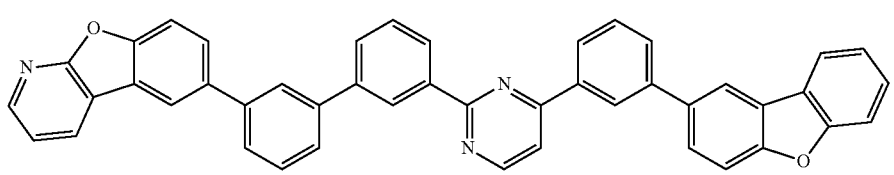
(237)
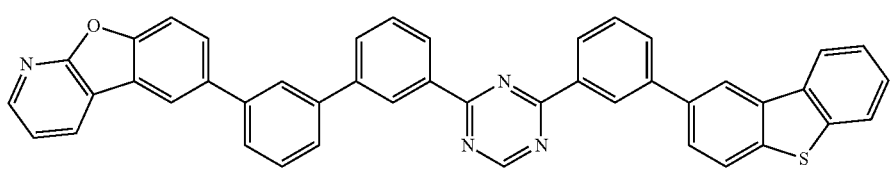
(238)

-continued
(239)
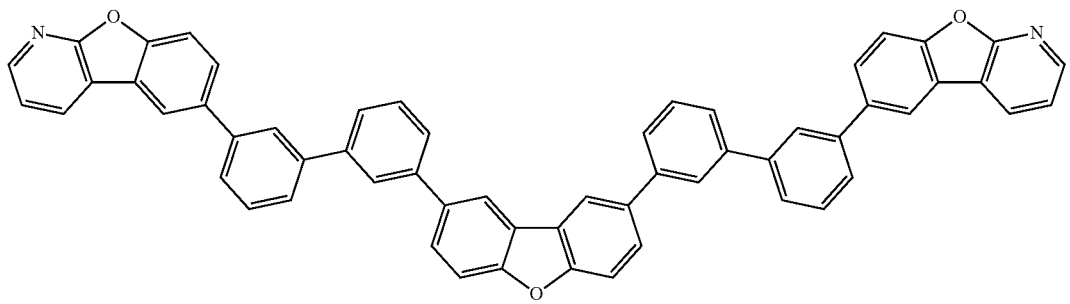
(240)
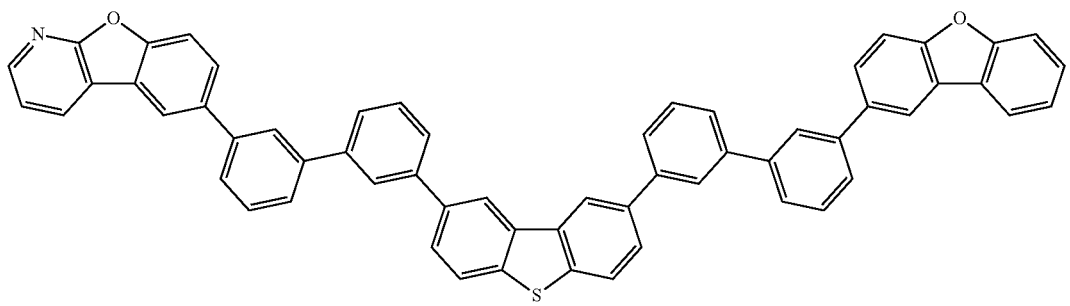
(241)
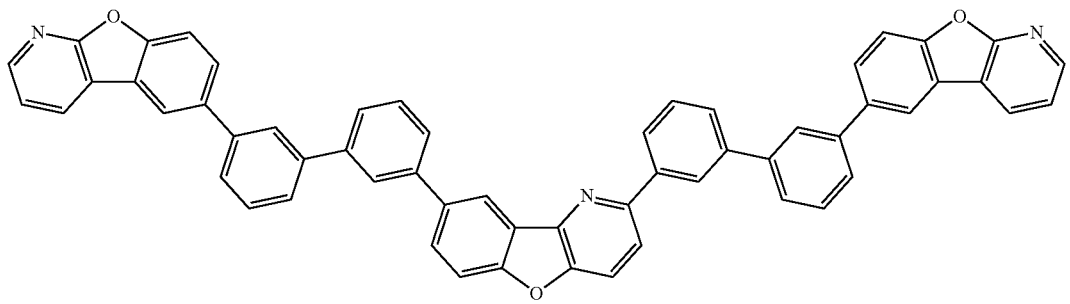
(242)
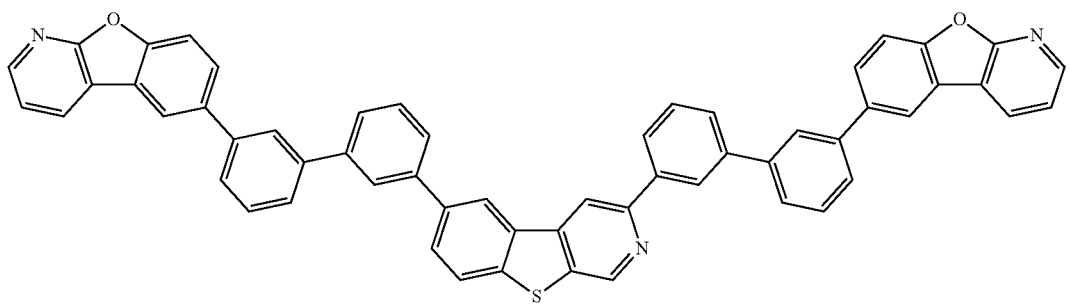
(243)
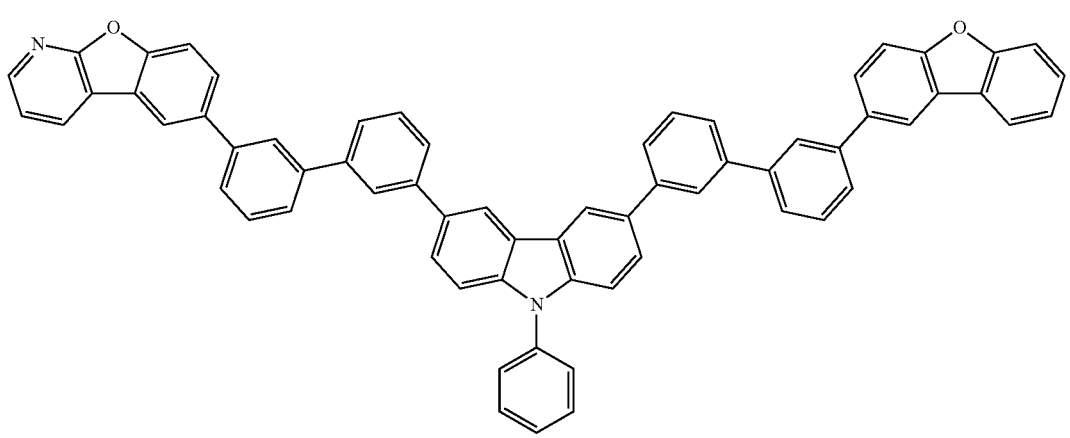

-continued
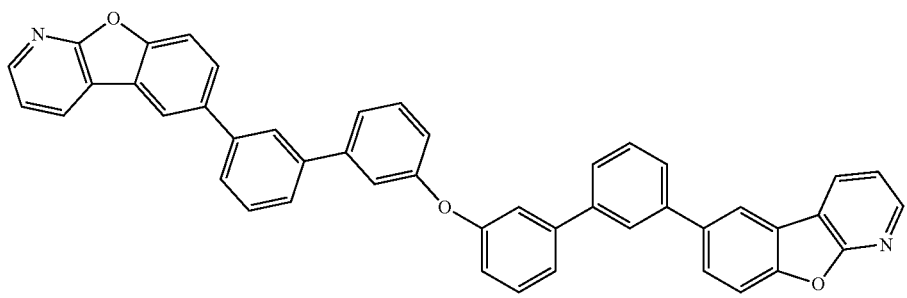
(244)
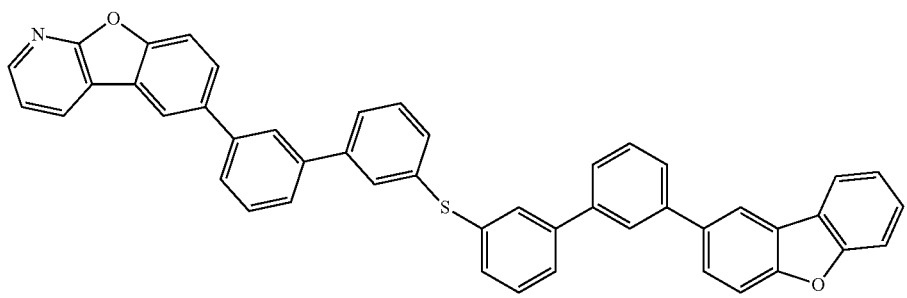
(245)
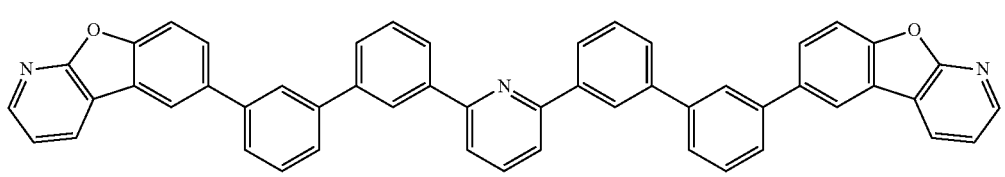
(246)
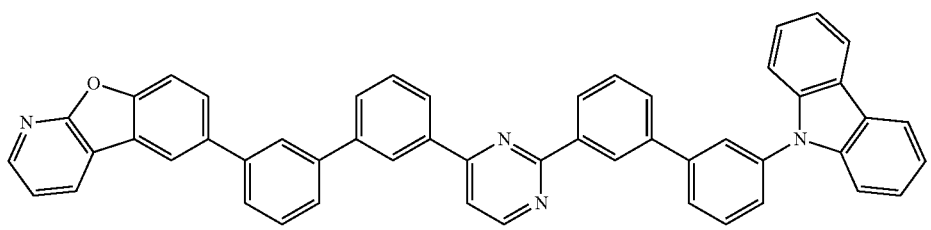
(247)
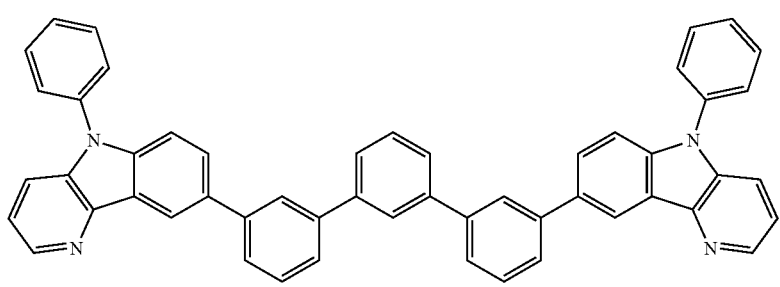
(248)

(249)
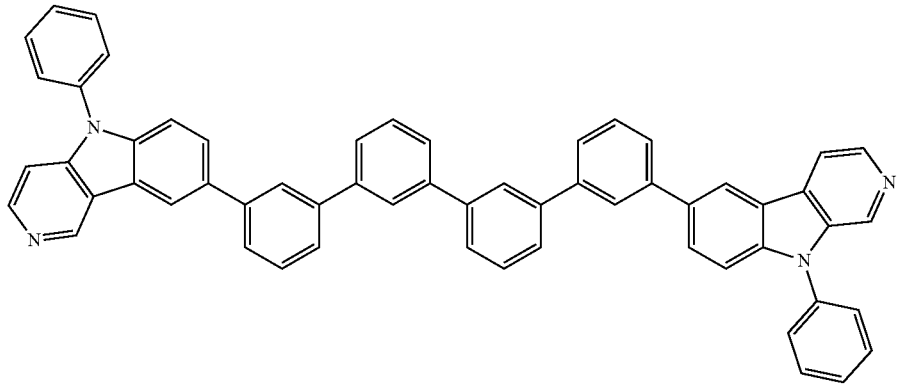
(250)
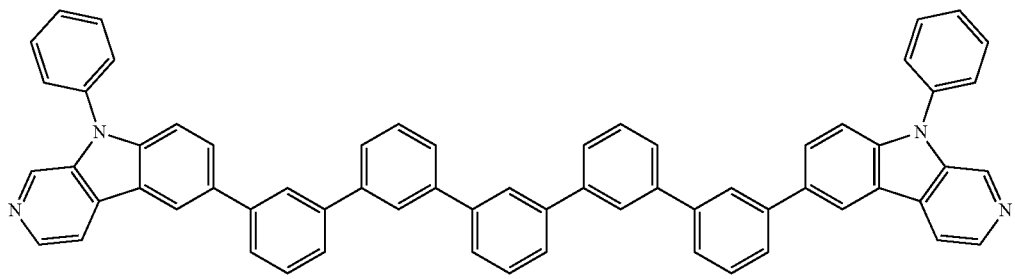
(251)
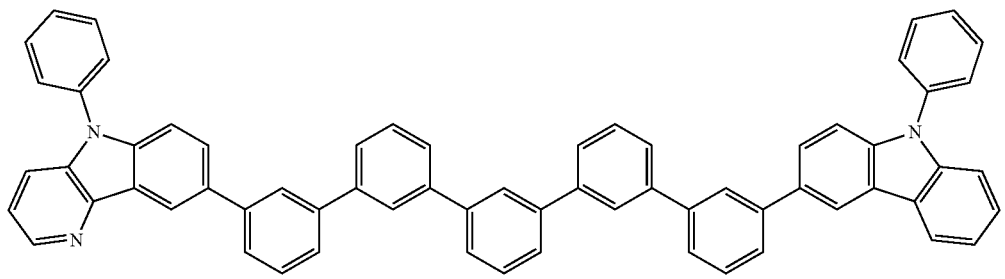
(252)
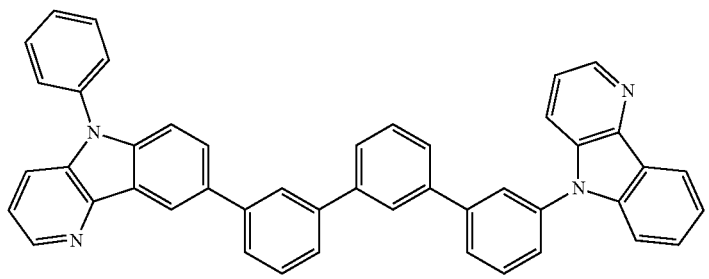
(253)
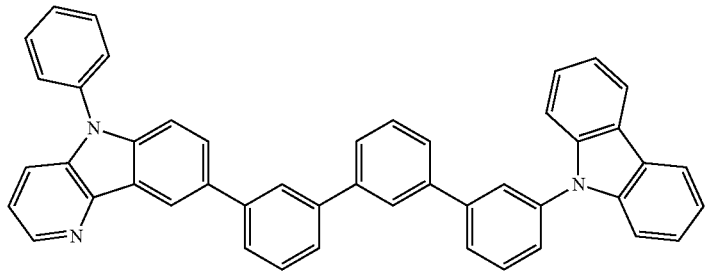

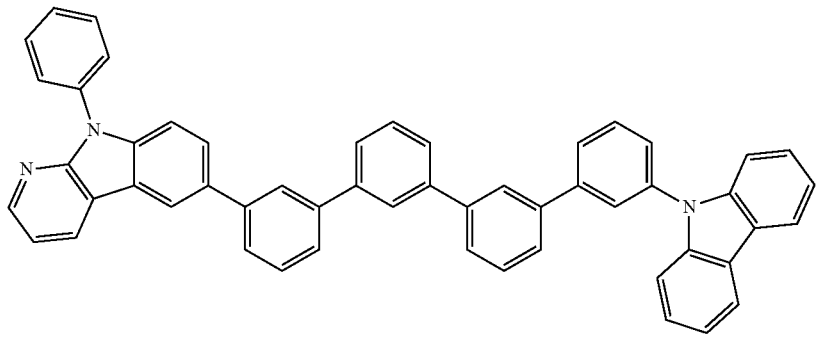
(254)
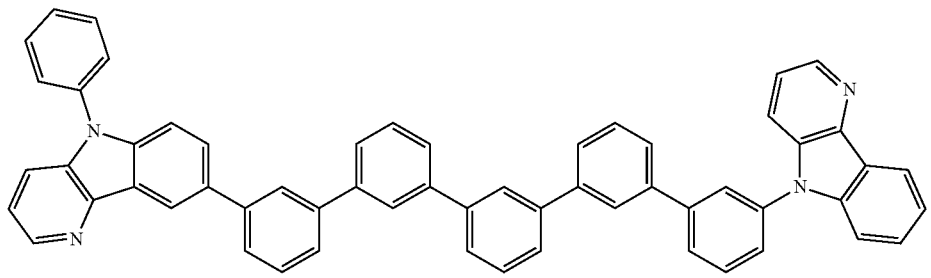
(255)
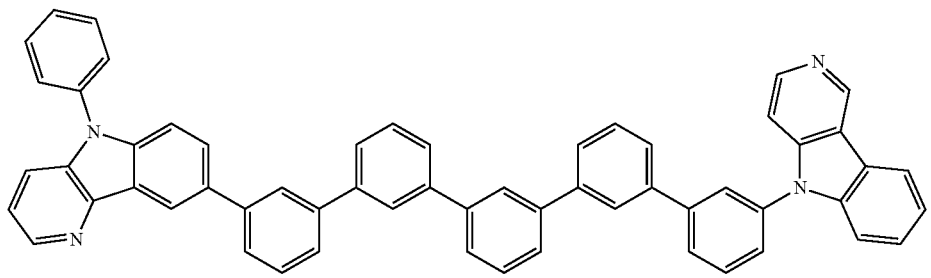
(256)
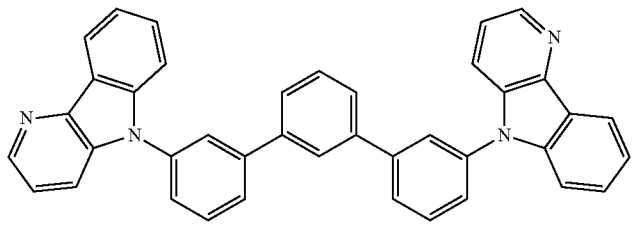
(257)
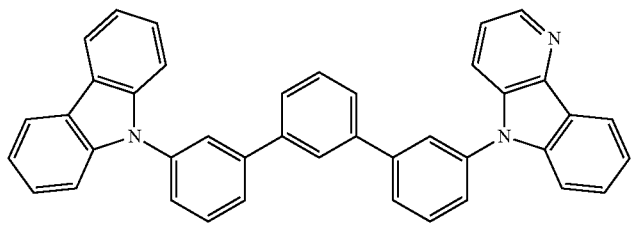
(258)

-continued
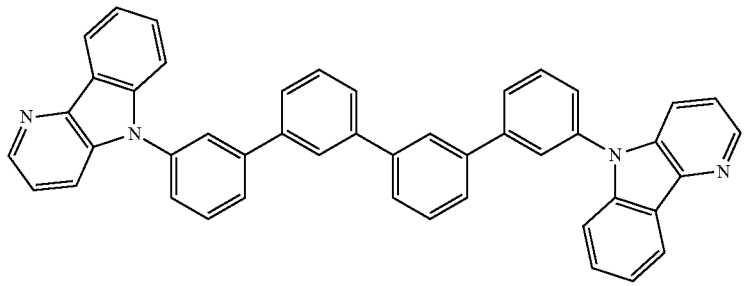
(259)
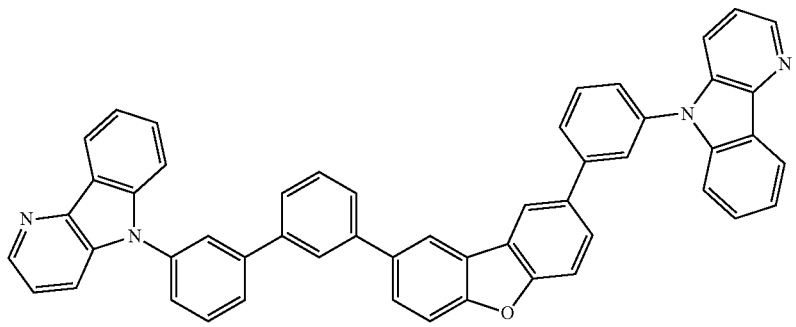
(260)
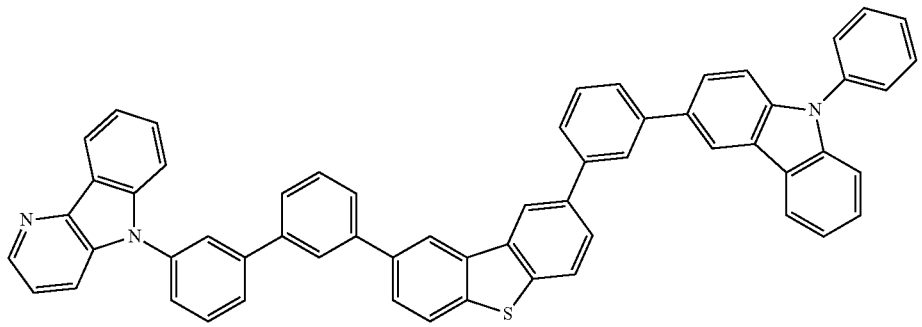
(261)
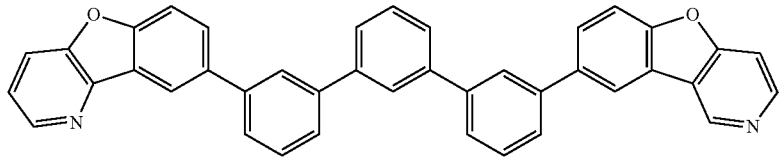
(262)
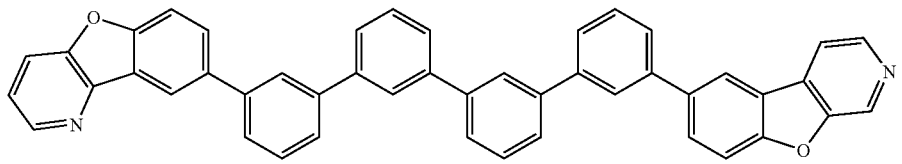
(263)
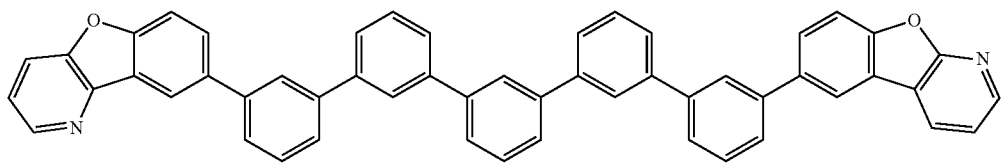
(264)

-continued
(265)
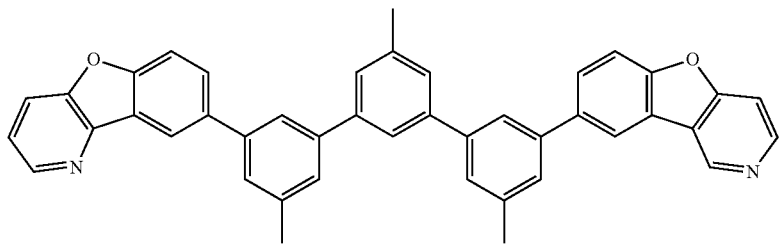
(266)
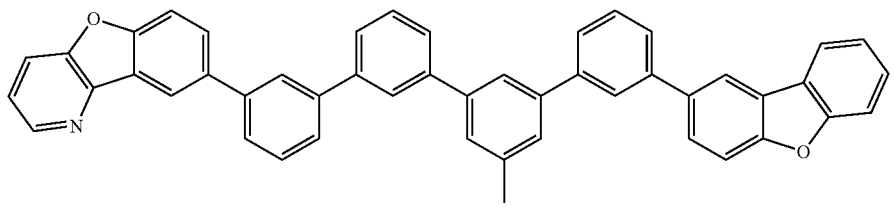
(267)
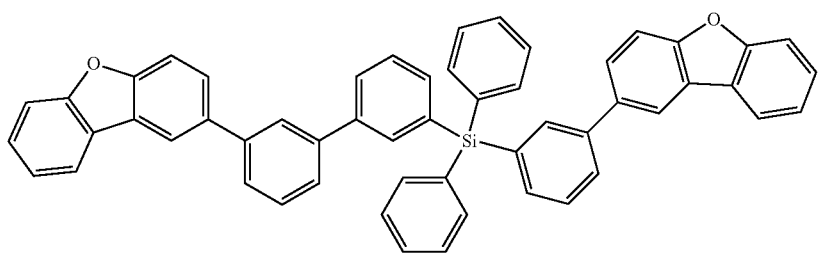
(268)
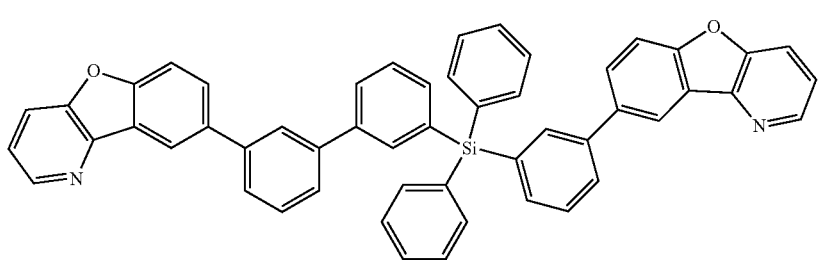
(269)
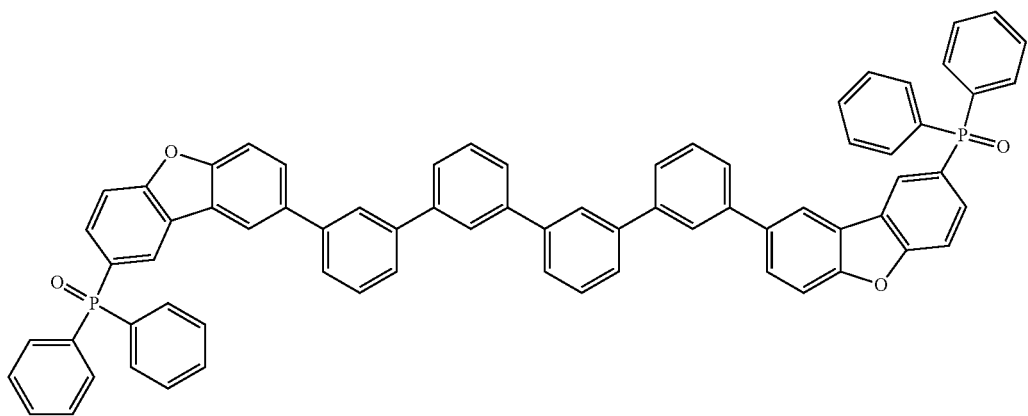

(270)
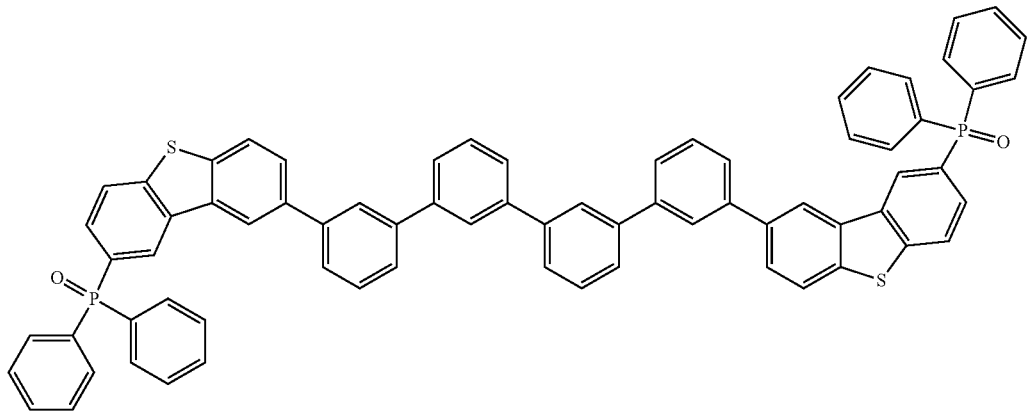
(271)
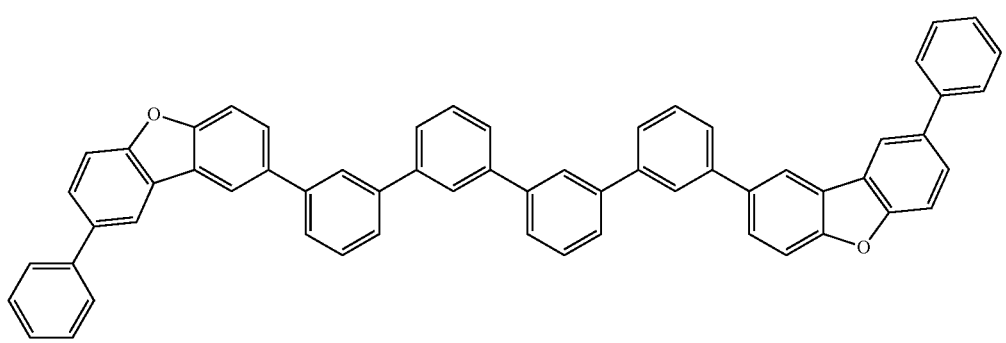
(272)
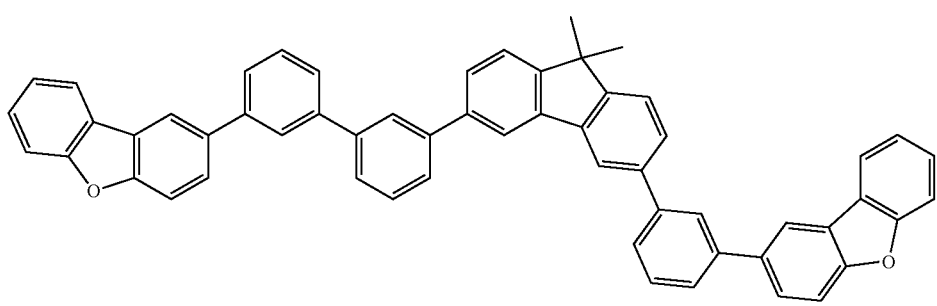
(273)
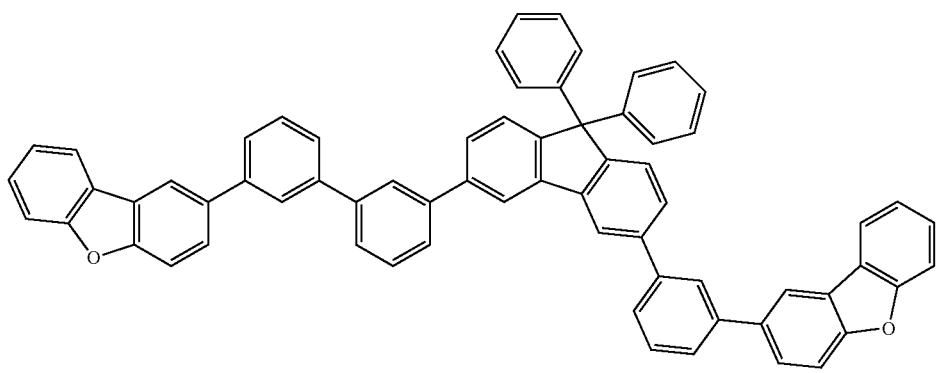

(274)
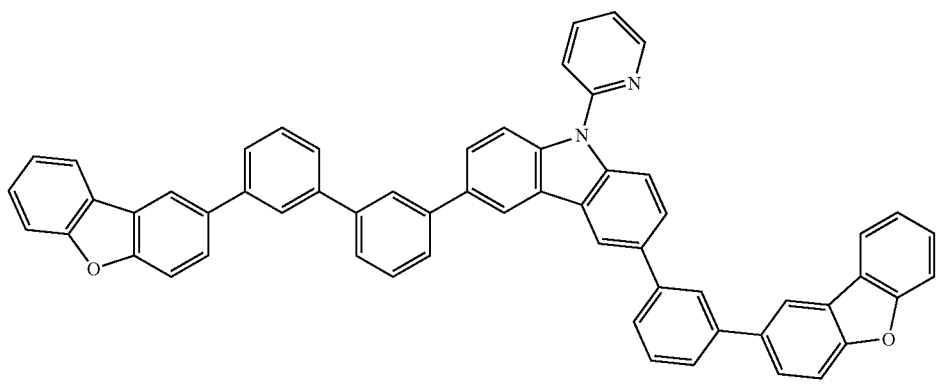
(275)
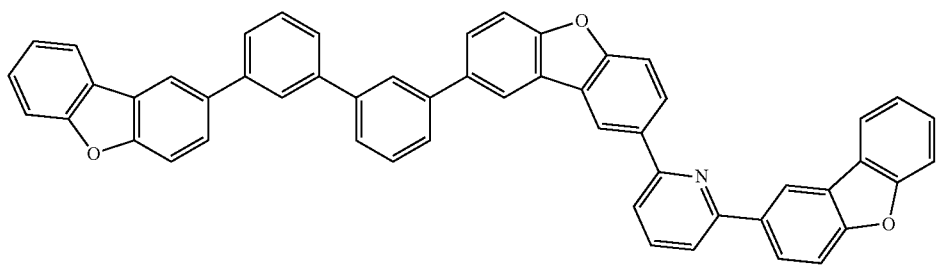
(276)
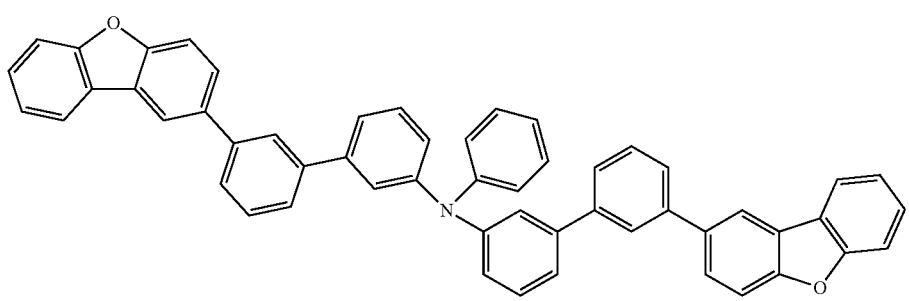
(277)
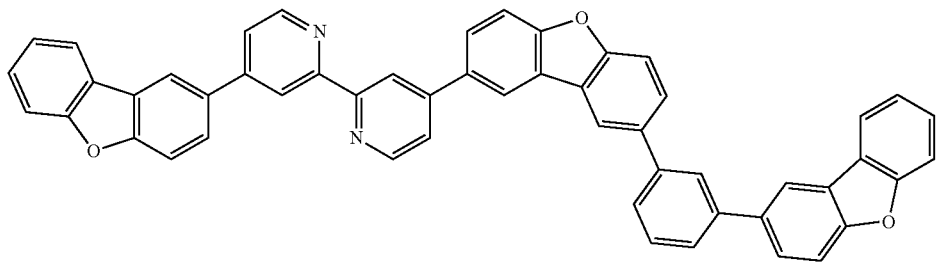
(278)
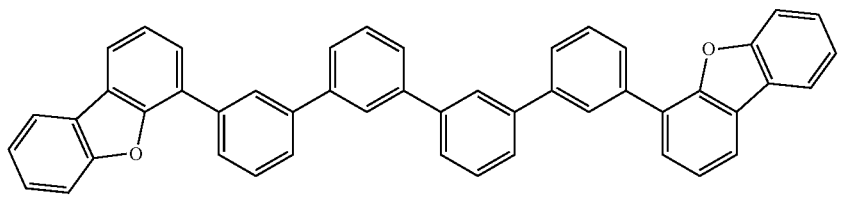

-continued
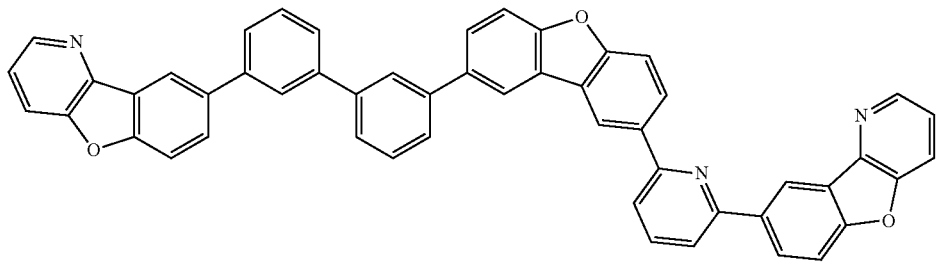
(279)
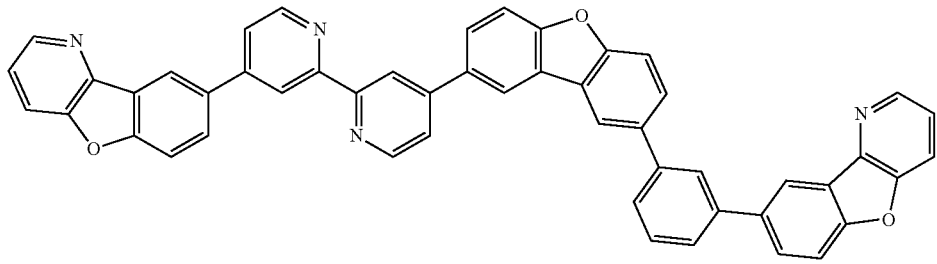
(280)
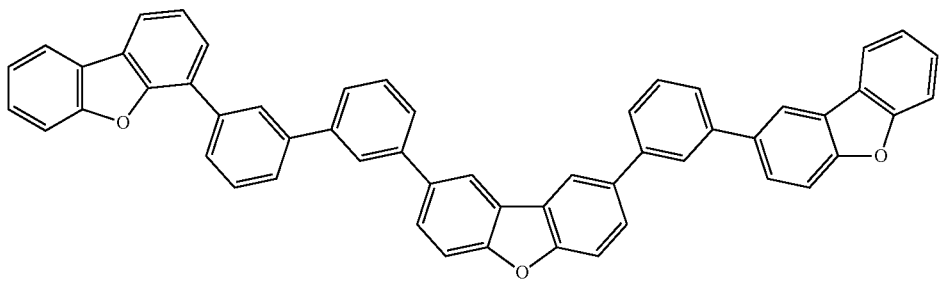
(281)
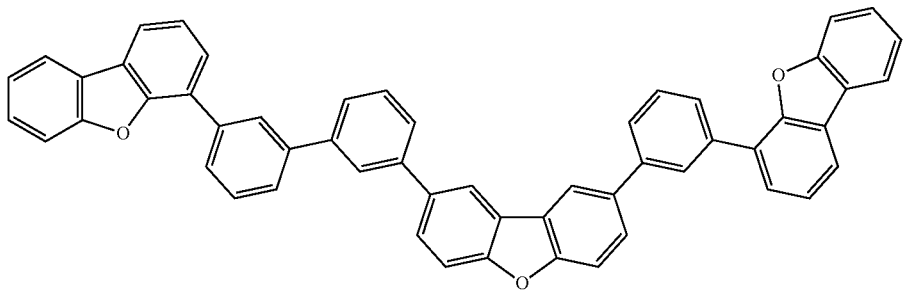
(282)
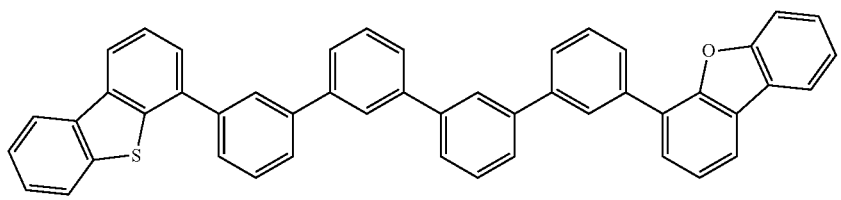
(283)
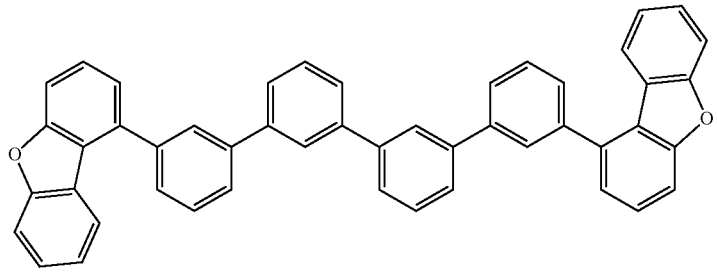
(284)

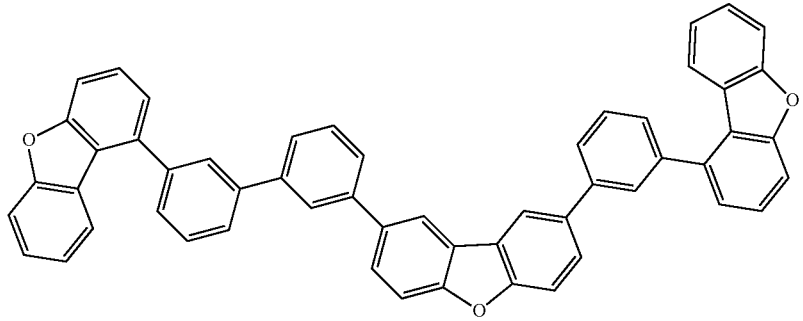
(285)
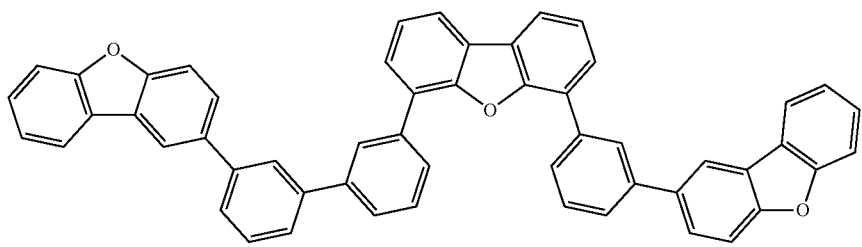
(286)
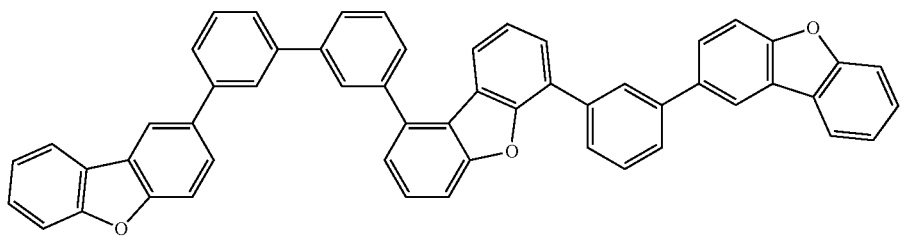
(287)
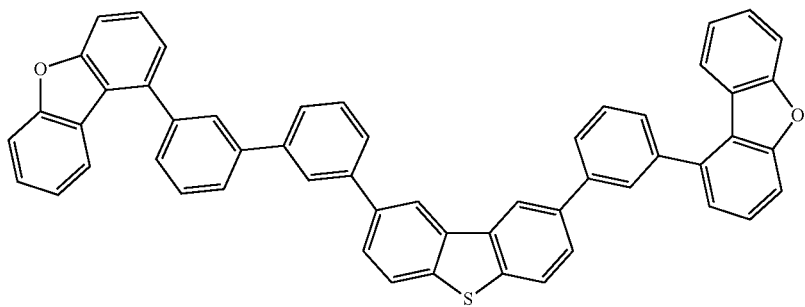
(288)
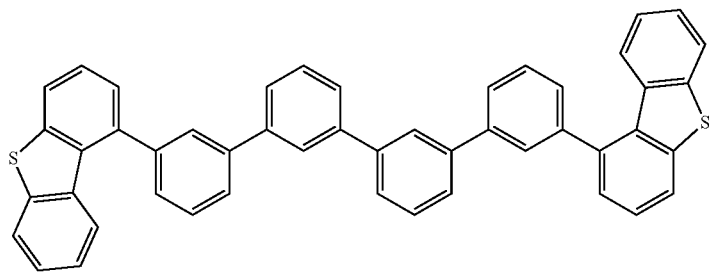
(289)

-continued
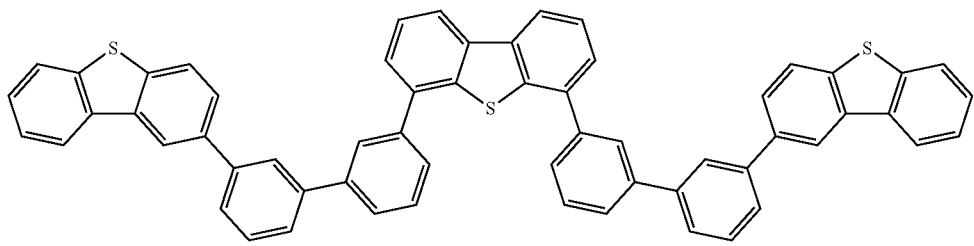
(290)
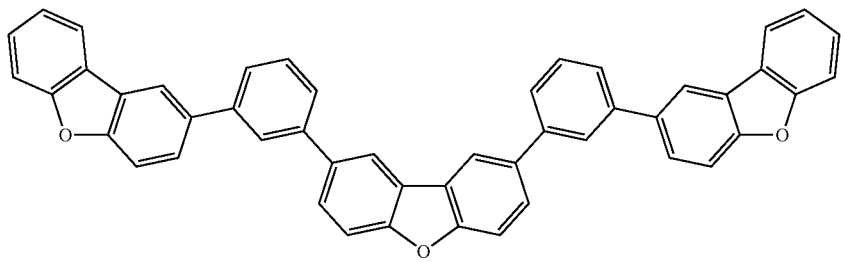
(291)
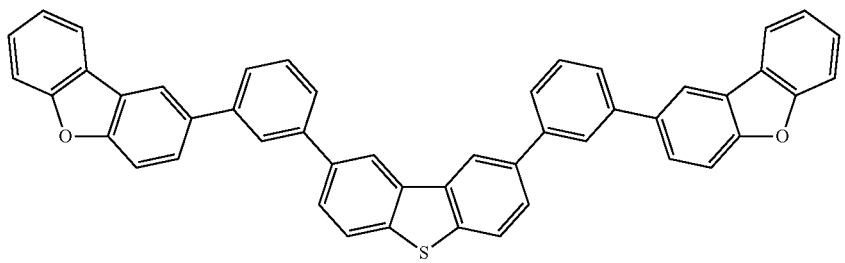
(292)
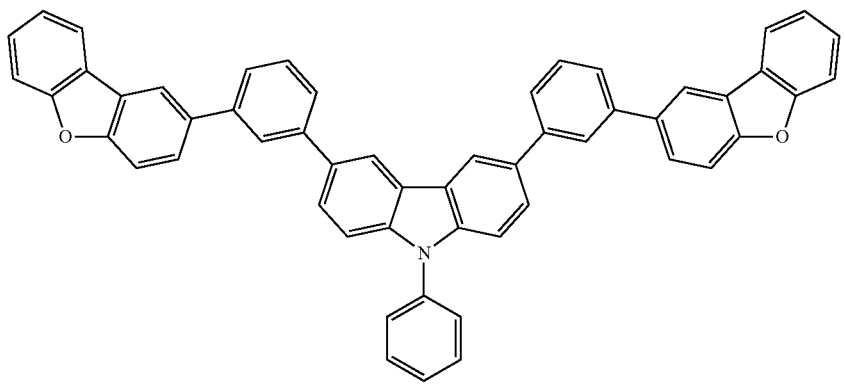
(293)
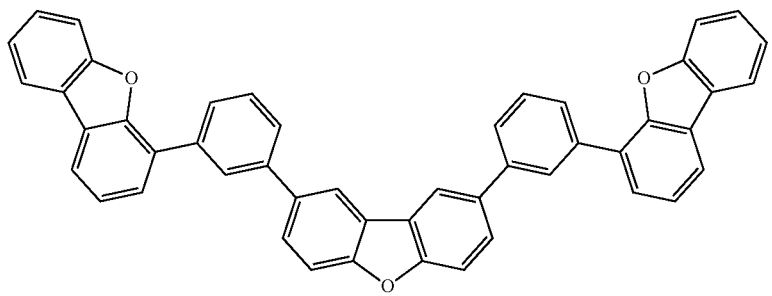
(294)

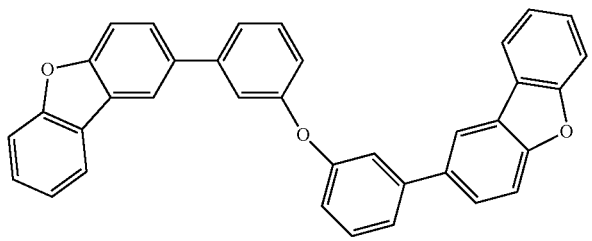
(295)
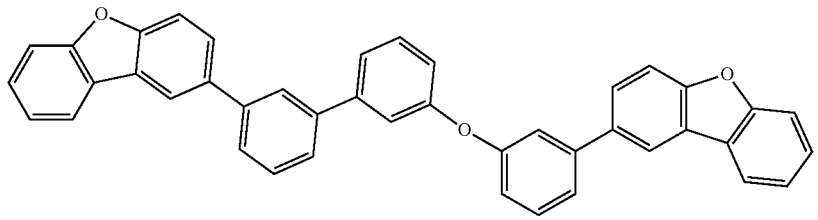
(296)
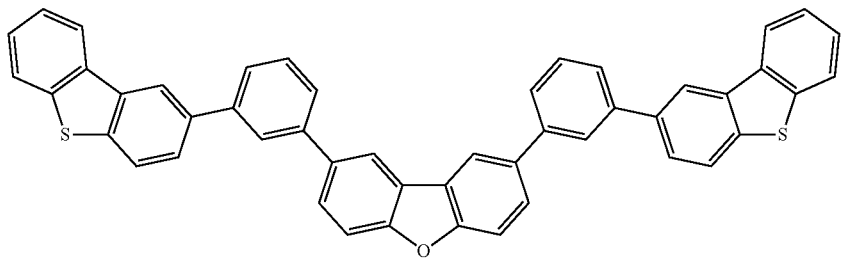
(297)
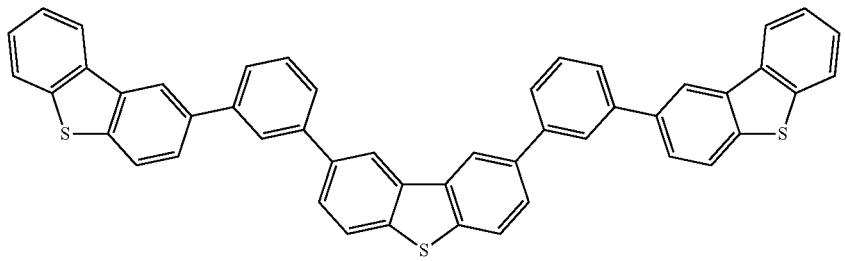
(298)
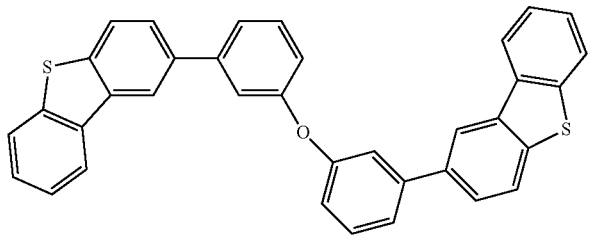
(299)
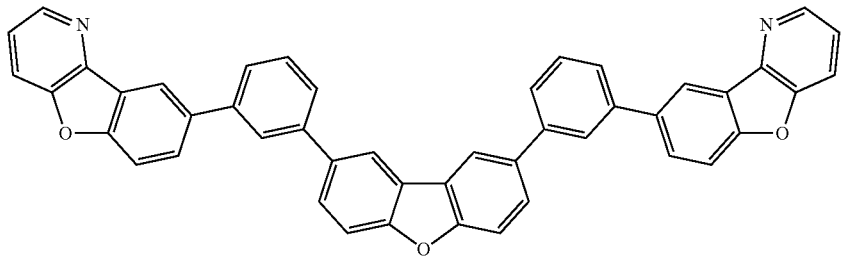
(300)

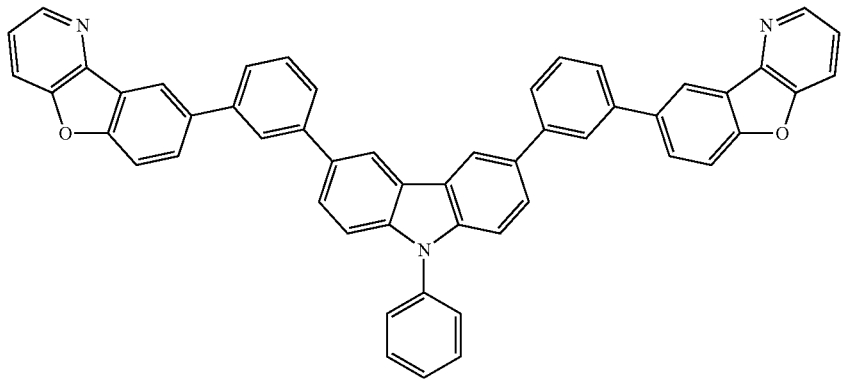
(301)

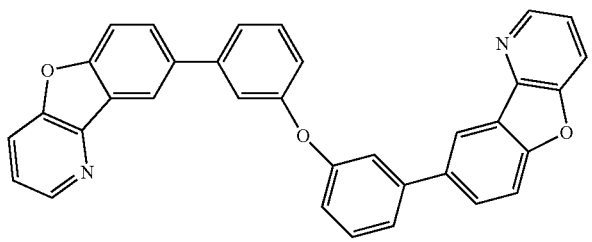
(302)

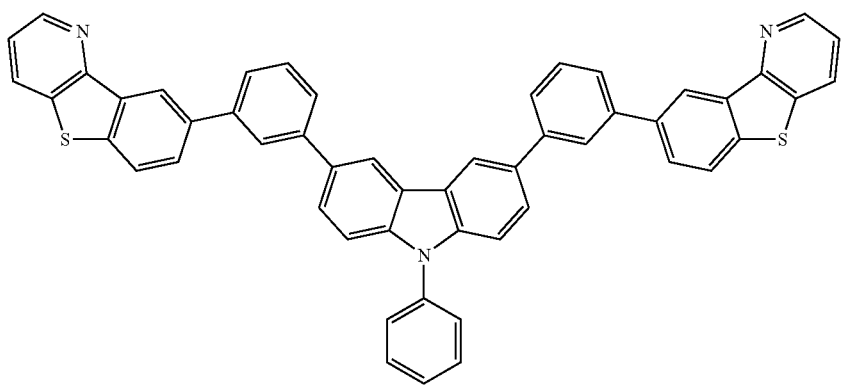
(303)

The compound of the invention is highly heat-resistant because of the structure represented by formula (1-1) or (1-2).

The molecular weight of the compound of the invention is preferably 1000 or less.

The production method of the compound of the invention is not particularly limited and can be produced by combining known synthesis methods, for example, by combining a cross-coupling reaction using a palladium and a boration reaction, as shown below. In the following formulae, Ar is an aromatic group such as an aryl group and a heteroaryl group.

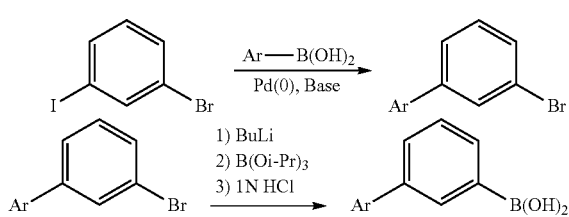

-continued

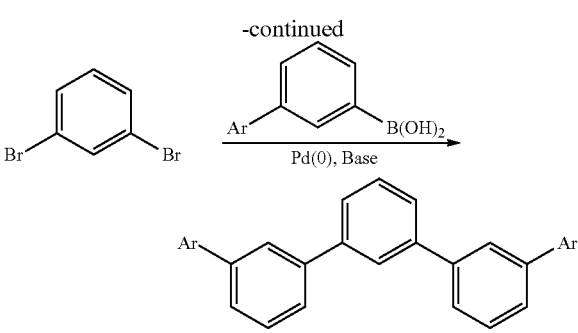

The organic EL device of the invention will be described below in detail.

Structure of Organic EL Device

The device structure of the organic EL device is first described.

Typical examples of the device structure of organic EL device include:

(1) anode/light emitting layer/cathode;

(2) anode/hole injecting layer/light emitting layer/cathode;

(3) anode/light emitting layer/electron injecting/transporting layer/cathode;
(4) anode/hole injecting layer/light emitting layer/electron injecting/transporting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting/transporting layer/light emitting layer/electron injecting/transporting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting/transporting layer/light emitting layer/insulating layer/cathode; and
(13) anode/insulating layer/hole injecting/transporting layer/light emitting layer/electron injecting/transporting layer/cathode.

Of the above, the structure (8) is preferably used, although not limited thereto.

An example of the device structure of the organic EL device of the invention is schematically shown in FIG. 1.

The organic EL device 1 includes a transparent substrate 2, an anode 3, a cathode 4, and an organic thin-film layer 10 disposed between the anode 3 and the cathode 4.

The organic thin-film layer 10 includes a phosphorescent light emitting layer 5 including a phosphorescent host as a host material and a phosphorescent dopant as a phosphorescent material. A layer, such as a hole injecting/transporting layer 6, may be provided between the phosphorescent light emitting layer 5 and the anode 3 while a layer, such as an electron injecting/transporting layer 7, may be provided between the phosphorescent light emitting layer 5 and the cathode 4.

An electron blocking layer may be provided on the anode 3 side of the phosphorescent light emitting layer 5 while a hole blocking layer may be provided on the cathode 4 side of the phosphorescent light emitting layer 5.

With these blocking layers, electrons and holes can be confined in the phosphorescent light emitting layer 5, thereby enhancing the exciton generation in the phosphorescent light emitting layer 5.

In the present invention, a host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures.

Namely, in the present invention, the term "fluorescent host" means a material for constituting a fluorescent emitting layer containing a fluorescent dopant and does not mean a material that can be utilized only as a host for a fluorescent material.

Similarly, the term "phosphorescent host" means a material for constituting a phosphorescent emitting layer containing a phosphorescent dopant and does not mean a material that can be utilized only as a host for a phosphorescent material.

The term "hole injecting/transporting layer" as used herein refers to at least one of a hole injecting layer and a hole transporting layer, and the term "electron injecting/transporting layer" as used herein refers to at least one of an electron injecting layer and an electron transporting layer.

The compound of the invention or the material for organic EL device comprising the compound of the invention is usable in any of a light emitting layer, an electron blocking layer, a hole blocking layer, an electron injecting/transporting layer, and a hole injecting/transporting layer, and preferably used in any of a light emitting layer, an electron blocking layer, and a hole blocking layer.

When the compound of the invention or the material for organic EL device comprising the compound of the invention is used in any of a light emitting layer, an electron blocking layer, and a hole blocking layer, an emission with high efficiency is expected if the following energy relationship:

$$E^T d < E^T h$$

wherein $E^T d$ is the triplet energy of the phosphorescent dopant in the light emitting layer and $E^T h$ is the triplet energy of the compound used in the light emitting layer, the electron blocking layer, or the hole blocking layer, is satisfied, because the triplet excitons of phosphorescent dopant are confined (not diffuse to other molecules) and the energy deactivation process other than the emission on the phosphorescent dopant is prevented. However, even in case of satisfying the relationship of $E^T d < E^T h$, the triplet excitons may move into other molecules if the energy difference ($\Delta E^T = E^T h - E^T d$) is small, because the energy difference $\Delta E^T$ may be overcome by the absorption of ambient heat energy when driving a device at around room temperature as generally employed in practical device driving. As compared with the fluorescent emission, the phosphorescent emission is relatively likely to be affected by the diffusion of excitons due to the heat absorption, because the lifetime of triplet excitons is longer. The compound of the invention is effective for preventing the diffusion of excitons, to provide a highly efficient phosphorescent device. As for the energy difference $\Delta E^T$, the larger as compared with the heat energy of room temperature, the better. Therefore, the energy difference $\Delta E^T$ is preferably 0.2 eV or more. When the compound of the invention is used in the light emitting layer, the electron blocking layer, or the hole blocking layer, the charge injection from the adjacent layer may increase the driving voltage of the organic EL device if $\Delta E^T$ is excessively large. Therefore, $\Delta E^T$ is preferably 1.0 eV or less.

In order to make the device highly efficient, the triplet energy of the compound of the invention is preferably wide-gap to confine the excitons of the emission material. As compared with fluorescent materials, red, green and blue phosphorescent materials have large triplet energies. To allow the efficient emission of such phosphorescent materials, the triplet energy of the compound of the invention is preferably 2.9 eV or more. However, as noted above, the charge injection from the adjacent layer may increase the driving voltage of the device if the triplet energy is excessively large. Therefore, the triplet energy of the compound of the invention is preferably 3.2 eV or less.

To make the triplet energy large, the ring A in formula (1-1), (1-2), or (7), is preferably bonded to one of $A_1$, $A_3$, $A_8$, and $A_8$, and the ring B is preferably bonded to one of $A_9$, $A_{11}$, $A_{14}$, and $A_{16}$. To make the triplet energy larger, the ring A is more preferably bonded to $A_3$ or $A_8$, and the ring B is more preferably bonded to $A_{11}$ or $A_{14}$.

When the compound represented by formula (1-1), (1-2), (7), (8), (9), (10), or (11) is used in the hole blocking layer, at least one of $A_1$ to $A_{16}$ is preferably a nitrogen atom.

Transparent Substrate

The organic EL device of the invention is formed on a light-transmissive substrate. The light-transmissive substrate serves as a support for the organic EL device and preferably a flat substrate having a transmittance of 50% or more to 400 nm to 700 nm visible light.

Examples of the substrate include a glass plate and a polymer plate.

The glass plate may include a plate made of soda-lime glass, barium-strontium-containing glass, lead glass, aluminosilicate glass, borosilicate glass, barium borosilicate glass, or quartz.

The polymer plate may include a plate made of polycarbonate, acryl, polyethylene terephthalate, polyether sulfide, or polysulfone.

Anode and Cathode

The anode of the organic EL device injects holes to the hole injecting layer, the hole transporting layer or the light emitting layer, and an anode having a work function of 4.5 eV or more is effective.

Examples of the material for anode include indium tin oxide alloy (ITO), tin oxide (NESA), indium zinc oxide alloy, gold, silver, platinum, and copper.

The anode is formed by making the electrode material into a thin film by a method, such as a vapor deposition method or a sputtering method.

When getting the light emitted from the light emitting layer through the anode as in the embodiment of the invention, the transmittance of anode to visible light is preferably 10% or more. The sheet resistance of anode is preferably several hundreds Ω/□ or less. The film thickness of anode depends upon the kind of material and generally 10 nm to 1 μm, preferably 10 nm to 200 nm.

The cathode is formed preferably from a material having a small work function in view of injecting electrons to the electron injecting layer, the electron transporting layer or the light emitting layer.

Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy.

Like the anode, the cathode is formed by making the material into a thin film by a method, such as the vapor deposition method and the sputtering method. The emitted light may be taken through the cathode.

Light Emitting Layer

The light emitting layer of the organic EL device combines the following functions:
(i) The injecting function: the function of allowing the injection of holes from the anode or the hole injecting layer and allowing the injection of electrons from the cathode or the electron injecting layer when an electric field is applied;
(ii) The transporting function: the function of transporting injected charges (i.e., electrons and holes) by the force of the electric field; and
(iii) The light emitting function: the function of providing the area for recombination of electrons and holes and leading the recombination to the emission of light.

The light emitting layer may be different in its easiness of hole injection and its easiness of electron injection, and also in the hole transporting ability and the electron transporting ability each being expressed by mobility.

The light emitting layer is formed, for example, by a known method, such as a vapor deposition method, a spin coating method, and LB method.

The light emitting layer is preferably a molecular deposit film.

The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The light emitting layer can be formed also by making a solution of a binder, such as resin, and the material for the light emitting layer in a solvent into a thin film by a method such as spin coating.

The organic EL device of the invention comprises at least one organic thin film layer between a cathode and an anode. The at least one organic thin film layer comprises a light emitting layer and at least one layer of the at least one organic thin film layer comprises the material for organic electroluminescence device of the invention.

In the organic EL device of the invention, at least one light emitting layer preferably comprises the material for organic electroluminescence device of the invention and at least one phosphorescent material. With such a light emitting layer, the device is capable of driving at low voltage with high efficiency and a long lifetime organic EL device excellent in heat resistance is obtained.

Phosphorescent Material

The organic EL device of the invention comprises an organometallic complex as the phosphorescent material. The organometallic complex preferably comprises a metal selected from Ir, Pt, Os, Au, Be, Cu, Re, and Ru and a ligand. The ligand is preferably ortho-metal bonded to the metal.

In view of obtaining a high phosphorescent quantum yield and further improving the external quantum efficiency of electroluminescence device, a metal compound comprising a metal selected from Ir, Os, and Pt is preferred, with a metal complex, such as an iridium complex, an osmium complex, and a platinum complex, being more preferred, an iridium complex and a platinum complex being still more preferred, and an ortho metallated iridium complex being most preferred.

Preferred examples of the organometallic complex are shown below.

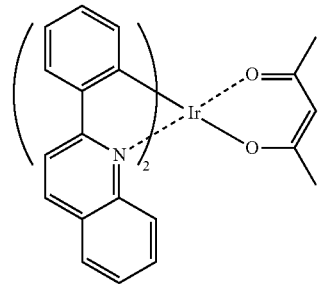

PQIr

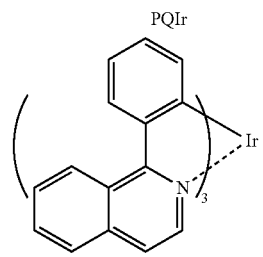

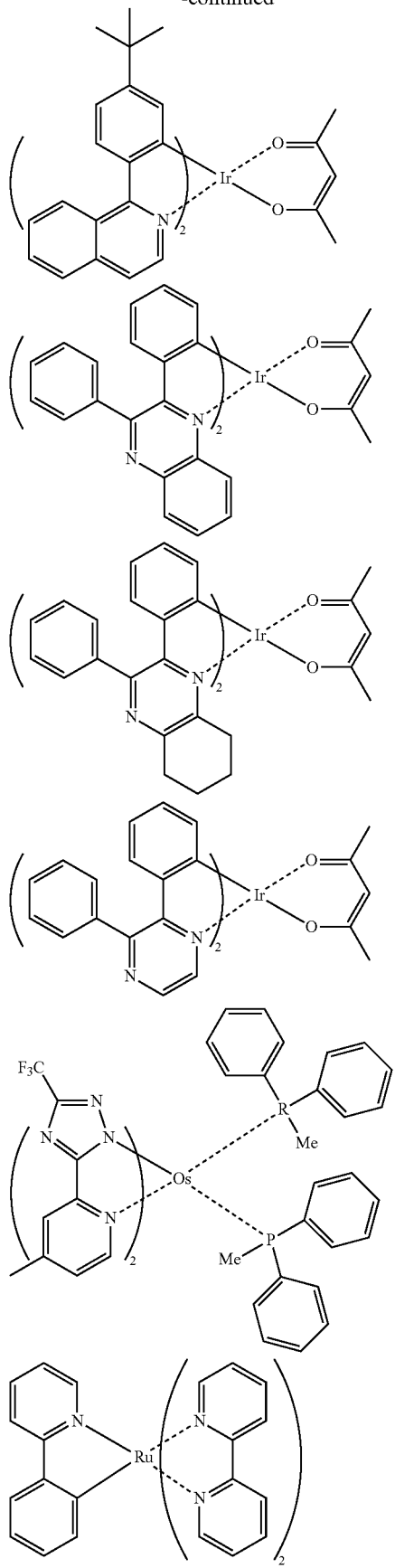
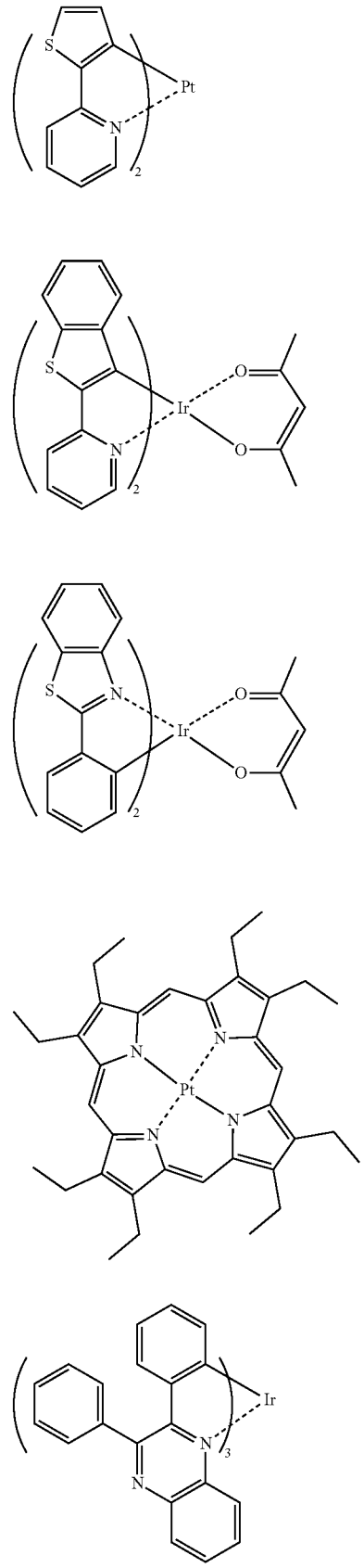

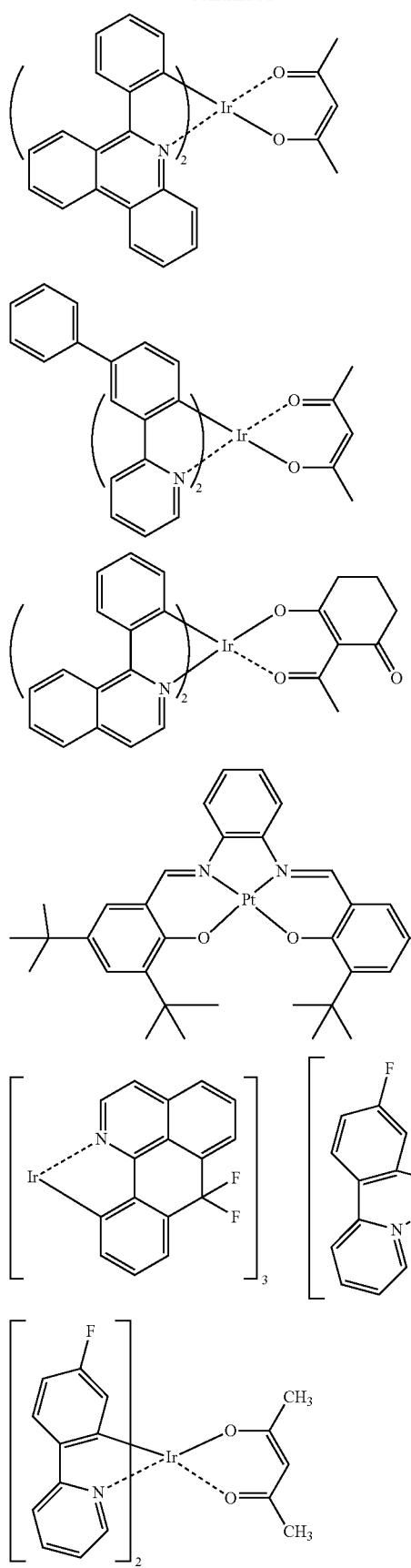
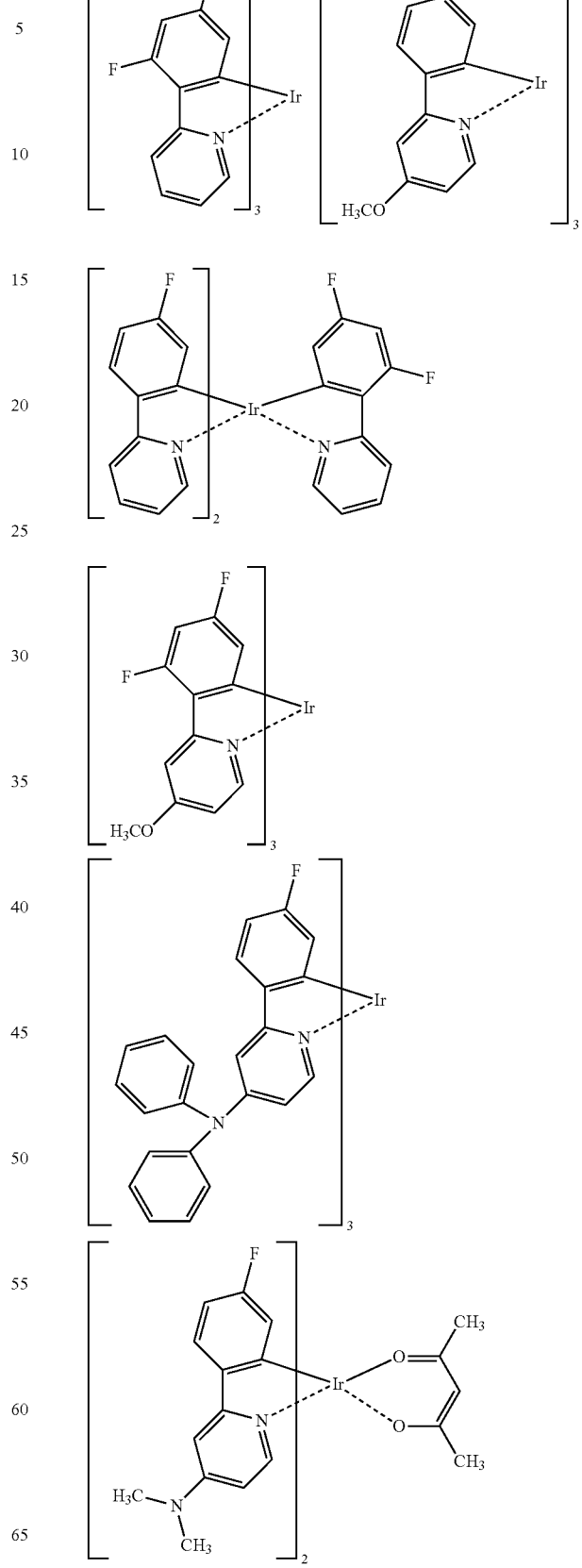

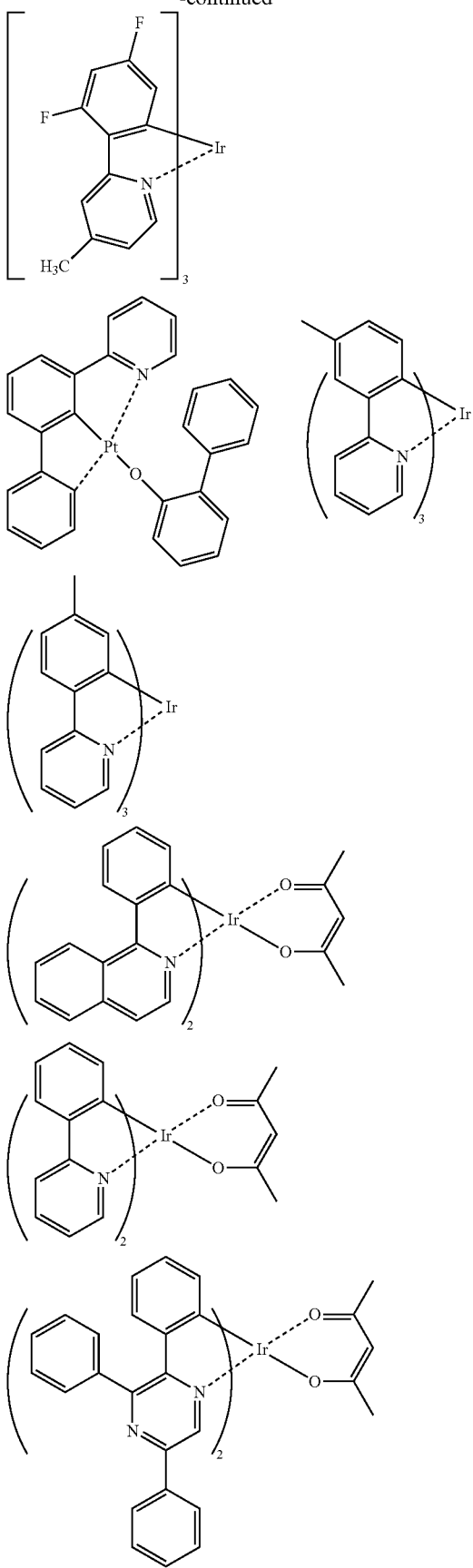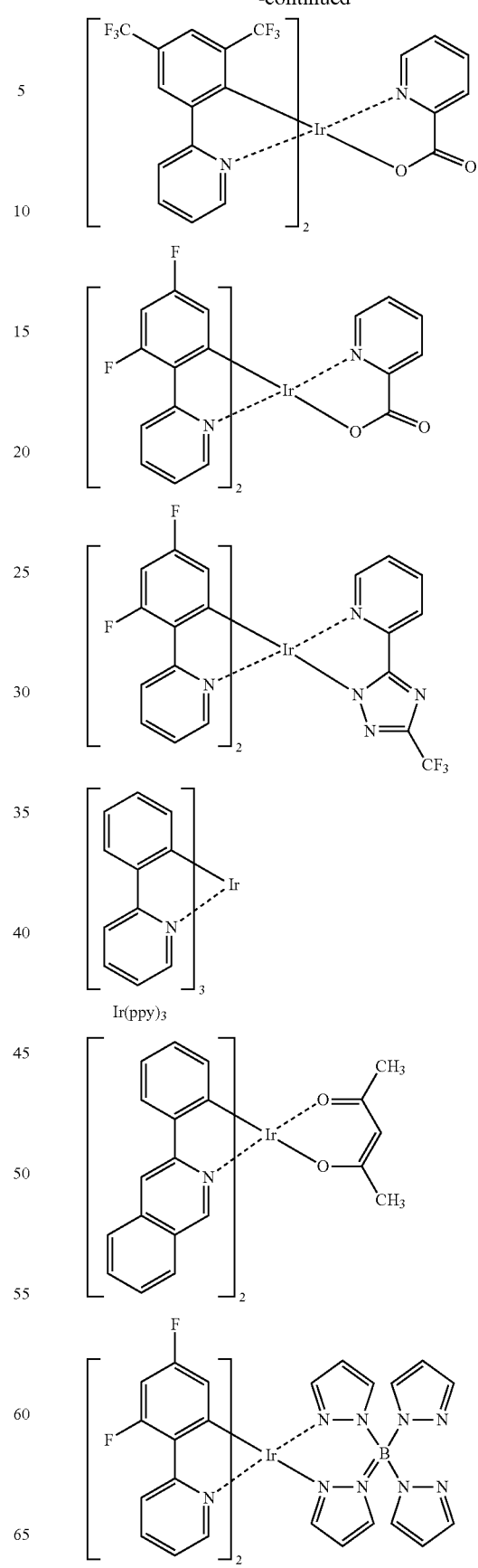

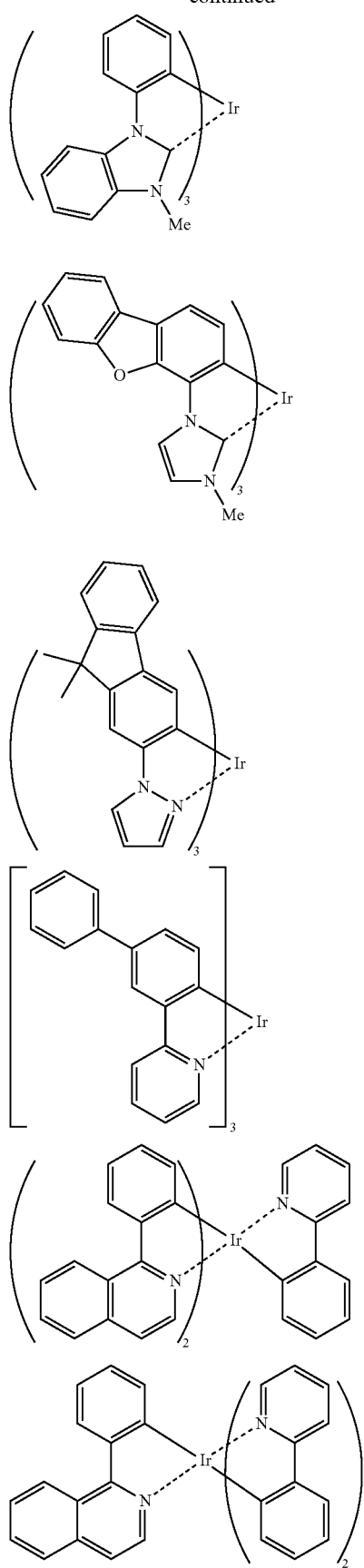
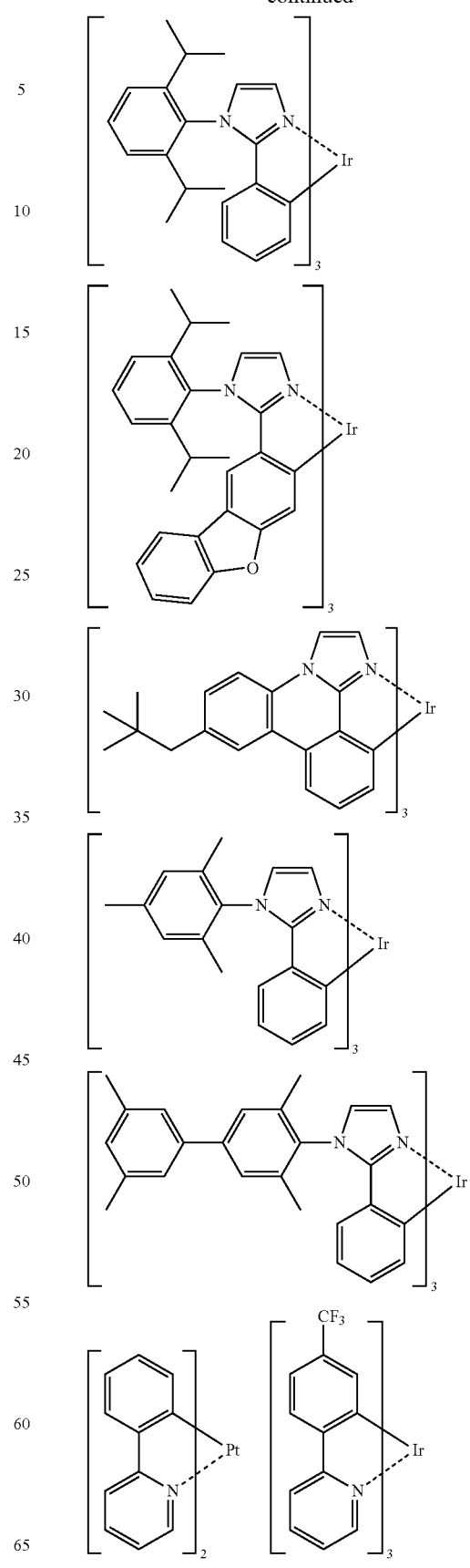

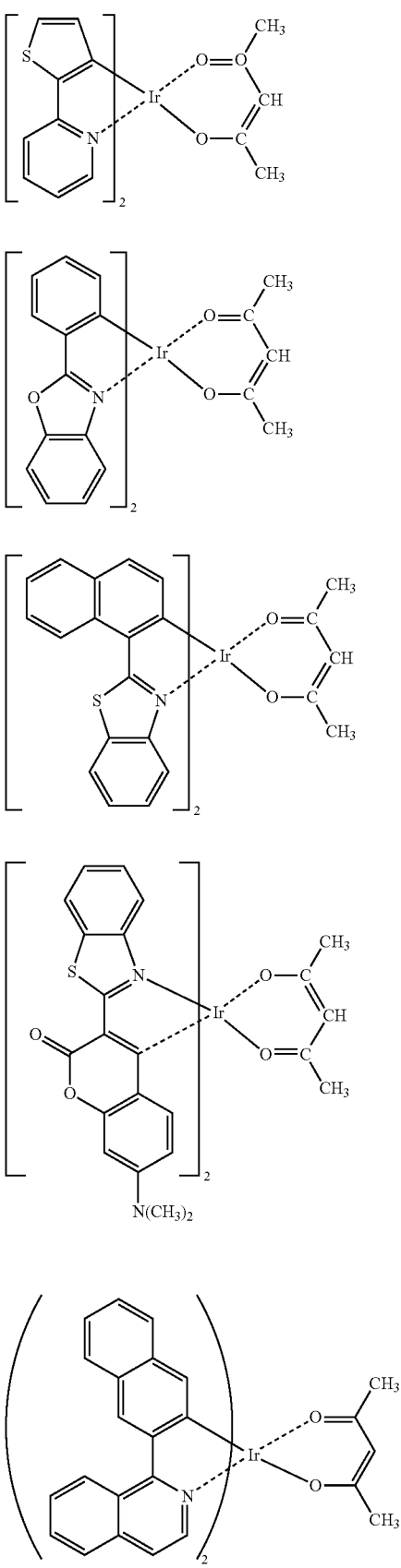

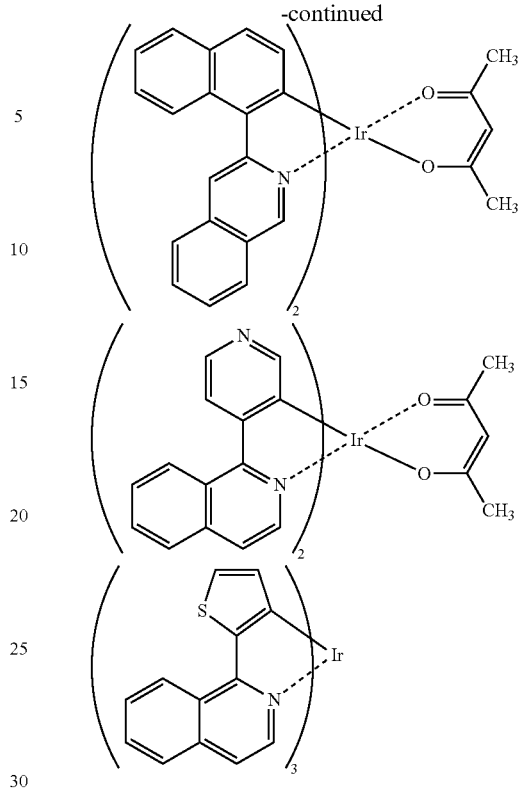

In a preferred embodiment of the invention, at least one of the phosphorescent materials used in the light emitting layer emit light having a maximum emission wavelength of preferably 450 nm or longer and 750 nm or shorter. In another preferred embodiment, the maximum emission wavelength is 450 nm or longer and 495 nm or shorter, 495 nm or longer and 590 nm or shorter, or 590 nm or longer and 750 nm or shorter.

By doping a specific host material used in the invention in the light emitting layer with the phosphorescent material (phosphorescent dopant) having a maximum emission wavelength within the above ranges, a high-efficiency organic EL device even at a low voltage drive having a long lifetime can be obtained.

Reducing Dopant

The organic EL device of the present invention preferably comprises a reducing dopant at an interfacial region between the cathode and the organic thin film layer.

With such a construction, the organic EL device has an improved luminance and an elongated lifetime.

Examples of the reducing dopant include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs.

Examples of the alkaline earth metal include Ca (work function: 2.9 eV), Sr (work function: 2.0 to 2.5 eV), and Ba (work function: 2.52 eV), with those having a work function of 2.9 eV or less being particularly preferred.

Examples of the rare earth metal include Sc, Y, Ce, Tb, and Yb, with those having a work function of 2.9 eV or less being particularly preferred.

The preferred metals described above have a particularly high reducing ability. Therefore, the emission luminance and life time of an organic EL device can be improved by adding a relatively small amount of the metal to an electron injecting region.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred.

Examples of the alkaline earth metal compound include BaO, SrO, CaO, and mixture thereof, such as $Ba_xSr_{1-x}O$ (0<x<1) and $Ba_xCa_{1-x}O$ (0<x<1), with BaO, SrO, and CaO being preferred.

Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal complex are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The reducing dopant is added to the interfacial region preferably into a form of layer or island. The reducing dopant is added preferably by co-depositing the reducing dopant with the organic compound (light emitting material, electron injecting material) for forming the interfacial region by a resistance heating deposition method, thereby dispersing the reducing dopant into the organic material. The disperse concentration expressed by the molar ratio of the organic material and the reducing dopant is 100:1 to 1:100 and preferably 5:1 to 1:5.

When the reducing dopant is formed into a form of layer, a light emitting material or an electron injecting material is made into a layer which serves as an organic layer in the interface, and then, the reducing dopant alone is deposited by a resistance heating deposition method into a layer having a thickness preferably 0.1 nm to 15 nm.

When the reducing dopant is formed into a form of island, a light emitting material or an electron injecting material is made into a form of island which serves as an organic layer in the interface, and then, the reducing dopant alone is deposited by a resistance heating deposition method into a form of island having a thickness preferably 0.05 nm to 1 nm.

The molar ratio of the main component and the reducing dopant in the organic electroluminescence device of the invention is preferably 5:1 to 1:5 and more preferably 2:1 to 1:2.

Electron Injecting Layer and Electron Transporting Layer

The electron injecting layer or the electron transporting layer is a layer that aids the injection of electrons into the light emitting layer, and has a large electron mobility. The electron injecting layer is provided for adjusting an energy level, for example, for reducing an abrupt change in energy level.

It is preferred that the organic EL device of the present invention comprises an electron injecting layer between the light emitting layer and the cathode, and the electron injecting layer comprises a nitrogen-containing ring derivative as a main component. The electron injecting layer may function as the electron transporting layer.

The phrase "as a main component" used herein means that the content of the nitrogen-containing ring derivative in the electron injecting layer is 50 mass % or more.

An aromatic heterocyclic compound having one or more heteroatoms in a molecule thereof is preferably used as an electron transporting material used in the electron injecting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

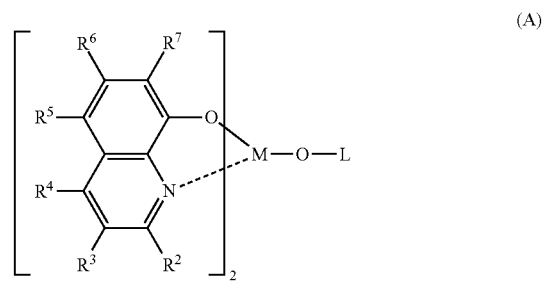

(A)

wherein each of $R^2$ to $R^7$ independently represents a hydrogen atom, a deuterium atom, a halogen atom, a hydroxyl group, an amino group, a hydrocarbon group having 1 to 40 carbon atoms, an alkoxy group, an aryloxy group, an alkoxycarbonyl group, or an aromatic heterocyclic group, each being optionally substituted.

The halogen atom may include fluorine, chlorine, bromine, and iodine. The substituted amino group may include an alkylamino group, an arylamino group, and an aralkylamino group.

The alkoxycarbonyl group is represented by —COOY', wherein Y' is selected from the alkyl groups mentioned above. The alkylamino group and the aralkylamino group are represented by —NQ$^1$Q$^2$. Examples and preferred examples of Q$^1$ and Q$^2$ are independently selected from the alkyl groups and aralkyl groups mentioned above. One of Q$^1$ and Q$^2$ may be a hydrogen atom or a deuterium atom.

The arylamino group is represented by —NAr$^1$Ar$^2$, wherein Ar$^1$ and Ar$_2$ are independently selected from the aryl group mentioned above. One of Ar$^1$ and Ar$^2$ may be a hydrogen atom or a deuterium atom.

M is aluminum (Al), gallium (Ga), or indium (In), with In being preferred.

L in formula (A) is a group represented by formula (A') or (A''):

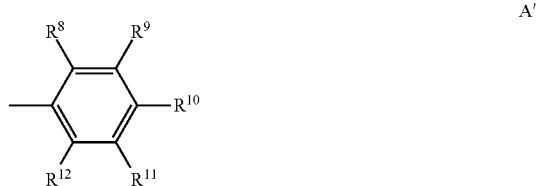

A'

-continued

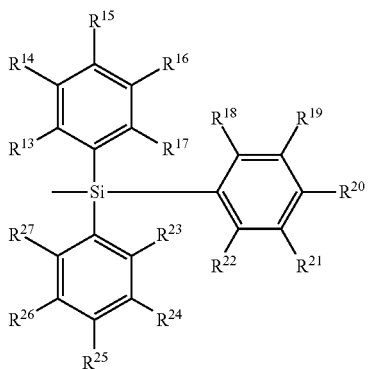

A″

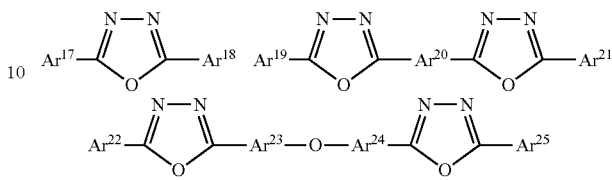

wherein each $R^8$ to $R^{12}$ independently represents a hydrogen atom, a deuterium atom, or a substituted or unsubstituted hydrocarbon group having 1 to 40 carbon atoms. The adjacent two groups may form a ring structure. Each of $R^{13}$ to $R^{27}$ independently represents a hydrogen atom, a deuterium atom, or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A″) are the same as those described above with respect to $R^2$ to $R^7$ of formula (A).

Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron injecting layer or the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include phenyl group, naphthyl group, biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group, and $Ar^{23}$ and $Ar^{24}$ may be the same or different.

Examples of the bivalent aromatic hydrocarbon group or the bivalent fused aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

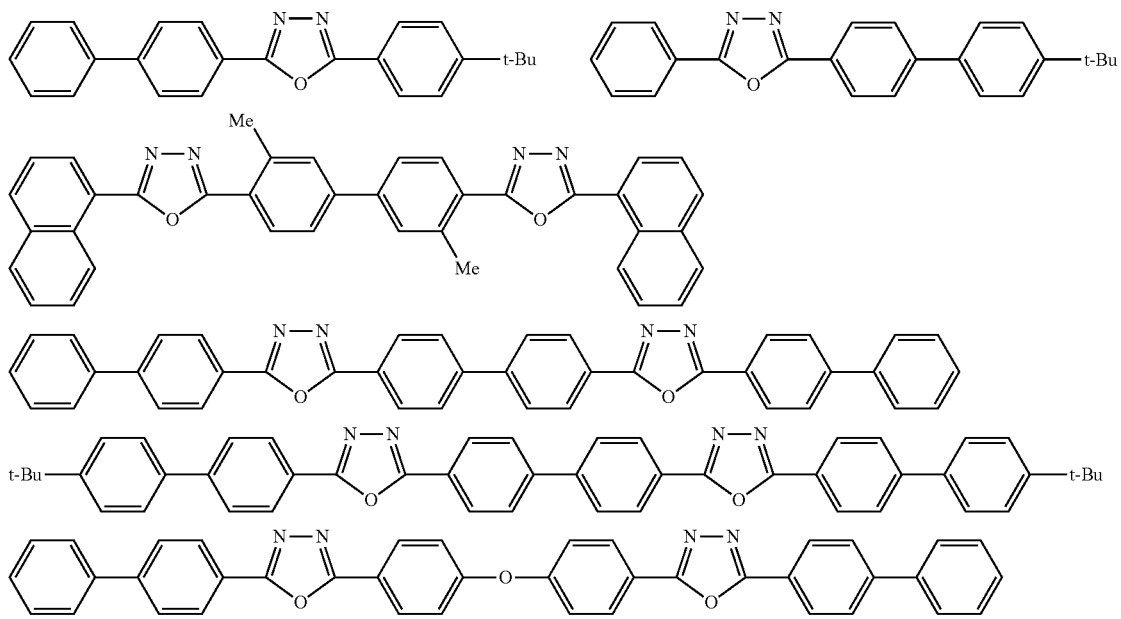

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

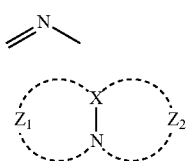

(B)

(C)

wherein X is a carbon atom or a nitrogen atom and each of $Z_1$ and $Z_2$ independently represents a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

(D)

The nitrogen-containing group of the nitrogen-containing aromatic polycyclic compound is selected, for example, from the nitrogen-containing heterocyclic groups shown below:

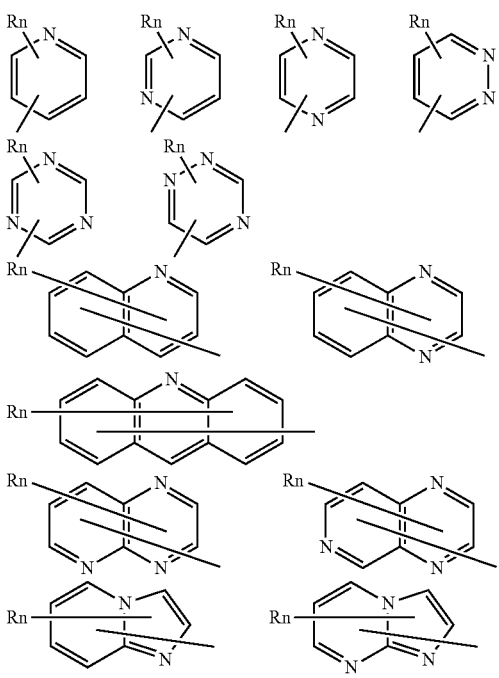

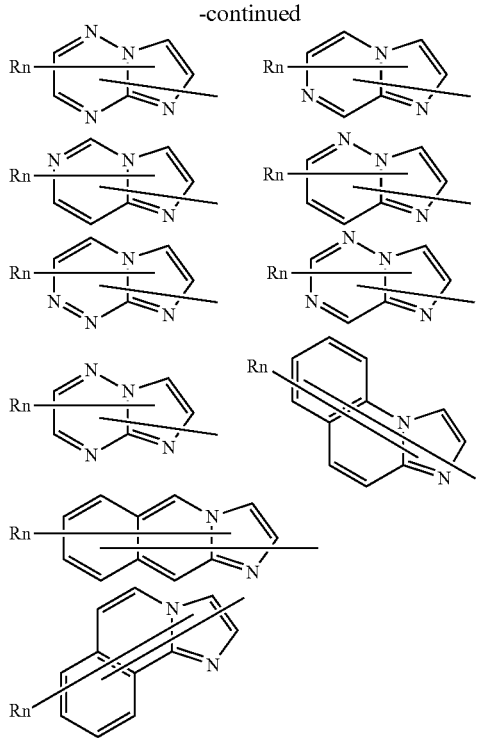

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

$$\text{HAr-}L^1\text{-Ar}^1\text{—Ar}^2$$

wherein HAr is a substitute or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substitute or unsubstituted divalent aromatic hydrocarbon group having 6 to 40 carbon atoms; and $Ar^2$ is a substitute or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

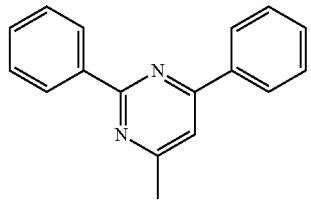 [SMILES: Cc1cc(-c2ccccc2)nc(-c2ccccn2)c1]

149
-continued
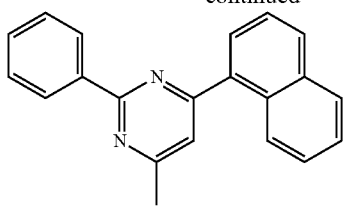
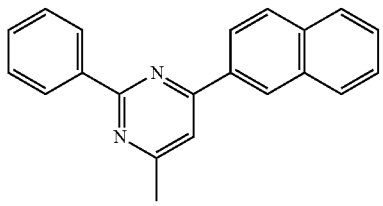
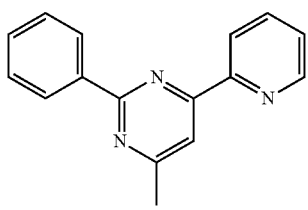
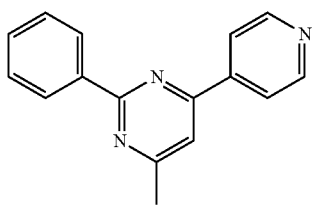
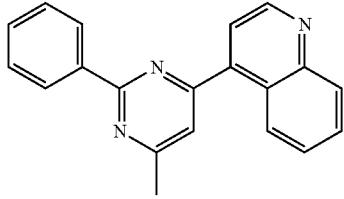
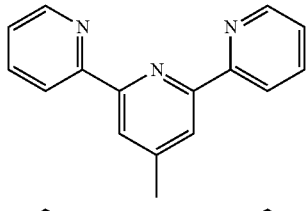
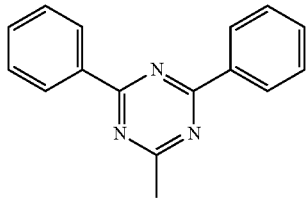
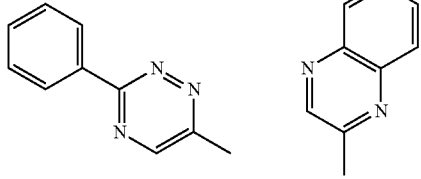
150
-continued
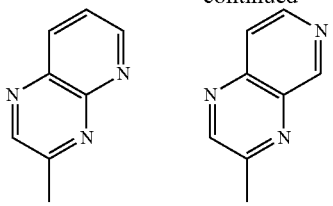
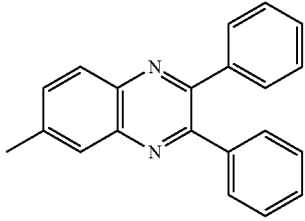
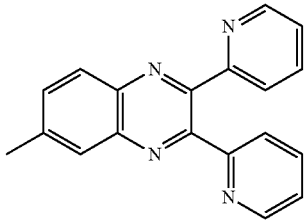
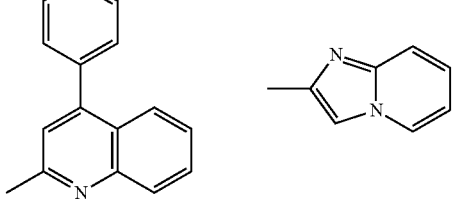
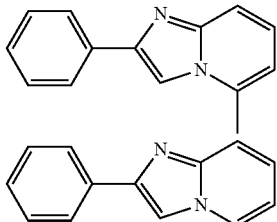
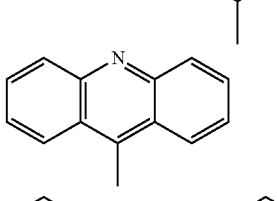
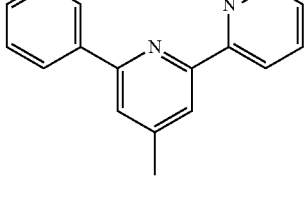
$L^1$ is selected, for example, from the following groups:
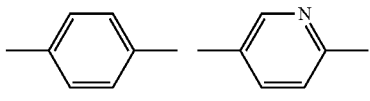

$Ar^1$ is selected, for example, from the following arylanthranyl groups:

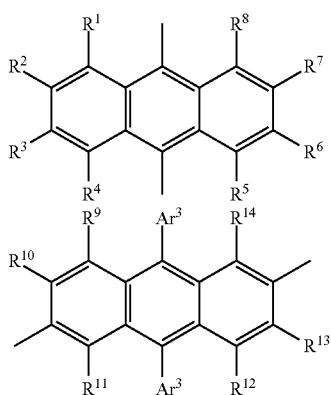

wherein $R^1$ to $R^{14}$ are each independently a hydrogen atom, a deuterium atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar^3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

$R^1$ to $R^8$ may be selected from a hydrogen atom and a deuterium atom.

$Ar^2$ is selected, for example, from the following groups:

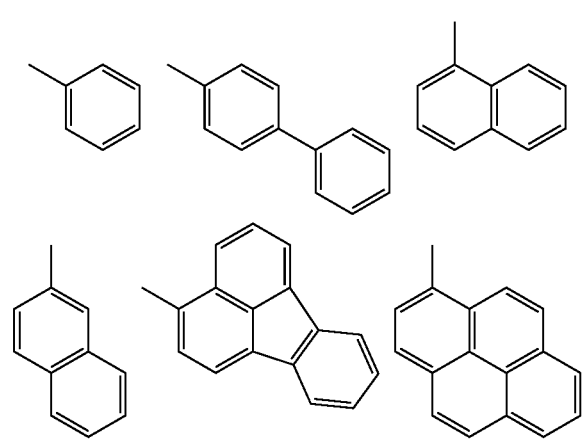

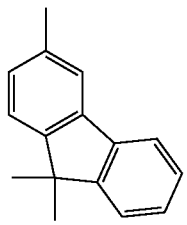

In addition, the following compound is preferably used as the nitrogen-containing aromatic polycyclic compound for use as the electron transporting compound:

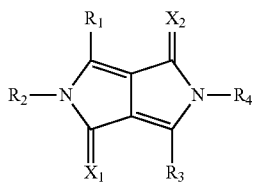

wherein $R_1$ to $R_4$ each independently represent a hydrogen atom, a deuterium atom, a substituted or unsubstituted aliphatic group, a substituted or unsubstituted alicyclic group, a substituted or unsubstituted aromatic hydrocarbon group, or a substituted or unsubstituted heterocyclic group; and $X_1$ and $X_2$ each independently represent an oxygen atom, a sulfur atom, or dicyanomethylene group.

Further, the following compound is also suitable as the electron transporting compound:

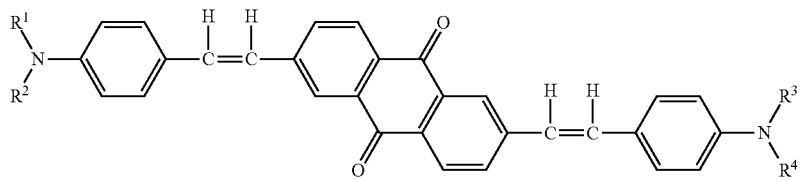

wherein $R^1$, $R^2$, $R^3$, and $R^4$ may be the same or different and each represents an aromatic hydrocarbon group or a fused aromatic hydrocarbon group each represented by the following formula:

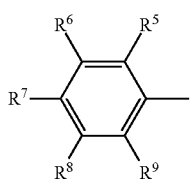

wherein $R^5$, $R^6$, $R^7$, $R^8$, and $R^9$ may be the same or different and each represents a hydrogen atom or a deuterium atom, and at least one of $R^5$, $R^6$, $R^7$, $R^8$, and $R^9$ represents a saturated or unsaturated alkoxyl group, alkyl group, amino group, or alkylamino group.

Further, a polymer having the nitrogen-containing heterocyclic group or the nitrogen-containing heterocyclic derivative is also usable as the electron transporting compound.

The electron transporting layer preferably comprises at least one compound selected from the nitrogen-containing heterocyclic derivatives represented by formulae (201) to (203):

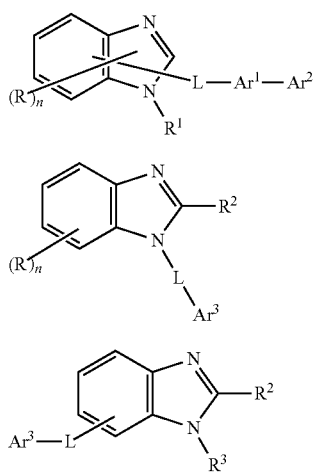

(201)

(202)

(203)

wherein R is a hydrogen atom, a deuterium atom, a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms;

n is an integer of 0 to 4;

$R^1$ is a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms;

$R^2$ and $R^3$ are each independently a hydrogen atom, a deuterium atom, a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms;

L is a substituted or unsubstituted aromatic hydrocarbon group or fused aromatic hydrocarbon group having 6 to 60 carbon atoms, a substituted or unsubstituted pyridinylene group, a substituted or unsubstituted quinolinylene group, or a substituted or unsubstituted fluorenylene group;

$Ar^1$ is a substituted or unsubstituted aromatic hydrocarbon group or fused aromatic hydrocarbon group having 6 to 60 carbon atoms, a substituted or unsubstituted pyridinylene group, or a substituted or unsubstituted quinolinylene group;

$Ar^2$ is a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms; and $Ar^3$ is a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —$Ar^1$—$Ar^2$ wherein $Ar^3$ and $Ar^2$ are the same as defined above.

In formulae (201) to (203), R is hydrogen atom, a deuterium atom, a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

The thickness of the electron injecting layer or the electron transporting layer is preferably, but not particularly limited to, 1 nm to 100 nm.

It is preferred that the electron injecting layer comprises an inorganic compound, such as an insulating material and a semiconductor, in addition to the nitrogen-containing ring derivative. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 nm to 15 nm. The electron injecting layer in the invention may contain the reducing dopant mentioned above.

Hole Injecting Layer and Hole Transporting Layer

The hole injecting layer or the hole transporting layer (inclusive of a hole injecting/transporting layer) preferably comprises an aromatic amine compound, for example, an aromatic amine derivative represented by formula (I):

(I)

wherein each of $Ar^1$ to $Ar^4$ is a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group.
Examples of the compound represented by formula (I) are shown below, although not limited thereto.
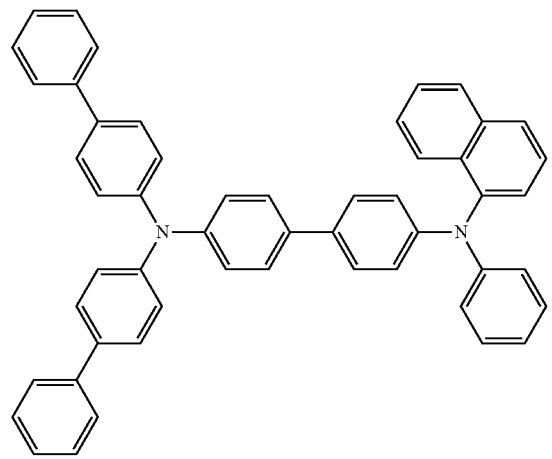
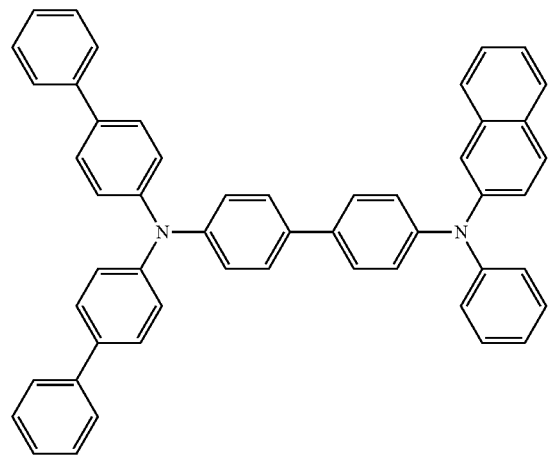
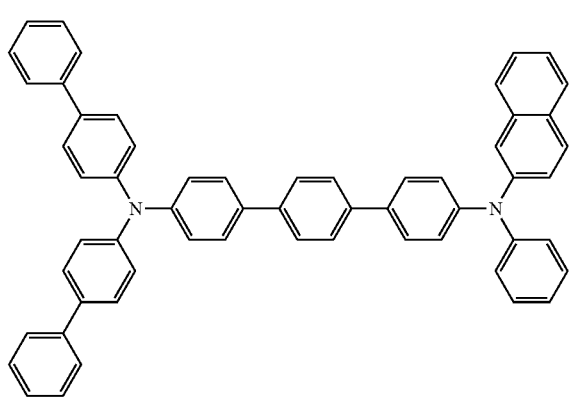
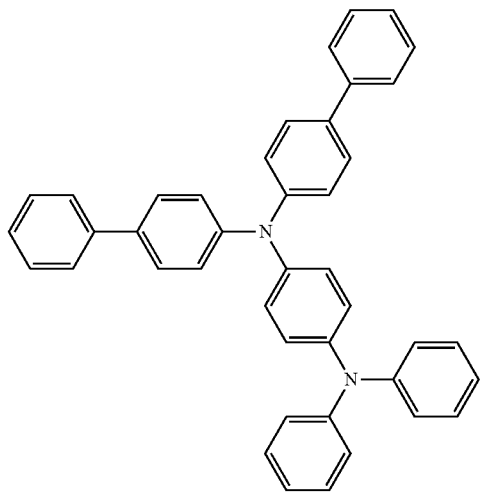
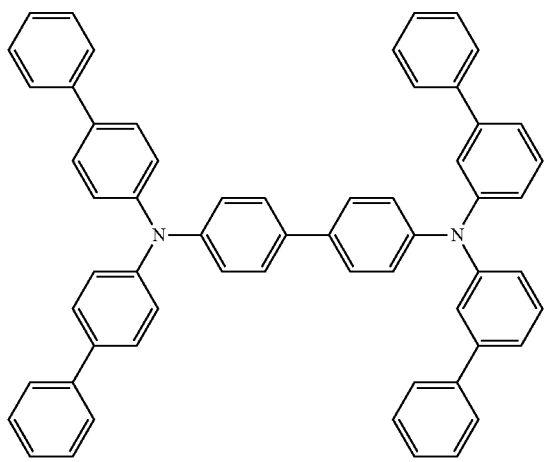
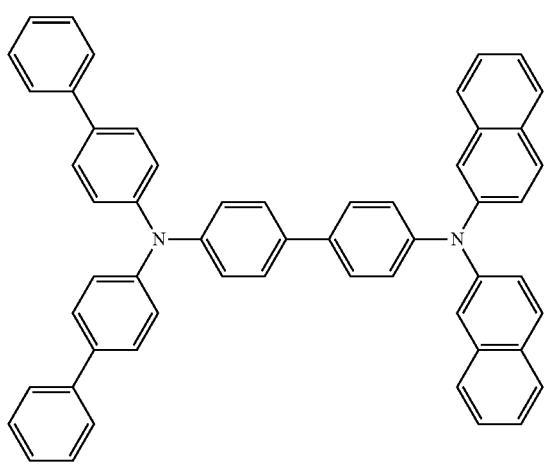

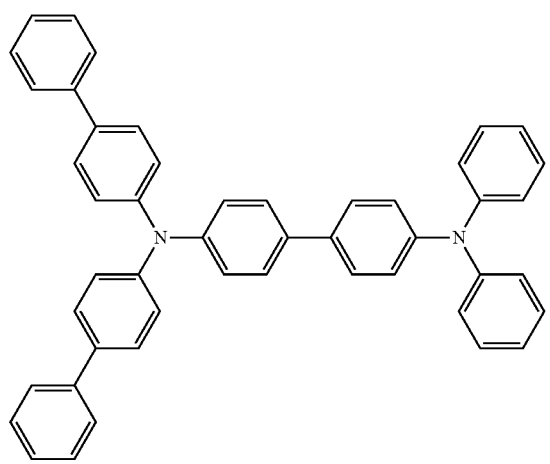
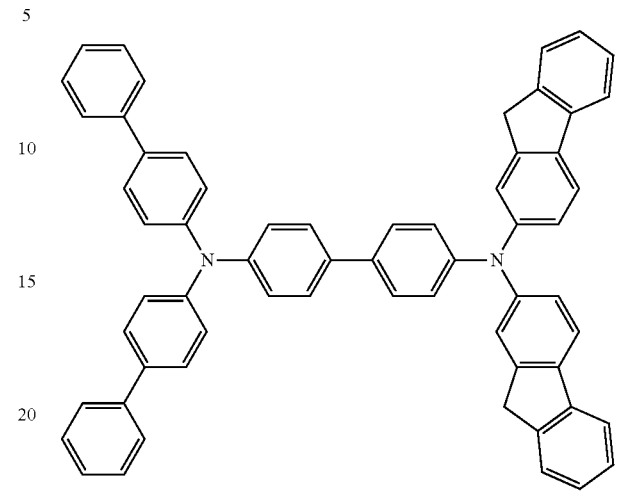
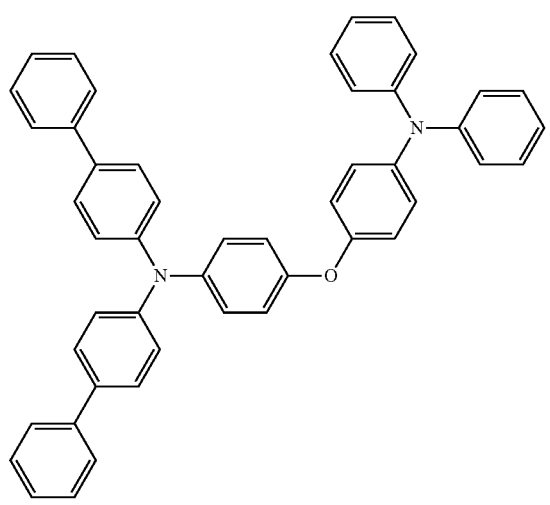
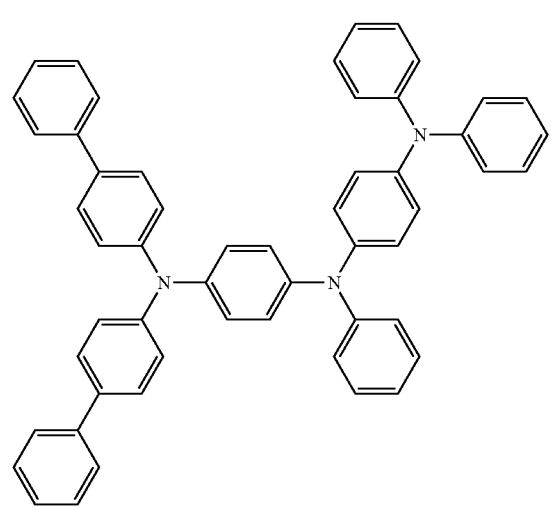
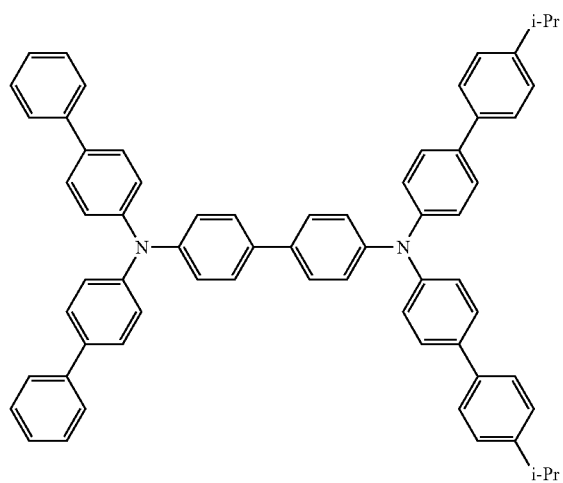
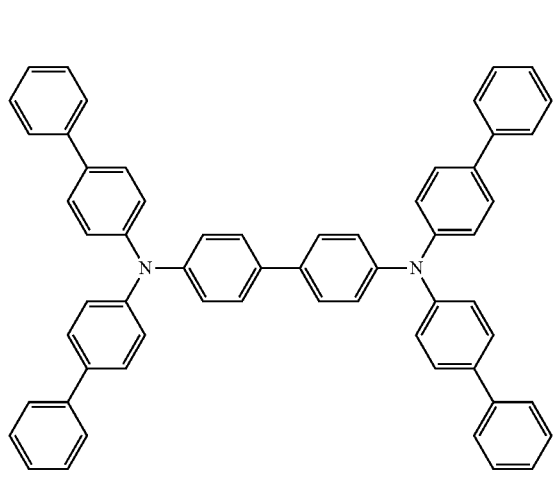

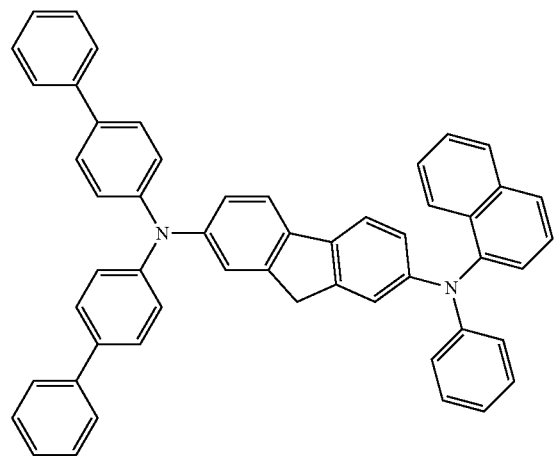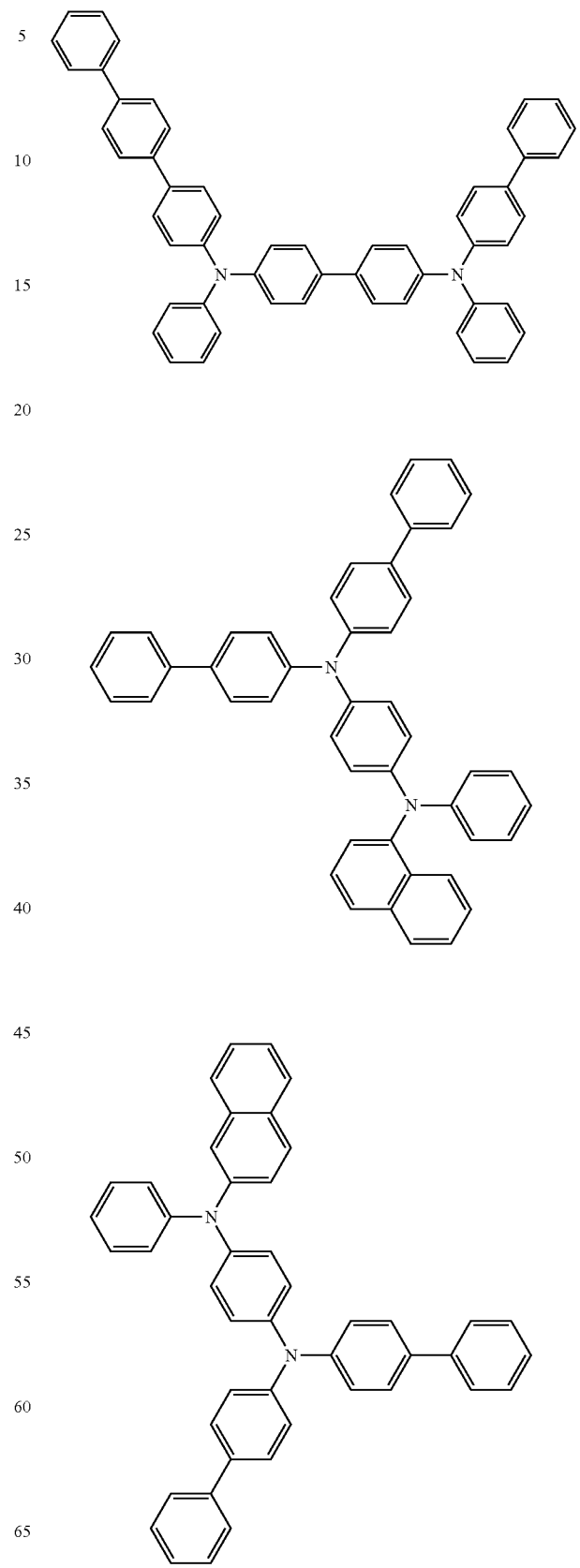

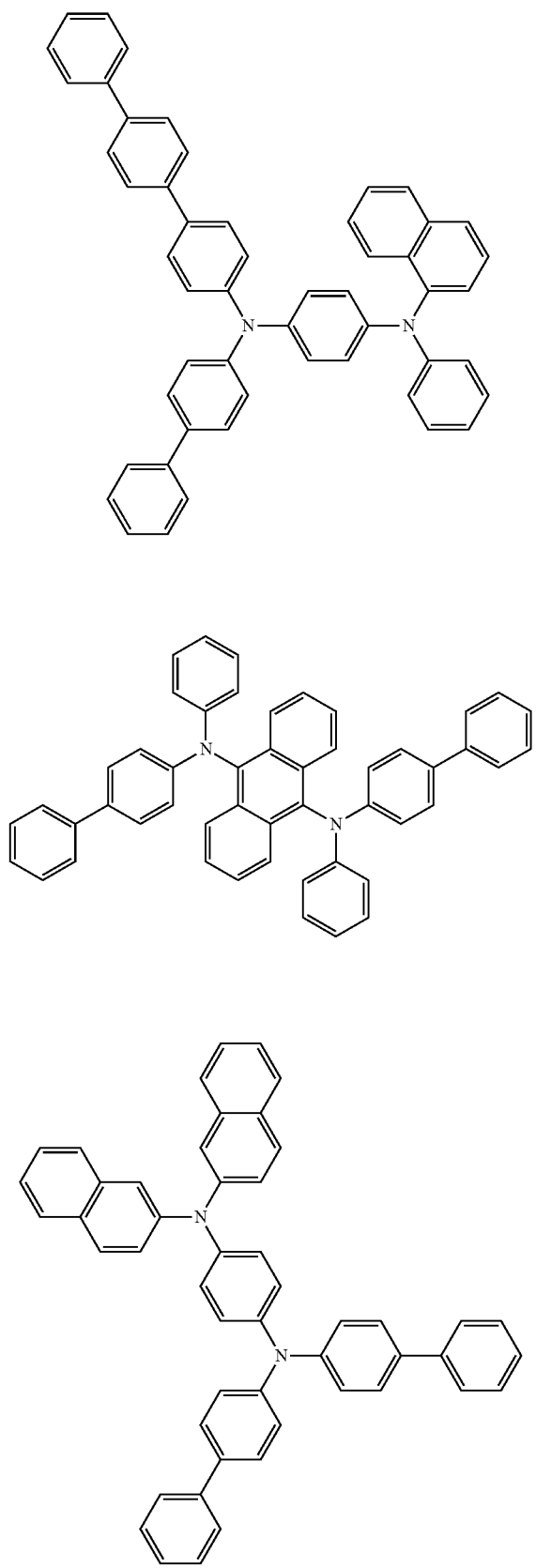
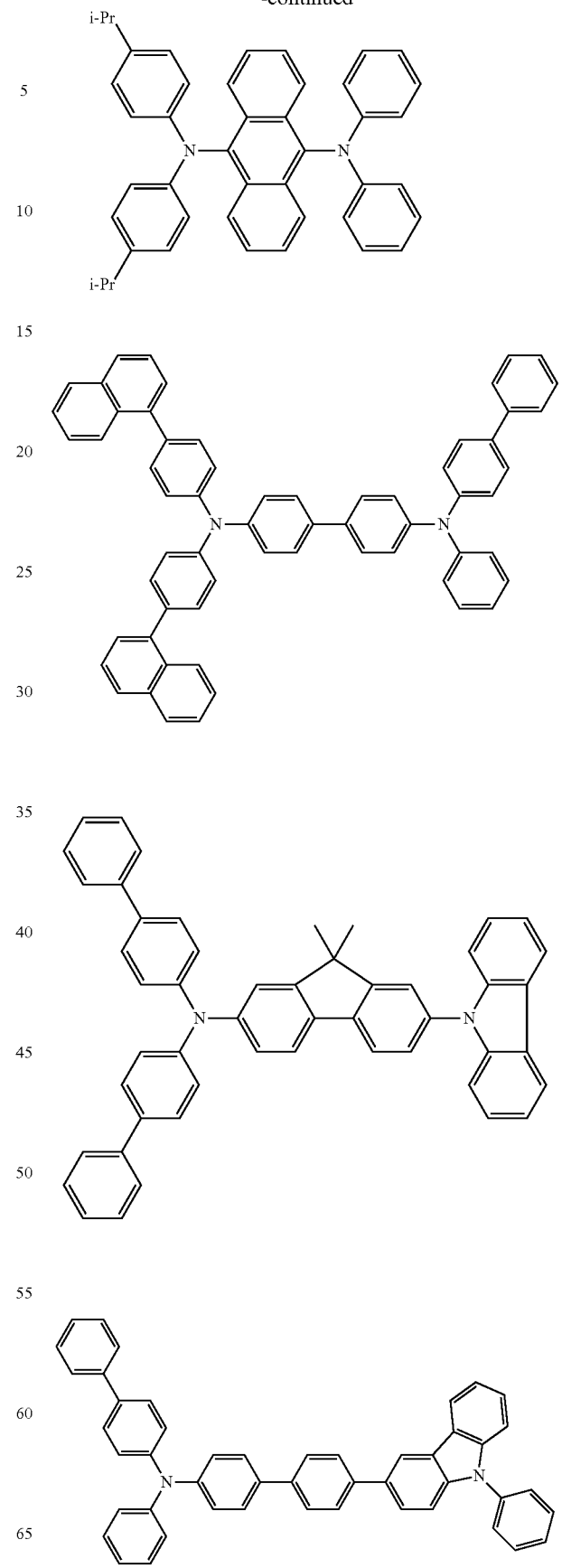

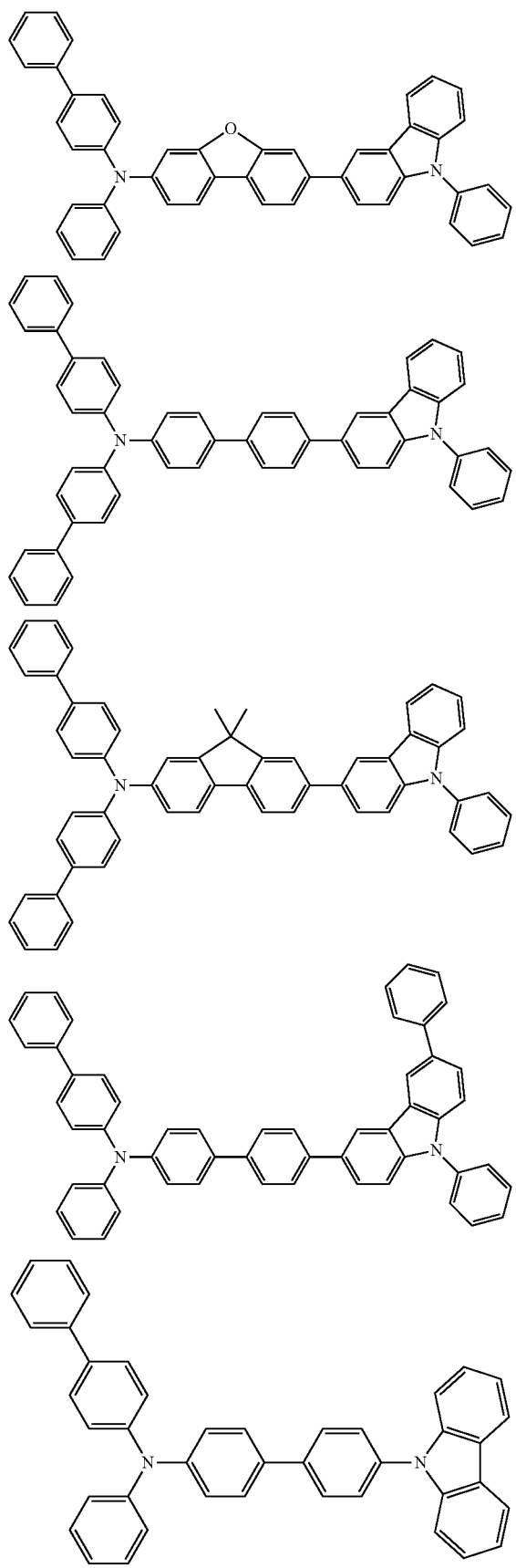
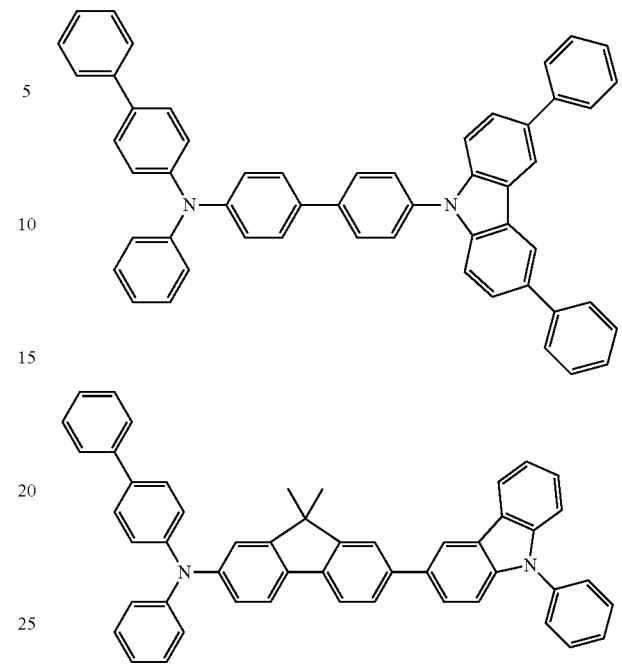

An aromatic amine represented by formula (II) is also preferably used to form the hole injecting layer or the hole transporting layer:

$$Ar^2-N\begin{matrix}Ar^1\\ \\Ar^3\end{matrix} \quad (II)$$

wherein $Ar^1$ to $Ar^3$ are the same as defined with respect to $Ar^1$ to $Ar^4$ of formula (I). Examples of the compound represented by formula (II) are shown below, although not limited thereto.

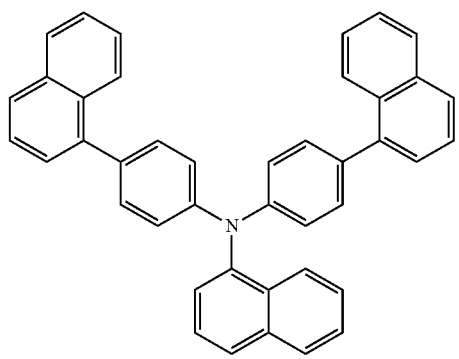

165
-continued
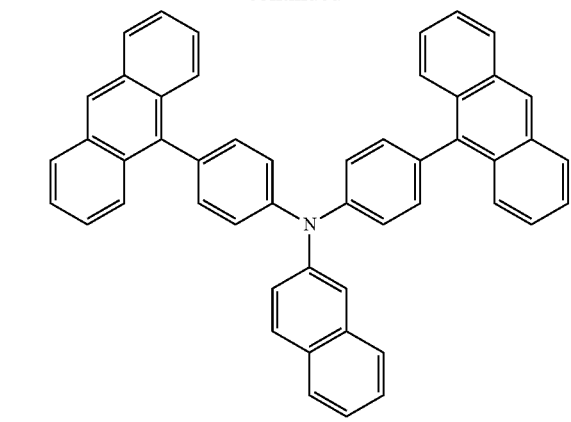
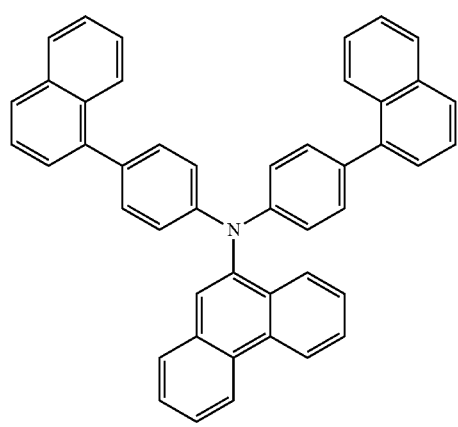
166
-continued
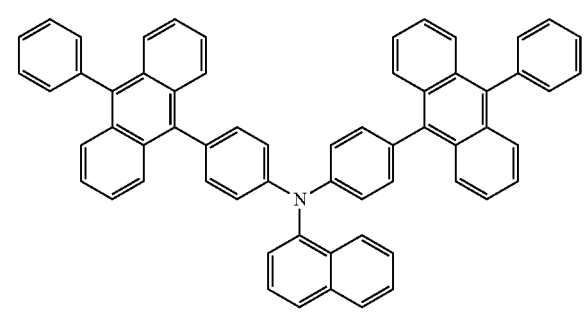
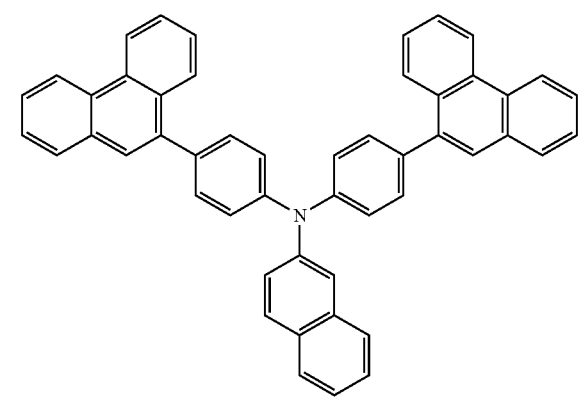
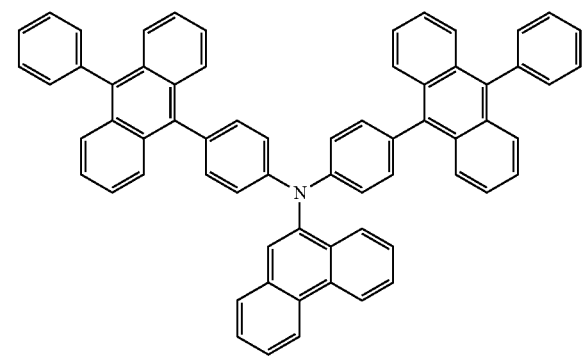
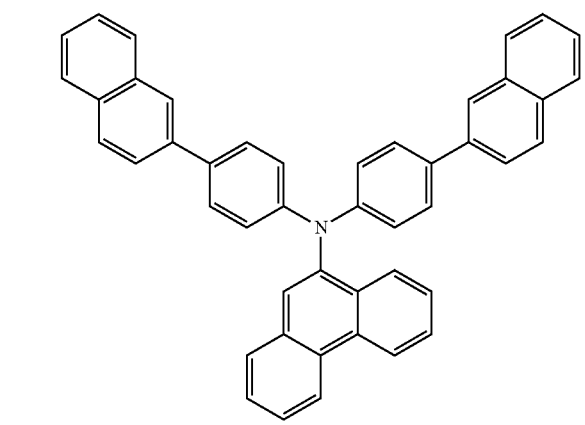

167
-continued
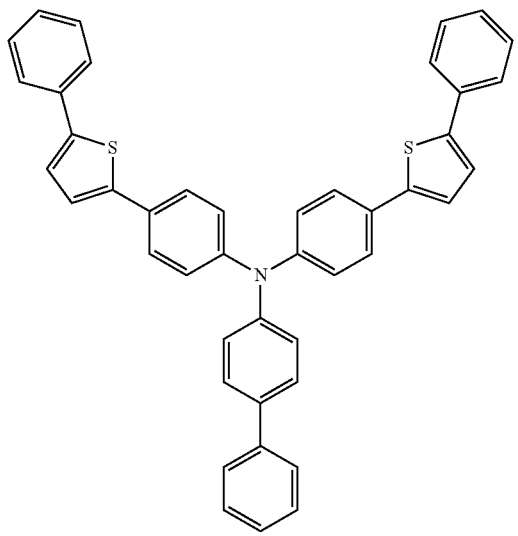
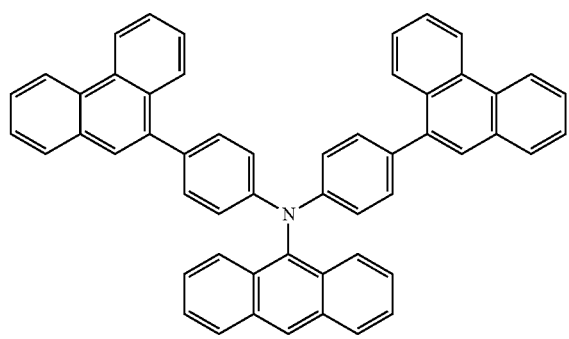
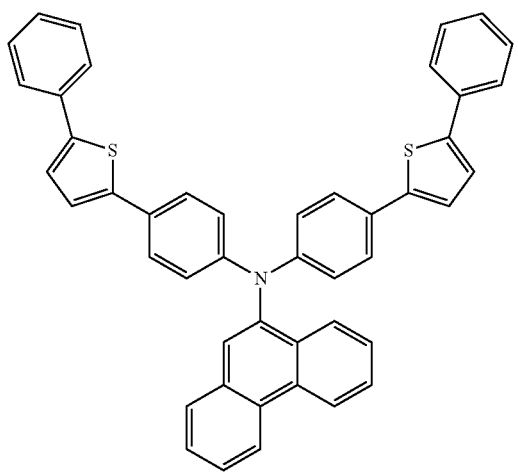
168
-continued
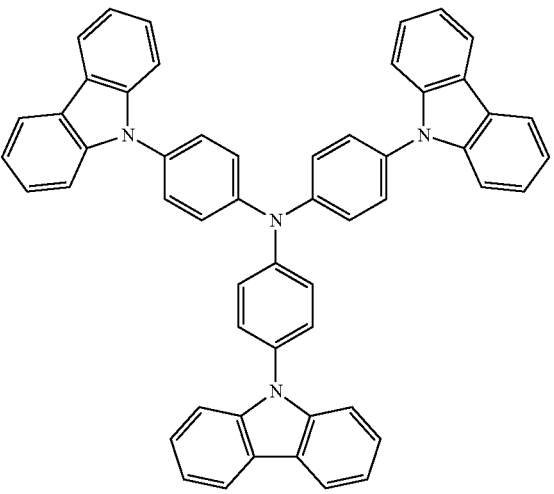
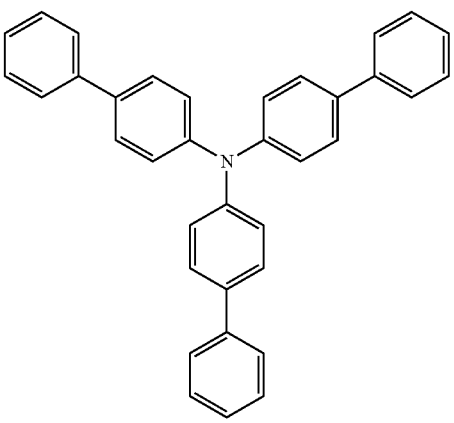
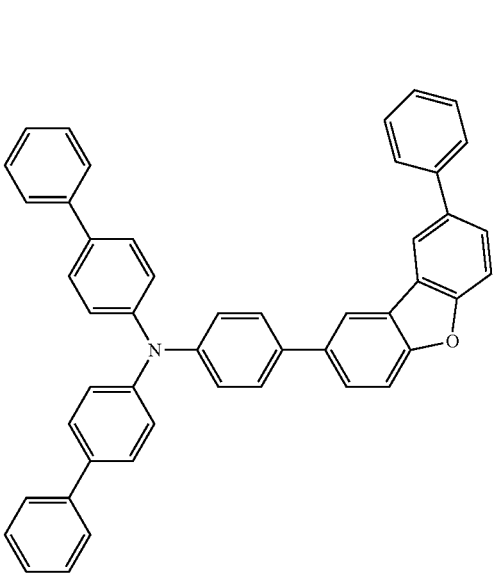

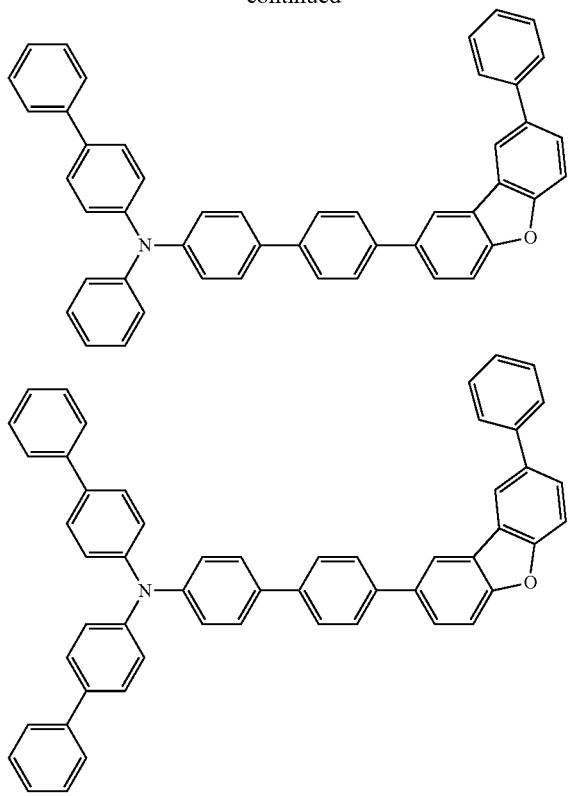

It should be noted that the present invention is not limited to those described above and it will be understood that variations and modifications can be effected within the spirit and scope of the invention.

For example, the following embodiment is one of preferred modifications of the invention.

In the present invention, the light emitting layer preferably comprises a charge injection aid.

When a host material having a wide energy gap is used in the light emitting layer, the difference between the ionization potential (Ip) of the host material and Ip of the hole injecting/transporting layer, etc. becomes large, this making the hole injection into the light emitting layer difficult to likely to increase the driving voltage for obtaining a sufficient luminance.

By adding a hole injecting/transporting charge injection aid into the light emitting layer, the hole injection into the light emitting layer is facilitated and the driving voltage can be reduced.

For example, a hole injecting/transporting material generally known can be used as the charge injection aid.

Examples thereof include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, a polysilane-based copolymer, an aniline-based copolymer, and an electroconductive high-molecular oligomer (particularly, thiophene oligomer).

In addition to the above hole injecting materials, a porphyrin compound, an aromatic tertiary amine compound, and a styryl amine compound are also preferably used, with an aromatic tertiary amine compound being particularly preferred.

Also usable are a compound having two fused aromatic rings in its molecule, for example, 4,4'-bis(N-(1-naphthyl)-N-phenylamino)biphenyl (NPD), and a compound having three triphenylamine units connected in star burst configuration, for example, 4,4',4''-tris(N-(3-methylphenyl)-N-phenylamino)triphenylamine (MTDATA).

Further, a hexaazatriphenylene derivative is preferably used as the hole injecting material.

An inorganic compound, such as p-type Si and p-type SiC, is also usable as the hole injecting material.

Each layer of the organic EL device of the invention may be formed by any one of known methods such as a vacuum vapor deposition method and a spin coating method, although not particularly limited. The organic thin-film layer containing the compound represented by formula (1) in the organic EL device is formed by a known method such as a vacuum vapor deposition method, a molecular beam epitaxy method (MBE method) and a coating method, for example, a dipping method, a spin coating method, a casting method, a bar coating method and a roll coating method each using a solution of the compound in a solvent.

The thickness of each organic thin film layer in the organic EL device of the invention is not particularly limited and preferably several nanometers to 1 μm because an excessively small thickness may cause defects such as pin holes and an excessively large thickness may require a high driving voltage.

EXAMPLES

The present invention will be described in more detail with reference to the synthetic examples and the examples. However, it should be noted that the scope of the invention is not limited to the following examples.

Synthesis Example 1

Synthesis of Compound (1)

(1) Synthesis of Compound (1-a)

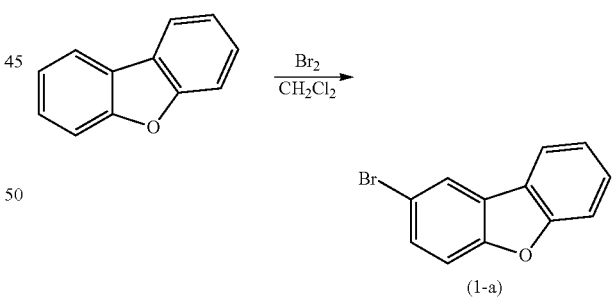

Into a three-necked flask, 269.1 g (1600 mmol) of dibenzofuran and 1280 ml of dichloromethane were charged. The reaction vessel was cooled to 0° C. in a nitrogen atmosphere. After adding 100 ml of a dichloromethane solution of 204.6 g of bromine dropwise into the reaction vessel over 40 min, the contents were stirred at room temperature for 12 h. After the reaction, the reaction vessel was cooled to 0° C. and then 500 ml of water and 100 ml of a 20% aqueous solution of NaHSO$_4$ were added. The reaction solution was extracted with several portions of dichloromethane in a separatory funnel. The extract was washed with 300 ml of a 1 N aqueous solution of sodium hydroxide, dried over anhydrous magnesium sulfate, filtered, and concentrated. The concentrate was dispersed in hexane for washing, to obtain a white solid.

The yield was 136 g and the percent yield was 55%.

(2) Synthesis of Compound (1-b)

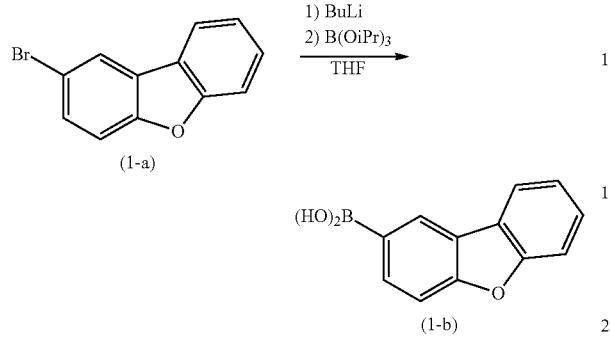

Into a three-necked flask, 20.0 g (80.9 mmol) of Compound (1-a) and 200 ml of dehydrated tetrahydrofuran were charged, and the reaction vessel was cooled to −70° C. in a nitrogen atmosphere. Into the reaction vessel, 53 ml (88.9 mmol) of a 1.68 M hexane solution of n-butyllithium was added dropwise and the contents were stirred at −70° C. for one hour. After adding 37.3 ml (162 mmol) of triisopropyl borate, the contents were stirred at room temperature for 6 h. After the reaction, 100 ml of a 1 N hydrochloric acid was added and the contents were stirred for 30 min. The resultant solution was extracted with several portions of dichloromethane in a separatory funnel. The extract was dried over anhydrous magnesium sulfate, filtered, and concentrated. The concentrate was dispersed in hexane for washing, to obtain a white solid.

The yield was 15.9 g and the percent yield was 93%.

(3) Synthesis of Compound (1-c)

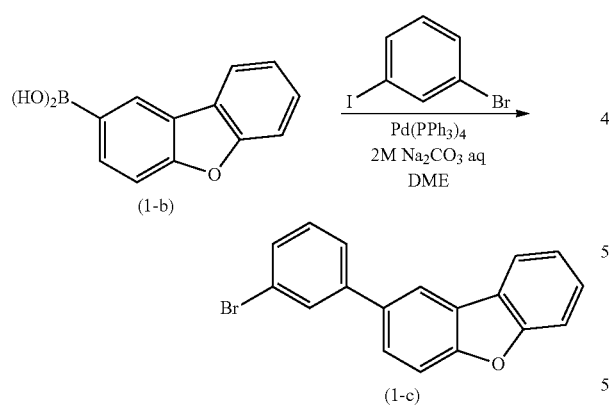

Into a three-necked flask, 15.5 g (73.1 mmol) of Compound (1-b), 30.8 g (109 mmol) of 3-bromoiodobenzene, 110 ml of a 2 M aqueous solution of sodium carbonate, 220 ml of 1,2-dimethoxyethane, and 1.70 g (1.46 mmol) of Pd(PPh$_3$)$_4$ were charged, and the contents were refluxed for 12 h.

After the reaction, the reaction solution was extracted with several portions of dichloromethane in a separatory funnel. The extract was dried over anhydrous magnesium sulfate, filtered, and concentrated. The concentrate was purified by silica gel chromatography (hexane:dichloromethane=20:1), to obtain a colorless viscous matter.

The yield was 13.2 g and the percent yield was 56%.

(4) Synthesis of Compound (1-d)

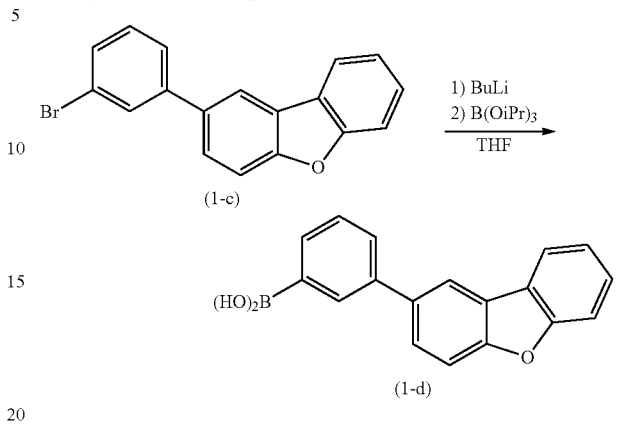

Into a three-necked flask, 13.2 g (40.8 mmol) of Compound (1-c) and 100 ml of dehydrated tetrahydrofuran were charged, and the reaction vessel was cooled to −70° C. in a nitrogen atmosphere. Into the reaction vessel, 27 ml (44.9 mmol) of a 1.67 M hexane solution of n-butyllithium was added dropwise, and the contents were stirred at −70° C. for one hour. After adding 18.8 ml (81.6 mmol) of triisopropyl borate, the stirring was further continued at room temperature for 6 h. After the reaction, 100 ml of a 1 N hydrochloric acid was added and the contents were stirred for 30 min. The resultant solution was extracted with several portions of dichloromethane in a separatory funnel. The extract was dried over anhydrous magnesium sulfate, filtered, and concentrated. The concentrate was dispersed in hexane for washing, to obtain a white solid.

The yield was 8.24 g and the percent yield was 70%.

(5) Synthesis of Compound (1-e)

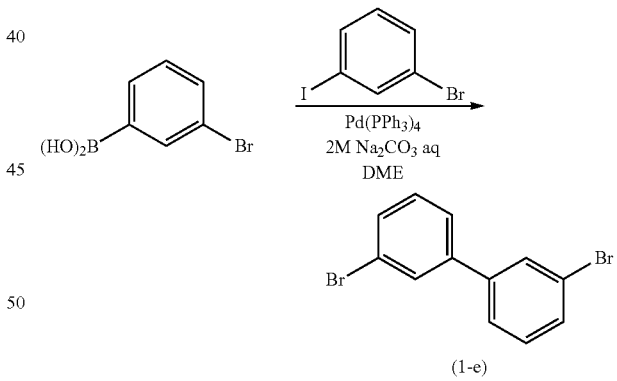

Into a three-necked flask, 12.0 g (59.8 mmol) of 3-bromophenylboronic acid, 25.3 g (89.6 mmol) of 3-bromoiodobenzene, 90 ml of a 2 M aqueous solution of sodium carbonate, 180 ml of 1,2-dimethoxyethane, and 1.38 g (1.20 mmol) of Pd(PPh$_3$)$_4$ were charged, and the contents were refluxed for 12 h in a nitrogen atmosphere.

After the reaction, the reaction solution was extracted with several portions of dichloromethane in a separatory funnel. The extract was dried over anhydrous magnesium sulfate, filtered, and concentrated. The concentrate was purified by silica gel chromatography (hexane), to obtain a white solid.

The yield was 11.2 g and the percent yield was 60%.

(6) Synthesis of Compound (1)

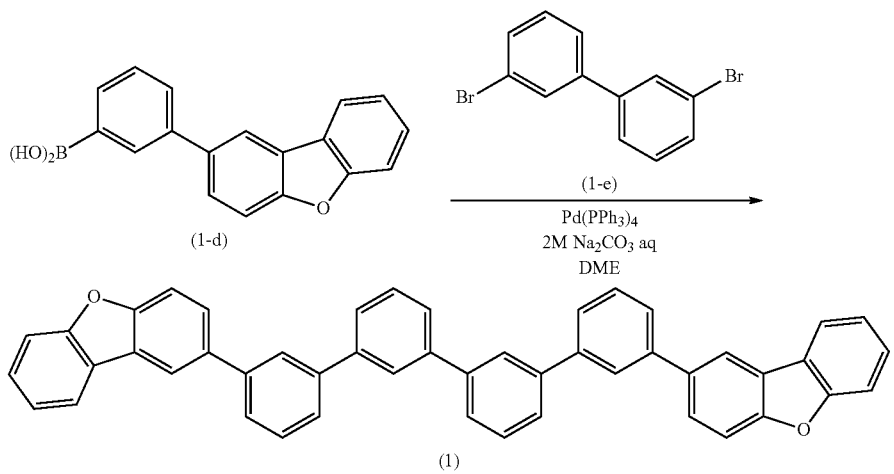

Into a three-necked flask, 4.11 g (14.3 mmol) of Compound (1-d), 1.85 g (5.96 mmol) of Compound (1-e), 22 ml of a 2 M aqueous solution of sodium carbonate, 44 ml of 1,2-dimethoxyethane, and 0.688 g (0.596 mmol) of Pd(PPh$_3$)$_4$ were charged, and the contents were refluxed for 12 h in a nitrogen atmosphere.

After the reaction, the reaction solution was added with 100 ml of methanol and ultrasonically washed for 10 min. The precipitate was separated by filtration and washed with methanol, water, and then hexane. After drying, the precipitate was further ultrasonically washed for 30 min in a hexane:ethyl acetate=1:1 mixed solvent, to obtain a white solid. The identification was based on the molecular weight measurement by FD/MS, which showed m/e=638 for the molecular weight of 638. The yield was 1.85 g and the percent yield was 49%.

Synthesis Example 2

Synthesis of Compound (2)

(1) Synthesis of Compound (2-a)

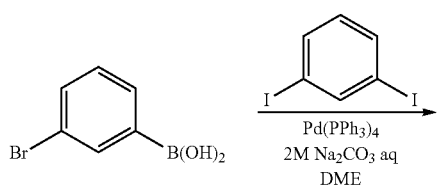

-continued

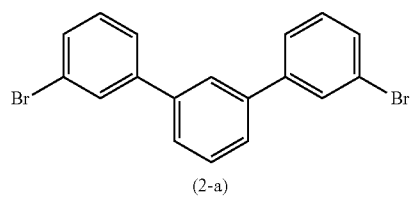

Into a three-necked flask, 12.0 g (36.4 mmol) of 1,3-diiodobenzene, 18.3 g (90.9 mmol) of 3-bromoiodobenzene, 125 ml of a 2 M aqueous solution of sodium carbonate, 250 ml of 1,2-dimethoxyethane, and 2.10 g (1.82 mmol) of Pd(PPh$_3$)$_4$ were charged, and the contents were refluxed for 12 h in a nitrogen atmosphere.

After the reaction, the reaction solution was extracted with several portions of dichloromethane in a separatory funnel. The extract was dried over anhydrous magnesium sulfate, filtered, and concentrated. The concentrate was purified by silica gel chromatography (hexane:dichloromethane=20:1), to obtain a colorless viscous matter.

The yield was 4.20 g and the percent yield was 30%.

(2) Synthesis of Compound (2)

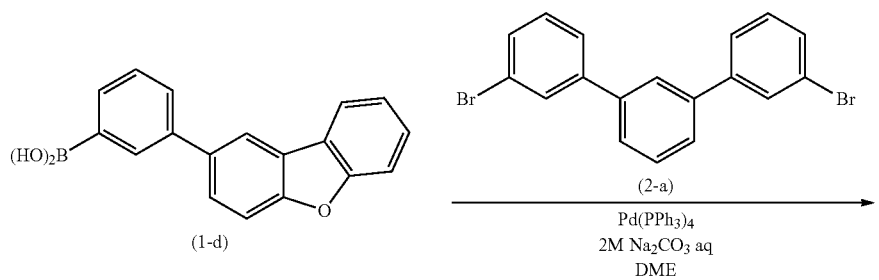

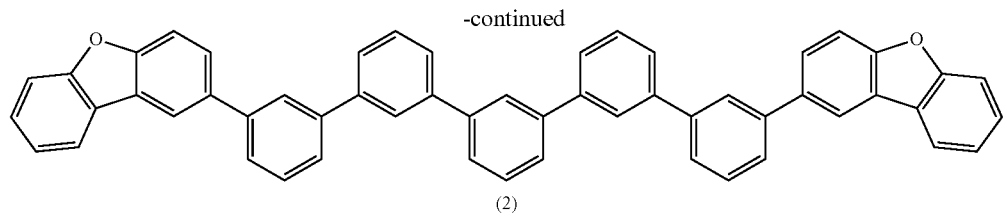

(2)

Into a three-necked flask, 5.93 g (20.6 mmol) of Compound (1-d), 3.20 g (8.25 mmol) of Compound (2-a), 30 ml of a 2 M aqueous solution of sodium carbonate, 60 ml of 1,2-dimethoxyethane, and 1.19 g (1.03 mmol) of Pd(PPh$_3$)$_4$ were charged, and the contents were refluxed for 12 h in a nitrogen atmosphere.

After the reaction, the reaction solution was added with 100 ml of methanol and ultrasonically washed for 10 min. The precipitate was separated by filtration and washed with methanol, water, and then hexane. After drying, the precipitate was dispersed in a hexane:ethyl acetate=1:1 mixed solution for washing, to obtain a white solid. The identification was based on the molecular weight measurement by FD/MS, which showed m/e=714 for the molecular weight of 714. The yield was 2.52 g and the percent yield was 43%.

Synthesis Example 3

Synthesis of Compound (4)

(1) Synthesis of Compound (4-a)

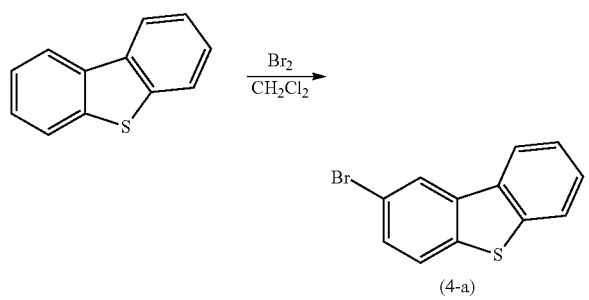

(4-a)

Into a three-necked flask, 15.0 g (81.4 mmol) of dibenzothiophene and 90 ml of chloroform were charged, and the reaction vessel was cooled to 0° C. in a nitrogen atmosphere. After adding 20 ml of dichloromethane solution of 13.1 g of bromine into the reaction vessel dropwise over 15 min, the contents were stirred at room temperature for 12 h. After the reaction, the reaction vessel was cooled to 0° C. and added with 100 ml of water and then 30 ml of a 20% aqueous solution of NaHSO$_4$. The reaction solution was extracted with several portions of dichloromethane in a separatory funnel. The extract was washed with 30 ml of a 1 N aqueous solution of sodium hydroxide, dried over anhydrous magnesium sulfate, filtered, and concentrated. The concentrate was dispersed in hexane and then methanol for washing, to obtain a white solid.

The yield was 10.7 g and the percent yield was 50%.

(2) Synthesis of Compound (4-b)

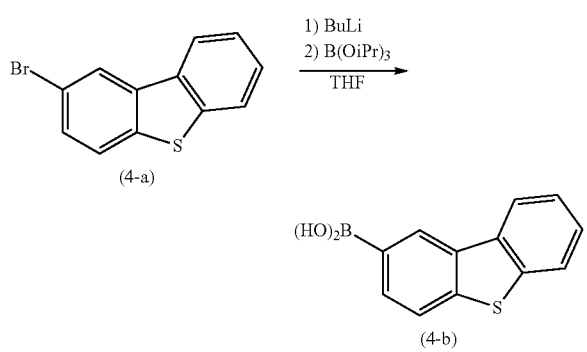

Into a three-necked flask, 7.00 g (26.6 mmol) of Compound (4-a) and 80 ml of a dehydrated tetrahydrofuran: dehydrated toluene=1:1 mixed solution were charged and the reaction vessel was cooled to −70° C. in a nitrogen atmosphere. After adding 23 ml (37.2 mmol) of a 1.60 M hexane solution of n-butyllithium dropwise into the reaction vessel, the contents were stirred at −70° C. for one hour. After further adding 12.3 ml (53.2 mmol) of triisopropyl borate, the contents were stirred at room temperature for 6 h. After the reaction, the reaction solution was added with 50 ml of a 1 N hydrochloric acid, stirred for 30 min, and extracted with several portions of dichloromethane in a separatory funnel. The extract was dried over anhydrous magnesium sulfate, filtered, and concentrated. The concentrate was dispersed in hexane for washing, to obtain a white solid.

The yield was 5.76 g and the percent yield was 95%.

(3) Synthesis of Compound (4-c)

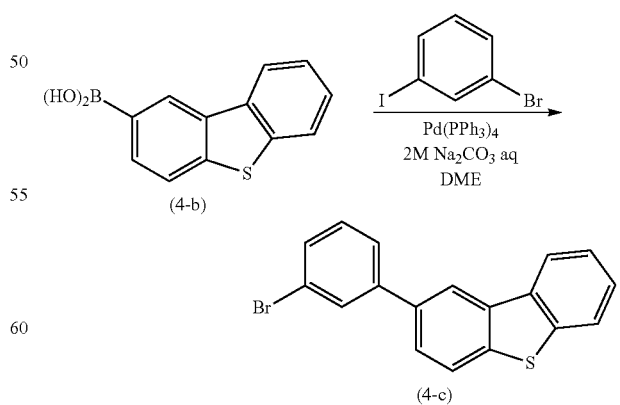

Into a three-necked flask, 5.76 g (25.3 mmol) of Compound (4-b), 10.7 g (38.0 mmol) of 3-bromoiodobenzene, 38 ml of a 2 M aqueous solution of sodium carbonate, 76 ml of 1,2-dimethoxyethane, and 1.46 g (1.23 mmol) of Pd(PPh$_3$)$_4$ were charged, and the contents were refluxed for 12 h in a nitrogen atmosphere.

After the reaction, the reaction solution was extracted with several portions of dichloromethane in a separatory funnel. The extract was dried over anhydrous magnesium sulfate, filtered, and concentrated. The concentrate was purified by silica gel chromatography (hexane:dichloromethane=20:1), to obtain a colorless viscous matter.

The yield was 6.87 g and the percent yield was 80%.

(4) Synthesis of Compound (4-d)

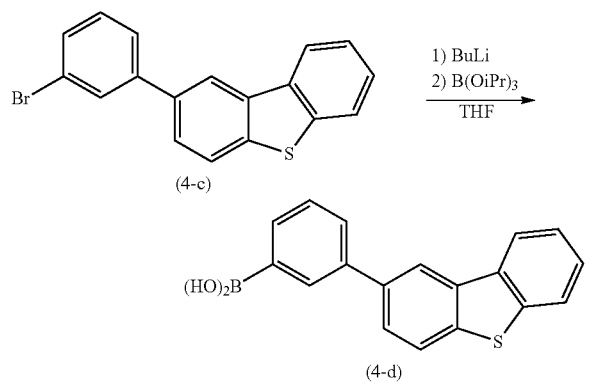

Into a three-necked flask, 6.87 g (20.3 mmol) of Compound (4-c) and 50 ml of dehydrated tetrahydrofuran were charged, and the reaction vessel was cooled to −70° C. in a nitrogen atmosphere. After adding 13 ml (22.3 mmol) of a 1.67 M hexane solution of n-butyllithium dropwise into the reaction vessel, the contents were stirred at −70° C. for one hour. After further adding 9.4 ml (40.6 mmol) of triisopropyl borate, the contents were stirred at room temperature for 6 h. After the reaction, the reaction solution was added with 50 ml of a 1 N hydrochloric acid, stirred for 30 min, and extracted with several portions of dichloromethane in a separatory funnel. The extract was dried over anhydrous magnesium sulfate, filtered, and concentrated. The concentrate was dispersed in hexane for washing, to obtain a white solid.

The yield was 5.43 g and the percent yield was 88%.

(5) Synthesis of Compound (4)

Into a three-necked flask, 5.00 g (16.4 mmol) of Compound (4-d), 2.13 g (6.83 mmol) of Compound (1-e), 25 ml of a 2 M aqueous solution of sodium carbonate, 50 ml of 1,2-dimethoxyethane, and 1.90 g (1.64 mmol) of Pd(PPh$_3$)$_4$ were charged, and the contents were refluxed for 12 h in a nitrogen atmosphere.

After the reaction, the reaction solution was added with 100 ml of methanol and ultrasonically washed for 10 min. The precipitate was separated by filtration and washed with methanol, water, and then hexane. After drying, the precipitate was further ultrasonically washed for 30 min in a hexane:ethyl acetate=1:1 mixed solvent, to obtain a white solid. The identification was based on the molecular weight measurement by FD/MS, which showed m/e=670 for the molecular weight of 670. The yield was 2.06 g and the percent yield was 45%.

Synthesis Example 4

Synthesis of Compound (37)

(1) Synthesis of Compound (37-a)

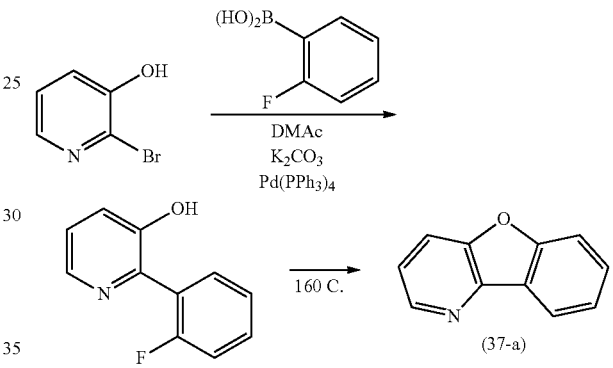

Into a three-necked flask, 100.1 g (575 mmol) of 2-bromo-3-hydroxypyridine, 88.5 g (632.5 mmol) of 2-fluorophenylboronic acid, 88.5 g (2300 mmol) of potassium carbonate, 1150 ml of N,N-dimethylacetamide, and 13.3 g (11.5 mmol) of Pd(PPh$_3$)$_4$ were charged, and the contents were stirred at 90° C. for 12 h under heating in a nitrogen atmosphere and then stirred at 160° C. for 8 h under heating.

After the reaction, the reaction solution was cooled to room temperature, added with 1 L of toluene and 1 L of water, and shaken well in a separatory funnel. The toluene

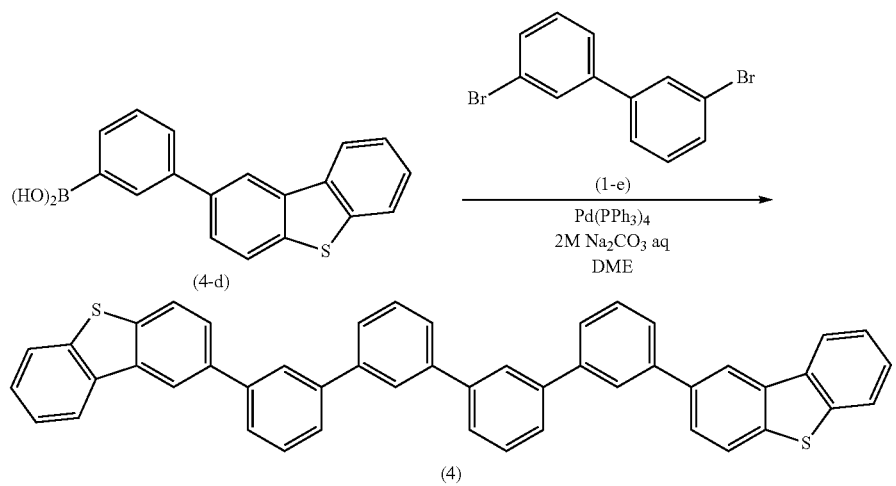

phase was recovered and the water phase was extracted with several portions of toluene. The combined toluene solution was washed with several portions of water, dried over anhydrous magnesium sulfate, passed through a silica gel short column, and concentrated. The obtained concentrate was recrystallized from 200 ml of hexane, to obtain a pale yellowish solid.

The identification was done by $^1$H-NMR. The yield was 54.4 g and the percent yield was 56%.

(2) Synthesis of Compound (37-b)

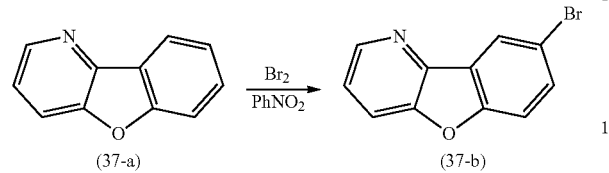

Into a three-necked flask, 52.6 g (310 mmol) of Compound (37-a), 155 ml of nitrobenzene, and 19.1 ml (372 mmol) of bromine were charged, and the contents were stirred at 140° C. for 12 h under stirring in the atmosphere.

After the reaction, the temperature was lowered to room temperature. An aqueous solution of sodium thiosulfate was added to the reaction solution under cooling in an iced water bath to deactivate the remaining bromine. Then, an aqueous solution of sodium hydroxide was added so as to adjust pH of the resultant solution to 10. The resultant solution was extracted with several portions of toluene in a separatory funnel. The extract was dried over anhydrous magnesium sulfate, filtered, and concentrated. The concentrate was purified by silica gel chromatography (dichloromethane:ethyl acetate=8:2). The purified product was dispersed in hexane for washing, separated by filtration, and vacuum-dried (at 40° C. for 6 h) to obtain a pale yellowish solid.

The identification was done by $^1$H-NMR. The yield was 32.1 g and the percent yield was 42%.

(3) Synthesis of Compound (37-c)

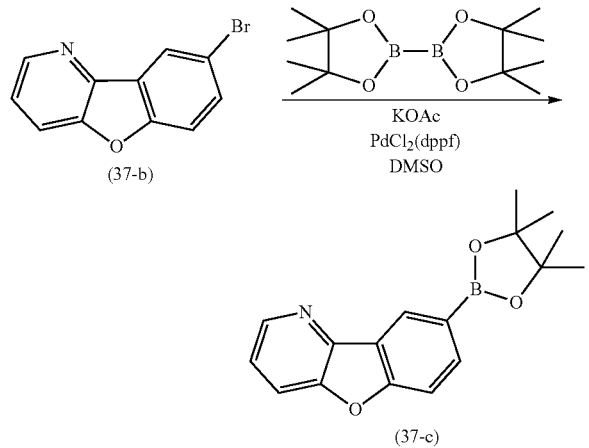

Into a three-necked flask, 18.0 g (72.6 mmol) of Compound (37-b), 27.6 g (108.9 mmol) of bispinacolate diboron, 21.4 g (217.8 mmol) of potassium acetate, 2.96 g (3.63 mmol) of PdCl$_2$(dppf), and 150 ml of dimethylsulfoxide were charged, and the contents were stirred at 80° C. for 16 h in a nitrogen atmosphere.

After the reaction, the reaction solution was filtered through celite, added with 300 ml of water, and extracted with several portions of toluene in a separatory funnel. The extract was dried over anhydrous magnesium sulfate, filtered, and concentrated. The concentrate was purified by silica gel chromatography (hexane:ethyl acetate=1:5) and recrystallized from hexane, to obtain a white solid.

The yield was 4.20 g and the percent yield was 20%.

(4) Synthesis of Compound (37-d)

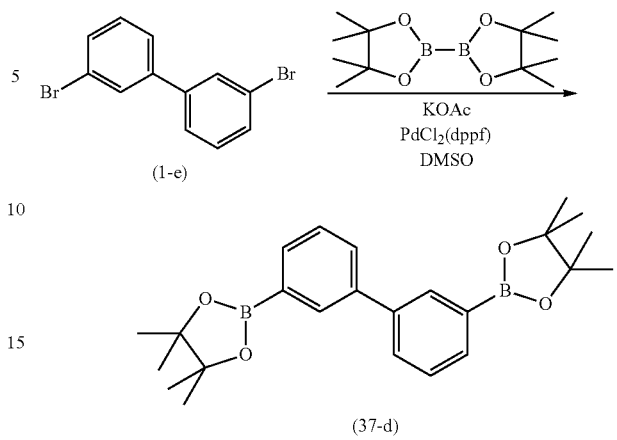

Into a three-necked flask, 6.00 g (19.2 mmol) of Compound (1-e), 14.6 g (57.6 mmol) of bispinacolate diboron, 12.2 g (124.8 mmol) of potassium acetate, 1.57 g (1.92 mmol) of PdCl$_2$(dppf), and 100 ml of dimethylsulfoxide were charged, and the contents were stirred at 80° C. for 16 h in a nitrogen atmosphere.

After the reaction, the reaction solution was filtered through celite, added with 100 ml of water, and extracted with several portions of dichloromethane in a separatory funnel. The extract was dried over anhydrous magnesium sulfate, filtered, and concentrated. The concentrate was purified by silica gel chromatography (hexane:ethyl acetate=20:1) and recrystallized from hexane, to obtain a while solid.

The yield was 5.44 g and the percent yield was 70%.

(5) Synthesis of Compound (37-e)

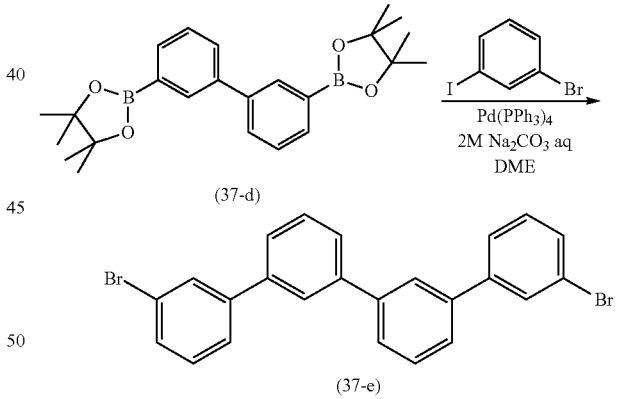

Into a three-necked flask, 5.40 g (13.3 mmol) of Compound (37-d), 11.3 g (39.9 mmol) of 3-bromoiodobenzene, 40 ml of a 2 M aqueous solution of sodium carbonate, 80 ml of 1,2-dimethoxyethane, 1.54 g (1.33 mmol) of Pd(PPh$_3$)$_4$ were charged, and the contents were refluxed for 12 h in a nitrogen atmosphere.

After the reaction, the reaction solution was extracted with several portions of dichloromethane in a separatory funnel. The extract was dried over anhydrous magnesium sulfate, filtered, and concentrated. The concentrate was purified by silica gel chromatography (hexane:dichloromethane=20:1), to obtain a white solid.

The yield was 4.90 g and the percent yield was 79%.

(6) Synthesis of Compound (37)

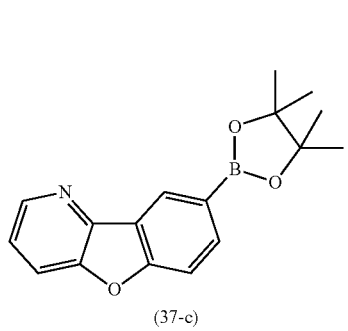 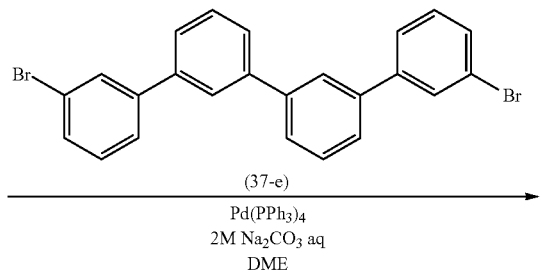

Into a three-necked flask, 4.10 g (13.9 mmol) of Compound (37-c), 2.58 g (5.56 mmol) of Compound (37-e), 20 ml of a 2 M aqueous solution of sodium carbonate, 40 ml of 1,2-dimethoxyethane, and 1.61 g (1.39 mmol) of Pd(PPh$_3$)$_4$ were charged, and the contents were refluxed for 12 h in a nitrogen atmosphere.

After the reaction, the reaction solution was added with 100 ml of methanol and ultrasonically washed for 10 min. The precipitate was separated by filtration and washed with methanol, water, and then hexane. The washed precipitate was dried and dispersed in ethyl acetate for washing. The obtained solid was recrystallized from toluene, to obtain a white solid. The identification was based on the molecular weight measurement by FD/MS, which showed m/e=640 for the molecular weight of 640. The yield was 2.46 g and the percent yield was 69%.

Synthesis Example 5

Synthesis of Compound (16)

(1) Synthesis of Compound (16-a)

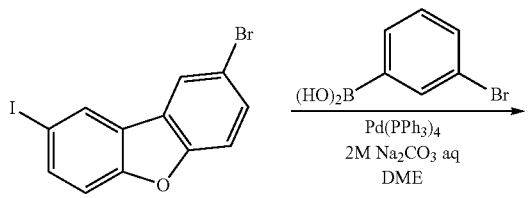

-continued

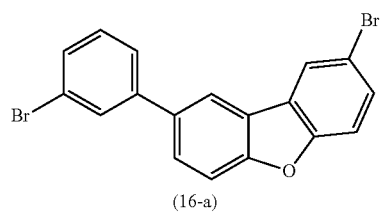

Into a three-necked flask, 10.0 g (26.8 mmol) of 2-bromo-8-iododibenzofuran, 6.46 g (32.2 mmol) of 3-bromophenylboronic acid, 50 ml of a 2 M aqueous solution of sodium carbonate, 100 ml of 1,2-dimethoxyethane, and 1.55 g (1.34 mmol) of Pd(PPh$_3$)$_4$ were charged, and the contents were refluxed for 10 h in a nitrogen atmosphere.

After the reaction, the reaction solution was extracted with several portions of dichloromethane in a separatory funnel. The extract was dried over anhydrous magnesium sulfate, filtered, and concentrated. The concentrate was purified by silica gel chromatography (hexane:dichloromethane=50:1), to obtain a white solid.

The yield was 2.30 g and the percent yield was 21%.

(2) Synthesis of Compound (16)

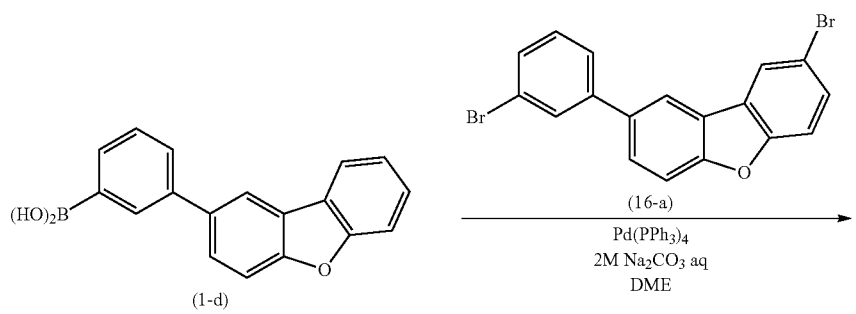

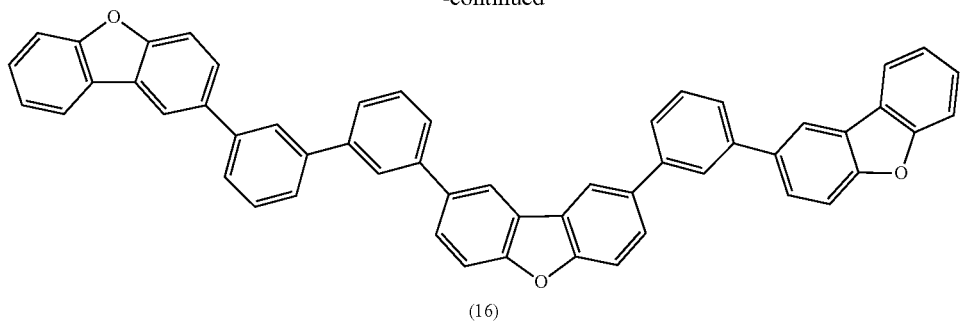

(16)

Into a three-necked flask, 3.96 g (13.7 mmol) of Compound (1-d), 2.30 g (5.72 mmol) of Compound (16-a), 20 ml of a 2 M aqueous solution of sodium carbonate, 40 ml of 1,2-dimethoxyethane, and 0.661 g (0.572 mmol) of Pd(PPh$_3$)$_4$ were charged, and the contents were refluxed for 12 h in a nitrogen atmosphere.

After the reaction, the reaction solution was added with 100 ml of methanol and ultrasonically washed for 10 min. The precipitate was separated by filtration and washed with methanol, water, and then hexane. The washed precipitate was dried and purified by silica gel chromatography (hexane:dichloromethane=5:1), to obtain a white solid. The identification was based on the molecular weight measurement by FD/MS, which showed m/e=728 for the molecular weight of 728. The yield was 2.31 g and the percent yield was 55%.

Synthesis Example 6
Synthesis of Compound (291)

(1) Synthesis of Compound (291-a)

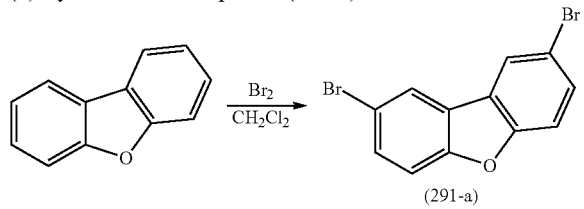

Into a three-necked flask, 168.1 g (1000 mmol) of dibenzofuran and 1600 ml of dichloromethane were charged, and the reaction vessel was cooled to 0° C. in a nitrogen atmosphere. After adding 125 ml of a dichloromethane solution of 255.8 g of bromine dropwise into the reaction vessel over 40 min, the contents were stirred at room temperature for 12 h. After the reaction, the reaction vessel was cooled to 0° C. and then 500 ml of water and 100 ml of a 20% aqueous solution of NaHSO$_4$ were added. The resultant solution was extracted with several portions of dichloromethane in a separatory funnel. The extract was washed with 300 ml of a 1 N aqueous solution of sodium hydroxide, dried over anhydrous magnesium sulfate, filtered, and concentrated. The concentrate was dispersed in hexane for washing, to obtain a white solid.

The yield was 212 g and the percent yield was 65%.

(2) Synthesis of Compound (291)

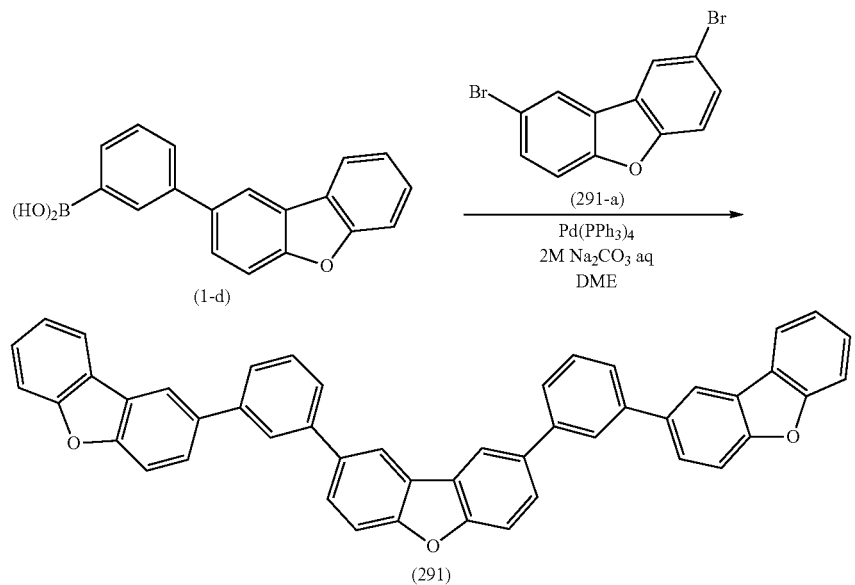

Into a three-necked flask, 10.6 g (36.8 mmol) of Compound (1-d), 5.00 g (15.3 mmol) of Compound (291-a), 55 ml of a 2 M aqueous solution of sodium carbonate, 110 ml of 1,2-dimethoxyethane, and 1.77 g (1.53 mmol) of Pd(PPh$_3$)$_4$ were charged, and the contents were refluxed for 12 h in a nitrogen atmosphere.

After the reaction, the reaction solution was added with 100 ml of methanol and ultrasonically washed for 10 min. The precipitate was separated by filtration and washed with methanol, water, and then hexane. The washed precipitate was dried and dispersed in ethyl acetate for washing, to obtain a white solid. The identification was based on the molecular weight measurement by FD/MS, which showed m/e=652 for the molecular weight of 652. The yield was 5.75 g and the percent yield was 58%.

Synthesis Example 7

Synthesis of Compound (300)

(1) Synthesis of Compound (300-a)

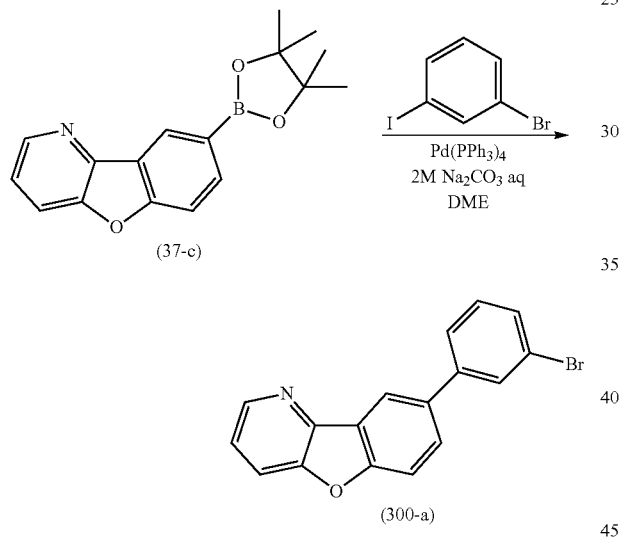

Into a three-necked flask, 5.75 g (19.5 mmol) of Compound (37-c), 8.26 g (29.2 mmol) of 3-bromoiodobenzene, 30 ml of a 2 M aqueous solution of sodium carbonate, 60 ml of 1,2-dimethoxyethane, and 2.25 g (1.95 mmol) of Pd(PPh$_3$)$_4$ were charged, and the contents were refluxed for 8 h in a nitrogen atmosphere.

After the reaction, the reaction solution was extracted with several portions of ethyl acetate in a separatory funnel. The extract was dried over anhydrous magnesium sulfate, filtered, and concentrated. The concentrate was purified by silica gel chromatography (hexane:dichloromethane=25:1 to 2:1), to obtain a white solid.

The yield was 5.62 g and the percent yield was 89%.

(2) Synthesis of Compound (300-b)

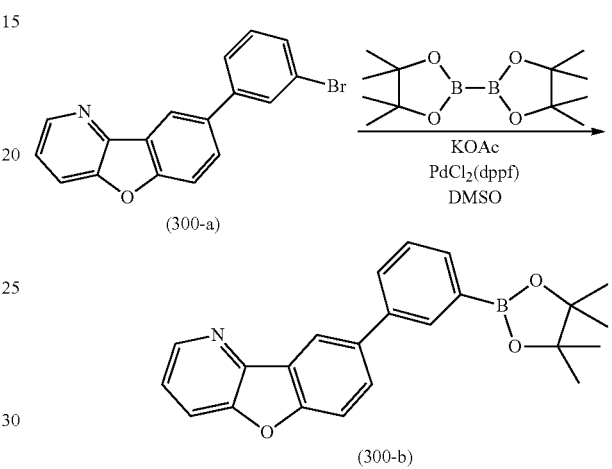

Into a three-necked flask, 5.62 g (17.3 mmol) of Compound (300-a), 6.60 g (26.0 mmol) of bispinacolate diboron, 5.09 g (51.9 mmol) of potassium acetate, 1.41 g (1.73 mmol) of PdCl$_2$(dppf), and 40 ml of dimethylsulfoxide, and the contents were stirred at 120° C. for 16 h in a nitrogen atmosphere.

After the reaction, the reaction solution was filtered through celite and added with 300 ml of water. The resultant solution was extracted with several portions of ethyl acetate in a separatory funnel. The extract was dried over anhydrous magnesium sulfate, filtered, and concentrated. The concentrate was purified by silica gel chromatography (hexane: ethyl acetate=20:1 to 5:1 to 2:1) and recrystallized from hexane, to obtain a white solid.

The yield was 3.84 g and the percent yield was 60%.

(3) Synthesis of Compound (300)

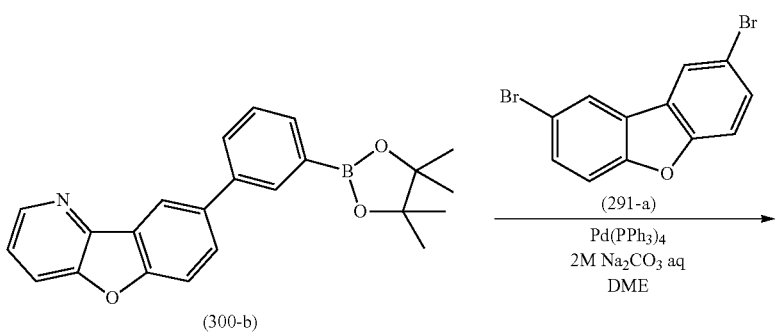

-continued

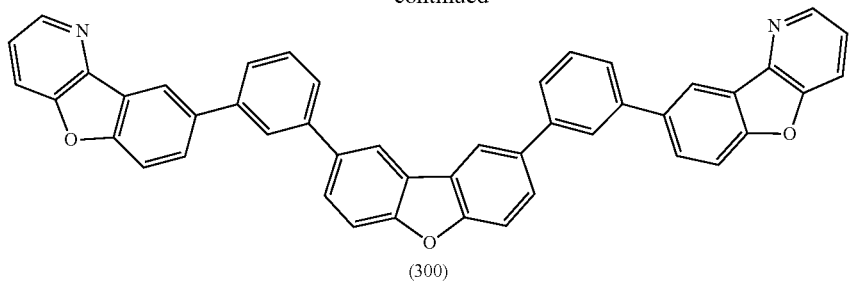
(300)

Into a three-necked flask, 3.80 g (10.2 mmol) of Compound (300-b), 1.39 g (4.25 mmol) of Compound (291-a), 15 ml of a 2 M aqueous solution of sodium carbonate, 30 ml of 1,2-dimethoxyethane, and 0.368 g (0.425 mmol) of Pd(PPh$_3$)$_4$ were charged, and the contents were refluxed for 12 h in a nitrogen atmosphere.

After the reaction, the reaction solution was added with 100 ml of methanol and ultrasonically washed for 10 min. The precipitate was separated by filtration and washed with methanol, water, and then hexane. The washed precipitate was dried, dispersed in ethyl acetate for washing, and recrystallized from toluene, to obtain a white solid. The identification was based on the molecular weight measurement by FD/MS, which showed m/e=654 for the molecular weight of 654. The yield was 1.50 g and the percent yield was 54%.

Example 1

A glass substrate having an ITO electrode line with a thickness of 130 nm (manufactured by Geomatec Company) was cleaned by ultrasonic cleaning in isopropyl alcohol for 5 min and then UV ozone cleaning for 30 min.

The cleaned glass substrate with the ITO electrode line was mounted on the substrate holder of a vacuum deposition apparatus. The compound (HI1) was vapor-deposited by resistance heating into a thickness of 20 nm so as to cover the ITO electrode line, and then, the compound (HT1) was vapor-deposited by resistance heating into a thickness of 60 nm, thereby successively forming thin films. The film-forming rate was 1 Å/s. These thin films work as a hole injecting layer and a hole transporting layer, respectively.

On the hole injecting/transporting layer, the compound (1) and the compound (BD1) were co-deposited by resistance heating to form a thin film with a thickness of 50 nm. The deposited amount of the compound (BD1) was 20% by mass of the total mass of the compound (1) and the compound (BD1). The film-forming rates were 1.2 Å/s and 0.3 Å/s, respectively. The obtained thin film works as a phosphorescent emitting layer.

Next, on the phosphorescent emitting layer, the compound (H1) was vapor-deposited by resistance heating to form a thin film with a thickness of 10 nm. The film-forming rate was 1.2 Å/s. The obtained thin film works as a blocking layer.

Next, on the blocking layer, the compound (ET1) was vapor-deposited by resistance heating to form a thin film with a thickness of 10 nm. The film-forming rate was 1 Å/s. The obtained thin film works as an electron injecting layer.

Next, LiF was vapor-deposited on the electron injecting layer to form a LiF film with a thickness of 1.0 nm at a film-forming rate of 0.1 Å/s.

Then, metallic Al was vapor-deposited on the LiF film at a film-forming rate of 8.0 Å/s to form a metallic cathode with a thickness of 80 nm, thereby obtaining an organic EL device.

The organic EL devices obtained above were evaluated as follows.

(1) External Quantum Efficiency (%)

The external quantum efficiency at a luminance of 1000 cd/m$^2$ was measured by a spectroradiometer (CS-1000 manufactured by Minolta) at 23° C. in a dry nitrogen gas atmosphere.

(2) Half Lifetime (h)

The time taken until the initial luminance (1000 cd/m$^2$) was reduced by half was measured while continuously passing direct current.

(3) Voltage (V)

Using Keithly 236 Source Measure Unit, a voltage was applied to a device which was electrically wired, to cause light emission at 23° C. in a dry nitrogen gas atmosphere. The voltage applied to the device was determined by subtracting the voltage applied to the wiring resistance other than the device. The voltage at a luminance of 100 cd/m$^2$ was also read, while measuring the luminance using a luminance meter (spectroradiometer CS-1000 manufactured by Minolta) simultaneously with the measurement of the applied voltage.

Examples 2 to 5 and Comparative Examples 1

Each organic EL device was produced in the same manner as in Example 1 except for forming the light emitting layer by using the compound listed in Table 1 in place of the compound (1).

TABLE 1

|  | Light emitting layer | Voltage (V) | External quantum efficiency (%) | Half lifetime (h) |
|---|---|---|---|---|
| Examples |  |  |  |  |
| 1 | compound (1) | 4.9 | 15.8 | 3,200 |
| 2 | compound (2) | 4.7 | 13.9 | 3,000 |
| 3 | compound (4) | 4.8 | 14.9 | 3,000 |

TABLE 1-continued

| | Light emitting layer | Voltage (V) | External quantum efficiency (%) | Half lifetime (h) |
|---|---|---|---|---|
| 4 | compound (16) | 4.4 | 15.5 | 3,500 |
| 5 | compound (291) | 4.3 | 15.0 | 3,600 |
| Comparative Example | | | | |
| 1 | compound (H2) | 5.5 | 16.2 | 600 |

Examples 6-7 and Comparative Examples 2-3

Each organic EL device was produced in the same manner as in Example 1 except for forming the phosphorescent emitting layer by using the compound (H1) in place of the compound (1) and forming the hole blocking layer by using the compound listed in Table 2 in place of the compound (H1).

TABLE 2

| | Blocking layer | Voltage (V) | External quantum efficiency (%) | Half lifetime (h) |
|---|---|---|---|---|
| Examples | | | | |
| 6 | compound (37) | 4.8 | 14.7 | 4,800 |
| 7 | compound (300) | 4.8 | 16.5 | 5,500 |
| Comparative Examples | | | | |
| 2 | compound (H2) | 6.0 | 16.7 | 2,300 |
| 3 | compound (H3) | 4.8 | 16.4 | 2,500 |

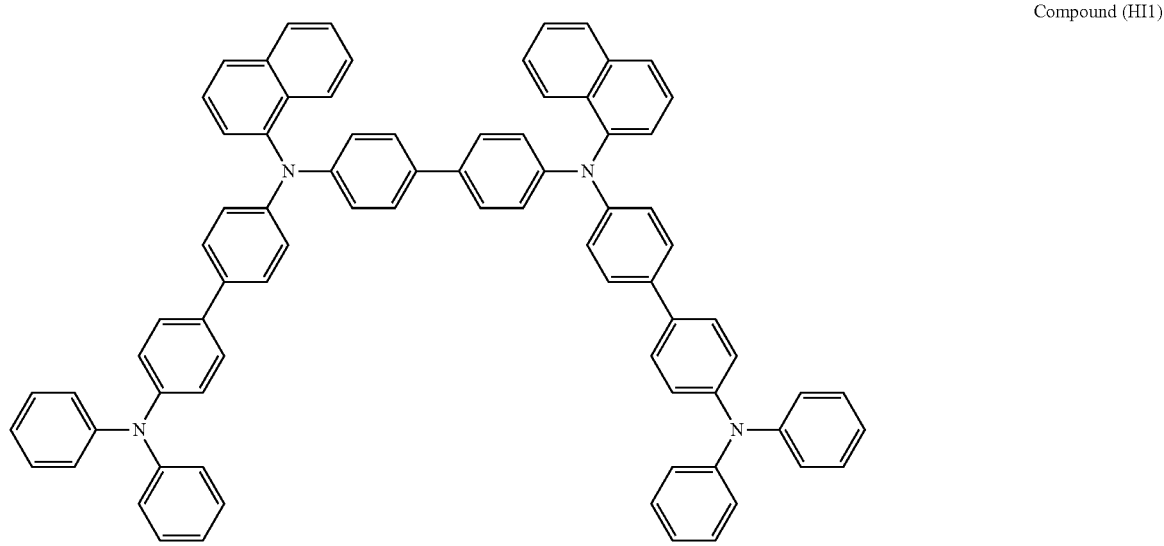

Compound (HI1)

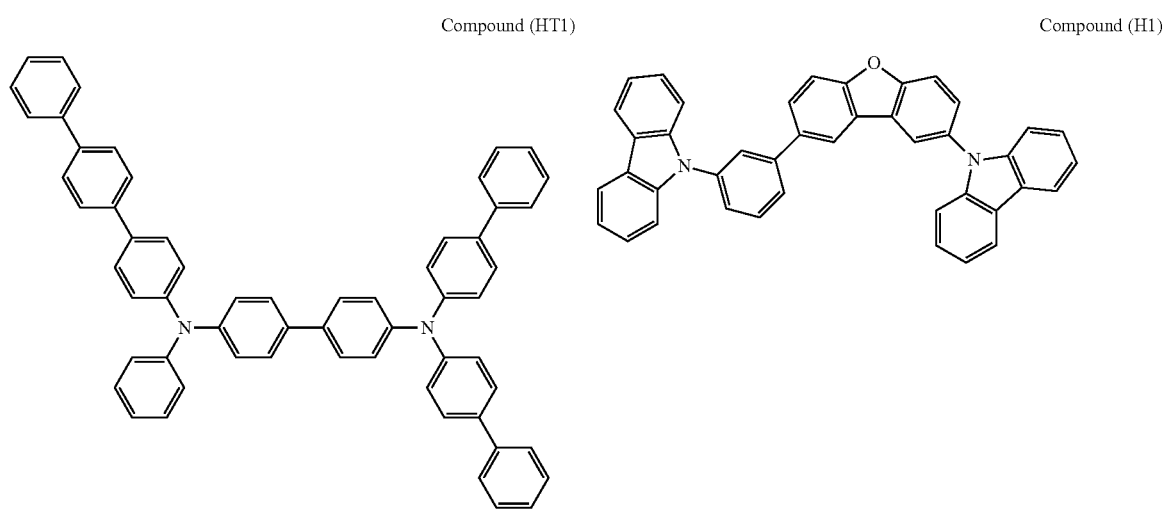

Compound (HT1)

Compound (H1)

-continued

Compound (H2)

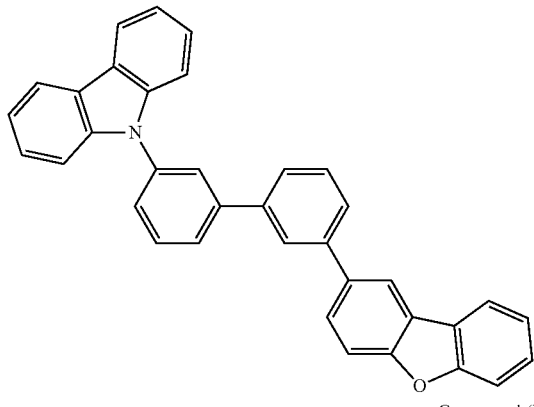

Compound (H3)

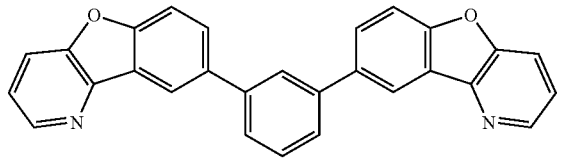

Compound (BD1)

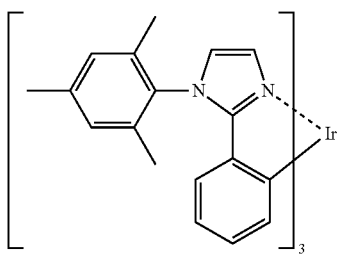

Compound (ET1)

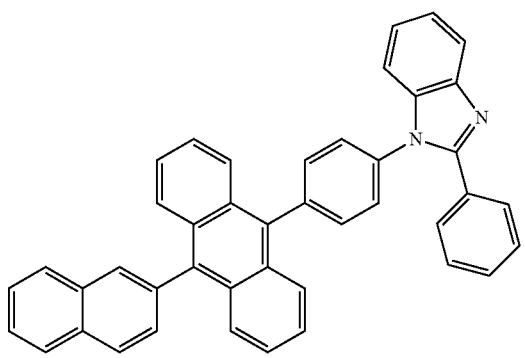

The triplet energies of the materials for organic electroluminescence device of the invention are shown in Table 3. The triplet energy referred to herein was determined as follows. A sample was dissolved in EPA solvent (diethyl ether:isopentane:ethanol=5:5:2 (by volume)) in a concentration of 10 μmmol/L to prepare a specimen for phosphorescence measurement. The specimen for phosphorescence measurement was placed in a quartz cell and irradiated with excitation ray at 77 K, and the emitted phosphorescence was measured. Using the wavelength of the rising portion at the short-wavelength side, the triplet energy was determined as the value calculated from the following conversion formula:

$E^T(eV)=1239.85/\lambda_{edge}$ wherein $\lambda_{edge}$ is determined as follows.

On the phosphorescence spectrum with a vertical axis of phosphorescent intensity and a horizontal axis of wavelength, a line tangent to the rising portion at the short-wavelength side of the phosphorescent spectrum was drawn, and the wavelength (nm) at the intersection of the tangent line and the horizontal axis was expressed by "$\lambda_{edge}$." In the following examples, the phosphorescence spectrum was measured by a commercially available apparatus, F-4500 manufactured by Hitachi, Ltd.

The glass transition point was determined by heating and cooling about 3 mg of sample according to the following 2-cycle heating/cooling process (1) to (6) using DSC 8500 manufactured by Perkin Elmer Inc. and reading the temperature of the inflection point where the base line of DSC curve in the temperature-rising step (6) changed stepwise, thereby determining the glass transition point:
(1) keeping the sample at 30° C. for one minute;
(2) heating the sample from 30° C. to a given temperature lower than the thermal decomposition temperature of the sample at a temperature rising speed of 10° C./min;
(3) keeping the sample at the given temperature for 3 min;
(4) cooling the sample from the given temperature to 0° C. at a cooling speed of 200° C./min;
(5) keeping the sample at 0° C. for 10 min; and
(6) heating the sample from 0° C. to 200° C. at a temperature rising speed of 10° C./min.

TABLE 3

|  | Triplet energy (eV) | Glass transition point (° C.) |
| --- | --- | --- |
| Compound (1) | 2.92 | 95 |
| Compound (2) | 2.92 | 103 |
| Compound (4) | 2.91 | 100 |
| Compound (16) | 2.96 | 117 |
| Compound (37) | 2.91 | 104 |
| Compound (291) | 2.94 | 109 |
| Compound (300) | 2.95 | 125 |
| Compound (H2) | 2.92 | 75 |
| Compound (H3) | 3.03 | 70 |
| Compound (BD1) | 2.64 | — |

The results of Tables 1 and 2 show that the organic EL devices employing the compound or the material for organic electroluminescence device of the invention have long lifetimes and are capable of driving at lower voltage as compared with the devices employing the comparative compounds.

It can be also seen that the lifetime of the organic EL device employing the compound or the material for organic EL device of the invention is prolonged, because the compound and the material for organic EL device have a high glass transition point, and therefore, are excellent in heat resistance.

INDUSTRIAL APPLICABILITY

The material for organic EL device is useful for the production of an organic EL device having long lifetime and high emission efficiency and capable of driving at low voltage which is required for reducing power consumption.

REFERENCE NUMERALS

1: Organic electroluminescence device
2: Substrate
3: Anode
4: Cathode
5: Phosphorescent light emitting layer
6: Hole injecting/transporting layer
7: Electron injecting/transporting layer
10: Organic thin film layers

What is claimed is:
1. An organic electroluminescence device, comprising:
   a cathode;
   an anode; and
   at least one organic thin film layer between the cathode and the anode;
   wherein
   the at least one organic thin film layer comprises a light emitting layer,
   an electron transporting layer between the light emitting layer and the cathode, and
   a hole blocking layer between the light emitting layer and the electron transporting layer, and
   wherein
   the hole blocking layer comprises;
   a compound of formula (1-1) or formula (1-2):

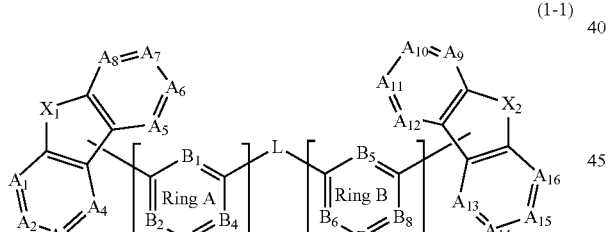

(1-1)

wherein in formula (1-1):
   $X_1$ represents an oxygen atom, a sulfur atom, or —N($R_A$)—;
   $X_2$ represents an oxygen atom, a sulfur atom, or —N($R_B$)—;
   each of $A_1$ to $A_8$ independently represents =C($R_A$)— or =N—;
   each of $A_9$ to $A_{16}$ independently represents =C($R_B$)— or =N—;
   each of $B_1$ to $B_8$ independently represents =C(R)— or =N—;
   each of m and n independently represents an integer of 1 to 3;
   L represents an oxygen atom, a sulfur atom, —N(R)—, —Si($R_1$)($R_2$)— or a linker represented by any one of formulae (2-1), (3-1), (4-1), (5-1), and (6-1):

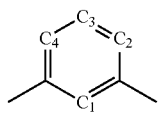
(2-1)

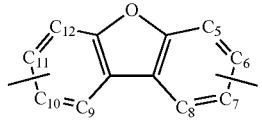
(3-1)

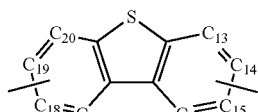
(4-1)

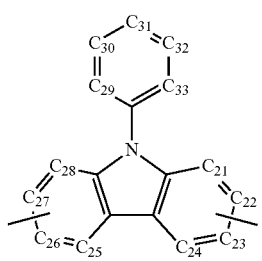
(5-1)

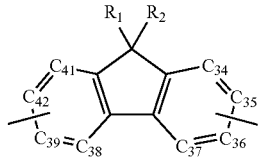
(6-1)

wherein in formulae (2-1), (3-1), (4-1), (5-1), and (6-1):
   each of $C_1$ to $C_4$ and $C_{29}$ to $C_{33}$ independently represents =C(R)—;
   each of $C_5$ to $C_8$, $C_{13}$ to $C_{16}$, $C_{21}$ to $C_{24}$, and $C_{34}$ to $C_{37}$ independently represents =C(R)—;
   each of $C_9$ to $C_{12}$, $C_{17}$ to $C_{20}$, $C_{25}$ to $C_{28}$ and $C_{38}$ to $C_{41}$ independently represents =C($R_A$)—;
   provided that when m=n=1 and both of $X_1$ and $X_2$ represent oxygen atoms, L does not represent the formula (2-1);
   when m=n=1 and both of $X_1$ and $X_2$ represent sulfur atoms, L does not represent the formula (2-1); and
   when m=n=1 or m=n=2, $X_1$ and $X_2$ are not both nitrogen atoms;
   R represents a hydrogen atom, a deuterium atom, or $R_C$;
   each of $R_1$ and $R_2$ independently represents a hydrogen atom, a deuterium atom or $R_C$, or $R_1$ and $R_2$ are bonded to each other to represent a divalent group represented by —($CR_3R_4$)$_p$—;
   $R_A$ represents a hydrogen atom, a deuterium atom, $R_C$, or a single bond bonded to ring A;
   $R_B$ represents a hydrogen atom, a deuterium atom, $R_C$, or a single bond bonded to ring B;
   $R_C$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atom, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or —P(=O)$R_3R_4$;

each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and p represents an integer of 5 to 8;

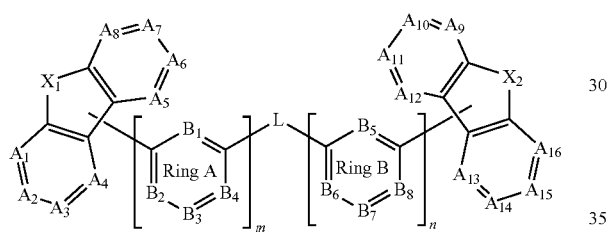
(1-2)

wherein in formula (1-2):
$X_1$ represents an oxygen atom, a sulfur atom, or —N($R_A$)—;
$X_2$ represents an oxygen atom, a sulfur atom, or —N($R_B$)—;
each of $A_1$ to $A_8$ independently represents =C($R_A$)— or =N—;
each of $A_9$ to $A_{16}$ independently represents =C($R_B$)— or =N—;
at least one of $A_1$ to $A_{16}$ represents =N—;
each of $B_1$ to $B_8$ independently represents =C(R)— or =N—;
each of m and n independently represents an integer of 1 to 3;
L represents an oxygen atom, a sulfur atom, —N(R)—, —Si($R_1$)($R_2$)—, or a linker represented by any one of formulae (2-2), (3-2), (4-2), (5-2), and (6-2):

(2-2)

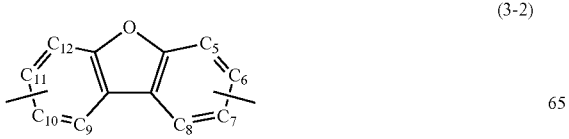
(3-2)

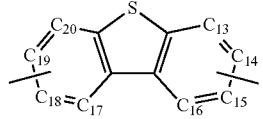
(4-2)

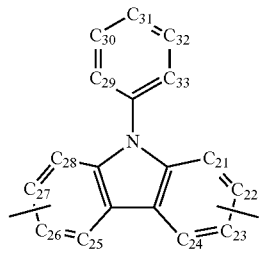
(5-2)

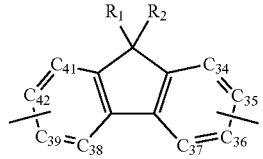
(6-2)

wherein in formulae (2-2), (3-2), (4-2), (5-2), and (6-2):
each of $C_1$ to $C_4$ and $C_{29}$ to $C_{33}$ independently represents =C(R)— or =N—;
each of $C_5$ to $C_8$, $C_{13}$ to $C_{16}$, $C_{21}$ to $C_{24}$ and $C_{34}$ to $C_{37}$ independently represents =C($R_B$)— or =N—; and
each of $C_9$ to $C_{12}$, $C_{17}$ to $C_{20}$, $C_{25}$ to $C_{28}$, and $C_{38}$ to $C_{41}$ independently represents =C($R_A$)— or =N—;
R represents a hydrogen atom, a deuterium atom, or $R_C$;
each of $R_1$ and $R_2$ independently represents a hydrogen atom, a deuterium atom or $R_C$, or $R_1$ and $R_2$ are bonded to each other to represent a divalent group represented by —(CR$_3$R$_4$)$_p$—;
$R_A$ represents a hydrogen atom, a deuterium atom, $R_C$, or a single bond bonded to ring A;
$R_B$ represents a hydrogen atom, a deuterium atom, $R_C$, or a single bond bonded to ring B;
$R_C$ independently represents, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or —P(=O)$R_3R_4$;

each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and p represents an integer of 5 to 8.

2. An organic electroluminescence device, comprising:
a cathode;
an anode; and
at least one organic thin film layer between the cathode and the anode;
wherein
the at least one organic thin film layer comprises:
a light emitting layer,
a hole transporting layer between the light emitting layer and the anode, and
an electron blocking layer between the light emitting layer and the hole transporting layer, and wherein
the electron blocking layer comprises;
a compound of formula (1-1) or formula (1-2):

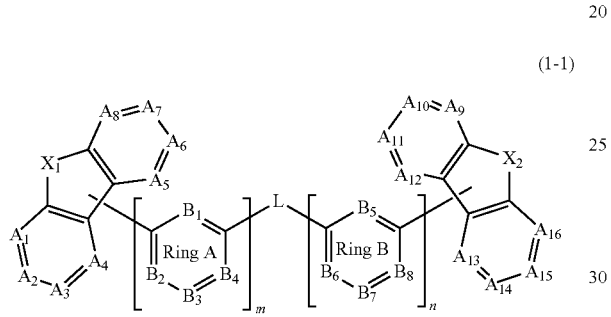

(1-1)

wherein in formula (1-1):
$X_1$ represents an oxygen atom, a sulfur atom, or —N($R_A$)—;
$X_2$ represents an oxygen atom, a sulfur atom, or —N($R_B$)—;
each of $A_1$ to $A_8$ independently represents =C($R_A$)— or =N—;
each of $A_9$ to $A_{16}$ independently represents =C($R_B$)— or =N—;
each of $B_1$ to $B_9$ independently represents =C(R)— or =N—;
each of m and n independently represents an integer of 1 to 3;
L represents an oxygen atom, a sulfur atom, —N(R)—, —Si($R_1$)($R_2$)— or a linker represented by any one of formulae (2-1), (3-1), (4-1), (5-1), and (6-1):

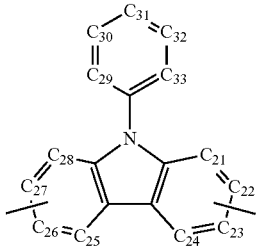

(2-1)

(3-1)

(4-1)

(5-1)

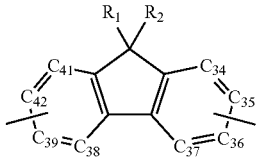

(6-1)

wherein in formulae (2-1), (3-1), (4-1), (5-1), and (6-1):
each of $C_1$ to $C_4$ and $C_{29}$ to $C_{33}$ independently represents =C(R)—;
each of $C_5$ to $C_8$, $C_{13}$ to $C_{16}$, $C_{21}$ to $C_{24}$, and $C_{34}$ to $C_{37}$ independently represents =C($R_B$)—;
each of $C_9$ to $C_{12}$, $C_{17}$ to $C_{20}$, $C_{25}$ to $C_{28}$ and $C_{38}$ to $C_{41}$ independently represents =C($R_A$)—;
provided that when m=n=1 and both of $X_1$ and $X_2$ represent oxygen atoms, L does not represent the formula (2-1);
when m=n=1 and both of $X_1$ and $X_2$ represent sulfur atoms, L does not represent the formula (2-1); and
when m=n=1 or m=n=2, $X_1$ and $X_2$ are not both nitrogen atoms;
R represents a hydrogen atom, a deuterium atom, or $R_C$;
each of $R_1$ and $R_2$ independently represents a hydrogen atom, a deuterium atom or $R_C$, or $R_1$ and $R_2$ are bonded to each other to represent a divalent group represented by —(CR$_3$R$_4$)$_p$—;
$R_A$ represents a hydrogen atom, a deuterium atom, $R_C$, or a single bond bonded to ring A;
$R_B$ represents a hydrogen atom, a deuterium atom, $R_C$, or a single bond bonded to ring B;
$R_C$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atom, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or —P(=O)R$_3$R$_4$;
each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and p represents an integer of 5 to 8;

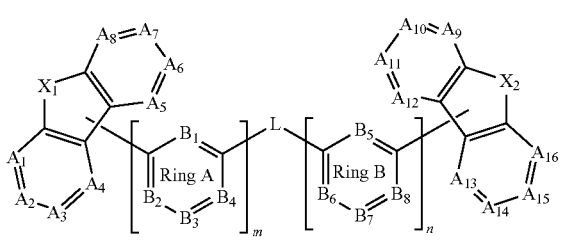
(1-2)

wherein in formula (1-2):
$X_1$ represents an oxygen atom, a sulfur atom, or —N($R_A$)—;
$X_2$ represents an oxygen atom, a sulfur atom, or —N($R_B$)—;
each of $A_1$ to $A_8$ independently represents =C($R_A$)— or =N—;
each of $A_9$ to $A_{16}$ independently represents =C($R_B$)— or =N—;
at least one of $A_1$ to $A_{16}$ represents =N—;
each of $B_1$ to $B_8$ independently represents =C(R)— or =N—;
each of m and n independently represents an integer of 1 to 3;
L represents an oxygen atom, a sulfur atom, —N(R)—, —Si($R_1$)($R_2$)—, or a linker represented by any one of formulae (2-2), (3-2), (4-2), (5-2), and (6-2):

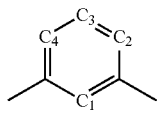
(2-2)

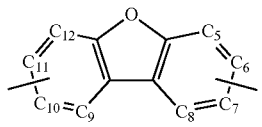
(3-2)

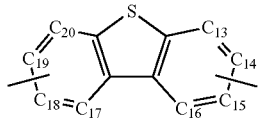
(4-2)

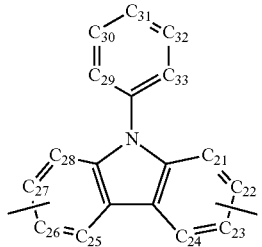
(5-2)

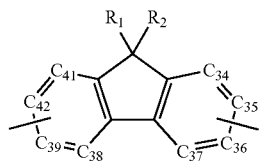
(6-2)

wherein in formulae (2-2), (3-2), (4-2), (5-2), and (6-2):
each of $C_1$ to $C_4$ and $C_{29}$ to $C_{33}$ independently represents =C(R)— or =N—;
each of $C_5$ to $C_8$, $C_{13}$ to $C_{16}$, $C_{21}$ to $C_{24}$, and $C_{34}$ to $C_{37}$ independently represents =C($R_B$)— or =N—; and
each of $C_9$ to $C_{12}$, $C_{17}$ to $C_{20}$, $C_{25}$ to $C_{28}$, and $C_{38}$ to $C_{41}$ independently represents =C($R_A$)— or =N—;
R represents a hydrogen atom, a deuterium atom, or $R_C$;
each of $R_1$ and $R_2$ independently represents a hydrogen atom, a deuterium atom or $R_C$, or $R_1$ and $R_2$ are bonded to each other to represent a divalent group represented by —(CR$_3$R$_4$)$_p$—;
$R_A$ represents a hydrogen atom, a deuterium atom, $R_C$, or a single bond bonded to ring A;
$R_B$ represents a hydrogen atom, a deuterium atom, $R_C$, or a single bond bonded to ring B;
$R_C$ independently represents, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or —P(=O)R$_3$R$_4$;
each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and
p represents an integer of 5 to 8.

3. The organic electroluminescence device according to claim 1, wherein an interfacial region between the cathode and the organic thin film layer comprises a reducing dopant.

4. An organic electroluminescence device, comprising:
a cathode;
an anode; and
at least one organic thin film layer between the cathode and the anode;

wherein
the at least one organic thin film layer comprises:
a light emitting layer, and
a hole transporting layer between the light emitting layer and the anode,
and wherein the hole transporting layer comprises:
a compound of formula (1-1) or formula (1-2):

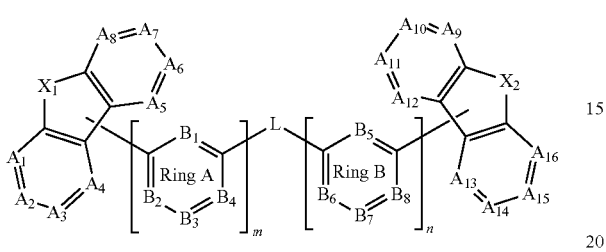
(1-1)

wherein in formula (1-1):
$X_1$ represents an oxygen atom, a sulfur atom, or —N($R_A$)—;
$X_2$ represents an oxygen atom, a sulfur atom, or —N($R_B$)—;
each of $A_1$ to $A_8$ independently represents =C($R_A$)— or =N—;
each of $A_9$ to $A_{16}$ independently represents =C($R_B$)— or =N—;
each of $B_1$ to $B_8$ independently represents =C(R)— or =N—;
each of m and n independently represents an integer of 1 to 3;
L represents an oxygen atom, a sulfur atom, —N(R)—, —Si($R_1$)($R_2$)— or a linker represented by any one of formulae (2-1), (3-1), (4-1), (5-1), and (6-1):

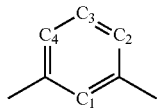
(2-1)

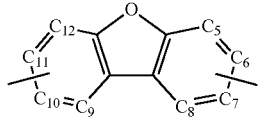
(3-1)

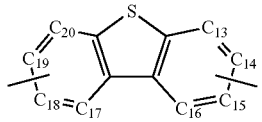
(4-1)

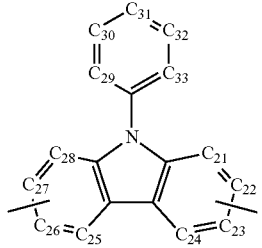
(5-1)

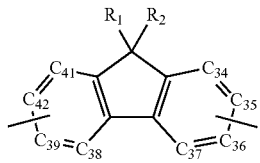
(6-1)

wherein in formulae (2-1), (3-1), (4-1), (5-1), and (6-1):
each of $C_1$ to $C_4$ and $C_{29}$ to $C_{33}$ independently represents =C(R)—;
each of $C_5$ to $C_8$, $C_{13}$ to $C_{16}$, $C_{21}$ to $C_{24}$, and $C_{34}$ to $C_{37}$ independently represents =C(R)—;
each of $C_9$ to $C_{12}$, $C_{17}$ to $C_{20}$, $C_{25}$ to $C_{28}$ and $C_{38}$ to $C_{41}$ independently represents =C($R_A$);
provided that when m=n=1 and both of $X_1$ and $X_2$ represent oxygen atoms, L does not represent the formula (2-1);
when m=n=1 and both of $X_1$ and $X_2$ represent sulfur atoms, L does not represent the formula (2-1); and
when m=n=1 or m=n=2, $X_1$ and $X_2$ are not both nitrogen atoms;
R represents a hydrogen atom, a deuterium atom, or $R_C$;
each of $R_1$ and $R_2$ independently represents a hydrogen atom, a deuterium atom or $R_C$, or $R_1$ and $R_2$ are bonded to each other to represent a divalent group represented by —(CR$_3$R$_4$)$_p$—;
$R_A$ represents a hydrogen atom, a deuterium atom, $R_C$, or a single bond bonded to ring A;
$R_B$ represents a hydrogen atom, a deuterium atom, $R_C$, or a single bond bonded to ring B;
$R_C$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atom, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or —P(=O)R$_3$R$_4$;
each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and p represents an integer of 5 to 8:

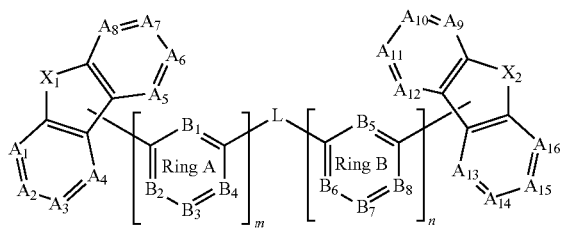
(1-2)

wherein in formula (1-2):
$X_1$ represents an oxygen atom, a sulfur atom, or —N($R_A$)—;
$X_2$ represents an oxygen atom, a sulfur atom, or —N($R_B$)—;
each of $A_1$ to $A_8$ independently represents =C($R_A$)— or =N—;
each of $A_9$ to $A_{16}$ independently represents =C($R_B$)— or =N—;
at least one of $A_1$ to $A_{16}$ represents =N—;
each of $B_1$ to $B_8$ independently represents =C(R)— or =N—;
each of m and n independently represents an integer of 1 to 3;
L represents an oxygen atom, a sulfur atom, —N(R)—, —Si($R_1$)($R_2$)—, or a linker represented by any one of formulae (2-2), (3-2), (4-2), (5-2), and (6-2):

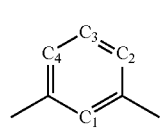
(2-2)

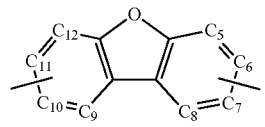
(3-2)

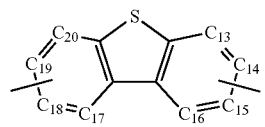
(4-2)

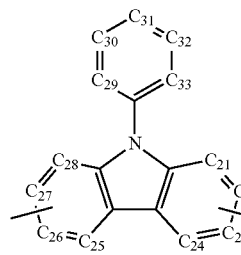
(5-2)

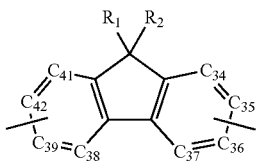
(6-2)

wherein in formulae (2-2), (3-2)(4-2), (5-2), and (6-2);
each of $C_1$ to $C_4$ and $C_{29}$ to $C_{33}$ independently represents =C(R)— or =N—;
each of $C_5$ to $C_8$, $C_{13}$ to $C_{16}$, $C_{21}$ to $C_{24}$ and $C_{34}$ to $C_{37}$ independently represents =C($R_B$)— or =N—; and
each of $C_9$ to $C_{12}$, $C_{17}$ to $C_{20}$, $C_{25}$ to $C_{28}$ and $C_{38}$ to $C_{41}$ independently represents =C($R_A$)— or =N—;
R represents a hydrogen atom, a deuterium atom, or $R_C$;
each of $R_1$ and $R_2$ independently represents a hydrogen atom, a deuterium atom or $R_C$, or $R_1$ and $R_2$ are bonded to each other to represent a divalent group represented by —(C$R_3R_4$)$_p$—;
$R_A$ represents a hydrogen atom, a deuterium atom, $R_C$, or a single bond bonded to ring A;
$R_B$ represents a hydrogen atom, a deuterium atom, $R_C$, or a single bond bonded to ring B;
$R_C$ independently represents, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a silyl group substituted with a substituted or unsubstituted alkyl group having 1 to 30 carbon atoms and/or an unsubstituted aryl group having 6 to 30 ring carbon atoms, an unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a hydroxyl group, a nitro group, an amino group substituted with a substituted or unsubstituted alkyl group having 1 to 30 carbon atoms and/or an unsubstituted aryl group having 6 to 30 ring carbon atoms, an unsubstituted amino group, a carboxyl group, or —P(=O)$R_3R_4$;
each of $R_3$ and $R_4$ independently represents a hydrogen atom, a deuterium atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, or a substituted or unsubstituted fluoroalkyl group having 1 to 30 carbon atoms; and
p represents an integer of 5 to 8.

5. The organic electroluminescence device according to claim 1, wherein each of R, $R_1$, $R_2$, $R_A$, and $R_B$ independently represents a hydrogen atom, a deuterium atom, a single bond, a substituted or unsubstituted alkyl group having 1 to 5 carbon atoms, a substituted or unsubstituted aryl group having 6 to 18 ring carbon atoms, a substituted or unsubstituted heteroaryl group having 5 to 18 ring atoms, or —P(=O)($R_3$)($R_4$).

6. The organic electroluminescence device according to claim 1, wherein at least one of m and n is 2 or 3.

7. The organic electroluminescence device according to claim 1, wherein the compound of formula (1-1) or formula (1-2) is of formula (7):

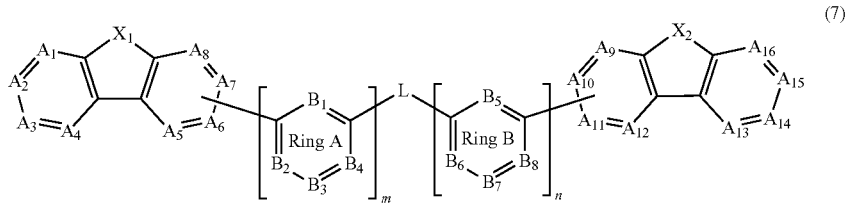

(7)

wherein $X_1$, $X_2$, $A_1$ to $A_{16}$, $B_1$ to $B_8$, L, m, and n are the same as defined with respect to $X_1$, $X_2$, $A_1$ to $A_{16}$, $B_1$ to $B_8$, L, m, and n of the formula (1-1), or $X_1$, $X_2$, $A_1$ to $A_{16}$, $B_1$ to $B_8$, L, m, and n of the formula (1-2).

8. The organic electroluminescence device according to claim 1, wherein the compound of formula (1-1) or of formula (1-2) is of formula (8):

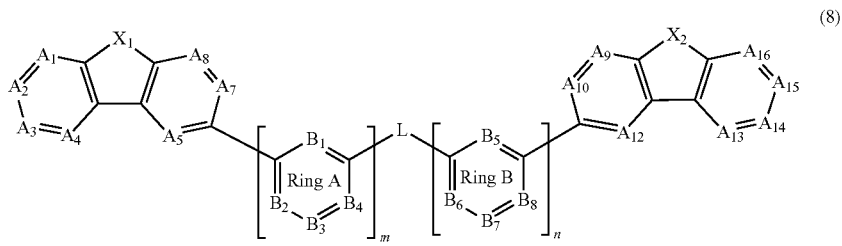

(8)

wherein $X_1$, $X_2$, $A_1$ to $A_5$, $A_7$ to $A_{10}$, $A_{12}$ to $A_{16}$, $B_1$ to $B_8$, L, m, and n are the same as defined with respect to $X_1$, $X_2$, $A_1$ to $A_5$, $A_7$ to $A_{10}$, $A_{12}$ to $A_{16}$, $B_1$ to $B_8$, L, m, and n of the formula (1-1), or $X_1$, $X_2$, $A_1$ to $A_5$, $A_7$ to $A_{10}$, $A_{12}$ to $A_{16}$, $B_1$ to $B_8$, L, m, and n of the formula (1-2).

9. The organic electroluminescence device according to claim 1, wherein the compound of formula (1-1) or of formula (1-2) is of formula (9):

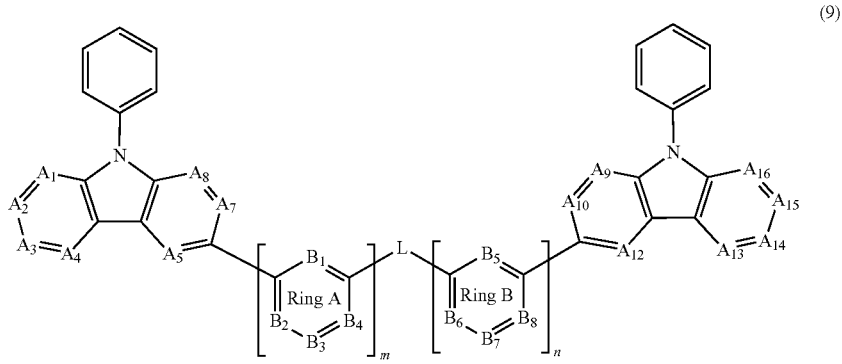

(9)

wherein $A_1$ to $A_5$, $A_7$ to $A_{10}$, $A_{12}$ to $A_{16}$, $B_1$ to $B_8$, L, m, and n are the same as defined with respect to $A_1$ to $A_5$, $A_7$ to $A_{10}$, $A_{12}$ to $A_{16}$, $B_1$ to $B_8$, L, m, and n of the formula (1-1), or $A_1$ to $A_5$, $A_7$ to $A_{10}$, $A_{12}$ to $A_{16}$, $B_1$ to $B_8$, L, m, and n of the formula (1-2).

10. The organic electroluminescence device according to claim 1, wherein the compound of formula (1-1) or of formula (1-2) is of formula (10):

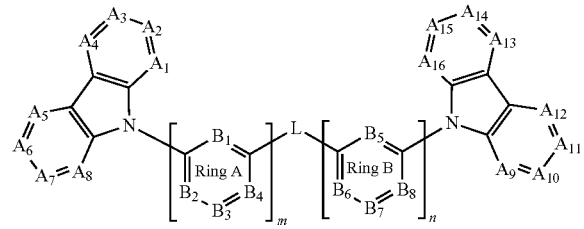

(10)

wherein $A_1$ to $A_{16}$, $B_1$ to $B_8$, L, m, and n are the same as defined with respect to $A_1$ to $A_{16}$, $B_1$ to $B_8$, L, m, and n of the formula (1-1), or $A_1$ to $A_{16}$, $B_1$ to $B_8$, L, m, and n of the formula (1-2).

11. The organic electroluminescence device according to claim 1, wherein the compound of formula (1-1) or of formula (1-2) has a molecular weight of 1000 or less.

12. The organic electroluminescence device according to claim 2, wherein each of R, $R_1$, $R_2$, $R_4$, and $R_B$ independently represents a hydrogen atom, a deuterium atom, a single bond, a substituted or unsubstituted alkyl group having 1 to 5 carbon atoms, a substituted or unsubstituted aryl group having 6 to 18 ring carbon atoms, a substituted or unsubstituted heteroaryl group having 5 to 18 ring atoms, or —P(=O)($R_3$)($R_4$).

13. The organic electroluminescence device according to claim 2, wherein at least one of m and n is 2 or 3.

14. The organic electroluminescence device according to claim 2, wherein the compound of formula (1-1) or of formula (1-2) is of formula (8):

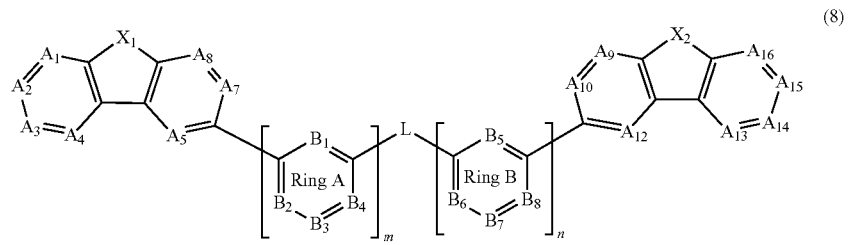

(8)

wherein $X_1$, $X_2$, $A_1$ to $A_5$, $A_7$ to $A_{10}$, $A_{12}$ to $A_{16}$, $B_1$ to $B_8$, L, m, and n are the same as defined with respect to $X_1$, $X_2$, $A_1$ to $A_5$, $A_7$ to $A_{10}$, $A_{12}$ to $A_{16}$, $B_1$ to $B_8$, L, m, and n of the formula (1-1), or $X_1$, $X_2$, $A_1$ to $A_5$, $A_7$ to $A_{10}$, $A_{12}$ to $A_{16}$, $B_1$ to $B_8$, L, m, and n of the formula (1-2).

15. The organic electroluminescence device according to claim 2, wherein the compound of formula (1-1) or of formula (1-2) is of formula (9):

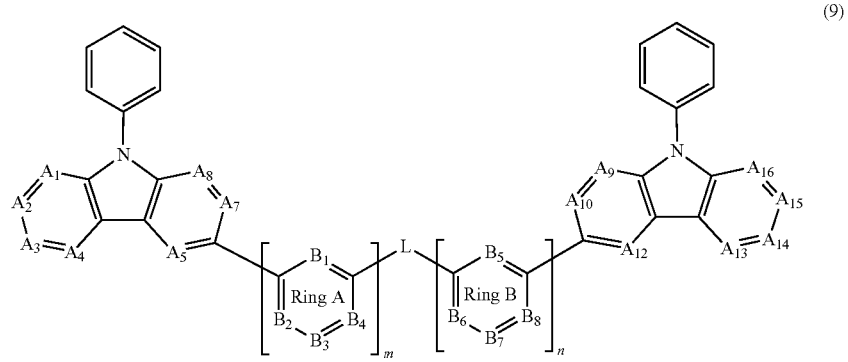

(9)

wherein $A_1$ to $A_5$, $A_7$ to $A_{10}$, $A_{12}$ to $A_{16}$, $B_1$ to $B_8$, L, m, and n are the same as defined with respect to $A_1$ to $A_5$, $A_7$ to $A_{10}$, $A_{12}$ to $A_{16}$, $B_1$ to $B_8$, L, m, and n of the formula (1-1), or $A_1$ to $A_5$, $A_7$ to $A_{10}$, $A_{12}$ to $A_{16}$, $B_1$ to $B_8$, L, m, and n of the formula (1-2).

16. The organic electroluminescence device according to claim 2, wherein the compound of formula (1-1) or of formula (1-2) is of formula (10):

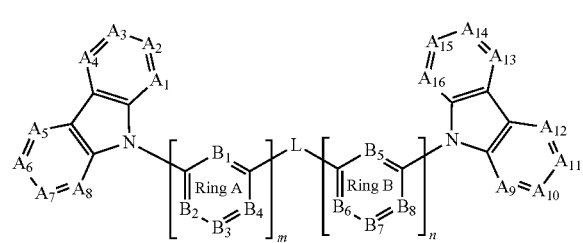

(10)

wherein $A_1$ to $A_{16}$, $B_1$ to $B_8$, L, m, and n are the same as defined with respect to $A_1$ to $A_{16}$, $B_1$ to $B_8$, L, m, and n of the formula (1-1), or $A_1$ to $A_{16}$, $B_1$ to $B_8$, L, m, and n of the formula (1-2).

17. The organic electroluminescence device according to claim 4, wherein each of R, $R_1$, $R_2$, $R_A$, and $R_B$ independently represents a hydrogen atom, a deuterium atom, a single bond, a substituted or unsubstituted alkyl group having 1 to 5 carbon atoms, a substituted or unsubstituted aryl group having 6 to 18 ring carbon atoms, a substituted or unsubstituted heteroaryl group having 5 to 18 ring atoms, or $-P(=O)(R_3)(R_4)$.

18. The organic electroluminescence device according to claim 4, wherein at least one of m and n is 2 or 3.

19. The organic electroluminescence device according to claim 4, wherein the compound of formula (1-1) or of formula (1-2) is of formula (8):

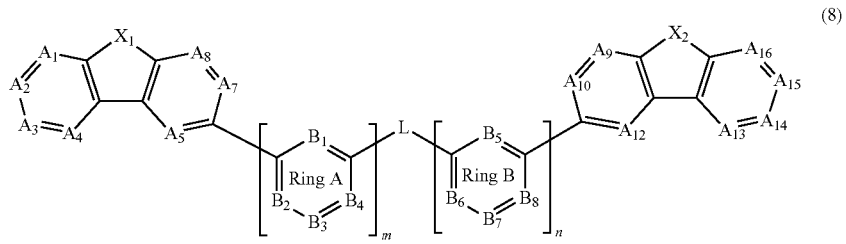

(8)

wherein $X_1$, $X_2$, $A_1$ to $A_5$, $A_7$ to $A_{10}$, $A_{12}$ to $A_{16}$, $B_1$ to $B_8$, L, m, and n are the same as defined with respect to $X_1$, $X_2$, $A_1$ to $A_5$, $A_7$ to $A_{10}$, $A_{12}$ to $A_{16}$, $B_1$ to $B_8$, L, m, and n of the formula (1-1), or $X_1$, $X_2$, $A_1$ to $A_5$, $A_7$ to $A_{10}$, $A_{12}$ to $A_{16}$, $B_1$ to $B_8$, L, m, and n of the formula (1-2).

20. The organic electroluminescence device according to claim 4, wherein the compound of formula (1-1) or of formula (1-2) is of formula (9):

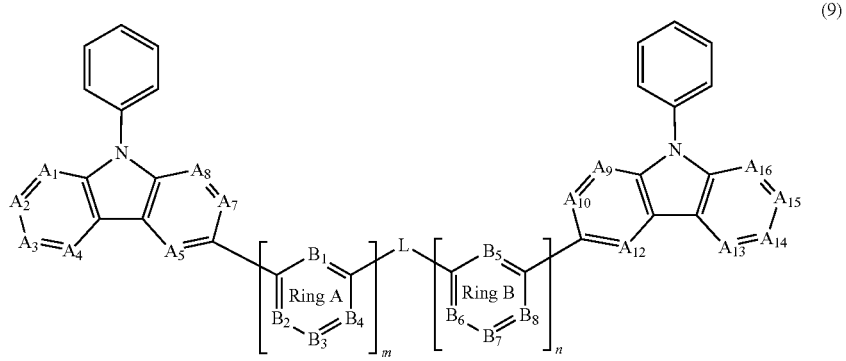

(9)

wherein $A_1$ to $A_5$, $A_7$ to $A_{10}$, $A_{12}$ to $A_{16}$, $B_1$ to $B_8$, L, m, and n are the same as defined with respect to $A_1$ to $A_5$, $A_7$ to $A_{10}$, $A_{12}$ to $A_{16}$, $B_1$ to $B_8$, L, m, and n of the formula (1-1), or $A_1$ to $A_5$, $A_7$ to $A_{10}$, $A_{12}$ to $A_{16}$, $B_1$ to $B_8$, L, m, and n of the formula (1-2).

21. The organic electroluminescence device according to claim 4, wherein the compound of formula (1-1) or of formula (1-2) is of formula (10):

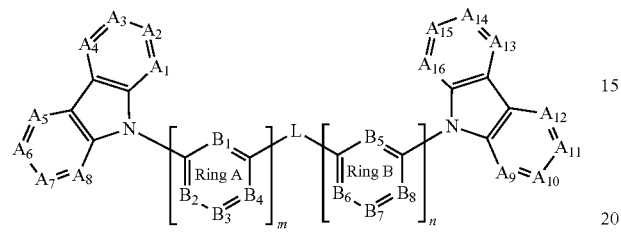

(10)

wherein $A_1$ to $A_{16}$, $B_1$ to $B_8$, L, m, and n are the same as defined with respect to $A_1$ to $A_{16}$, $B_1$ to $B_8$, L, m, and n of the formula (1-1), or $A_1$ to $A_{16}$, $B_1$ to $B_8$, L, m, and n of the formula (1-2).

* * * * *